US011821012B2

(12) United States Patent
Wessells et al.

(10) Patent No.: US 11,821,012 B2
(45) **Date of Patent: *Nov. 21, 2023**

(54) GENE EDITING SYSTEMS COMPRISING AN RNA GUIDE TARGETING HYDROXYACID OXIDASE 1 (HAO1) AND USES THEREOF

(71) Applicant: Arbor Biotechnologies, Inc., Cambridge, MA (US)

(72) Inventors: Quinton Norman Wessells, Cambridge, MA (US); Jeffrey Raymond Haswell, Needham, MA (US); Tia Marie Ditommaso, Newton, MA (US); Noah Michael Jakimo, San Francisco, CA (US); Sejuti Sengupta, Ashland, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,801

(22) Filed: Nov. 4, 2022

(65) Prior Publication Data

US 2023/0212541 A1 Jul. 6, 2023

Related U.S. Application Data

(63) Continuation of application No. 17/832,038, filed on Jun. 3, 2022.

(60) Provisional application No. 63/300,727, filed on Jan. 19, 2022, provisional application No. 63/292,889, filed on Dec. 22, 2021, provisional application No. 63/225,046, filed on Jul. 23, 2021, provisional application No. 63/197,073, filed on Jun. 4, 2021.

(51) Int. Cl.

| | |
|---|---|
| ***C12N 9/22*** | (2006.01) |
| ***A61P 13/12*** | (2006.01) |
| ***A61K 31/7105*** | (2006.01) |
| ***A61K 38/16*** | (2006.01) |
| ***C12N 15/11*** | (2006.01) |
| ***C12N 15/86*** | (2006.01) |
| ***C12N 15/90*** | (2006.01) |
| ***A61K 48/00*** | (2006.01) |
| ***A61K 38/46*** | (2006.01) |

(52) U.S. Cl.

CPC ............ *C12N 9/22* (2013.01); *A61K 31/7105* (2013.01); *A61K 38/465* (2013.01); *A61P 13/12* (2018.01); *C12N 15/11* (2013.01); *C12N 15/86* (2013.01); *C12N 15/907* (2013.01); *A61K 48/00* (2013.01); *C12N 2310/20* (2017.05); *C12N 2750/14143* (2013.01); *C12N 2800/80* (2013.01)

(58) Field of Classification Search

None

See application file for complete search history.

(56) References Cited

FOREIGN PATENT DOCUMENTS

| | | |
|---|---|---|
| WO | WO 2015/100436 A1 | 7/2015 |
| WO | WO 2019/178427 A1 | 9/2019 |
| WO | WO 2020/028327 A1 | 2/2020 |
| WO | WO 2021/202800 A1 | 10/2021 |
| WO | WO 2021/257730 A2 | 12/2021 |

OTHER PUBLICATIONS

Slaymaker et al. Rationally Engineered Cas9 Nucleases With Improved Specificity. Science, 2016. 351(6268): pp. 84-88, with Supplement (Year: 2016).*

Gao et al., Engineered Cpf1 Variants with Altered PAM Specificities. Nature Biotechnology, 2016. 35(8): pp. 789-793, with Supplement (Year: 2016).*

Strecker et al., Engineering of CRISPR-12b for Human Genome Editing. Nature Communications, 2019. 10 (212): 8 pages, with Supplement. https://doi.org/10.1038/s41467-018-08224-4 (Year: 2019).*

Huang et al., Structural Basis for Two Metal-Ion Catalysis of DNA Cleavage by Cas12i2. Nature Communications, 2020. 11 (5241): 14 pages, with Supplement. https://doi.org/10.1038/s41467-020-19072-6 (Year: 2020).*

[No Author Listed], Cas12i nickase variant Cas12i2-6.1, Seq ID No. 18. Geneseq Database Accession No. BIV42112. From CN 112195164 A. Jan. 8, 2021. 5 pages.

Mcgaw et al., Engineered Cas12i2 is a versatile high-efficiency platform for therapeutic genome editing. Nat Commun. May 20, 2022;13(1):2833(1-11).

Zheng et al., CRISPR/Cas9-mediated metabolic pathway reprogramming in a novel humanized rat model ameliorates primary hyperoxaluria type 1. Kidney Int. Oct. 2020;98(4):947-957. Epub May 25, 2020.

±U.S. Appl. No. 17/832,038, filed Jun. 3, 2022, Wessells et al.

* cited by examiner

*Primary Examiner* — Allison M Fox
*Assistant Examiner* — Kimberly A Aron
(74) *Attorney, Agent, or Firm* — McDermott, Will & Emery LLP

(57) ABSTRACT

Provided herein are gene editing systems and/or compositions comprising RNA guides targeting HAO1 for use in genetic editing of the HAO1 gene. Also provide herein are methods of using the gene editing system for introducing edits to the HAO1 gene and/or for treatment of primary hyperoxaluria (PH), and processes for characterizing the gene editing system.

22 Claims, 10 Drawing Sheets

Specification includes a Sequence Listing.

GENE EDITING SYSTEMS COMPRISING AN RNA GUIDE TARGETING HYDROXYACID OXIDASE 1 (HAO1) AND USES THEREOF

CROSS REFERENCE TO RELATED APPLICATIONS

The present application is a continuation of U.S. application Ser. No. 17/832,038, filed Jun. 3, 2022, which claims the benefit under 35 U.S.C. § 119(e) of U.S. Provisional Application No. 63/197,073, filed Jun. 4, 2021, U.S. Provisional Application No. 63/225,046, filed Jul. 23, 2021, U.S. Provisional Application No. 63/292,889, filed Dec. 22, 2021, and U.S. Provisional Application No. 63/300,727, filed Jan. 19, 2022, the contents of each of which are incorporated by reference herein in their entirety.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SEQUENCE LISTING

The instant application contains a Sequence Listing which has been filed electronically in XML format and is hereby incorporated by reference in its entirety. Said XML copy, created on Mar. 21, 2023, is named 116928-0047-0004US01_SUBSEQ.xml and is 1,465,049 bytes in size.

SUMMARY OF THE INVENTION

The present disclosure is based, at least in part, on the development of a system for genetic editing of a hydroxyacid oxidase 1 (HAO1) gene. The system involves a Cas12i CRISPR nuclease polypeptide (e.g., a Cas12i2 polypeptide) and an RNA guide mediating cleavage at a genetic site within the HAO1 gene by the CRISPR nuclease polypeptide. As reported herein, the gene editing system disclosed herein has achieved successful editing of HAO1 gene with high editing efficiency and accuracy.

Without being bound by theory, the gene editing system disclosed herein may further exhibit one or more of the following advantageous features. Compared to SpCas9 and Cas12a, Cas12i effectors are smaller (1033 to 1093 aa), which, in conjunction with their short mature crRNA (40-43 nt), is preferable in terms of delivery and cost of synthesis. Cas12i cleavage results in larger deletions compared to the small deletions and +1 insertions induced by Cas9 cleavage. Cas12i PAM sequences also differ from those of Cas9. Therefore, larger and different portions of genetic sites of interest can be disrupted with a Cas12i polypeptide and RNA guide compared to Cas9. Using an unbiased approach of tagmentation-based tag integration site sequencing (TTISS), more potential off-target sites with a higher number of unique integration events were identified for SpCas9 compared to Cas12i2. See WO/2021/202800. Therefore, Cas12i such as Cas12i2 may be more specific than Cas9.

Accordingly, provided herein are gene editing systems for editing HAO1 gene, pharmaceutical compositions or kits comprising such, methods of using the gene editing systems to produce genetically modified cells, and the resultant cells thus produced. Also provided herein are uses of the gene editing systems disclosed herein, the pharmaceutical compositions and kits comprising such, and/or the genetically modified cells thus produced for treating primary hyperoxaluria (PH) in a subject.

In some aspects, the present disclosure features system for genetic editing of a hydroxyacid oxidase 1 (HAO1) gene, comprising (i) a Cas12i polypeptide or a first nucleic acid encoding the Cas12i polypeptide, and (ii) an RNA guide or a second nucleic acid encoding the RNA guide. The RNA guide comprises a spacer sequence specific to a target sequence within an HAO1 gene, the target sequence being adjacent to a protospacer adjacent motif (PAM) comprising the motif of 5'-TTN-3', which is located 5' to the target sequence.

In some embodiments, the Cas12i polypeptide can be a Cas12i2 polypeptide. In other embodiments, the Cas12i polypeptide can be a Cas12i4 polypeptide.

In some embodiments, the Cas12i polypeptide is a Cas12i2 polypeptide, which comprises an amino acid sequence at least 95% identical to SEQ ID NO: 922 and comprises one or more mutations relative to SEQ ID NO: 922. In some embodiments, the one or more mutations in the Cas12i2 polypeptide are at positions D581, G624, F626, P868, I926, V1030, E1035, and/or S1046 of SEQ ID NO: 922. In some examples, the one or more mutations are amino acid substitutions, which optionally is D581R, G624R, F626R, P868T, I926R, V1030G, E1035R, S1046G, or a combination thereof.

In one example, the Cas12i2 polypeptide comprises mutations at positions D581, D911, I926, and V1030 (e.g., amino acid substitutions of D581R, D911R, I926R, and V1030G). In another example, the Cas12i2 polypeptide comprises mutations at positions D581, I926, and V1030 (e.g., amino acid substitutions of D581R, I926R, and V1030G). In yet another example, the Cas12i2 polypeptide comprises mutations at positions D581, I926, V1030, and S1046 (e.g., amino acid substitutions of D581R, I926R, V1030G, and S1046G). In still another example, the Cas12i2 polypeptide comprises mutations at positions D581, G624, F626, I926, V1030, E1035, and S1046 (e.g., amino acid substitutions of D581R, G624R, F626R, I926R, V1030G, E1035R, and S1046G). In another example, the Cas12i2 polypeptide comprises mutations at positions D581, G624, F626, P868, I926, V1030, E1035, and S1046 (e.g., amino acid substitutions of D581R, G624R, F626R, P868T, I926R, V1030G, E1035R, and S1046G).

Exemplary Cas12i2 polypeptides for use in any of the gene editing systems disclosed herein may comprise the amino acid sequence of any one of SEQ ID NOs: 923-927. In one example, the exemplary Cas12i2 polypeptide for use in any of the gene editing systems disclosed herein comprises the amino acid sequence of SEQ ID NO: 924. In another example, the exemplary Cas12i2 polypeptide for use in any of the gene editing systems disclosed herein comprises the amino acid sequence of SEQ ID NO: 927.

In some embodiments, the gene editing system may comprise the first nucleic acid encoding the Cas12i polypeptide (e.g., the Cas12i2 polypeptide as disclosed herein). In some instances, the first nucleic acid is located in a first vector (e.g., a viral vector such as an adeno-associated viral vector or AAV vector). In some instances, the first nucleic acid is a messenger RNA (mRNA). In some instances, the nucleic acid encoding the Cas12i polypeptide (e.g., the Cas12i2 polypeptide as disclosed herein) is codon-optimized.

In some embodiments, the target sequence may be within exon 1 or exon 2 of the HAO1 gene. In some examples, the target sequence comprises 5'-CAAAGTCTATATATGACTAT-3' (SEQ ID NO: 1025), 5'-GGAAGTACTGATTTAGCATG-3' (SEQ ID NO: 1026), 5'-TAGATGGAAGCTGTATCCAA-3' (SEQ ID NO: 1046), 5'-CGGAGCATCCTTGGATACAG-3' (SEQ ID NO: 1047), or 5'-AGGACAGAGGGTCAGCATGC-3' (SEQ ID NO: 1052). In specific examples, the target sequence can be the nucleotide sequence of SEQ ID NO: 1047.

In some embodiments, the spacer sequence may be 20-30-nucleotide in length. In some examples, the spacer sequence is 20-nucleotide in length. In some examples, the spacer sequence comprises 5'-CAAAGUCUAUAUAUGACUAU-3' (SEQ ID NO: 1093); 5'-GGAAGUACUGAUUUAGCAUG-3' (SEQ ID NO: 1094); 5'-UAGAUGGAAGCUGUAUCCAA-3' (SEQ ID NO: 1095); 5'-CGGAGCAUCCUUGGAUACAG-3' (SEQ ID NO: 1096); or 5'-AGGACAGAGGGUCAGCAUGC-3 (SEQ ID NO: 1097). In specific examples, the spacer sequence may comprise SEQ ID NO: 1096.

In some embodiments, the RNA guide comprises the spacer and a direct repeat sequence. In some examples, the direct repeat sequence is 23-36-nucleotide in length. In one example, the direct repeat sequence is at least 90% identical to any one of SEQ ID NOs: 1-10 or a fragment thereof that is at least 23-nucleotide in length. In some specific examples, the direct repeat sequence is any one of SEQ ID NOs: 1-10, or a fragment thereof that is at least 23-nucleotide in length. By way of non-limiting example, the direct repeat sequence is 5'-AGAAAUCCGUCUUUCAUUGACGG-3' (SEQ ID NO: 10).

In specific examples, the RNA guide may comprise the nucleotide sequence of 5'-AGAAAUCCGUCUUUCAUUGACGGCAAAGUCUAUAUAUGACUAU-3' (SEQ ID NO: 967), 5'-AGAAAUCCGUCUUUCAUUGACGGGGAAGUACUGAUUUAGCAUG-3' (SEQ ID NO: 968), 5'-AGAAAUCCGUCUUUCAUUGACGGUAGAUGGAAGCUGUAUCCAA-3' (SEQ ID NO: 988), 5'-AGAAAUCCGUCUUUCAUUGACGGCGGAGCAUCCUUGGAUACAG-3' (SEQ ID NO: 989), or 5'-AGAAAUCCGUCUUUCAUUGACGGAGGACAGAGGGUCAGCAUGC-3' (SEQ ID NO: 994). In specific examples, the RNA guide may comprise SEQ ID NO: 989.

In some embodiments, the system may comprise the second nucleic acid encoding the RNA guide. In some examples, the nucleic acid encoding the RNA guide may be located in a viral vector. In some examples, the viral vector comprises the both the first nucleic acid encoding the Cas12i2 polypeptide and the second nucleic acid encoding the RNA guide.

In some embodiments, any of the systems described herein may comprise the first nucleic acid encoding the Cas12i2 polypeptide, which is located in a first vector, and the second nucleic acid encoding the RNA guide, which is located on a second vector. In some examples, the first and/or second vector is a viral vector. In some specific examples, the first and second vectors are the same vector. In other examples, the first and second vectors are different vectors.

In some embodiments, any of the systems described herein may comprise one or more lipid nanoparticles (LNPs), which encompass the Cas12i2 polypeptide or the first nucleic acid encoding the Cas12i2 polypeptide, the RNA guide or the second nucleic acid encoding the RNA guide, or both.

In some embodiments, the system described herein may comprise a LNP, which encompass the Cas12i2 polypeptide or the first nucleic acid encoding the Cas12i2 polypeptide, and a viral vector comprising the second nucleic acid encoding the RNA guide. In some examples, the viral vector is an AAV vector. In other embodiments, the system described herein may comprise a LNP, which encompass the RNA guide or the second nucleic acid encoding the RNA guide, and a viral vector comprising the first nucleic acid encoding the Cas12i2 polypeptide. In some examples, the viral vector is an AAV vector.

In some aspects, the present disclosure also provides a pharmaceutical composition comprising any of the gene editing systems disclosed herein, or a kit comprising the components of the gene editing system.

In other aspects, the present disclosure also features a method for editing a hydroxyacid oxidase 1 (HAO1) gene in a cell, the method comprising contacting a host cell with any of the systems disclosed herein to genetically edit the HAO1 gene in the host cell. In some examples, the host cell is cultured in vitro. In other examples, the contacting step is performed by administering the system for editing the HAO1 gene to a subject comprising the host cell.

Also within the scope of the present disclosure is a cell comprising a disrupted a hydroxyacid oxidase 1 (HAO1) gene, which can be produced by contacting a host cell with the system disclosed herein genetically edit the HAO1 gene in the host cell.

Still in other aspects, the present disclosure provides a method for treating primary hyperoxaluria (PH) in a subject. The method may comprise administering to a subject in need thereof any of the systems for editing a hydroxyacid oxidase 1 (HAO1) gene or any of the modified cells disclosed herein. In some embodiments, the subject may be a human patient having the PH. In some examples, the PH is PH1, PH2, or PH3. In a specific example, the PH is PH1.

Also provided herein is an RNA guide, comprising (i) a spacer sequence as disclosed herein that is specific to a target sequence in a hydroxyacid oxidase 1 (HAO1) gene, wherein the target sequence is adjacent to a protospacer adjacent motif (PAM) comprising the motif of 5'-TTN-3', which is located 5' to the target sequence; and (ii) a direct repeat sequence.

In some embodiments, the spacer may be 20-30-nucleotide in length. In some examples, the spacer is 20-nucleotide in length.

In some embodiments, the direct repeat sequence may be 23-36-nucleotide in length. In some examples, the direct repeat sequence is 23-nucleotide in length.

In some embodiments, the target sequence may be within exon 1 or exon 2 of the HAO1 gene. In some examples, the target sequence comprises 5'-CAAAGTCTATATATGACTAT-3' (SEQ ID NO: 1025), 5'-GGAAGTACTGATTTAGCATG-3' (SEQ ID NO: 1026), 5'-TAGATGGAAGCTGTATCCAA-3' (SEQ ID NO: 1046), 5'-CGGAGCATCCTTGGATACAG-3' (SEQ ID NO: 1047), or 5'-AGGACAGAGGGTCAGCATGC-3' (SEQ ID NO: 1052). In specific examples, the target sequence may comprise SEQ ID NO: 1047.

In some embodiments, the spacer sequence may be set forth as 5'-CAAAGUCUAUAUAUGACUAU-3' (SEQ ID NO: 1093); 5'-GGAAGUACUGAUUUAGCAUG-3' (SEQ ID NO:1094); 5'-UAGAUGGAAGCUGUAUCCAA-3' (SEQ ID NO: 1095); 5'-CGGAGCAUCCUUGGAUACAG-3' (SEQ ID NO: 1096); or 5'-AGGACAGAGGGUCAGCAUGC-3 (SEQ ID NO: 1097). In specific examples, the spacer sequence may comprise SEQ ID NO: 1096.

In some embodiments, the direct repeat sequence may be at least 90% identical to any one of SEQ ID NOs: 1-10 or a fragment thereof that is at least 23-nucleotide in length. In some examples, the direct repeat sequence is any one of SEQ ID NOs: 1-10, or a fragment thereof that is at least 23-nucleotide in length. By way of non-limiting example, the direct repeat sequence is 5'-AGAAAUCCGUCUUUCAUUGACGG-3' (SEQ ID NO: 10).

In some embodiments, the RNA guide may comprise the nucleotide sequence of 5'-AGAAAUCCGUCUUUCAUUGACGGCAAAGUCUAUAUAUGACUAU-3' (SEQ ID NO: 967), 5'-AGAAAUCCGUCUUUCAUUGACGGGGAAGUACUGAUUUAGCAUG-3' (SEQ ID NO: 968), 5'-AGAAAUCCGUCUUUCAUUGACGGUAGAUGGAAGCUGUAUCCAA-3' (SEQ ID NO: 988), 5'-AGAAAUCCGUCUUUCAUUGACGGCGGAGCAUCCUUGGAUACAG-3' (SEQ ID NO: 989), or 5'-AGAAAUCCGUCUUUCAUUGACGGAGGACAGAGGGUCAGCAUGC-3' (SEQ ID NO: 994). In specific examples, the RNA guide may comprise SEQ ID NO: 989.

Also provided herein are any of the gene editing systems disclosed herein, pharmaceutical compositions or kits comprising such, or genetically modified cells generated by the gene editing system for use in treating PH in a subject, as well as uses of the gene editing systems disclosed herein, pharmaceutical compositions or kits comprising such, or genetically modified cells generated by the gene editing system for manufacturing a medicament for treatment of PH in a subject.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

DETAILED DESCRIPTION

Figure 1:
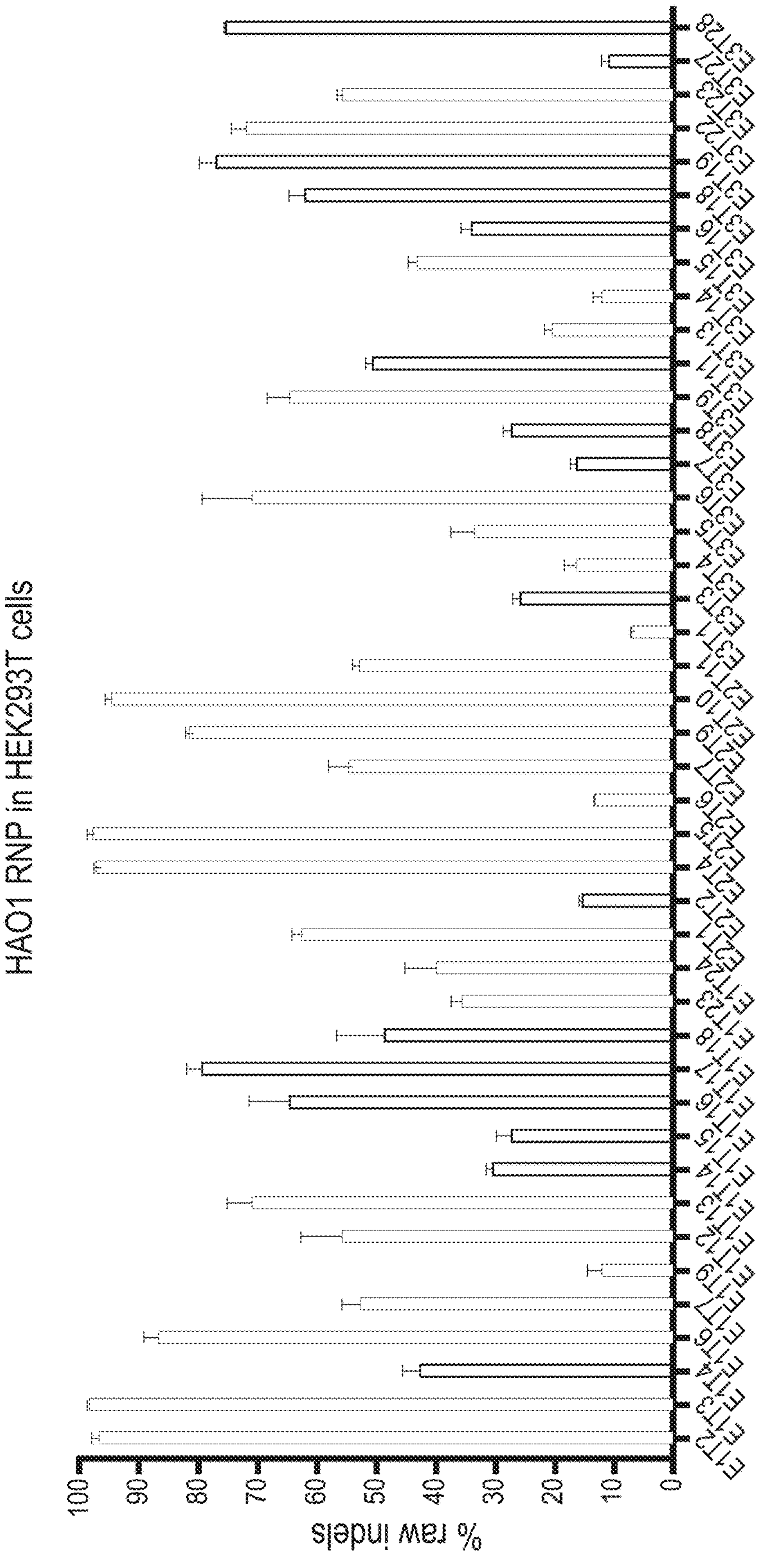
FIG. 1 is a graph showing the ability of RNPs prepared with a Cas12i2 polypeptide and a crRNA to edit the HAO1 gene in HEK293 cells. The darker grey bars represent target sequences with perfect homology to both rhesus macaque (*Macaca mulatta*) and crab-eating macaque (*Macaca fascicularis*) sequences.

The present disclosure relates to a system for genetic editing of a hydroxyacid oxidase 1 (HAO1) gene (a.k.a., glycolate oxidase gene), which comprises (i) a Cas12i polypeptide or a first nucleic acid encoding the Cas12i polypeptide, and (ii) an RNA guide or a second nucleic acid encoding the RNA guide, wherein the RNA guide comprises a spacer sequence specific to a target sequence within an HAO1 gene, the target sequence being adjacent to a protospacer adjacent motif (PAM) comprising the motif of 5'-TTN-3', which is located 5' to the target sequence. Also provided in the present disclosure are a pharmaceutical composition or a kit comprising such system as well as uses thereof. Further disclosed herein are a method for editing a HAO1 gene in a cell, a cell so produced that comprises a disrupted a HAO1 gene, a method of treating primary hyperoxaluria (PH) in a subject, and an RNA guide that comprises (i) a spacer that is specific to a target sequence in a HAO1 gene, wherein the target sequence is adjacent to a protospacer adjacent motif (PAM) comprising the motif of 5'-TTN-3', which is located 5' to the target sequence; and (ii) a direct repeat sequence as well as uses thereof.

The Cas12i polypeptide for use in the gene editing system disclosed herein may be a Cas12i2 polypeptide, e.g., a wild-type Cas12i polypeptide or a variant thereof as those disclosed herein. In some examples, the Cas12i2 polypeptide comprises an amino acid sequence at least 95% identical to SEQ ID NO: 922 and comprises one or more mutations relative to SEQ ID NO: 922. In other examples, the Cas12i polypeptide may be a Cas12i4 polypeptide, which is also disclosed herein.

Definitions

The present disclosure will be described with respect to particular embodiments and with reference to certain Figures, but the disclosure is not limited thereto but only by the claims. Terms as set forth hereinafter are generally to be understood in their common sense unless indicated otherwise.

As used herein, the term "activity" refers to a biological activity. In some embodiments, activity includes enzymatic activity, e.g., catalytic ability of a Cas12i polypeptide. For example, activity can include nuclease activity.

As used herein the term "HAO1" refers to "glycolate oxidase 1," which is also known as "hydroxyacid oxidase." HAO1 is a peroxisome protein expressed primarily in the liver and pancreas, and its activities include oxidation of glycolate and 2-hydroxy fatty acids. SEQ ID NO: 928 as set forth herein provides an example of an HAO1 gene sequence.

As used herein, the term "Cas12i polypeptide" (also referred to herein as Cas12i) refers to a polypeptide that binds to a target sequence on a target nucleic acid specified by an RNA guide, wherein the polypeptide has at least some amino acid sequence homology to a wild-type Cas12i polypeptide. In some embodiments, the Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 1-5 and 11-18 of U.S. Pat. No. 10,808,245, which is incorporated by reference for the subject matter and purpose referenced herein. In some embodiments, a Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 8, 2, 11, and 9 of the present application. In some embodiments, a Cas12i polypeptide of the disclosure is a Cas12i2 polypeptide as described in WO/2021/202800, the relevant disclosures of which are incorporated by reference for the subject matter and purpose referenced herein. In some embodiments, the Cas12i polypeptide cleaves a target nucleic acid (e.g., as a nick or a double strand break).

As used herein, the term "adjacent to" refers to a nucleotide or amino acid sequence in close proximity to another nucleotide or amino acid sequence. In some embodiments, a nucleotide sequence is adjacent to another nucleotide sequence if no nucleotides separate the two sequences (i.e., immediately adjacent). In some embodiments, a nucleotide sequence is adjacent to another nucleotide sequence if a small number of nucleotides separate the two sequences (e.g., about 1, 2, 3, 4, 5, 6, 7, 8, 9, 10, 11, 12, 13, 14, 15, 16, 17, 18, 19, or 20 nucleotides). In some embodiments, a first sequence is adjacent to a second sequence if the two sequences are separated by about 5, 6, 7, 8, 9, 10, 11, 12, 13, 14, or 15 nucleotides. In some embodiments, a first sequence is adjacent to a second sequence if the two sequences are separated by up to 2 nucleotides, up to 5 nucleotides, up to 8 nucleotides, up to 10 nucleotides, up to 12 nucleotides, or up to 15 nucleotides. In some embodiments, a first sequence is adjacent to a second sequence if the two sequences are separated by 2-5 nucleotides, 4-6 nucleotides, 4-8 nucleotides, 4-10 nucleotides, 6-8 nucleotides, 6-10 nucleotides, 6-12 nucleotides, 8-10 nucleotides, 8-12 nucleotides, 10-12 nucleotides, 10-15 nucleotides, or 12-15 nucleotides.

As used herein, the term "complex" refers to a grouping of two or more molecules. In some embodiments, the complex comprises a polypeptide and a nucleic acid molecule interacting with (e.g., binding to, coming into contact with, adhering to) one another. For example, the term "complex" can refer to a grouping of an RNA guide and a polypeptide (e.g., a Cas12i polypeptide). Alternatively, the term "complex" can refer to a grouping of an RNA guide, a polypeptide, and the complementary region of a target sequence. In another example, the term "complex" can refer to a grouping of an HAO1-targeting RNA guide and a Cas12i polypeptide.

As used herein, the term "protospacer adjacent motif" or "PAM" refers to a DNA sequence adjacent to a target sequence (e.g., an HAO1 target sequence) to which a complex comprising an RNA guide (e.g., an HAO1-targeting RNA guide) and a Cas12i polypeptide binds. In a double-stranded DNA molecule, the strand containing the PAM motif is called the "PAM-strand" and the complementary strand is called the "non-PAM strand." The RNA guide binds to a site in the non-PAM strand that is complementary to a target sequence disclosed herein.

In some embodiments, the PAM strand is a coding (e.g., sense) strand. In other embodiments, the PAM strand is a non-coding (e.g., antisense strand). Since an RNA guide binds the non-PAM strand via base-pairing, the non-PAM strand is also known as the target strand, while the PAM strand is also known as the non-target strand.

As used herein, the term "target sequence" refers to a DNA fragment adjacent to a PAM motif (on the PAM strand). The complementary region of the target sequence is on the non-PAM strand. A target sequence may be immediately adjacent to the PAM motif. Alternatively, the target sequence and the PAM may be separately by a small sequence segment (e.g., up to 5 nucleotides, for example, up to 4, 3, 2, or 1 nucleotide). A target sequence may be located at the 3' end of the PAM motif or at the 5' end of the PAM motif, depending upon the CRISPR nuclease that recognizes the PAM motif, which is known in the art. For example, a target sequence is located at the 3' end of a PAM motif for a Cas12i polypeptide (e.g., a Cas12i2 polypeptide such as those disclosed herein). In some embodiments, the target sequence is a sequence within an HAO1 gene sequence, including, but not limited to, the sequence set forth in SEQ ID NO: 928.

As used herein, the term "adjacent to" refers to a nucleotide or amino acid sequence in close proximity to another nucleotide or amino acid sequence. In some embodiments, a nucleotide sequence is adjacent to another nucleotide sequence if no nucleotides separate the two sequences (i.e., immediately adjacent). In some embodiments, a nucleotide sequence is adjacent to another nucleotide sequence if a small number of nucleotides separate the two sequences (e.g., about 1, 2, 3, 4, 5, 6, 7, 8, 9, 10, 11, 12, 13, 14, 15, 16, 17, 18, 19, or 20 nucleotides). In some embodiments, a first sequence is adjacent to a second sequence if the two sequences are separated by about 5, 6, 7, 8, 9, 10, 11, 12, 13, 14, or 15 nucleotides. In some embodiments, a first sequence is adjacent to a second sequence if the two sequences are separated by up to 2 nucleotides, up to 5 nucleotides, up to 8 nucleotides, up to 10 nucleotides, up to 12 nucleotides, or up to 15 nucleotides. In some embodiments, a first sequence is adjacent to a second sequence if the two sequences are separated by 2-5 nucleotides, 4-6 nucleotides, 4-8 nucleotides, 4-10 nucleotides, 6-8 nucleotides, 6-10 nucleotides, 6-12 nucleotides, 8-10 nucleotides, 8-12 nucleotides, 10-12 nucleotides, 10-15 nucleotides, or 12-15 nucleotides.

As used herein, the term "spacer" or "spacer sequence" is a portion in an RNA guide that is the RNA equivalent of the target sequence (a DNA sequence). The spacer contains a sequence capable of binding to the non-PAM strand via base-pairing at the site complementary to the target sequence (in the PAM strand). Such a spacer is also known as specific to the target sequence. In some instances, the spacer may be at least 75% identical to the target sequence (e.g., at least 80%, at least 85%, at least 90%, at least 95%, at least 98%, or at least 99%), except for the RNA-DNA sequence difference. In some instances, the spacer may be 100% identical to the target sequence except for the RNA-DNA sequence difference.

As used herein, the term "RNA guide" or "RNA guide sequence" refers to any RNA molecule or a modified RNA molecule that facilitates the targeting of a polypeptide (e.g., a Cas12i polypeptide) described herein to a target sequence (e.g., a sequence of an HAO1 gene). For example, an RNA guide can be a molecule that is designed to be complementary to a specific nucleic acid sequence (a target sequence such as a target sequence with an HAO1 gene). An RNA guide may comprise a spacer sequence and a direct repeat (DR) sequence. In some instances, the RNA guide can be a modified RNA molecule comprising one or more deoxyribonucleotides, for example, in a DNA-binding sequence contained in the RNA guide, which binds a sequence complementary to the target sequence. In some examples, the DNA-binding sequence may contain a DNA sequence or a DNA/RNA hybrid sequence. The terms CRISPR RNA (crRNA), pre-crRNA and mature crRNA are also used herein to refer to an RNA guide.

As used herein, the term "complementary" refers to a first polynucleotide (e.g., a spacer sequence of an RNA guide) that has a certain level of complementarity to a second polynucleotide (e.g., the complementary sequence of a target sequence) such that the first and second polynucleotides can form a double-stranded complex via base-pairing to permit an effector polypeptide that is complexed with the first polynucleotide to act on (e.g., cleave) the second polynucleotide. In some embodiments, the first polynucleotide may be substantially complementary to the second polynucleotide, i.e., having at least about 80%, 81%, 82%, 83%, 84%, 85%, 86%, 87%, 88%, 89%, 90%, 91%, 92%, 93%, 94%, 95%, 96%, 97%, 98%, or 99% complementarity to the second polynucleotide. In some embodiments, the first polynucleotide is completely complementary to the second polynucleotide, i.e., having 100% complementarity to the second polynucleotide.

The "percent identity" (a.k.a., sequence identity) of two nucleic acids or of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, word length=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

As used herein, the term "edit" refers to one or more modifications introduced into a target nucleic acid, e.g., within the HAO1 gene. The edit can be one or more substitutions, one or more insertions, one or more deletions, or a combination thereof. As used herein, the term "substitution" refers to a replacement of a nucleotide or nucleotides with a different nucleotide or nucleotides, relative to a reference sequence. As used herein, the term "insertion" refers to a gain of a nucleotide or nucleotides in a nucleic acid sequence, relative to a reference sequence. As used herein, the term "deletion" refers to a loss of a nucleotide or nucleotides in a nucleic acid sequence, relative to a reference sequence.

No particular process is implied in how to make a sequence comprising a deletion. For instance, a sequence comprising a deletion can be synthesized directly from individual nucleotides. In other embodiments, a deletion is made by providing and then altering a reference sequence. The nucleic acid sequence can be in a genome of an organism. The nucleic acid sequence can be in a cell. The nucleic acid sequence can be a DNA sequence. The deletion can be a frameshift mutation or a non-frameshift mutation. A deletion described herein refers to a deletion of up to several kilobases.

As used herein, the terms "upstream" and "downstream" refer to relative positions within a single nucleic acid (e.g., DNA) sequence in a nucleic acid molecule. "Upstream" and "downstream" relate to the 5' to 3' direction, respectively, in which RNA transcription occurs. A first sequence is upstream of a second sequence when the 3' end of the first sequence occurs before the 5' end of the second sequence. A first sequence is downstream of a second sequence when the 5' end of the first sequence occurs after the 3' end of the second sequence. In some embodiments, the 5'-NTTN-3' or 5'-TTN-3' sequence is upstream of an indel described herein, and a Cas12i-induced indel is downstream of the 5'-NTTN-3' or 5'-TTN-3' sequence.

I. Gene Editing Systems

In some aspects, the present disclosure provides gene editing systems comprising an RNA guide targeting an HAO1 gene. Such a gene editing system can be used to edit the HAO1 target gene, e.g., to disrupt the HAO1 gene.

Hydroxyacid oxidase 1 (HAO1, also known as glycolate oxidase [GOX or GO]), converts glycolate into glyoxylate. It has been proposed that inhibition of HAO1 in individuals with PH1 would block formation of glyoxylate, and excess glycolate would be excreted through the urine. The idea of treating PH1 by inhibition of HAO1 is further supported that some individuals with abnormal splice variants of HAO1 are asymptomatic for glycolic aciduria, whereby there was increased urinary glycolic acid excretion without apparent kidney pathology. Thus, inhibition of HAO1 expression would block production of glyoxylate, and in turn block production of its metabolite, oxalate. Accordingly, the gene editing systems disclosed here, targeting the HAO1 gene, could be used to treat primary hyperoxaluria (PH) in a subject in need of the treatment.

In some embodiments, the RNA guide is comprised of a direct repeat component and a spacer component. In some embodiments, the RNA guide binds a Cas12i polypeptide. In some embodiments, the spacer component is specific to an HAO1 target sequence, wherein the HAO1 target sequence is adjacent to a 5'-NTTN-3' or 5'-TTN-3' PAM sequence as described herein. In the case of a double-stranded target, the RNA guide binds to a first strand of the target (i.e., the non-PAM strand) and a PAM sequence as described herein is present in the second, complementary strand (i.e., the PAM strand).

In some embodiments, the present disclosure provides compositions comprising a complex, wherein the complex comprises an RNA guide targeting HAO1. In some embodiments, the present disclosure comprises a complex comprising an RNA guide and a Cas12i polypeptide. In some embodiments, the RNA guide and the Cas12i polypeptide bind to each other in a molar ratio of about 1:1. In some embodiments, a complex comprising an RNA guide and a Cas12i polypeptide binds to the complementary region of a target sequence within an HAO1 gene. In some embodiments, a complex comprising an RNA guide targeting HAO1 and a Cas12i polypeptide binds to the complementary region of a target sequence within an HAO1 gene at a molar ratio of about 1:1. In some embodiments, the complex comprises enzymatic activity, such as nuclease activity, that can cleave the HAO1 target sequence and/or the complementary sequence. The RNA guide, the Cas12i polypeptide, and the complementary region of the HAO1 target sequence, either alone or together, do not naturally occur. In some embodiments, the RNA guide in the complex comprises a direct repeat and/or a spacer sequence described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, the RNA guide has a sequence of any one of SEQ ID NOs: 967-1023.

In some embodiments, the present disclosure described herein comprises compositions comprising an RNA guide as described herein and/or an RNA encoding a Cas12i polypeptide as described herein. In some embodiments, the RNA guide and the RNA encoding a Cas12i polypeptide are comprised together within the same composition. In some embodiments, the RNA guide and the RNA encoding a Cas12i polypeptide are comprised within separate compositions. In some embodiments, the RNA guide comprises a direct repeat and/or a spacer sequence described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, the RNA guide has a sequence of any one of SEQ ID NOs: 967-1023.

Use of the gene editing systems disclosed herein has advantages over those of other known nuclease systems. Cas12i polypeptides are smaller than other nucleases. For example, Cas12i2 is 1,054 amino acids in length, whereas *S. pyogenes* Cas9 (SpCas9) is 1,368 amino acids in length, *S. thermophilus* Cas9 (StCas9) is 1,128 amino acids in length, FnCpf1 is 1,300 amino acids in length, AsCpf1 is 1,307 amino acids in length, and LbCpf1 is 1,246 amino acids in length. Cas12i RNA guides, which do not require a trans-activating CRISPR RNA (tracrRNA), are also smaller than Cas9 RNA guides. The smaller Cas12i polypeptide and RNA guide sizes are beneficial for delivery. Compositions comprising a Cas12i polypeptide also demonstrate decreased off-target activity compared to compositions comprising an SpCas9 polypeptide. See PCT/US2021/025257, which is incorporated by reference in its entirety. Furthermore, indels induced by compositions comprising a Cas12i polypeptide differ from indels induced by compositions comprising an SpCas9 polypeptide. For example, SpCas9 polypeptides primarily induce insertions and deletions of 1 nucleotide in length. However, Cas12i polypeptides induce larger deletions, which can be beneficial in disrupting a larger portion of a gene such as HAO1.

Also provided herein is a system for genetic editing of a hydroxyacid oxidase 1 (HAO1) gene, which comprises (i) a Cas12i polypeptide (e.g., a Cas12i2 polypeptide) or a first nucleic acid encoding the Cas12i polypeptide (e.g., a Cas12i2 polypeptide comprises an amino acid sequence at least 95% identical to SEQ ID NO: 922, which may and comprises one or more mutations relative to SEQ ID NO: 922); and (ii) an RNA guide or a second nucleic acid encoding the RNA guide, wherein the RNA guide comprises a spacer sequence specific to a target sequence within an HAO1 gene (e.g., within exon 1 or exon 2 of the HAO1 gene), the target sequence being adjacent to a protospacer adjacent motif (PAM) comprising the motif of 5'-TTN-3' (5'-NTTN-3'), which is located 5' to the target sequence.

A. RNA Guides

In some embodiments, the gene editing system described herein comprises an RNA guide targeting a HAO1 gene, for example, targeting exon 1 or exon 2 of the HAO1 gene. In some embodiments, the gene editing system described herein may comprise two or more (e.g., 2, 3, 4, 5, 6, 7, 8, 9, or more) RNA guides targeting HAO1.

The RNA guide may direct the Cas12i polypeptide contained in the gene editing system as described herein to an HAO1 target sequence. Two or more RNA guides may direct two or more separate Cas12i polypeptides (e.g., Cas12i polypeptides having the same or different sequence) as described herein to two or more (e.g., 2, 3, 4, 5, 6, 7, 8, 9, or more) HAO1 target sequences.

Those skilled in the art reading the below examples of particular kinds of RNA guides will understand that, in some embodiments, an RNA guide is HAO1 target-specific. That is, in some embodiments, an RNA guide binds specifically to one or more HAO1 target sequences (e.g., within a cell) and not to non-targeted sequences (e.g., non-specific DNA or random sequences within the same cell).

In some embodiments, the RNA guide comprises a spacer sequence followed by a direct repeat sequence, referring to the sequences in the 5' to 3' direction. In some embodiments, the RNA guide comprises a first direct repeat sequence followed by a spacer sequence and a second direct repeat sequence, referring to the sequences in the 5' to 3' direction. In some embodiments, the first and second direct repeats of such an RNA guide are identical. In some embodiments, the first and second direct repeats of such an RNA guide are different.

In some embodiments, the spacer sequence and the direct repeat sequence(s) of the RNA guide are present within the same RNA molecule. In some embodiments, the spacer and direct repeat sequences are linked directly to one another. In some embodiments, a short linker is present between the spacer and direct repeat sequences, e.g., an RNA linker of 1, 2, or 3 nucleotides in length. In some embodiments, the spacer sequence and the direct repeat sequence(s) of the RNA guide are present in separate molecules, which are joined to one another by base pairing interactions.

Additional information regarding exemplary direct repeat and spacer components of RNA guides is provided as follows.

(i). Direct Repeat

In some embodiments, the RNA guide comprises a direct repeat sequence. In some embodiments, the direct repeat sequence of the RNA guide has a length of between 12-100, 13-75, 14-50, or 15-40 nucleotides (e.g., 15, 16, 17, 18, 19, 20, 21, 22, 23, 24, 25, 26, 27, 28, 29, 30, 31, 32, 33, 34, 35, 36, 37, 38, 39, or 40 nucleotides).

In some embodiments, the direct repeat sequence is a sequence of Table 1 or a portion of a sequence of Table 1. The direct repeat sequence can comprise nucleotide 1 through nucleotide 36 of any one of SEQ ID NOs: 1, 2, 3, 4, 5, 6, 7, or 8. The direct repeat sequence can comprise nucleotide 2 through nucleotide 36 of any one of SEQ ID NOs: 1, 2, 3, 4, 5, 6, 7, or 8. The direct repeat sequence can comprise nucleotide 3 through nucleotide 36 of any one of SEQ ID NOs: 1, 2, 3, 4, 5, 6, 7, or 8. The direct repeat sequence can comprise nucleotide 4 through nucleotide 36 of any one of SEQ ID NOs: 1, 2, 3, 4, 5, 6, 7, or 8. The direct repeat sequence can comprise nucleotide 5 through nucleotide 36 of any one of SEQ ID NOs: 1, 2, 3, 4, 5, 6, 7, or 8. The direct repeat sequence can comprise nucleotide 6 through nucleotide 36 of any one of SEQ ID NOs: 1, 2, 3, 4, 5, 6, 7, or 8. The direct repeat sequence can comprise nucleotide 7 through nucleotide 36 of any one of SEQ ID NOs: 1, 2, 3, 4, 5, 6, 7, or 8. The direct repeat sequence can comprise nucleotide 8 through nucleotide 36 of any one of SEQ ID NOs: 1, 2, 3, 4, 5, 6, 7, or 8. The direct repeat sequence can comprise nucleotide 9 through nucleotide 36 of any one of SEQ ID NOs: 1, 2, 3, 4, 5, 6, 7, or 8. The direct repeat sequence can comprise nucleotide 10 through nucleotide 36 of any one of SEQ ID NOs: 1, 2, 3, 4, 5, 6, 7, or 8. The direct repeat sequence can comprise nucleotide 11 through nucleotide 36 of any one of SEQ ID NOs: 1, 2, 3, 4, 5, 6, 7, or 8. The direct repeat sequence can comprise nucleotide 12 through nucleotide 36 of any one of SEQ ID NOs: 1, 2, 3, 4, 5, 6, 7, or 8. The direct repeat sequence can comprise nucleotide 13 through nucleotide 36 of any one of SEQ ID NOs: 1, 2, 3, 4, 5, 6, 7, or 8. The direct repeat sequence can comprise nucleotide 14 through nucleotide 36 of any one of SEQ ID NOs: 1, 2, 3, 4, 5, 6, 7, or 8.

The direct repeat sequence can comprise nucleotide 1 through nucleotide 34 of SEQ ID NO: 9. The direct repeat sequence can comprise nucleotide 2 through nucleotide 34 of SEQ ID NO: 9. The direct repeat sequence can comprise nucleotide 3 through nucleotide 34 of SEQ ID NO: 9. The direct repeat sequence can comprise nucleotide 4 through nucleotide 34 of SEQ ID NO: 9. The direct repeat sequence can comprise nucleotide 5 through nucleotide 34 of SEQ ID NO: 9. The direct repeat sequence can comprise nucleotide 6 through nucleotide 34 of SEQ ID NO: 9. The direct repeat sequence can comprise nucleotide 7 through nucleotide 34 of SEQ ID NO: 9. The direct repeat sequence can comprise nucleotide 8 through nucleotide 34 of SEQ ID NO: 9. The direct repeat sequence can comprise nucleotide 9 through nucleotide 34 of SEQ ID NO: 9. The direct repeat sequence can comprise nucleotide 10 through nucleotide 34 of SEQ ID NO: 9. The direct repeat sequence can comprise nucleotide 11 through nucleotide 34 of SEQ ID NO: 9. The direct repeat sequence can comprise nucleotide 12 through nucleotide 34 of SEQ ID NO: 9. In some embodiments, the direct repeat sequence is set forth in SEQ ID NO: 10. In some embodiments, the direct repeat sequence comprises a portion of the sequence set forth in SEQ ID NO: 10.

In some embodiments, the direct repeat sequence has at least 90% identity (e.g., at least 90%, 91%, 92%, 93%, 94%, 95%, 96%, 97%, 98% or 99% identity) to a sequence of Table 1 or a portion of a sequence of Table 1. The direct repeat sequence can have at least 90% identity to a sequence comprising nucleotide 1 through nucleotide 36 of any one of SEQ ID NOs: 1, 2, 3, 4, 5, 6, 7, or 8. The direct repeat sequence can have at least 90% identity to a sequence comprising 2 through nucleotide 36 of any one of SEQ ID NOs: 1, 2, 3, 4, 5, 6, 7, or 8. The direct repeat sequence can have at least 90% identity to a sequence comprising 3 through nucleotide 36 of any one of SEQ ID NOs: 1, 2, 3, 4, 5, 6, 7, or 8. The direct repeat sequence can have at least 90% identity to a sequence comprising 4 through nucleotide 36 of any one of SEQ ID NOs: 1, 2, 3, 4, 5, 6, 7, or 8. The direct repeat sequence can have at least 90% identity to a sequence comprising 5 through nucleotide 36 of any one of SEQ ID NOs: 1, 2, 3, 4, 5, 6, 7, or 8. The direct repeat sequence can have at least 90% identity to a sequence comprising 6 through nucleotide 36 of any one of SEQ ID NOs: 1, 2, 3, 4, 5, 6, 7, or 8. The direct repeat sequence can have at least 90% identity to a sequence comprising 7 through nucleotide 36 of any one of SEQ ID NOs: 1, 2, 3, 4, 5, 6, 7, or 8. The direct repeat sequence can have at least 90% identity to a sequence comprising 8 through nucleotide 36 of any one of SEQ ID NOs: 1, 2, 3, 4, 5, 6, 7, or 8. The direct repeat sequence can have at least 90% identity to a sequence comprising 9 through nucleotide 36 of any one of SEQ ID NOs: 1, 2, 3, 4, 5, 6, 7, or 8. The direct repeat sequence can have at least 90% identity to a sequence comprising 10 through nucleotide 36 of any one of SEQ ID NOs: 1, 2, 3, 4, 5, 6, 7, or 8. The direct repeat sequence can have at least 90% identity to a sequence comprising 11 through nucleotide 36 of any one of SEQ ID NOs: 1, 2, 3, 4, 5, 6, 7, or 8. The direct repeat sequence can have at least 90% identity to a sequence comprising 12 through nucleotide 36 of any one of SEQ ID NOs: 1, 2, 3, 4, 5, 6, 7, or 8. The direct repeat sequence can have at least 90% identity to a sequence comprising 13 through nucleotide 36 of any one of SEQ ID NOs: 1, 2, 3, 4, 5, 6, 7, or 8. The direct repeat sequence can have at least 90% identity to a sequence comprising 14 through nucleotide 36 of any one of SEQ ID NOs: 1, 2, 3, 4, 5, 6, 7, or 8. The direct repeat sequence can have at least 90% identity to a sequence comprising 1 through nucleotide 34 of SEQ ID NO: 9. The direct repeat sequence can have at least 90% identity to a sequence comprising 2 through nucleotide 34 of SEQ ID NO: 9. The direct repeat sequence can have at least 90% identity to a sequence comprising 3 through nucleotide 34 of SEQ ID NO: 9.

The direct repeat sequence can have at least 90% identity to a sequence comprising 4 through nucleotide 34 of SEQ ID NO: 9. The direct repeat sequence can have at least 90% identity to a sequence comprising 5 through nucleotide 34 of SEQ ID NO: 9. The direct repeat sequence can have at least 90% identity to a sequence comprising 6 through nucleotide 34 of SEQ ID NO: 9. The direct repeat sequence can have at least 90% identity to a sequence comprising 7 through nucleotide 34 of SEQ ID NO: 9. The direct repeat sequence can have at least 90% identity to a sequence comprising 8 through nucleotide 34 of SEQ ID NO: 9. The direct repeat sequence can have at least 90% identity to a sequence comprising 9 through nucleotide 34 of SEQ ID NO: 9. The direct repeat sequence can have at least 90% identity to a sequence comprising 10 through nucleotide 34 of SEQ ID NO: 9. The direct repeat sequence can have at least 90% identity to a sequence comprising 11 through nucleotide 34 of SEQ ID NO: 9.

The direct repeat sequence can have at least 90% identity to a sequence comprising 12 through nucleotide 34 of SEQ ID NO: 9. In some embodiments, the direct repeat sequence has at least 90% identity (e.g., at least 90%, 91%, 92%, 93%, 94%, 95%, 96%, 97%, 98% or 99% identity) to SEQ ID NO: 10. In some embodiments, the direct repeat sequence has at least 90% identity to a portion of the sequence set forth in SEQ ID NO: 10.

In some embodiments, compositions comprising a Cas12i2 polypeptide and an RNA guide comprising the direct repeat of SEQ ID NO: 10 and a spacer length of 20 nucleotides are capable of introducing indels into an HAO1 target sequence. See, e.g., Example 1, where indels were measured at forty-four HAO1 target sequences following delivery of an RNA guide and a Cas12i2 polypeptide of SEQ ID NO: 924 to HEK293T cells by RNP; Example 2, where indels were measured at eleven HAO1 target sequences following delivery of an RNA guide and a Cas12i2 polypeptide of SEQ ID NO: 924 to HepG2 cells by RNP; and Example 3, where indels were measured at five HAO1 target sequences following delivery of an RNA guide and a Cas12i2 polypeptide of SEQ ID NO: 924 to primary hepatocytes by RNP.

In some embodiments, the direct repeat sequence is at least 90% identical to the reverse complement of any one of SEQ ID NOs: 1-10 (see, Table 1). In some embodiments, the direct repeat sequence is the reverse complement of any one of SEQ ID NOs: 1-10.

TABLE 1

Cas12i2 Direct Repeat Sequences

| Sequence identifier | Direct Repeat Sequence |
|---|---|
| SEQ ID NO: 1 | GUUGCAAAACCCAAGAAAUCCGUCUUUCAUUGACGG |
| SEQ ID NO: 2 | AAUAGCGGCCCUAAGAAAUCCGUCUUUCAUUGACGG |
| SEQ ID NO: 3 | AUUGGAACUGGCGAGAAAUCCGUCUUUCAUUGACGG |
| SEQ ID NO: 4 | CCAGCAACACCUAAGAAAUCCGUCUUUCAUUGACGG |
| SEQ ID NO: 5 | CGGCGCUCGAAUAGGAAAUCCGUCUUUCAUUGACGG |
| SEQ ID NO: 6 | GUGGCAACACCUAAGAAAUCCGUCUUUCAUUGACGG |
| SEQ ID NO: 7 | GUUGCAACACCUAAGAAAUCCGUCUUUCAUUGACGG |
| SEQ ID NO: 8 | GUUGCAAUGCCUAAGAAAUCCGUCUUUCAUUGACGG |
| SEQ ID NO: 9 | GCAACACCUAAGAAAUCCGUCUUUCAUUGACGGG |
| SEQ ID NO: 10 | AGAAAUCCGUCUUUCAUUGACGG |

In some embodiments, the direct repeat sequence is a sequence of Table 2 or a portion of a sequence of Table 2. The direct repeat sequence can comprise nucleotide 1 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 2 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 3 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 4 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 5 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 6 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 7 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 8 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 9 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 10 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 11 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 12 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 13 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 14 through nucleotide 36 of any one of SEQ ID NOs: 936, 937, 938, 939, 940, 941, 942, 943, 944, 945, 946, 947, 948, 949, 950, 951, 952, or 953.

In some embodiments, the direct repeat sequence has at least 95% identity (e.g., at least 95%, 96%, 97%, 98% or 99% identity) to a sequence of Table 2 or a portion of a sequence of Table 2. The direct repeat sequence can have at least 95% identity to a sequence comprising nucleotide 1 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 2 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 3 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 4 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 5 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 6 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 7 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 8 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 9 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 10 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 11 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 12 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 13 through nucleotide 36 of any one of SEQ ID NOs: 936, 937, 938, 939, 940, 941, 942, 943, 944, 945, 946, 947, 948, 949, 950, 951, 952, or 953.

In some embodiments, the direct repeat sequence has at least 90% identity (e.g., at least 90%, 91%, 92%, 93%, 94%, 95%, 96%, 97%, 98% or 99% identity) to a sequence of Table 2 or a portion of a sequence of Table 2. The direct repeat sequence can have at least 90% identity to a sequence comprising nucleotide 1 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 2 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 3 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 4 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 5 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 6 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 7 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 8 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 9 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 10 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 11 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 12 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 13 through nucleotide 36 of any one of SEQ ID NOs: 936, 937, 938, 939, 940, 941, 942, 943, 944, 945, 946, 947, 948, 949, 950, 951, 952, or 953.

In some embodiments, the direct repeat sequence is at least 90% identical to the reverse complement of any one of SEQ ID NOs: 936, 937, 938, 939, 940, 941, 942, 943, 944, 945, 946, 947, 948, 949, 950, 951, 952, or 953. In some embodiments, the direct repeat sequence is at least 95% identical to the reverse complement of any one of SEQ ID NOs: 936, 937, 938, 939, 940, 941, 942, 943, 944, 945, 946, 947, 948, 949, 950, 951, 952, or 953. In some embodiments, the direct repeat sequence is the reverse complement of any one of SEQ ID NOs: 936, 937, 938, 939, 940, 941, 942, 943, 944, 945, 946, 947, 948, 949, 950, 951, 952, or 953.

In some embodiments, the direct repeat sequence is at least 90% identical to SEQ ID NO: 954 or a portion of SEQ ID NO: 954. In some embodiments, the direct repeat sequence is at least 95% identical to SEQ ID NO: 954 or a portion of SEQ ID NO: 954. In some embodiments, the direct repeat sequence is 100% identical to SEQ ID NO: 954 or a portion of SEQ ID NO: 954.

TABLE 2

Cas12i4 Direct Repeat Sequences

| Sequence identifier | Direct Repeat Sequence |
|---|---|
| SEQ ID NO: 936 | UCUCAACGAUAGUCAGACAUGUGUCCUCAGUGACAC |
| SEQ ID NO: 937 | UUUUAACAACACUCAGGCAUGUGUCCACAGUGACAC |
| SEQ ID NO: 938 | UUGAACGGAUACUCAGACAUGUGUUUCCAGUGACAC |
| SEQ ID NO: 939 | UGCCCUCAAUAGUCAGAUGUGUGUCCACAGUGACAC |
| SEQ ID NO: 940 | UCUCAAUGAUACUUAGAUACGUGUCCUCAGUGACAC |
| SEQ ID NO: 941 | UCUCAAUGAUACUCAGACAUGUGUCCCCAGUGACAC |
| SEQ ID NO: 942 | UCUCAAUGAUACUAAGACAUGUGUCCUCAGUGACAC |
| SEQ ID NO: 943 | UCUCAACUAUACUCAGACAUGUGUCCUCAGUGACAC |
| SEQ ID NO: 944 | UCUCAACGAUACUCAGACAUGUGUCCUCAGUGACAC |
| SEQ ID NO: 945 | UCUCAACGAUACUAAGAUAUGUGUCCUCAGCGACAC |
| SEQ ID NO: 946 | UCUCAACGAUACUAAGAUAUGUGUCCCCAGUGACAC |
| SEQ ID NO: 947 | UCUCAACGAUACUAAGAUAUGUGUCCACAGUGACAC |
| SEQ ID NO: 948 | UCUCAACAAUACUCAGACAUGUGUCCCCAGUGACAC |
| SEQ ID NO: 949 | UCUCAACAAUACUAAGGCAUGUGUCCCCAGUGACCC |
| SEQ ID NO: 950 | UCUCAAAGAUACUCAGACACGUGUCCCCAGUGACAC |
| SEQ ID NO: 951 | UCUCAAAAAUACUCAGACAUGUGUCCUCAGUGACAC |
| SEQ ID NO: 952 | GCGAAACAACAGUCAGACAUGUGUCCCCAGUGACAC |
| SEQ ID NO: 953 | CCUCAACGAUAUUAAGACAUGUGUCCGCAGUGACAC |
| SEQ ID NO: 954 | AGACAUGUGUCCUCAGUGACAC |

In some embodiments, the direct repeat sequence is a sequence of Table 3 or a portion of a sequence of Table 3. In some embodiments, the direct repeat sequence has at least 95% identity (e.g., at least 95%, 96%, 97%, 98% or 99% identity) to a sequence of Table 3 or a portion of a sequence of Table 3. In some embodiments, the direct repeat sequence has at least 90% identity (e.g., at least 90%, 91%, 92%, 93%, 94%, 95%, 96%, 97%, 98% or 99% identity) to a sequence of Table 3 or a portion of a sequence of Table 3. In some embodiments, the direct repeat sequence is at least 90% identical to the reverse complement of any one of SEQ ID NOs: 959-961. In some embodiments, the direct repeat sequence is at least 95% identical to the reverse complement of any one of SEQ ID NOs: 959-961. In some embodiments, the direct repeat sequence is the reverse complement of any one of SEQ ID NOs: 959-961.

TABLE 3

| Cas12i1 Direct Repeat Sequences | |
|---|---|
| Sequence identifier | Direct Repeat Sequence |
| SEQ ID NO: 959 | GUUGGAAUGACUAAUUUUUGUGCCCACCGUUGGCAC |
| SEQ ID NO: 960 | AAUUUUUGUGCCCAUCGUUGGCAC |
| SEQ ID NO: 961 | AUUUUUGUGCCCAUCGUUGGCAC |

In some embodiments, the direct repeat sequence is a sequence of Table 4 or a portion of a sequence of Table 4. In some embodiments, the direct repeat sequence has at least 95% identity (e.g., at least 95%, 96%, 97%, 98% or 99% identity) to a sequence of Table 4 or a portion of a sequence of Table 4. In some embodiments, the direct repeat sequence has at least 90% identity (e.g., at least 90%, 91%, 92%, 93%, 94%, 95%, 96%, 97%, 98% or 99% identity) to a sequence of Table 4 or a portion of a sequence of Table 4. In some embodiments, the direct repeat sequence is at least 90% identical to the reverse complement of any one of SEQ ID NOs: 962-964. In some embodiments, the direct repeat sequence is at least 95% identical to the reverse complement of any one of SEQ ID NOs: 962-964. In some embodiments, the direct repeat sequence is the reverse complement of any one of SEQ ID NOs: 962-964.

TABLE 4

| Cas12i3 Direct Repeat Sequences | |
|---|---|
| Sequence identifier | Direct Repeat Sequence |
| SEQ ID NO: 962 | CUAGCAAUGACCUAAUAGUGUGUCCUUAGUUGACAU |
| SEQ ID NO: 963 | CCUACAAUACCUAAGAAAUCCGUCCUAAGUUGACGG |
| SEQ ID NO: 964 | AUAGUGUGUCCUUAGUUGACAU |

In some embodiments, a direct repeat sequence described herein comprises an uracil (U). In some embodiments, a direct repeat sequence described herein comprises a thymine (T). In some embodiments, a direct repeat sequence according to Tables 1-4 comprises a sequence comprising a thymine in one or more places indicated as uracil in Tables 1-4.

(ii). Spacer Sequence

In some embodiments, the RNA guide comprises a DNA targeting or spacer sequence. In some embodiments, the spacer sequence of the RNA guide has a length of between 12-100, 13-75, 14-50, or 15-30 nucleotides (e.g., 15, 16, 17, 18, 19, 20, 21, 22, 23, 24, 25, 26, 27, 28, 29, or 30 nucleotides) and is complementary to a non-PAM strand sequence. In some embodiments, the spacer sequence is designed to be complementary to a specific DNA strand, e.g., of a genomic locus.

In some embodiments, the RNA guide spacer sequence is substantially identical to a complementary strand of a target sequence. In some embodiments, the RNA guide comprises a sequence (e.g., a spacer sequence) having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a reference nucleic acid sequence, e.g., a target sequence. The percent identity between two such nucleic acids can be determined manually by inspection of the two optimally aligned nucleic acid sequences or by using software programs or algorithms (e.g., BLAST, ALIGN, CLUSTAL) using standard parameters.

In some embodiments, the RNA guide comprises a spacer sequence that has a length of between 12-100, 13-75, 14-50, or 15-30 nucleotides (e.g., 15, 16, 17, 18, 19, 20, 21, 22, 23, 24, 25, 26, 27, 28, 29, or 30 nucleotides) and at least 80%, at least 90%, at least 95%, at least 96%, at least 97%, at least 98%, at least 99% complementary to a region on the non-PAM strand that is complementary to the target sequence. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence. In some embodiments, the RNA guide comprises a sequence, e.g., RNA sequence, that is a length of up to 50 and at least 80%, at least 90%, at least 95%, at least 96%, at least 97%, at least 98%, at least 99% complementary to a region on the non-PAM strand that is complementary to the target sequence. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence.

In some embodiments, the spacer sequence is a sequence of Table 5 or a portion of a sequence of Table 5. It should be understood that an indication of SEQ ID NOs: 466-920 should be considered as equivalent to a listing of SEQ ID NOs: 466-920, with each of the intervening numbers present in the listing, i.e., 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, and 920.

The spacer sequence can comprise nucleotide 1 through nucleotide 16 of any one of SEQ ID NOs: 466-920. The spacer sequence can comprise nucleotide 1 through nucleotide 17 of any one of SEQ ID NOs: 466-920. The spacer sequence can comprise nucleotide 1 through nucleotide 18 of any one of SEQ ID NOs: 466-920. The spacer sequence can comprise nucleotide 1 through nucleotide 19 of any one of SEQ ID NOs: 466-920. The spacer sequence can comprise nucleotide 1 through nucleotide 20 of any one of SEQ ID NOs: 466-920. The spacer sequence can comprise nucleotide 1 through nucleotide 21 of any one of SEQ ID NOs: 466-920. The spacer sequence can comprise nucleotide 1 through nucleotide 22 of any one of SEQ ID NOs: 466-920. The spacer sequence can comprise nucleotide 1 through nucleotide 23 of any one of SEQ ID NOs: 466-920. The spacer sequence can comprise nucleotide 1 through nucleotide 24 of any one of SEQ ID NOs: 466-920. The spacer sequence can comprise nucleotide 1 through nucleotide 25 of any one of SEQ ID NOs: 466-920. The spacer sequence can comprise nucleotide 1 through nucleotide 26 of any one of SEQ ID NOs: 466-920. The spacer sequence can comprise nucleotide 1 through nucleotide 27 of any one of SEQ ID NOs: 466-920. The spacer sequence can comprise nucleotide 1 through nucleotide 28 of any one of SEQ ID NOs: 466-920. The spacer sequence can comprise nucleotide 1 through nucleotide 29 of any one of SEQ ID NOs: 466-920. The spacer sequence can comprise nucleotide 1 through nucleotide 30 of any one of SEQ ID NOs: 466-920.

In some embodiments, the spacer sequence has at least 90% identity (e.g., at least 90%, 91%, 92%, 93%, 94%, 95%, 96%, 97%, 98% or 99% identity) to a sequence of Table 5 or a portion of a sequence of Table 5. The spacer sequence can have at least 90% identity to a sequence comprising nucleotide 1 through nucleotide 16 of any one of SEQ ID NOs: 466-920. The spacer sequence can have at least 90% identity to a sequence comprising nucleotide 1 through nucleotide 17 of any one of SEQ ID NOs: 466-920. The spacer sequence can have at least 90% identity to a sequence comprising nucleotide 1 through nucleotide 18 of any one of SEQ ID NOs: 466-920. The spacer sequence can have at least 90% identity to a sequence comprising nucleotide 1 through nucleotide 19 of any one of SEQ ID NOs: 466-920. The spacer sequence can have at least 90% identity to a sequence comprising nucleotide 1 through nucleotide 20 of any one of SEQ ID NOs: 466-920. The spacer sequence can have at least 90% identity to a sequence comprising nucleotide 1 through nucleotide 21 of any one of SEQ ID NOs: 466-920. The spacer sequence can have at least 90% identity to a sequence comprising nucleotide 1 through nucleotide 22 of any one of SEQ ID NOs: 466-920. The spacer sequence can have at least 90% identity to a sequence comprising nucleotide 1 through nucleotide 23 of any one of SEQ ID NOs: 466-920. The spacer sequence can have at least 90% identity to a sequence comprising nucleotide 1 through nucleotide 24 of any one of SEQ ID NOs: 466-920.

The spacer sequence can have at least 90% identity to a sequence comprising nucleotide 1 through nucleotide 25 of any one of SEQ ID NOs: 466-920. The spacer sequence can have at least 90% identity to a sequence comprising nucleotide 1 through nucleotide 26 of any one of SEQ ID NOs: 466-920. The spacer sequence can have at least 90% identity to a sequence comprising nucleotide 1 through nucleotide 27 of any one of SEQ ID NOs: 466-920. The spacer sequence can have at least 90% identity to a sequence comprising nucleotide 1 through nucleotide 28 of any one of SEQ ID NOs: 466-920. The spacer sequence can have at least 90% identity to a sequence comprising nucleotide 1 through nucleotide 29 of any one of SEQ ID NOs: 466-920. The spacer sequence can have at least 90% identity to a sequence comprising nucleotide 1 through nucleotide 30 of any one of 466-920.

TABLE 5

Target and Spacer Sequences

| HAO1 | Strand | PAM* | SEQ ID NO | Target Sequence | SEQ ID NO | Spacer Sequence |
|---|---|---|---|---|---|---|
| HAO1_exon1 | + | **CTTA** | 11 | CCTGGAAAATGCTGCAA TATTATCAGGCAA | 466 | CCUGGAAAAUGCUGCAAUA UUAUCAGCCAA |
| HAO1_exon1 | + | **ATTT** | 12 | TCTTACCTGGAAAATGC TGCAATATTATCA | 467 | UCUUACCUGGAAAAUGCUG CAAUAUUAUCA |
| HAO1_exon1 | + | **TTTT** | 13 | CTTACCTGGAAAATGCT GCAATATTATCAG | 468 | CUUACCUGGAAAAUGCUGC AAUAUUAUCAG |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon1 | + | **TTTC** | 14 | TTACCTGGAAAATGCTG CAATATTATCAGC | 469 | UUACCUGGAAAAUGCUGCA AUAUUAUCAGC |
| HAO1_exon1 | + | **ATTA** | 15 | TCAGCCAAAGTTTCTTC ATCATTTGCCCCA | 470 | UCAGCCAAAGUUUCUUCAU CAUUUGCCCCA |
| HAO1_exon1 | + | **GTTT** | 16 | CTTCATCATTTGCCCCA GACCTGTAATAGT | 471 | CUUCAUCAUUUGCCCCAGA CCUGUAAUAGU |
| HAO1_exon1 | + | **TTTC** | 17 | TTCATCATTTGCCCCAG ACCTGTAATAGTC | 472 | UUCAUCAUUUGCCCCAGAC CUGUAAUAGUC |
| HAO1_exon1 | + | **CTTC** | 18 | ATCATTTGCCCCAGACC TGTAATAGTCATA | 473 | AUCAUUUGCCCCAGACCUG UAAUAGUCAUA |
| HAO1_exon1 | + | **ATTT** | 19 | GCCCCAGACCTGTAATA GTCATATATAGAC | 474 | GCCCCAGACCUGUAAUAGU CAUAUAUAGAC |
| HAO1_exon1 | + | **TTTG** | 20 | CCCCAGACCTGTAATAG TCATATATAGACT | 475 | CCCCAGACCUGUAAUAGUC AUAUAUAGACU |
| HAO1_exon1 | + | **TTTT** | 21 | AAAAAATAAATTTTCTT ACCTGGAAAATGC | 476 | AAAAAAUAAAUUUUCUUAC CUGGAAAAUGC |
| HAO1_exon1 | + | **CTTT** | 22 | GGAAGTACTGATTTAGC ATGTTGTTCATAA | 477 | GGAAGUACUGAUUUAGCAU GUUGUUCAUAA |
| HAO1_exon1 | + | **ATTT** | 23 | AGCATGTTGTTCATAAT CATTGATACAAAT | 478 | AGCAUGUUGUUCAUAAUCA UUGAUACAAAU |
| HAO1_exon1 | + | **TTTA** | 24 | GCATGTTGTTCATAATC ATTGATACAAATT | 479 | GCAUGUUGUUCAUAAUCAU UGAUACAAAUU |
| HAO1_exon1 | + | **GTTG** | 25 | TTCATAATCATTGATAC AAATTAGCCGGGG | 480 | UUCAUAAUCAUUGAUACAA AUUAGCCGGGG |
| HAO1_exon1 | + | **GTTC** | 26 | ATAATCATTGATACAAA TTAGCCGGGGGAG | 481 | AUAAUCAUUGAUACAAAUU AGCCGGGGGAG |
| HAO1_exon1 | + | **ATTG** | 27 | ATACAAATTAGCCGGGG GAGCATTTTCACA | 482 | AUACAAAUUAGCCGGGGGA GCAUUUUCACA |
| HAO1_exon1 | + | **ATTA** | 28 | GCCGGGGGAGCATTTTC ACAGGTTATTGCT | 483 | GCCGGGGGAGCAUUUUCAC AGGUUAUUGCU |
| HAO1_exon1 | + | **ATTT** | 29 | TCACAGGTTATTGCTAT CCCAGATGGAGTT | 484 | UCACAGGUUAUUGCUAUCC CAGAUGGAGUU |
| HAO1_exon1 | + | **TTTT** | 30 | CACAGGTTATTGCTATC CCAGATGGAGTTC | 485 | CACAGGUUAUUGCUAUCCC AGAUGGAGUUC |
| HAO1_exon1 | + | **TTTC** | 31 | ACAGGTTATTGCTATCC CAGATGGAGTTCG | 486 | ACAGGUUAUUGCUAUCCCA GAUGGAGUUCG |
| HAO1_exon1 | + | **TTTG** | 32 | GAAGTACTGATTTAGCA TGTTGTTCATAAT | 487 | GAAGUACUGAUUUAGCAUG UUGUUCAUAAU |
| HAO1_exon1 | + | **ATTT** | 33 | TAAAAAATAAATTTTCT TACCTGGAAAATG | 488 | UAAAAAAUAAAUUUUCUUA CCUGGAAAAUG |
| HAO1_exon1 | + | **TTTA** | 34 | AAAAATAAATTTTCTTA CCTGGAAAATGCT | 489 | AAAAAUAAAUUUUCUUACC UGGAAAAUGCU |
| HAO1_exon1 | + | **TTTT** | 35 | AAAACATGATTTTAAAA AATAAATTTTCTT | 490 | AAAACAUGAUUUUAAAAAA UAAAUUUUCUU |
| HAO1_exon1 | - | **TTTG** | 36 | TATCAATGATTATGAAC AACATGCTAAATC | 491 | UAUCAAUGAUUAUGAACAA CAUGCUAAAUC |
| HAO1_exon1 | - | **ATTA** | 37 | TGAACAACATGCTAAAT CAGTACTTCCAAA | 492 | UGAACAACAUGCUAAAUCA GUACUUCCAAA |
| HAO1_exon1 | - | **CTTC** | 38 | CAAAGTCTATATATGAC TATTACAGGTCTG | 493 | CAAAGUCUAUAUAUGACUA UUACAGGUCUG |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon1 | - | **ATTA** | 39 | CAGGTCTGGGGCAAATG ATGAAGAAACTTT | 494 | CAGGUCUGGGGCAAAUGAU GAAGAAACUUU |
| HAO1_exon1 | - | **CTTT** | 40 | GGCTGATAATATTGCAG CATTTTCCAGGTA | 495 | GGCUGAUAAUAUUGCAGCA UUUUCCAGGUA |
| HAO1_exon1 | - | **TTTG** | 41 | GCTGATAATATTGCAGC ATTTTCCAGGTAA | 496 | GCUGAUAAUAUUGCAGCAU UUUCCAGGUAA |
| HAO1_exon1 | - | **ATTG** | 42 | CAGCATTTTCCAGGTAA GAAAATTTATTTT | 497 | CAGCAUUUUCCAGGUAAGA AAAUUUAUUUU |
| HAO1_exon1 | - | **ATTT** | 43 | TCCAGGTAAGAAAATTT ATTTTTTAAAATC | 498 | UCCAGGUAAGAAAAUUUAU UUUUUAAAAUC |
| HAO1_exon1 | - | **TTTT** | 44 | CCAGGTAAGAAAATTTA TTTTTTAAAATCA | 499 | CCAGGUAAGAAAAUUUAUU UUUUAAAAUCA |
| HAO1_exon1 | + | **TTTA** | 45 | AAACATGATTTTAAAAA ATAAATTTTCTTA | 500 | AAACAUGAUUUUAAAAAAU AAAUUUUCUUA |
| HAO1_exon1 | - | **ATTT** | 46 | ATTTTTTAAAATCATGT TTTAAAATTACAC | 501 | AUUUUUUAAAAUCAUGUUU UAAAAUUACAC |
| HAO1_exon1 | - | **TTTC** | 47 | CAGGTAAGAAAATTTAT TTTTTAAAATCAT | 502 | CAGGUAAGAAAAUUUAUUU UUUAAAAUCAU |
| HAO1_exon1 | - | **ATTT** | 48 | TTTAAAATCATGTTTTA AAATTACACAAAG | 503 | UUUAAAAUCAUGUUUUAAA AUUACACAAAG |
| HAO1_exon1 | - | **TTTT** | 49 | TTAAAATCATGTTTTAA AATTACACAAAGA | 504 | UUAAAAUCAUGUUUUAAAA UUACACAAAGA |
| HAO1_exon1 | - | **TTTT** | 50 | TAAAATCATGTTTTAAA ATTACACAAAGAC | 505 | UAAAAUCAUGUUUUAAAAU UACACAAAGAC |
| HAO1_exon1 | - | **TTTT** | 51 | AAAATCATGTTTTAAAA TTACACAAAGACC | 506 | AAAAUCAUGUUUUAAAAUU ACACAAAGACC |
| HAO1_exon1 | - | **TTTA** | 52 | AAATCATGTTTTAAAAT TACACAAAGACCG | 507 | AAAUCAUGUUUUAAAAUUA CACAAAGACCG |
| HAO1_exon1 | + | **CTTT** | 53 | GTGTAATTTTAAAACAT GATTTTAAAAAAT | 508 | GUGUAAUUUUAAAACAUGA UUUUAAAAAAU |
| HAO1_exon1 | + | **TTTG** | 54 | TGTAATTTTAAAACATG ATTTTAAAAAATA | 509 | UGUAAUUUUAAAACAUGAU UUUAAAAAAUA |
| HAO1_exon1 | + | **ATTT** | 55 | TAAAACATGATTTTAAA AAATAAATTTTCT | 510 | UAAAACAUGAUUUUAAAAA AUAAAUUUUCU |
| HAO1_exon1 | - | **TTTA** | 56 | TTTTTTAAAATCATGTT TTAAAATTACACA | 511 | UUUUUUAAAAUCAUGUUUU AAAAUUACACA |
| HAO1_exon1 | - | **ATTT** | 57 | GTATCAATGATTATGAA CAACATGCTAAAT | 512 | GUAUCAAUGAUUAUGAACA ACAUGCUAAAU |
| HAO1_exon1 | + | **GTTA** | 58 | TTGCTATCCCAGATGGA GTTCGTT | 513 | UUGCUAUCCCAGAUGGAGU UCGUU |
| HAO1_exon1 | + | **ATTG** | 59 | CTATCCCAGATGGAGTT CGTT | 514 | CUAUCCCAGAUGGAGUUCG UU |
| HAO1_exon2 | - | **TTTA** | 60 | TTTTTTAATTCTAGATG GAAGCTGTATCCA | 515 | UUUUUUAAUUCUAGAUGGA AGCUGUAUCCA |
| HAO1_exon2 | - | **TTTT** | 61 | ATTTTATTTTTTAATTC TAGATGGAAGCTG | 516 | AUUUUAUUUUUUAAUUCUA GAUGGAAGCUG |
| HAO1_exon2 | - | **TTTT** | 62 | ATTTTTTAATTCTAGAT GGAAGCTGTATCC | 517 | AUUUUUUAAUUCUAGAUGG AAGCUGUAUCC |
| HAO1_exon2 | - | **ATTT** | 63 | TATTTTTTAATTCTAGA TGGAAGCTGTATC | 518 | UAUUUUUUAAUUCUAGAUG GAAGCUGUAUC |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon2 | - | **TTTA** | 64 | TTTTATTTTTTAATTCT AGATGGAAGCTGT | 519 | UUUUAUUUUUUAAUUCUAG AUGGAAGCUGU |
| HAO1_exon2 | + | **ATTA** | 65 | AAAAATAAAATAAAATA AAAGGCTTTAGAG | 520 | AAAAAUAAAAUAAAAUAAA AGGCUUUAGAG |
| HAO1_exon2 | - | **TTTT** | 66 | ATTTTATTTTATTTTTT AATTCTAGATGGA | 521 | AUUUUAUUUUAUUUUUUAA UUCUAGAUGGA |
| HAO1_exon2 | - | **CTTT** | 67 | TATTTTATTTTATTTTT TAATTCTAGATGG | 522 | UAUUUUAUUUUAUUUUUUA AUUCUAGAUGG |
| HAO1_exon2 | - | **ATTC** | 68 | TGAAACTCTAAAGCCTT TTATTTTATTTTA | 523 | UGAAACUCUAAAGCCUUUU AUUUUAUUUUA |
| HAO1_exon2 | - | **ATTT** | 69 | TTTAATTCTAGATGGAA GCTGTATCCAAGG | 524 | UUUAAUUCUAGAUGGAAGC UGUAUCCAAGG |
| HAO1_exon2 | - | **TTTA** | 70 | TTTTATTTTATTTTTTA ATTCTAGATGGAA | 525 | UUUUAUUUUAUUUUUUAAU UCUAGAUGGAA |
| HAO1_exon2 | - | **TTTT** | 71 | TTAATTCTAGATGGAAG CTGTATCCAAGGA | 526 | UUAAUUCUAGAUGGAAGCU GUAUCCAAGGA |
| HAO1_exon2 | - | **ATTT** | 72 | TATTTTATTTTTTAATT CTAGATGGAAGCT | 527 | UAUUUUAUUUUUUAAUUCU AGAUGGAAGCU |
| HAO1_exon2 | + | **CTTC** | 73 | CATCTAGAATTAAAAAA TAAAATAAAATAA | 528 | CAUCUAGAAUUAAAAAAUA AAAUAAAAUAA |
| HAO1_exon2 | - | **TTTT** | 74 | TAATTCTAGATGGAAGC TGTATCCAAGGAT | 529 | UAAUUCUAGAUGGAAGCUG UAUCCAAGGAU |
| HAO1_exon2 | - | **TTTT** | 75 | AATTCTAGATGGAAGCT GTATCCAAGGATG | 530 | AAUUCUAGAUGGAAGCUGU AUCCAAGGAUG |
| HAO1_exon2 | - | **TTTA** | 76 | ATTCTAGATGGAAGCTG TATCCAAGGATGC | 531 | AUUCUAGAUGGAAGCUGUA UCCAAGGAUGC |
| HAO1_exon2 | - | **ATTC** | 77 | TAGATGGAAGCTGTATC CAAGGATGCTCCG | 532 | UAGAUGGAAGCUGUAUCCA AGGAUGCUCCG |
| HAO1_exon2 | - | **GTTG** | 78 | CTGAAACAGATCTGTCG ACTTCTGTTTTAG | 533 | CUGAAACAGAUCUGUCGAC UUCUGUUUUAG |
| HAO1_exon2 | - | **GTTT** | 79 | TAGGACAGAGGGTCAGC ATGCCAATATGTG | 534 | UAGGACAGAGGGUCAGCAU GCCAAUAUGUG |
| HAO1_exon2 | - | **TTTT** | 80 | AGGACAGAGGGTCAGCA TGCCAATATGTGT | 535 | AGGACAGAGGGUCAGCAUG CCAAUAUGUGU |
| HAO1_exon2 | - | **TTTA** | 81 | GGACAGAGGGTCAGCAT GCCAATATGTGTG | 536 | GGACAGAGGGUCAGCAUGC CAAUAUGUGUG |
| HAO1_exon2 | - | **GTTG** | 82 | CCACTGTGAGAGGTAGG AGGAAGATTGTCA | 537 | CCACUGUGAGAGGUAGGAG GAAGAUUGUCA |
| HAO1_exon2 | - | **CTTC** | 83 | TGTTTTAGGACAGAGGG TCAGCATGCCAAT | 538 | UGUUUUAGGACAGAGGGUC AGCAUGCCAAU |
| HAO1_exon2 | + | **GTTA** | 84 | GCCTCCTTCTGTCCCTG TGGTGACAATCTT | 539 | GCCUCCUUCUGUCCCUGUG GUGACAAUCUU |
| HAO1_exon2 | - | **ATTG** | 85 | TCACCACAGGGACAGAA GGAGGCTAACGTT | 540 | UCACCACAGGGACAGAAGG AGGCUAACGUU |
| HAO1_exon2 | + | **ATTC** | 86 | CGGAGCATCCTTGGATA CAGCTTCCATCTA | 541 | CGGAGCAUCCUUGGAUACA GCUUCCAUCUA |
| HAO1_exon2 | + | **TTTC** | 87 | AGCAACATTCCGGAGCA TCCTTGGATACAG | 542 | AGCAACAUUCCGGAGCAUC CUUGGAUACAG |
| HAO1_exon2 | + | **GTTT** | 88 | CAGCAACATTCCGGAGC ATCCTTGGATACA | 543 | CAGCAACAUUCCGGAGCAU CCUUGGAUACA |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon2 | + | **GTTG** | 89 | GATACAGCTTCCATCTA GAATTAAAAAATA | 544 | GAUACAGCUUCCAUCUAGA AUUAAAAAAUA |
| HAO1_exon2 | + | **CTTC** | 90 | CTCCTACCTCTCACAGT GGCAAGCTCGCCG | 545 | CUCCUACCUCUCACAGUGG CAAGCUCGCCG |
| HAO1_exon2 | + | **CTTC** | 91 | TGTCCCTGTGGTGACAA TCTTCCTCCTACC | 546 | UGUCCCUGUGGUGACAAUC UUCCUCCUACC |
| HAO1_exon2 | + | **ATTG** | 92 | GCATGCTGACCCTCTGT CCTAAAACAGAAG | 547 | GCAUGCUGACCCUCUGUCC UAAAACAGAAG |
| HAO1_exon3 | - | **CTTA** | 93 | CCTGGGCAACCGTCTGG ATGATGTGCGTAA | 548 | CCUGGGCAACCGUCUGGAU GAUGUGCGUAA |
| HAO1_exon3 | + | **TTTG** | 94 | AATCTGTTACGCACATC ATCCAGACGGTTG | 549 | AAUCUGUUACGCACAUCAU CCAGACGGUUG |
| HAO1_exon3 | + | **GTTT** | 95 | GAATCTGTTACGCACAT CATCCAGACGGTT | 550 | GAAUCUGUUACGCACAUCA UCCAGACGGUU |
| HAO1_exon3 | + | **GTTG** | 96 | TGGCGGCAGTTTGAATC TGTTACGCACATC | 551 | UGGCGGCAGUUUGAAUCUG UUACGCACAUC |
| HAO1_exon3 | + | **GTTA** | 97 | CCTGAGTTGTGGCGGCA GTTTGAATCTGTT | 552 | CCUGAGUUGUGGCGGCAGU UUGAAUCUGUU |
| HAO1_exon3 | + | **TTTC** | 98 | GCCTCAGCTCGGGGCCC ACATGATCATGGT | 553 | GCCUCAGCUCGGGGCCCAC AUGAUCAUGGU |
| HAO1_exon3 | + | **CTTT** | 99 | CGCCTCAGCTCGGGGCC CACATGATCATGG | 554 | CGCCUCAGCUCGGGGCCCA CAUGAUCAUGG |
| HAO1_exon3 | - | **ATTC** | 100 | AAACTGCCGCCACAACT CAGGTAACCATGA | 555 | AAACUGCCGCCACAACUCA GGUAACCAUGA |
| HAO1_exon3 | - | **TTTG** | 101 | TGACAGTGGACACACCT TACCTGGGCAACC | 556 | UGACAGUGGACACACCUUA CCUGGGCAACC |
| HAO1_exon3 | - | **CTTG** | 102 | ATCATCCCCTTTCTTTC TCAGCCTGTCAGT | 557 | AUCAUCCCCUUUCUUUCUC AGCCUGUCAGU |
| HAO1_exon3 | - | **GTTG** | 103 | GCTGCAACTGTATATCT ACAAGGACCGAGA | 558 | GCUGCAACUGUAUAUCUAC AAGGACCGAGA |
| HAO1_exon3 | - | **ATTG** | 104 | AAGAAGTGGCGGAAGCT GGTCCTGAGGCAC | 559 | AAGAAGUGGCGGAAGCUGG UCCUGAGGCAC |
| HAO1_exon3 | - | **GTTC** | 105 | CTGGGCCACCTCCTCAA TTGAAGAAGTGGC | 560 | CUGGGCCACCUCCUCAAUU GAAGAAGUGGC |
| HAO1_exon3 | - | **GTTG** | 106 | AGTTCCTGGGCCACCTC CTCAATTGAAGAA | 561 | AGUUCCUGGGCCACCUCCU CAAUUGAAGAA |
| HAO1_exon3 | - | **TTTC** | 107 | TCAGCCTGTCAGTCCCT GGGAACGGGCATG | 562 | UCAGCCUGUCAGUCCCUGG GAACGGGCAUG |
| HAO1_exon3 | - | **CTTT** | 108 | CTCAGCCTGTCAGTCCC TGGGAACGGGCAT | 563 | CUCAGCCUGUCAGUCCCUG GGAACGGGCAU |
| HAO1_exon3 | - | **TTTC** | 109 | TTTCTCAGCCTGTCAGT CCCTGGGAACGGG | 564 | UUUCUCAGCCUGUCAGUCC CUGGGAACGGG |
| HAO1_exon3 | - | **CTTT** | 110 | CTTTCTCAGCCTGTCAG TCCCTGGGAACGG | 565 | CUUUCUCAGCCUGUCAGUC CCUGGGAACGG |
| HAO1_exon3 | + | **GTTA** | 111 | CGCACATCATCCAGACG GTTGCCCAGGTAA | 566 | CGCACAUCAUCCAGACGGU UGCCCAGGUAA |
| HAO1_exon3 | - | **ATTT** | 112 | GTGACAGTGGACACACC TTACCTGGGCAAC | 567 | GUGACAGUGGACACACCUU ACCUGGGCAAC |
| HAO1_exon3 | + | **GTTG** | 113 | CCCAGGTAAGGTGTGTC CACTGTCACAAAT | 568 | CCCAGGUAAGGUGUGUCCA CUGUCACAAAU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon3 | - | **CTTC** | 114 | GTTGGCTGCAACTGTAT ATCTACAAGGACC | 569 | GUUGGCUGCAACUGUAUAU CUACAAGGACC |
| HAO1_exon3 | + | **CTTC** | 115 | TCTGCCTGCCGCACTAG CTTCTTGGTGACT | 570 | UCUGCCUGCCGCACUAGCU UCUUGGUGACU |
| HAO1_exon3 | + | **CTTG** | 116 | TAGCCCATCTTCTCTGC CTGCCGCACTAGC | 571 | UAGCCCAUCUUCUCUGCCU GCCGCACUAGC |
| HAO1_exon3 | + | **GTTC** | 117 | CCAGGGACTGACAGGCT GAGAAAGAAAGGG | 572 | CCAGGGACUGACAGGCUGA GAAAGAAAGGG |
| HAO1_exon3 | + | **ATTG** | 118 | AGGAGGTGGCCCAGGAA CTCAACATCATGC | 573 | AGGAGGUGGCCCAGGAACU CAACAUCAUGC |
| HAO1_exon3 | + | **CTTC** | 119 | TTCAATTGAGGAGGTGG CCCAGGAACTCAA | 574 | UUCAAUUGAGGAGGUGGCC CAGGAACUCAA |
| HAO1_exon3 | + | **CTTC** | 120 | CGCCACTTCTTCAATTG AGGAGGTGGCCCA | 575 | CGCCACUUCUUCAAUUGAG GAGGUGGCCCA |
| HAO1_exon3 | + | **CTTC** | 121 | AATTGAGGAGGTGGCCC AGGAACTCAACAT | 576 | AAUUGAGGAGGUGGCCCAG GAACUCAACAU |
| HAO1_exon3 | + | **CTTG** | 122 | TAGATATACAGTTGCAG CCAACGAAGTGCC | 577 | UAGAUAUACAGUUGCAGCC AACGAAGUGCC |
| HAO1_exon3 | + | **CTTC** | 123 | TCGGTCCTTGTAGATAT ACAGTTGCAGCCA | 578 | UCGGUCCUUGUAGAUAUAC AGUUGCAGCCA |
| HAO1_exon3 | + | **CTTG** | 124 | GTGACTTCTCGGTCCTT GTAGATATACAGT | 579 | GUGACUUCUCGGUCCUUGU AGAUAUACAGU |
| HAO1_exon3 | + | **CTTC** | 125 | TTGGTGACTTCTCGGTC CTTGTAGATATAC | 580 | UUGGUGACUUCUCGGUCCU UGUAGAUAUAC |
| HAO1_exon3 | + | **GTTG** | 126 | CAGCCAACGAAGTGCCT CAGGACCAGCTTC | 581 | CAGCCAACGAAGUGCCUCA GGACCAGCUUC |
| HAO1_exon4 | - | **ATTT** | 127 | CTAATTTGGCAAATTTC TCATTTTATGCAT | 582 | CUAAUUUGGCAAAUUUCUC AUUUUAUGCAU |
| HAO1_exon4 | + | **TTTC** | 128 | ATCCTAAAATAAGAAAT GCATAAAATGAGA | 583 | AUCCUAAAAUAAGAAAUGC AUAAAAUGAGA |
| HAO1_exon4 | + | **ATTC** | 129 | AAGTAGAGAAATAAACG AACCTCTCAAAAT | 584 | AAGUAGAGAAAUAAACGAA CCUCUCAAAAU |
| HAO1_exon4 | - | **TTTC** | 130 | TCTACTTGAATTCATAC TGACTTTGTGATC | 585 | UCUACUUGAAUUCAUACUG ACUUUGUGAUC |
| HAO1_exon4 | - | **TTTC** | 131 | TAATTTGGCAAATTTCT CATTTTATGCATT | 586 | UAAUUUGGCAAAUUUCUCA UUUUAUGCAUU |
| HAO1_exon4 | - | **ATTT** | 132 | TATGCATTTCTTATTTT AGGATGAAAAATT | 587 | UAUGCAUUUCUUAUUUUAG GAUGAAAAAUU |
| HAO1_exon4 | - | **TTTG** | 133 | GCAAATTTCTCATTTTA TGCATTTCTTATT | 588 | GCAAAUUUCUCAUUUUAUG CAUUUCUUAUU |
| HAO1_exon4 | - | **ATTT** | 134 | CTCATTTTATGCATTTC TTATTTTAGGATG | 589 | CUCAUUUUAUGCAUUUCUU AUUUUAGGAUG |
| HAO1_exon4 | - | **TTTC** | 135 | TCATTTTATGCATTTCT TATTTTAGGATGA | 590 | UCAUUUUAUGCAUUUCUUA UUUUAGGAUGA |
| HAO1_exon4 | + | **TTTT** | 136 | CATCCTAAAATAAGAAA TGCATAAAATGAG | 591 | CAUCCUAAAAUAAGAAAUG CAUAAAAUGAG |
| HAO1_exon4 | - | **ATTT** | 137 | GGCAAATTTCTCATTTT ATGCATTTCTTAT | 592 | GGCAAAUUUCUCAUUUUAU GCAUUUCUUAU |
| HAO1_exon4 | + | **TTTT** | 138 | TCATCCTAAAATAAGAA ATGCATAAAATGA | 593 | UCAUCCUAAAAUAAGAAAU GCAUAAAAUGA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon4 | + | **ATTT** | 139 | TCCTCAGGAGAAAATGA TAAAGTACTGGTT | 594 | UCCUCAGGAGAAAAUGAUA AAGUACUGGUU |
| HAO1_exon4 | + | **TTTC** | 140 | AAAATTTTTCATCCTAA AATAAGAAATGCA | 595 | AAAAUUUUUCAUCCUAAAA UAAGAAAUGCA |
| HAO1_exon4 | + | **GTTT** | 141 | CAAAATTTTTCATCCTA AAATAAGAAATGC | 596 | CAAAAUUUUUCAUCCUAAA AUAAGAAAUGC |
| HAO1_exon4 | + | **TTTC** | 142 | CTCAGGAGAAAATGATA AAGTACTGGTTTC | 597 | CUCAGGAGAAAAUGAUAAA GUACUGGUUUC |
| HAO1_exon4 | + | **TTTT** | 143 | CCTCAGGAGAAAATGAT AAAGTACTGGTTT | 598 | CCUCAGGAGAAAAUGAUAA AGUACUGGUUU |
| HAO1_exon4 | - | **TTTT** | 144 | ATGCATTTCTTATTTTA GGATGAAAAATTT | 599 | AUGCAUUUCUUAUUUUAGG AUGAAAAAUUU |
| HAO1_exon4 | + | **TTTA** | 145 | GCCACATATGCAGCAAG TCCACTGTCGTCT | 600 | GCCACAUAUGCAGCAAGUC CACUGUCGUCU |
| HAO1_exon4 | + | **CTTT** | 146 | AGCCACATATGCAGCAA GTCCACTGTCGTC | 601 | AGCCACAUAUGCAGCAAGU CCACUGUCGUC |
| HAO1_exon4 | + | **ATTG** | 147 | CTTTAGCCACATATGCA GCAAGTCCACTGT | 602 | CUUUAGCCACAUAUGCAGC AAGUCCACUGU |
| HAO1_exon4 | + | **CTTC** | 148 | CCAGCTGATAGATGGGT CTATTGCTTTAGC | 603 | CCAGCUGAUAGAUGGGUCU AUUGCUUUAGC |
| HAO1_exon4 | + | **TTTG** | 149 | ATATCTTCCCAGCTGAT AGATGGGTCTATT | 604 | AUAUCUUCCCAGCUGAUAG AUGGGUCUAUU |
| HAO1_exon4 | + | **ATTT** | 150 | GATATCTTCCCAGCTGA TAGATGGGTCTAT | 605 | GAUAUCUUCCCAGCUGAUA GAUGGGUCUAU |
| HAO1_exon4 | + | **CTTC** | 151 | TCAGCCATTTGATATCT TCCCAGCTGATAG | 606 | UCAGCCAUUUGAUAUCUUC CCAGCUGAUAG |
| HAO1_exon4 | + | **ATTG** | 152 | GCAATGATGTCAGTCTT CTCAGCCATTTGA | 607 | GCAAUGAUGUCAGUCUUCU CAGCCAUUUGA |
| HAO1_exon4 | + | **ATTT** | 153 | TTCATCCTAAAATAAGA AATGCATAAAATG | 608 | UUCAUCCUAAAAUAAGAAA UGCAUAAAAUG |
| HAO1_exon4 | - | **TTTA** | 154 | TGCATTTCTTATTTTAG GATGAAAAATTTT | 609 | UGCAUUUCUUAUUUUAGGA UGAAAAAUUUU |
| HAO1_exon4 | - | **TTTA** | 155 | GGATGAAAAATTTTGAA ACCAGTACTTTAT | 610 | GGAUGAAAAAUUUUGAAAC CAGUACUUUAU |
| HAO1_exon4 | - | **TTTC** | 156 | TTATTTTAGGATGAAAA ATTTTGAAACCAG | 611 | UUAUUUUAGGAUGAAAAAU UUUGAAACCAG |
| HAO1_exon4 | - | **ATTG** | 157 | CCAATTGTTGCAAAGGG CATTTTGAGAGGT | 612 | CCAAUUGUUGCAAAGGGCA UUUUGAGAGGU |
| HAO1_exon4 | - | **ATTG** | 158 | TTGCAAAGGGCATTTTG AGAGGTTCGTTTA | 613 | UUGCAAAGGGCAUUUUGAG AGGUUCGUUUA |
| HAO1_exon4 | + | **CTTT** | 159 | GCAACAATTGGCAATGA TGTCAGTCTTCTC | 614 | GCAACAAUUGGCAAUGAUG UCAGUCUUCUC |
| HAO1_exon4 | - | **GTTG** | 160 | CAAAGGGCATTTTGAGA GGTTCGTTTATTT | 615 | CAAAGGGCAUUUUGAGAGG UUCGUUUAUUU |
| HAO1_exon4 | - | **ATTT** | 161 | TGAGAGGTTCGTTTATT TCTCTACTTGAAT | 616 | UGAGAGGUUCGUUUAUUUC UCUACUUGAAU |
| HAO1_exon4 | - | **TTTT** | 162 | GAGAGGTTCGTTTATTT CTCTACTTGAATT | 617 | GAGAGGUUCGUUUAUUUCU CUACUUGAAUU |
| HAO1_exon4 | - | **TTTG** | 163 | AGAGGTTCGTTTATTTC TCTACTTGAATTC | 618 | AGAGGUUCGUUUAUUUCUC UACUUGAAUUC |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon4 | - | **GTTC** | 164 | GTTTATTTCTCTACTTG AATTCATACTGAC | 619 | GUUUAUUUCUCUACUUGAA UUCAUACUGAC |
| HAO1_exon4 | - | **GTTT** | 165 | ATTTCTCTACTTGAATT CATACTGACTTTG | 620 | AUUUCUCUACUUGAAUUCA UACUGACUUUG |
| HAO1_exon4 | - | **TTTA** | 166 | TTTCTCTACTTGAATTC ATACTGACTTTGT | 621 | UUUCUCUACUUGAAUUCAU ACUGACUUUGU |
| HAO1_exon4 | - | **ATTT** | 167 | CTCTACTTGAATTCATA CTGACTTTGTGAT | 622 | CUCUACUUGAAUUCAUACU GACUUUGUGAU |
| HAO1_exon4 | - | **GTTG** | 168 | CTGCATATGTGGCTAAA GCAATAGACCCAT | 623 | CUGCAUAUGUGGCUAAAGC AAUAGACCCAU |
| HAO1_exon4 | - | **ATTT** | 169 | CTTATTTTAGGATGAAA AATTTTGAAACCA | 624 | CUUAUUUUAGGAUGAAAAA UUUUGAAACCA |
| HAO1_exon4 | - | **TTTG** | 170 | GAGACGACAGTGGACTT GCTGCATATGTGG | 625 | GAGACGACAGUGGACUUGC UGCAUAUGUGG |
| HAO1_exon4 | - | **ATTT** | 171 | TGGAGACGACAGTGGAC TTGCTGCATATGT | 626 | UGGAGACGACAGUGGACUU GCUGCAUAUGU |
| HAO1_exon4 | - | **TTTC** | 172 | TCCTGAGGAAAATTTTG GAGACGACAGTGG | 627 | UCCUGAGGAAAAUUUUGGA GACGACAGUGG |
| HAO1_exon4 | - | **TTTT** | 173 | CTCCTGAGGAAAATTTT GGAGACGACAGTG | 628 | CUCCUGAGGAAAAUUUUGG AGACGACAGUG |
| HAO1_exon4 | - | **ATTT** | 174 | TCTCCTGAGGAAAATTT TGGAGACGACAGT | 629 | UCUCCUGAGGAAAAUUUUG GAGACGACAGU |
| HAO1_exon4 | - | **TTTA** | 175 | TCATTTTCTCCTGAGGA AAATTTTGGAGAC | 630 | UCAUUUUCUCCUGAGGAAA AUUUUGGAGAC |
| HAO1_exon4 | - | **CTTT** | 176 | ATCATTTTCTCCTGAGG AAAATTTTGGAGA | 631 | AUCAUUUUCUCCUGAGGAA AAUUUUGGAGA |
| HAO1_exon4 | - | **TTTG** | 177 | AAACCAGTACTTTATCA TTTTCTCCTGAGG | 632 | AAACCAGUACUUUAUCAUU UUCUCCUGAGG |
| HAO1_exon4 | - | **TTTT** | 178 | GAAACCAGTACTTTATC ATTTTCTCCTGAG | 633 | GAAACCAGUACUUUAUCAU UUUCUCCUGAG |
| HAO1_exon4 | - | **ATTT** | 179 | TGAAACCAGTACTTTAT CATTTTCTCCTGA | 634 | UGAAACCAGUACUUUAUCA UUUUCUCCUGA |
| HAO1_exon4 | - | **TTTT** | 180 | AGGATGAAAAATTTTGA AACCAGTACTTTA | 635 | AGGAUGAAAAAUUUUGAAA CCAGUACUUUA |
| HAO1_exon4 | - | **ATTT** | 181 | TAGGATGAAAAATTTTG AAACCAGTACTTT | 636 | UAGGAUGAAAAAUUUUGAA ACCAGUACUUU |
| HAO1_exon4 | - | **CTTA** | 182 | TTTTAGGATGAAAAATT TTGAAACCAGTAC | 637 | UUUUAGGAUGAAAAAUUUU GAAACCAGUAC |
| HAO1_exon4 | - | **TTTT** | 183 | GGAGACGACAGTGGACT TGCTGCATATGTG | 638 | GGAGACGACAGUGGACUUG CUGCAUAUGUG |
| HAO1_exon4 | + | **TTTG** | 184 | CAACAATTGGCAATGAT GTCAGTCTTCTCA | 639 | CAACAAUUGGCAAUGAUGU CAGUCUUCUCA |
| HAO1_exon4 | - | **CTTG** | 185 | AATTCATACTGACTTTG TGATCCTTTGTG | 640 | AAUUCAUACUGACUUUGUG AUCCUUUGUG |
| HAO1_exon4 | - | **ATTC** | 186 | ATACTGACTTTGTGATC CTTTGTG | 641 | AUACUGACUUUGUGAUCCU UUGUG |
| HAO1_exon5 | - | **GTTA** | 187 | AGTTACAGTTTCCCTAA GGTGCTTGTTTTA | 642 | AGUUACAGUUUCCCUAAGG UGCUUGUUUUA |
| HAO1_exon5 | + | **ATTC** | 188 | AAGCCATGTTTAACAGC CTCCCTGGCATCA | 643 | AAGCCAUGUUUAACAGCCU CCCUGGCAUCA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon5 | + | **TTTA** | 189 | ACAGCCTCCCTGGCATC ATCACCTGGAGAG | 644 | ACAGCCUCCCUGGCAUCAU CACCUGGAGAG |
| HAO1_exon5 | + | **GTTT** | 190 | AACAGCCTCCCTGGCAT CATCACCTGGAGA | 645 | AACAGCCUCCCUGGCAUCA UCACCUGGAGA |
| HAO1_exon5 | + | **ATTC** | 191 | GACACCAAGATCCCATT CAAGCCATGTTTA | 646 | GACACCAAGAUCCCAUUCA AGCCAUGUUUA |
| HAO1_exon5 | + | **GTTG** | 192 | TCGAGCCCCATGATTCG ACACCAAGATCCC | 647 | UCGAGCCCCAUGAUUCGAC ACCAAGAUCCC |
| HAO1_exon5 | + | **GTTA** | 193 | GCGTCTGCCAAAACTCA CAGTGGCTGGCAC | 648 | GCGUCUGCCAAAACUCACA GUGGCUGGCAC |
| HAO1_exon5 | - | **TTTG** | 194 | GCAGACGCTAAGATTTC CTTTTGGAGTTCC | 649 | GCAGACGCUAAGAUUUCCU UUUGGAGUUCC |
| HAO1_exon5 | - | **GTTT** | 195 | TGGCAGACGCTAAGATT TCCTTTTGGAGTT | 650 | UGGCAGACGCUAAGAUUUC CUUUUGGAGUU |
| HAO1_exon5 | - | **GTTG** | 196 | GTGTCGAATCATGGGGC TCGACAACTCGAT | 651 | GUGUCGAAUCAUGGGGCUC GACAACUCGAU |
| HAO1_exon5 | - | **TTTT** | 197 | GGCAGACGCTAAGATTT CCTTTTGGAGTTC | 652 | GGCAGACGCUAAGAUUUCC UUUUGGAGUUC |
| HAO1_exon5 | - | **GTTA** | 198 | AACATGGCTTGAATGGG ATCTTGGTGTCGA | 653 | AACAUGGCUUGAAUGGGAU CUUGGUGUCGA |
| HAO1_exon5 | - | **TTTA** | 199 | CTCTCTCCAGGTGATGA TGCCAGGGAGGCT | 654 | CUCUCUCCAGGUGAUGAUG CCAGGGAGGCU |
| HAO1_exon5 | - | **TTTT** | 200 | ACTCTCTCCAGGTGATG ATGCCAGGGAGGC | 655 | ACUCUCUCCAGGUGAUGAU GCCAGGGAGGC |
| HAO1_exon5 | - | **GTTT** | 201 | TACTCTCTCCAGGTGAT GATGCCAGGGAGG | 656 | UACUCUCUCCAGGUGAUGA UGCCAGGGAGG |
| HAO1_exon5 | - | **GTTG** | 202 | TTTTACTCTCTCCAGGT GATGATGCCAGGG | 657 | UUUUACUCUCUCCAGGUGA UGAUGCCAGGG |
| HAO1_exon5 | - | **TTTC** | 203 | CCTAAGGTGCTTGTTTT ACTCTCTCCAGGT | 658 | CCUAAGGUGCUUGUUUUAC UCUCUCCAGGU |
| HAO1_exon5 | - | **GTTT** | 204 | CCCTAAGGTGCTTGTTT TACTCTCTCCAGG | 659 | CCCUAAGGUGCUUGUUUUA CUCUCUCCAGG |
| HAO1_exon5 | - | **GTTA** | 205 | CAGTTTCCCTAAGGTGC TTGTTTTACTCTC | 660 | CAGUUUCCCUAAGGUGCUU GUUUUACUCUC |
| HAO1_exon5 | - | **GTTG** | 206 | AATGGGATCTTGGTGTC GAATCATGGGGCT | 661 | AAUGGGAUCUUGGUGUCGA AUCAUGGGGCU |
| HAO1_exon5 | - | **ATTT** | 207 | CCTTTTGGAGTTCCCAT TTCCATC | 662 | CCUUUUGGAGUUCCCAUUU CCAUC |
| HAO1_exon5 | - | **TTTC** | 208 | CTTTTGGAGTTCCCATT TCCATC | 663 | CUUUUGGAGUUCCCAUUUC CAUC |
| HAO1_exon5 | + | **GTTA** | 209 | GGGAAACTGTAACTTAA CAGGCAG | 664 | GGGAAACUGUAACUUAACA GGCAG |
| HAO1_exon6 | - | **TTTA** | 210 | CAACTTTCTTTTCTTTT ATGATCTTTAAGT | 665 | CAACUUUCUUUUCUUUUAU GAUCUUUAAGU |
| HAO1_exon6 | - | **ATTC** | 211 | CGGTTGGCCATGGCTCT GAGTGGTAAGACT | 666 | CGGUUGGCCAUGGCUCUGA GUGGUAAGACU |
| HAO1_exon6 | - | **GTTG** | 212 | GCCATGGCTCTGAGTGG TAAGACTCATTCT | 667 | GCCAUGGCUCUGAGUGGUA AGACUCAUUCU |
| HAO1_exon6 | - | **ATTC** | 213 | TTGTTTACAACTTTCTT TTCTTTTATGATC | 668 | UUGUUUACAACUUUCUUUU CUUUUAUGAUC |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | - | **CTTG** | 214 | TTTACAACTTTCTTTTC TTTTATGATCTTT | 669 | UUUACAACUUUCUUUUCUU UUAUGAUCUUU |
| HAO1_exon6 | - | **GTTT** | 215 | ACAACTTTCTTTTCTTT TATGATCTTTAAG | 670 | ACAACUUUCUUUUCUUUUA UGAUCUUUAAG |
| HAO1_exon6 | + | **CTTA** | 216 | AAGATCATAAAAGAAAA GAAAGTTGTAAAC | 671 | AAGAUCAUAAAAGAAAAGA AAGUUGUAAAC |
| HAO1_exon6 | + | **GTTG** | 217 | TCTATTTTATATATTCA TTTCTTTGTCCAG | 672 | UCUAUUUUAUAUAUUCAUU UCUUUGUCCAG |
| HAO1_exon6 | + | **CTTA** | 218 | CCACTCAGAGCCATGGC CAACCGGAATTCT | 673 | CCACUCAGAGCCAUGGCCA ACCGGAAUUCU |
| HAO1_exon6 | + | **ATTC** | 219 | TTCCTTTAGTATCTCGA GGACATCTTGAAC | 674 | UUCCUUUAGUAUCUCGAGG ACAUCUUGAAC |
| HAO1_exon6 | + | **CTTC** | 220 | CTTTAGTATCTCGAGGA CATCTTGAACACC | 675 | CUUUAGUAUCUCGAGGACA UCUUGAACACC |
| HAO1_exon6 | + | **GTTT** | 221 | AGTATCTCGAGGACATC TTGAACACCTTTC | 676 | AGUAUCUCGAGGACAUCUU GAACACCUUUC |
| HAO1_exon6 | + | **TTTA** | 222 | GTATCTCGAGGACATCT TGAACACCTTTCT | 677 | GUAUCUCGAGGACAUCUUG AACACCUUUCU |
| HAO1_exon6 | - | **GTTC** | 223 | AAGATGTCCTCGAGATA CTAAAGGAAGAAT | 678 | AAGAUGUCCUCGAGAUACU AAAGGAAGAAU |
| HAO1_exon6 | + | **GTTG** | 224 | TAAACAAGAATGAGTCT TACCACTCAGAGC | 679 | UAAACAAGAAUGAGUCUUA CCACUCAGAGC |
| HAO1_exon6 | - | **GTTA** | 225 | GGGGGAGAAAGGTGTTC AAGATGTCCTCGA | 680 | GGGGGAGAAAGGUGUUCAA GAUGUCCUCGA |
| HAO1_exon6 | - | **GTTT** | 226 | CCAGGTAACTGGACAAA GAAATGAATATAT | 681 | CCAGGUAACUGGACAAAGA AAUGAAUAUAU |
| HAO1_exon6 | - | **TTTC** | 227 | ACTTGGTTAGGGGGAGA AAGGTGTTCAAGA | 682 | ACUUGGUUAGGGGGAGAAA GGUGUUCAAGA |
| HAO1_exon6 | - | **TTTT** | 228 | CACTTGGTTAGGGGGAG AAAGGTGTTCAAG | 683 | CACUUGGUUAGGGGGAGAA AGGUGUUCAAG |
| HAO1_exon6 | - | **GTTT** | 229 | TCACTTGGTTAGGGGGA GAAAGGTGTTCAA | 684 | UCACUUGGUUAGGGGGAGA AAGGUGUUCAA |
| HAO1_exon6 | - | **GTTC** | 230 | TGAATCACTCTGTATCT TTTCACTTGGTTA | 685 | UGAAUCACUCUGUAUCUUU UCACUUGGUUA |
| HAO1_exon6 | - | **TTTA** | 231 | GTTCTGAATCACTCTGT ATCTTTTCACTTG | 686 | GUUCUGAAUCACUCUGUAU CUUUUCACUUG |
| HAO1_exon6 | - | **ATTT** | 232 | AGTTCTGAATCACTCTG TATCTTTTCACTT | 687 | AGUUCUGAAUCACUCUGUA UCUUUUCACUU |
| HAO1_exon6 | - | **CTTG** | 233 | ACAGTAAAACAAATGAA TAAAACAAGTCAG | 688 | ACAGUAAAACAAAUGAAUA AAACAAGUCAG |
| HAO1_exon6 | - | **TTTC** | 234 | CAGGTAACTGGACAAAG AAATGAATATATA | 689 | CAGGUAACUGGACAAAGAA AUGAAUAUAUA |
| HAO1_exon6 | + | **CTTG** | 235 | AACACCTTTCTCCCCCT AACCAAGTGAAAA | 690 | AACACCUUUCUCCCCCUAA CCAAGUGAAAA |
| HAO1_exon6 | - | **CTTA** | 236 | GCTTTCCAGGTAACTGG ACAAAGAAATGAA | 691 | GCUUUCCAGGUAACUGGAC AAAGAAAUGAA |
| HAO1_exon6 | - | **TTTG** | 237 | GGGCTTAGCTTTCCAGG TAACTGGACAAAG | 692 | GGGCUUAGCUUUCCAGGUA ACUGGACAAAG |
| HAO1_exon6 | - | **GTTT** | 238 | GGGGCTTAGCTTTCCAG GTAACTGGACAAA | 693 | GGGGCUUAGCUUUCCAGGU AACUGGACAAA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | - | **TTTG** | 239 | TGGGGAGACCAATCGTT TGGGGCTTAGCTT | 694 | UGGGGAGACCAAUCGUUUG GGGCUUAGCUU |
| HAO1_exon6 | - | **GTTT** | 240 | GTGGGGAGACCAATCGT TTGGGGCTTAGCT | 695 | GUGGGGAGACCAAUCGUUU GGGGCUUAGCU |
| HAO1_exon6 | - | C**TTG** | 241 | GTTAGGGGGAGAAAGGT GTTCAAGATGTCC | 696 | GUUAGGGGGAGAAAGGUGU UCAAGAUGUCC |
| HAO1_exon6 | + | C**TTT** | 242 | CTCCCCCTAACCAAGTG AAAAGATACAGAG | 697 | CUCCCCCUAACCAAGUGAA AAGAUACAGAG |
| HAO1_exon6 | + | **GTTT** | 243 | TACTGTCAAGTTGTCTA TTTTATATATTCA | 698 | UACUGUCAAGUUGUCUAUU UUAUAUAUUCA |
| HAO1_exon6 | + | **ATTC** | 244 | AGAACTAAATCAGTCTG ACTTGTTTTATTC | 699 | AGAACUAAAUCAGUCUGAC UUGUUUUAUUC |
| HAO1_exon6 | + | **GTTC** | 245 | AATAATGTGACTCTATT AACACTGAATTGT | 700 | AAUAAUGUGACUCUAUUAA CACUGAAUUGU |
| HAO1_exon6 | + | **TTTC** | 246 | TGGCAGAACATCAATCT GGGGAAAGAAAAG | 701 | UGGCAGAACAUCAAUCUGG GGAAAGAAAAG |
| HAO1_exon6 | + | **ATTT** | 247 | CTGGCAGAACATCAATC TGGGGAAAGAAAA | 702 | CUGGCAGAACAUCAAUCUG GGGAAAGAAAA |
| HAO1_exon6 | + | **GTTC** | 248 | CACAGCCTCCACAATTT CTGGCAGAACATC | 703 | CACAGCCUCCACAAUUUCU GGCAGAACAUC |
| HAO1_exon6 | + | C**TTC** | 249 | CCTTCCACAGCCTCCAC AATTTCTGGCAGA | 704 | CCUUCCACAGCCUCCACAA UUUCUGGCAGA |
| HAO1_exon6 | + | **GTTC** | 250 | CACCTTCCCTTCCACAG CCTCCACAATTTC | 705 | CACCUUCCCUUCCACAGCC UCCACAAUUUC |
| HAO1_exon6 | + | **TTTC** | 251 | CGCACACCCCCGTCCAG GAAGACTTCCACC | 706 | CGCACACCCCCGUCCAGGA AGACUUCCACC |
| HAO1_exon6 | + | C**TTT** | 252 | CCGCACACCCCCGTCCA GGAAGACTTCCAC | 707 | CCGCACACCCCCGUCCAGG AAGACUUCCAC |
| HAO1_exon6 | + | **TTTC** | 253 | AGAACATCAGTGCCTTT CCGCACACCCCCG | 708 | AGAACAUCAGUGCCUUUCC GCACACCCCCG |
| HAO1_exon6 | + | C**TTT** | 254 | CAGAACATCAGTGCCTT TCCGCACACCCCC | 709 | CAGAACAUCAGUGCCUUUC CGCACACCCCC |
| HAO1_exon6 | + | C**TTG** | 255 | GCGCCAAGAGCCAGAGC TTTCAGAACATCA | 710 | GCGCCAAGAGCCAGAGCUU UCAGAACAUCA |
| HAO1_exon6 | + | **ATTG** | 256 | GTCTCCCCACAAACACA GCCTTGGCGCCAA | 711 | GUCUCCCCACAAACACAGC CUUGGCGCCAA |
| HAO1_exon6 | + | **GTTA** | 257 | CCTGGAAAGCTAAGCCC CAAACGATTGGTC | 712 | CCUGGAAAGCUAAGCCCCA AACGAUUGGUC |
| HAO1_exon6 | + | **TTTG** | 258 | TCCAGTTACCTGGAAAG CTAAGCCCCAAAC | 713 | UCCAGUUACCUGGAAAGCU AAGCCCCAAAC |
| HAO1_exon6 | + | C**TTT** | 259 | GTCCAGTTACCTGGAAA GCTAAGCCCCAAA | 714 | GUCCAGUUACCUGGAAAGC UAAGCCCCAAA |
| HAO1_exon6 | + | **TTTC** | 260 | TTTGTCCAGTTACCTGG AAAGCTAAGCCCC | 715 | UUUGUCCAGUUACCUGGAA AGCUAAGCCCC |
| HAO1_exon6 | + | **ATTT** | 261 | CTTTGTCCAGTTACCTG GAAAGCTAAGCCC | 716 | CUUUGUCCAGUUACCUGGA AAGCUAAGCCC |
| HAO1_exon6 | + | C**TTG** | 262 | TTTTATTCATTTGTTTT ACTGTCAAGTTGT | 717 | UUUUAUUCAUUUGUUUUAC UGUCAAGUUGU |
| HAO1_exon6 | + | **GTTT** | 263 | TATTCATTTGTTTTACT GTCAAGTTGTCTA | 718 | UAUUCAUUUGUUUUACUGU CAAGUUGUCUA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | + | **TTTT** | 264 | ATTCATTTGTTTTACTG TCAAGTTGTCTAT | 719 | AUUCAUUUGUUUUACUGUC AAGUUGUCUAU |
| HAO1_exon6 | + | **TTTA** | 265 | TTCATTTGTTTTACTGT CAAGTTGTCTATT | 720 | UUCAUUUGUUUUACUGUCA AGUUGUCUAUU |
| HAO1_exon6 | + | **ATTC** | 266 | ATTTGTTTTACTGTCAA GTTGTCTATTTTA | 721 | AUUUGUUUUACUGUCAAGU UGUCUAUUUUA |
| HAO1_exon6 | + | **ATTT** | 267 | GTTTTACTGTCAAGTTG TCTATTTTATATA | 722 | GUUUUACUGUCAAGUUGUC UAUUUUAUAUA |
| HAO1_exon6 | + | **TTTC** | 268 | TCCCCCTAACCAAGTGA AAAGATACAGAGT | 723 | UCCCCCUAACCAAGUGAAA AGAUACAGAGU |
| HAO1_exon6 | + | **TTTG** | 269 | TTTTACTGTCAAGTTGT CTATTTTATATAT | 724 | UUUUACUGUCAAGUUGUCU AUUUUAUAUAU |
| HAO1_exon6 | + | **TTTT** | 270 | ACTGTCAAGTTGTCTAT TTTATATATTCAT | 725 | ACUGUCAAGUUGUCUAUUU UAUAUAUUCAU |
| HAO1_exon6 | + | **TTTA** | 271 | CTGTCAAGTTGTCTATT TTATATATTCATT | 726 | CUGUCAAGUUGUCUAUUUU AUAUAUUCAUU |
| HAO1_exon6 | + | **ATTT** | 272 | TATATATTCATTTCTTT GTCCAGTTACCTG | 727 | UAUAUAUUCAUUUCUUUGU CCAGUUACCUG |
| HAO1_exon6 | + | **TTTT** | 273 | ATATATTCATTTCTTTG TCCAGTTACCTGG | 728 | AUAUAUUCAUUUCUUUGUC CAGUUACCUGG |
| HAO1_exon6 | + | **TTTA** | 274 | TATATTCATTTCTTTGT CCAGTTACCTGGA | 729 | UAUAUUCAUUUCUUUGUCC AGUUACCUGGA |
| HAO1_exon6 | + | **ATTC** | 275 | ATTTCTTTGTCCAGTTA CCTGGAAAGCTAA | 730 | AUUUCUUUGUCCAGUUACC UGGAAAGCUAA |
| HAO1_exon6 | - | **CTTG** | 276 | GCGCCAAGGCTGTGTTT GTGGGGAGACCAA | 731 | GCGCCAAGGCUGUGUUUGU GGGGAGACCAA |
| HAO1_exon6 | - | **GTTC** | 277 | TGAAAGCTCTGGCTCTT GGCGCCAAGGCTG | 732 | UGAAAGCUCUGGCUCUUGG CGCCAAGGCUG |
| HAO1_exon6 | - | **ATTG** | 278 | TGGAGGCTGTGGAAGGG AAGGTGGAAGTCT | 733 | UGGAGGCUGUGGAAGGGAA GGUGGAAGUCU |
| HAO1_exon6 | - | **ATTA** | 279 | TTGAACTTTTCTTTCCC CAGATTGATGTTC | 734 | UUGAACUUUUCUUUCCCCA GAUUGAUGUUC |
| HAO1_exon6 | - | **GTTC** | 280 | TGCCAGAAATTGTGGAG GCTGTGGAAGGGA | 735 | UGCCAGAAAUUGUGGAGGC UGUGGAAGGGA |
| HAO1_exon6 | - | **ATTG** | 281 | ATGTTCTGCCAGAAATT GTGGAGGCTGTGG | 736 | AUGUUCUGCCAGAAAUUGU GGAGGCUGUGG |
| HAO1_exon6 | - | **TTTC** | 282 | CCCAGATTGATGTTCTG CCAGAAATTGTGG | 737 | CCCAGAUUGAUGUUCUGCC AGAAAUUGUGG |
| HAO1_exon6 | - | **CTTT** | 283 | CCCCAGATTGATGTTCT GCCAGAAATTGTG | 738 | CCCCAGAUUGAUGUUCUGC CAGAAAUUGUG |
| HAO1_exon6 | - | **TTTC** | 284 | TTTCCCCAGATTGATGT TCTGCCAGAAATT | 739 | UUUCCCCAGAUUGAUGUUC UGCCAGAAAUU |
| HAO1_exon6 | - | **TTTT** | 285 | CTTTCCCCAGATTGATG TTCTGCCAGAAAT | 740 | CUUUCCCCAGAUUGAUGUU CUGCCAGAAAU |
| HAO1_exon6 | - | **CTTT** | 286 | TCTTTCCCCAGATTGAT GTTCTGCCAGAAA | 741 | UCUUUCCCCAGAUUGAUGU UCUGCCAGAAA |
| HAO1_exon6 | - | **ATTG** | 287 | AACTTTTCTTTCCCCAG ATTGATGTTCTGC | 742 | AACUUUUCUUUCCCCAGAU UGAUGUUCUGC |
| HAO1_exon6 | - | **GTTA** | 288 | ATAGAGTCACATTATTG AACTTTTCTTTCC | 743 | AUAGAGUCACAUUAUUGAA CUUUUCUUUCC |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | - | **ATTC** | 289 | AGTGTTAATAGAGTCAC ATTATTGAACTTT | 744 | AGUGUUAAUAGAGUCACAU UAUUGAACUUU |
| HAO1_exon6 | - | **GTTC** | 290 | CTGGACGGGGGTGTGCG GAAAGGCACTGAT | 745 | CUGGACGGGGGUGUGCGGA AAGGCACUGAU |
| HAO1_exon6 | - | **CTTT** | 291 | CTTTTCTTTTATGATCT TTAAGT | 746 | CUUUUCUUUUAUGAUCUUU AAGU |
| HAO1_exon6 | - | **TTTC** | 292 | TTTTCTTTTATGATCTT TAAGT | 747 | UUUUCUUUUAUGAUCUUUA AGU |
| HAO1_exon7 | - | **ATTT** | 293 | TTTCAGGGTGCCAGAAT GTGAAAGTCATCG | 748 | UUUCAGGGUGCCAGAAUGU GAAAGUCAUCG |
| HAO1_exon7 | - | **ATTA** | 294 | TTTTTTCAGGGTGCCAG AATGTGAAAGTCA | 749 | UUUUUUCAGGGUGCCAGAA UGUGAAAGUCA |
| HAO1_exon7 | - | **ATTG** | 295 | TAAGCTCAGGTTCAAAG TGTTGGTAATGCC | 750 | UAAGCUCAGGUUCAAAGUG UUGGUAAUGCC |
| HAO1_exon7 | - | **GTTC** | 296 | ATATTAAATGTATGCAT TATTTTTTCAGGG | 751 | AUAUUAAAUGUAUGCAUUA UUUUUUCAGGG |
| HAO1_exon7 | - | **ATTC** | 297 | AGTTCATATTAAATGTA TGCATTATTTTTT | 752 | AGUUCAUAUUAAAUGUAUG CAUUAUUUUUU |
| HAO1_exon7 | - | **TTTT** | 298 | TTCAGGGTGCCAGAATG TGAAAGTCATCGA | 753 | UUCAGGGUGCCAGAAUGUG AAAGUCAUCGA |
| HAO1_exon7 | - | **ATTA** | 299 | AATGTATGCATTATTTT TTCAGGGTGCCAG | 754 | AAUGUAUGCAUUAUUUUUU CAGGGUGCCAG |
| HAO1_exon7 | - | **TTTT** | 300 | TCAGGGTGCCAGAATGT GAAAGTCATCGAC | 755 | UCAGGGUGCCAGAAUGUGA AAGUCAUCGAC |
| HAO1_exon7 | - | **TTTG** | 301 | GCCGTTTCCAAGATCTG ACAGTGCACAATA | 756 | GCCGUUUCCAAGAUCUGAC AGUGCACAAUA |
| HAO1_exon7 | - | **TTTC** | 302 | AGGGTGCCAGAATGTGA AAGTCATCGACAA | 757 | AGGGUGCCAGAAUGUGAAA GUCAUCGACAA |
| HAO1_exon7 | - | **ATTG** | 303 | GTGAGGAAAAATCCTTT GGCCGTTTCCAAG | 758 | GUGAGGAAAAAUCCUUUGG CCGUUUCCAAG |
| HAO1_exon7 | - | **CTTT** | 304 | GGCCGTTTCCAAGATCT GACAGTGGACAAT | 759 | GGCCGUUUCCAAGAUCUGA CAGUGCACAAU |
| HAO1_exon7 | - | **ATTG** | 305 | CATTCAGTTCATATTAA ATGTATGCATTAT | 760 | CAUUCAGUUCAUAUUAAAU GUAUGCAUUAU |
| HAO1_exon7 | - | **GTTT** | 306 | CCAAGATCTGACAGTGC ACAATATTTTCCC | 761 | CCAAGAUCUGACAGUGCAC AAUAUUUUCCC |
| HAO1_exon7 | - | **TTTC** | 307 | CAAGATCTGACAGTGCA CAATATTTTCCCA | 762 | CAAGAUCUGACAGUGCACA AUAUUUUCCCA |
| HAO1_exon7 | - | **TTTT** | 308 | CAGGGTGCCAGAATGTG AAAGTCATCGACA | 763 | CAGGGUGCCAGAAUGUGAA AGUCAUCGACA |
| HAO1_exon7 | - | **ATTA** | 309 | TTGCATTCAGTTCATAT TAAATGTATGCAT | 764 | UUGCAUUCAGUUCAUAUUA AAUGUAUGCAU |
| HAO1_exon7 | - | **ATTG** | 310 | GAGGTAGCAAACACTAA GGTGAAAAGATAA | 765 | GAGGUAGCAAACACUAAGG UGAAAAGAUAA |
| HAO1_exon7 | - | **GTTT** | 311 | AGACAACGTCATCCCCT GGCAGGCTAAAGT | 766 | AGACAACGUCAUCCCCUGG CAGGCUAAAGU |
| HAO1_exon7 | - | **CTTA** | 312 | AATTGTAAGCTCAGGTT CAAAGTGTTGGTA | 767 | AAUUGUAAGCUCAGGUUCA AAGUGUUGGUA |
| HAO1_exon7 | - | **GTTC** | 313 | TTAAATTGTAAGCTCAG GTTCAAAGTGTTG | 768 | UUAAAUUGUAAGCUCAGGU UCAAAGUGUUG |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon7 | - | **TTTA** | 314 | AAACAGTGGTTCTTAAA TTGTAAGCTCAGG | 769 | AAACAGUGGUUCUUAAAUU GUAAGCUCAGG |
| HAO1_exon7 | - | **GTTT** | 315 | AAAACAGTGGTTCTTAA ATTGTAAGCTCAG | 770 | AAAACAGUGGUUCUUAAAU UGUAAGCUCAG |
| HAO1_exon7 | - | **TTTA** | 316 | CATGTCTTTAAAACAGT GGTTCTTAAATTG | 771 | CAUGUCUUUAAAACAGUGG UUCUUAAAUUG |
| HAO1_exon7 | - | **GTTT** | 317 | ACATGTCTTTAAAACAG TGGTTCTTAAATT | 772 | ACAUGUCUUUAAAACAGUG GUUCUUAAAUU |
| HAO1_exon7 | - | **ATTC** | 318 | TGTTTACATGTCTTTAA AACAGTGGTTCTT | 773 | UGUUUACAUGUCUUUAAAA CAGUGGUUCUU |
| HAO1_exon7 | - | **ATTA** | 319 | ACCTGTATTCTGTTTAC ATGTCTTTAAAAC | 774 | ACCUGUAUUCUGUUUACAU GUCUUUAAAAC |
| HAO1_exon7 | - | **TTTA** | 320 | TTAACCTGTATTCTGTT TACATGTCTTTAA | 775 | UUAACCUGUAUUCUGUUUA CAUGUCUUUAA |
| HAO1_exon7 | - | **GTTT** | 321 | ATTAACCTGTATTCTGT TTACATGTCTTTA | 776 | AUUAACCUGUAUUCUGUUU ACAUGUCUUUA |
| HAO1_exon7 | - | **ATTG** | 322 | TTTATTAACCTGTATTC TGTTTACATGTCT | 777 | UUUAUUAACCUGUAUUCUG UUUACAUGUCU |
| HAO1_exon7 | - | **ATTT** | 323 | TCCCATCTGTATTATTT TTTTTCAGCATGT | 778 | UCCCAUCUGUAUUAUUUUU UUUCAGCAUGU |
| HAO1_exon7 | - | **TTTA** | 324 | GTAAAATTGGAGGTAGC AAACACTAAGGTG | 779 | GUAAAAUUGGAGGUAGCAA ACACUAAGGUG |
| HAO1_exon7 | - | **GTTT** | 325 | AGTAAAATTGGAGGTAG CAAACACTAAGGT | 780 | AGUAAAAUUGGAGGUAGCA AACACUAAGGU |
| HAO1_exon7 | - | **TTTA** | 326 | GACAACGTCATCCCCTG GCAGGCTAAAGTG | 781 | GACAACGUCAUCCCCUGGC AGGCUAAAGUG |
| HAO1_exon7 | - | **ATTA** | 327 | TTATTGCATTCAGTTCA TATTAAATGTATG | 782 | UUAUUGCAUUCAGUUCAUA UUAAAUGUAUG |
| HAO1_exon7 | - | **TTTT** | 328 | CCCATCTGTATTATTTT TTTTCAGCATGTA | 783 | CCCAUCUGUAUUAUUUUUU UUCAGCAUGUA |
| HAO1_exon7 | - | **TTTT** | 329 | TTCAGCATGTATTACTT GACAAAGAGACAC | 784 | UUCAGCAUGUAUUACUUGA CAAAGAGACAC |
| HAO1_exon7 | - | **ATTA** | 330 | TTTTTTTTCAGCATGTA TTACTTGACAAAG | 785 | UUUUUUUUCAGCAUGUAUU ACUUGACAAAG |
| HAO1_exon7 | - | **TTTC** | 331 | ATTGCTTTTGACTTTTC AATGGGTGTCCTA | 786 | AUUGCUUUUGACUUUUCAA UGGGUGUCCUA |
| HAO1_exon7 | - | **ATTG** | 332 | CTTTTGACTTTTCAATG GGTGTCCTAGGAA | 787 | CUUUUGACUUUUCAAUGGG UGUCCUAGGAA |
| HAO1_exon7 | - | **CTTT** | 333 | TGACTTTTCAATGGGTG TCCTAGGAACCTT | 788 | UGACUUUUCAAUGGGUGUC CUAGGAACCUU |
| HAO1_exon7 | - | **TTTT** | 334 | GACTTTTCAATGGGTGT CCTAGGAACCTTT | 789 | GACUUUUCAAUGGGUGUCC UAGGAACCUUU |
| HAO1_exon7 | - | **TTTG** | 335 | ACTTTTCAATGGGTGTC CTAGGAACCTTTT | 790 | ACUUUUCAAUGGGUGUCCU AGGAACCUUUU |
| HAO1_exon7 | - | **CTTT** | 336 | TCAATGGGTGTCCTAGG AACCTTTTAGAAA | 791 | UCAAUGGGUGUCCUAGGAA CCUUUUAGAAA |
| HAO1_exon7 | - | **TTTT** | 337 | CAATGGGTGTCCTAGGA ACCTTTTAGAAAG | 792 | CAAUGGGUGUCCUAGGAAC CUUUUAGAAAG |
| HAO1_exon7 | - | **TTTC** | 338 | AATGGGTGTCCTAGGAA CCTTTTAGAAAGA | 793 | AAUGGGUGUCCUAGGAACC UUUUAGAAAGA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | - | **CTTT** | 339 | TAGAAAGAAATGGACTT TCATCCTGGAAAT | 794 | UAGAAAGAAAUGGACUUUC AUCCUGGAAAU |
| HAO1_exon7 | - | **TTTT** | 340 | AGAAAGAAATGGACTTT CATCCTGGAAATA | 795 | AGAAAGAAAUGGACUUUCA UCCUGGAAAUA |
| HAO1_exon7 | - | **TTTA** | 341 | GAAAGAAATGGACTTTC ATCCTGGAAATAT | 796 | GAAAGAAAUGGACUUUCAU CCUGGAAAUAU |
| HAO1_exon7 | - | **CTTT** | 342 | CATCCTGGAAATATATT AACTGTTAAAAAG | 797 | CAUCCUGGAAAUAUAUUAA CUGUUAAAAAG |
| HAO1_exon7 | - | **TTTC** | 343 | ATCCTGGAAATATATTA ACTGTTAAAAAGA | 798 | AUCCUGGAAAUAUAUUAAC UGUUAAAAAGA |
| HAO1_exon7 | - | **ATTA** | 344 | ACTGTTAAAAAGAAAAC ATTGAAAATGTGT | 799 | ACUGUUAAAAAGAAAACAU UGAAAAUGUGU |
| HAO1_exon7 | - | **GTTA** | 345 | AAAAGAAAACATTGAAA ATGTGTTTAGACA | 800 | AAAAGAAAACAUUGAAAAU GUGUUUAGACA |
| HAO1_exon7 | - | **ATTT** | 346 | CATTGCTTTTGACTTTT CAATGGGTGTCCT | 801 | CAUUGCUUUUGACUUUUCA AUGGGUGUCCU |
| HAO1_exon7 | - | **TTTC** | 347 | CCATCTGTATTATTTTT TTTCAGCATGTAT | 802 | CCAUCUGUAUUAUUUUUUU UCAGCAUGUAU |
| HAO1_exon7 | - | **TTTA** | 348 | TTTCATTGCTTTTGACT TTTCAATGGGTGT | 803 | UUUCAUUGCUUUUGACUUU UCAAUGGGUGU |
| HAO1_exon7 | - | **CTTT** | 349 | TATTTCATTGCTTTTGA CTTTTCAATGGGT | 804 | UAUUUCAUUGCUUUUGACU UUUCAAUGGGU |
| HAO1_exon7 | - | **ATTG** | 350 | AAAATGTGTTTAGACAA CGTCATCCCCTGG | 805 | AAAAUGUGUUUAGACAACG UCAUCCCCUGG |
| HAO1_exon7 | - | **ATTT** | 351 | TTTTTCAGCATGTATTA CTTGACAAAGAGA | 806 | UUUUUCAGCAUGUAUUACU UGACAAAGAGA |
| HAO1_exon7 | - | **TTTT** | 352 | TTTTCAGCATGTATTAC TTGACAAAGAGAC | 807 | UUUUCAGCAUGUAUUACUU GACAAAGAGAC |
| HAO1_exon7 | - | **TTTT** | 353 | TTTCAGCATGTATTACT TGACAAAGAGACA | 808 | UUUCAGCAUGUAUUACUUG ACAAAGAGACA |
| HAO1_exon7 | - | **TTTT** | 354 | TCAGCATGTATTACTTG ACAAAGAGACACT | 809 | UCAGCAUGUAUUACUUGAC AAAGAGACACU |
| HAO1_exon7 | - | **TTTT** | 355 | CAGCATGTATTACTTGA CAAAGAGACACTG | 810 | CAGCAUGUAUUACUUGACA AAGAGACACUG |
| HAO1_exon7 | - | **TTTC** | 356 | AGCATGTATTACTTGAC AAAGAGACACTGT | 811 | AGCAUGUAUUACUUGACAA AGAGACACUGU |
| HAO1_exon7 | - | **ATTA** | 357 | CTTGACAAAGAGACACT GTGCAGAGGGTGA | 812 | CUUGACAAAGAGACACUGU GCAGAGGGUGA |
| HAO1_exon7 | - | **CTTG** | 358 | ACAAAGAGACACTGTGC AGAGGGTGACCAC | 813 | ACAAAGAGACACUGUGCAG AGGGUGACCAC |
| HAO1_exon7 | - | **ATTC** | 359 | CCCACTTCAATACAAAG GGTGTCGTTCTTT | 814 | CCCACUUCAAUACAAAGGG UGUCGUUCUUU |
| HAO1_exon7 | - | **CTTC** | 360 | AATACAAAGGGTGTCGT TCTTTTCCAACAA | 815 | AAUACAAAGGGUGUCGUUC UUUUCCAACAA |
| HAO1_exon7 | - | **GTTC** | 361 | TTTTCCAACAAAATAGC AATCCCTTTTATT | 816 | UUUUCCAACAAAAUAGCAA UCCCUUUUAUU |
| HAO1_exon7 | - | **CTTT** | 362 | TCCAACAAAATAGCAAT CCCTTTTATTTCA | 817 | UCCAACAAAAUAGCAAUCC CUUUUAUUUCA |
| HAO1_exon7 | - | **TTTT** | 363 | CCAACAAAATAGCAATC CCTTTTATTTCAT | 818 | CCAACAAAAUAGCAAUCCC UUUUAUUUCAU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | - | **TTTC** | 364 | CAACAAAATAGCAATCC CTTTTATTTCATT | 819 | CAACAAAAUAGCAAUCCCU UUUAUUUCAUU |
| HAO1_exon7 | - | **TTTT** | 365 | ATTTCATTGCTTTTGAC TTTTCAATGGGTG | 820 | AUUUCAUUGCUUUUGACUU UUCAAUGGGUG |
| HAO1_exon7 | - | G**TTC** | 366 | AAAGTGTTGGTAATGCC TGATTCACAACTT | 821 | AAAGUGUUGGUAAUGCCUG AUUCACAACUU |
| HAO1_exon7 | + | **ATTT** | 367 | CTCTCTAAGAAGTAACA TACATCCTAAAAC | 822 | CUCUCUAAGAAGUAACAUA CAUCCUAAAAC |
| HAO1_exon7 | - | **ATTC** | 368 | ACAACTTTGAGAAGGTA GCACTGGAGAGAA | 823 | ACAACUUUGAGAAGGUAGC ACUGGAGAGAA |
| HAO1_exon7 | + | **TTTC** | 369 | ACCTTAGTGTTTGCTAC CTCCAATTTTACT | 824 | ACCUUAGUGUUUGCUACCU CCAAUUUUACU |
| HAO1_exon7 | + | C**TTA** | 370 | GTGTTTGCTACCTCCAA TTTTACTAAAGGA | 825 | GUGUUUGCUACCUCCAAUU UUACUAAAGGA |
| HAO1_exon7 | + | **GTTT** | 371 | GCTACCTCCAATTTTAC TAAAGGATACAGC | 826 | GCUACCUCCAAUUUUACUA AAGGAUACAGC |
| HAO1_exon7 | + | **TTTG** | 372 | CTACCTCCAATTTTACT AAAGGATACAGCA | 827 | CUACCUCCAAUUUUACUAA AGGAUACAGCA |
| HAO1_exon7 | + | **ATTT** | 373 | TACTAAAGGATACAGCA CTTTAGCCTGCCA | 828 | UACUAAAGGAUACAGCACU UUAGCCUGCCA |
| HAO1_exon7 | + | **TTTT** | 374 | ACTAAAGGATACAGCAC TTTAGCCTGCCAG | 829 | ACUAAAGGAUACAGCACUU UAGCCUGCCAG |
| HAO1_exon7 | + | **TTTA** | 375 | CTAAAGGATACAGCACT TTAGCCTGCCAGG | 830 | CUAAAGGAUACAGCACUUU AGCCUGCCAGG |
| HAO1_exon7 | + | C**TTT** | 376 | AGCCTGCCAGGGGATGA CGTTGTCTAAACA | 831 | AGCCUGCCAGGGGAUGACG UUGUCUAAACA |
| HAO1_exon7 | + | **TTTA** | 377 | GCCTGCCAGGGGATGAC GTTGTCTAAACAC | 832 | GCCUGCCAGGGGAUGACGU UGUCUAAACAC |
| HAO1_exon7 | + | **TTTT** | 378 | CACCTTAGTGTTTGCTA CCTCCAATTTTAC | 833 | CACCUUAGUGUUUGCUACC UCCAAUUUUAC |
| HAO1_exon7 | + | **GTTG** | 379 | TCTAAACACATTTTCAA TGTTTTCTTTTTA | 834 | UCUAAACACAUUUUCAAUG UUUUCUUUUUA |
| HAO1_exon7 | + | **TTTT** | 380 | CAATGTTTTCTTTTTAA CAGTTAATATATT | 835 | CAAUGUUUUCUUUUUAACA GUUAAUAUAUU |
| HAO1_exon7 | + | **TTTC** | 381 | AATGTTTTCTTTTTAAC AGTTAATATATTT | 836 | AAUGUUUUCUUUUUAACAG UUAAUAUAUUU |
| HAO1_exon7 | + | **GTTT** | 382 | TCTTTTTAACAGTTAAT ATATTTCCAGGAT | 837 | UCUUUUUAACAGUUAAUAU AUUUCCAGGAU |
| HAO1_exon7 | + | **TTTT** | 383 | CTTTTTAACAGTTAATA TATTTCCAGGATG | 838 | CUUUUUAACAGUUAAUAUA UUUCCAGGAUG |
| HAO1_exon7 | + | **TTTC** | 384 | TTTTTAACAGTTAATAT ATTTCCAGGATGA | 839 | UUUUUAACAGUUAAUAUAU UUCCAGGAUGA |
| HAO1_exon7 | + | **CTTT** | 385 | TTAACAGTTAATATATT TCCAGGATGAAAG | 840 | UUAACAGUUAAUAUAUUUC CAGGAUGAAAG |
| HAO1_exon7 | + | **TTTT** | 386 | TAACAGTTAATATATTT CCAGGATGAAAGT | 841 | UAACAGUUAAUAUAUUUCC AGGAUGAAAGU |
| HAO1_exon7 | + | **TTTT** | 387 | AACAGTTAATATATTTC CAGGATGAAAGTC | 842 | AACAGUUAAUAUAUUUCCA GGAUGAAAGUC |
| HAO1_exon7 | + | **TTTA** | 388 | ACAGTTAATATATTTCC AGGATGAAAGTCC | 843 | ACAGUUAAUAUAUUUCCAG GAUGAAAGUCC |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon7 | + | **ATTT** | 389 | TCAATGTTTTCTTTTTA ACAGTTAATATAT | 844 | UCAAUGUUUUCUUUUUAAC AGUUAAUAUAU |
| HAO1_exon7 | + | **GTTA** | 390 | ATATATTTCCAGGATGA AAGTCCATTTCTT | 845 | AUAUAUUUCCAGGAUGAAA GUCCAUUUCUU |
| HAO1_exon7 | + | **CTTT** | 391 | TCACCTTAGTGTTTGCT ACCTCCAATTTTA | 846 | UCACCUUAGUGUUUGCUAC CUCCAAUUUUA |
| HAO1_exon7 | + | **GTTA** | 392 | ATAAACAATGAGATCAT TATCTTTTCACCT | 847 | AUAAACAAUGAGAUCAUUA UCUUUUCACCU |
| HAO1_exon7 | + | **TTTC** | 393 | TCTCTAAGAAGTAACAT ACATCCTAAAACA | 848 | UCUCUAAGAAGUAACAUAC AUCCUAAAACA |
| HAO1_exon7 | + | **ATTT** | 394 | GGATATATTCAGACACT AAAGATGTGATTG | 849 | GGAUAUAUUCAGACACUAA AGAUGUGAUUG |
| HAO1_exon7 | + | **TTTG** | 395 | GATATATTCAGACACTA AAGATGTGATTGG | 850 | GAUAUAUUCAGACACUAAA GAUGUGAUUGG |
| HAO1_exon7 | + | **ATTC** | 396 | AGACACTAAAGATGTGA TTGGAAATCTACA | 851 | AGACACUAAAGAUGUGAUU GGAAAUCUACA |
| HAO1_exon7 | + | **ATTG** | 397 | GAAATCTACATTCAAAG AAGTATCACCAAT | 852 | GAAAUCUACAUUCAAAGAA GUAUCACCAAU |
| HAO1_exon7 | + | **ATTC** | 398 | AAAGAAGTATCACCAAT TACCGCCACCCAT | 853 | AAAGAAGUAUCACCAAUUA CCGCCACCCAU |
| HAO1_exon7 | + | **ATTA** | 399 | CCGCCACCCATTCCAAT TCTCTCCAGTGCT | 854 | CCGCCACCCAUUCCAAUUC UCUCCAGUGCU |
| HAO1_exon7 | + | **ATTC** | 400 | CAATTCTCTCCAGTGCT ACCTTCTCAAAGT | 855 | CAAUUCUCUCCAGUGCUAC CUUCUCAAAGU |
| HAO1_exon7 | + | **ATTC** | 401 | TCTCCAGTGCTACCTTC TCAAAGTTGTGAA | 856 | UCUCCAGUGCUACCUUCUC AAAGUUGUGAA |
| HAO1_exon7 | + | **ATTA** | 402 | TCTTTTCACCTTAGTGT TTGCTACCTCCAA | 857 | UCUUUUCACCUUAGUGUUU GCUACCUCCAA |
| HAO1_exon7 | + | **CTTC** | 403 | TCAAAGTTGTGAATCAG GCATTACCAACAC | 858 | UCAAAGUUGUGAAUCAGGC AUUACCAACAC |
| HAO1_exon7 | + | **ATTA** | 404 | CCAACACTTTGAACCTG AGCTTACAATTTA | 859 | CCAACACUUUGAACCUGAG CUUACAAUUUA |
| HAO1_exon7 | + | **CTTT** | 405 | GAACCTGAGCTTACAAT TTAAGAACCACTG | 860 | GAACCUGAGCUUACAAUUU AAGAACCACUG |
| HAO1_exon7 | + | **TTTG** | 406 | AACCTGAGCTTACAATT TAAGAACCACTGT | 861 | AACCUGAGCUUACAAUUUA AGAACCACUGU |
| HAO1_exon7 | + | **CTTA** | 407 | CAATTTAAGAACCACTG TTTTAAAGACATG | 862 | CAAUUUAAGAACCACUGUU UUAAAGACAUG |
| HAO1_exon7 | + | **ATTT** | 408 | AAGAACCACTGTTTTAA AGACATGTAAACA | 863 | AAGAACCACUGUUUUAAAG ACAUGUAAACA |
| HAO1_exon7 | + | **TTTA** | 409 | AGAACCACTGTTTTAAA GACATGTAAACAG | 864 | AGAACCACUGUUUUAAAGA CAUGUAAACAG |
| HAO1_exon7 | + | **GTTT** | 410 | TAAAGACATGTAAACAG AATACAGGTTAAT | 865 | UAAAGACAUGUAAACAGAA UACAGGUUAAU |
| HAO1_exon7 | + | **TTTT** | 411 | AAAGACATGTAAACAGA ATACAGGTTAATA | 866 | AAAGACAUGUAAACAGAAU ACAGGUUAAUA |
| HAO1_exon7 | + | **TTTA** | 412 | AAGACATGTAAACAGAA TACAGGTTAATAA | 867 | AAGACAUGUAAACAGAAUA CAGGUUAAUAA |
| HAO1_exon7 | + | **GTTG** | 413 | TGAATCAGGCATTACCA ACACTTTGAACCT | 868 | UGAAUCAGGCAUUACCAAC ACUUUGAACCU |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon7 | - | **GTTG** | 414 | GTAATGCCTGATTCACA ACTTTGAGAAGGT | 869 | GUAAUGCCUGAUUCACAAC UUUGAGAAGGU |
| HAO1_exon7 | + | **ATTT** | 415 | CCAGGATGAAAGTCCAT TTCTTTCTAAAAG | 870 | CCAGGAUGAAAGUCCAUUU CUUUCUAAAAG |
| HAO1_exon7 | + | **GTTT** | 416 | ATTTCTCTCTAAGAAGT AACATACATCCTA | 871 | AUUUCUCUCUAAGAAGUAA CAUACAUCCUA |
| HAO1_exon7 | + | **TTTC** | 417 | ACATTCTGGCACCCTGA AAAAATAATGCAT | 872 | ACAUUCUGGCACCCUGAAA AAAUAAUGCAU |
| HAO1_exon7 | + | **ATTC** | 418 | TGGCACCCTGAAAAAAT AATGCATACATTT | 873 | UGGCACCCUGAAAAAAUAA UGCAUACAUUU |
| HAO1_exon7 | + | **TTTA** | 419 | TTTCTCTCTAAGAAGTA ACATACATCCTAA | 874 | UUUCUCUCUAAGAAGUAAC AUACAUCCUAA |
| HAO1_exon7 | + | **CTTC** | 420 | CCAAAAATGCTTTATTT CTCTCTAAGAAGT | 875 | CCAAAAAUGCUUUAUUUCU CUCUAAGAAGU |
| HAO1_exon7 | - | **CTTC** | 421 | TTAGAGAGAAATAAAGC ATTTTTGGGAAGA | 876 | UUAGAGAGAAAUAAAGCAU UUUUGGGAAGA |
| HAO1_exon7 | - | **GTTA** | 422 | CTTCTTAGAGAGAAATA AAGCATTTTTGGG | 877 | CUUCUUAGAGAGAAAUAAA GCAUUUUUGGG |
| HAO1_exon7 | - | **TTTA** | 423 | GGATGTATGTTACTTCT TAGAGAGAAATAA | 878 | GGAUGUAUGUUACUUCUUA GAGAGAAAUAA |
| HAO1_exon7 | - | **TTTT** | 424 | AGGATGTATGTTACTTC TTAGAGAGAAATA | 879 | AGGAUGUAUGUUACUUCUU AGAGAGAAAUA |
| HAO1_exon7 | - | **GTTT** | 425 | TAGGATGTATGTTACTT CTTAGAGAGAAAT | 880 | UAGGAUGUAUGUUACUUCU UAGAGAGAAAU |
| HAO1_exon7 | + | **GTTT** | 426 | CACATTCTGGCACCCTG AAAAAATAATGCA | 881 | CACAUUCUGGCACCCUGAA AAAAUAAUGCA |
| HAO1_exon7 | - | **TTTA** | 427 | GTGTCTGAATATATCCA AATGTTTTAGGAT | 882 | GUGUCUGAAUAUAUCCAAA UGUUUUAGGAU |
| HAO1_exon7 | - | **TTTC** | 428 | CAATCACATCTTTAGTG TCTGAATATATCC | 883 | CAAUCACAUCUUUAGUGUC UGAAUAUAUCC |
| HAO1_exon7 | - | **ATTT** | 429 | CCAATCACATCTTTAGT GTCTGAATATATC | 884 | CCAAUCACAUCUUUAGUGU CUGAAUAUAUC |
| HAO1_exon7 | - | **TTTG** | 430 | AATGTAGATTTCCAATC ACATCTTTAGTGT | 885 | AAUGUAGAUUUCCAAUCAC AUCUUUAGUGU |
| HAO1_exon7 | - | **GTTT** | 431 | GAATGTAGATTTCCAAT CACATCTTTAGTG | 886 | GAAUGUAGAUUUCCAAUCA CAUCUUUAGUG |
| HAO1_exon7 | - | **CTTC** | 432 | TTTGAATGTAGATTTCC AATCACATCTTTA | 887 | UUUGAAUGUAGAUUUCCAA UCACAUCUUUA |
| HAO1_exon7 | - | **ATTG** | 433 | GTGATACTTCTTTGAAT GTAGATTTCCAAT | 888 | GUGAUACUUCUUUGAAUGU AGAUUUCCAAU |
| HAO1_exon7 | - | **ATTG** | 434 | GAATGGGTGGCGGTAAT TGGTGATACTTCT | 889 | GAAUGGGUGGCGGUAAUUG GUGAUACUUCU |
| HAO1_exon7 | - | **TTTG** | 435 | AGAAGGTAGCACTGGAG AGAATTGGAATGG | 890 | AGAAGGUAGCACUGGAGAG AAUUGGAAUGG |
| HAO1_exon7 | - | **GTTT** | 436 | GAGAAGGTAGCACTGGA GAGAATTGGAATG | 891 | GAGAAGGUAGCACUGGAGA GAAUUGGAAUG |
| HAO1_exon7 | - | **GTTT** | 437 | AGTGTCTGAATATATCC AAATGTTTTAGGA | 892 | AGUGUCUGAAUAUAUCCAA AUGUUUUAGGA |
| HAO1_exon7 | + | **TTTC** | 438 | CAGGATGAAAGTCCATT TCTTTCTAAAAGG | 893 | CAGGAUGAAAGUCCAUUUC UUUCUAAAAGG |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | + | **CTTG** | 439 | TCGATGACTTTCACATT CTGGCACCCTGAA | 894 | UCGAUGACUUUCACAUUCU GGCACCCUGAA |
| HAO1_exon7 | + | **TTTT** | 440 | CCTCACCAATGTCTTGT CGATGACTTTCAC | 895 | CCUCACCAAUGUCUUGUCG AUGACUUUCAC |
| HAO1_exon7 | + | **TTTC** | 441 | TTTCTAAAAGGTTCCTA GGACACCCATTGA | 896 | UUUCUAAAAGGUUCCUAGG ACACCCAUUGA |
| HAO1_exon7 | + | **CTTT** | 442 | CTAAAAGGTTCCTAGGA CACCCATTGAAAA | 897 | CUAAAAGGUUCCUAGGACA CCCAUUGAAAA |
| HAO1_exon7 | + | **TTTC** | 443 | TAAAAGGTTCCTAGGAC ACCCATTGAAAAG | 898 | UAAAAGGUUCCUAGGACAC CCAUUGAAAAG |
| HAO1_exon7 | + | **GTTC** | 444 | CTAGGACACCCATTGAA AAGTCAAAAGCAA | 899 | CUAGGACACCCAUUGAAAA GUCAAAAGCAA |
| HAO1_exon7 | + | **ATTG** | 445 | AAAAGTCAAAAGCAATG AAATAAAAGGGAT | 900 | AAAAGUCAAAAGCAAUGAA AUAAAAGGGAU |
| HAO1_exon7 | + | **ATTG** | 446 | CTATTTTGTTGGAAAAG AACGACACCCTTT | 901 | CUAUUUUGUUGGAAAAGAA CGACACCCUUU |
| HAO1_exon7 | + | **ATTT** | 447 | TGTTGGAAAAGAACGAC ACCCTTTGTATTG | 902 | UGUUGGAAAAGAACGACAC CCUUUGUAUUG |
| HAO1_exon7 | + | **TTTT** | 448 | GTTGGAAAAGAACGACA CCCTTTGTATTGA | 903 | GUUGGAAAAGAACGACACC CUUUGUAUUGA |
| HAO1_exon7 | + | **TTTG** | 449 | TTGGAAAAGAACGACAC CCTTTGTATTGAA | 904 | UUGGAAAAGAACGACACCC UUUGUAUUGAA |
| HAO1_exon7 | + | **TTTC** | 450 | CTCACCAATGTCTTGTC GATGACTTTCACA | 905 | CUCACCAAUGUCUUGUCGA UGACUUUCACA |
| HAO1_exon7 | + | **GTTG** | 451 | GAAAAGAACGACACCCT TTGTATTGAAGTG | 906 | GAAAAGAACGACACCCUUU GUAUUGAAGUG |
| HAO1_exon7 | + | **TTTG** | 452 | TATTGAAGTGGGGAATT ACAGACTGTGGTC | 907 | UAUUGAAGUGGGGAAUUAC AGACUGUGGUC |
| HAO1_exon7 | + | **ATTG** | 453 | AAGTGGGGAATTACAGA CTGTGGTCACCCT | 908 | AAGUGGGGAAUUACAGACU GUGGUCACCCU |
| HAO1_exon7 | + | **ATTA** | 454 | CAGACTGTGGTCACCCT CTGCACAGTGTCT | 909 | CAGACUGUGGUCACCCUCU GCACAGUGUCU |
| HAO1_exon7 | + | **CTTT** | 455 | GTCAAGTAATACATGCT GAAAAAAAATAAT | 910 | GUCAAGUAAUACAUGCUGA AAAAAAAUAAU |
| HAO1_exon7 | + | **TTTG** | 456 | TCAAGTAATACATGCTG AAAAAAAATAATA | 911 | UCAAGUAAUACAUGCUGAA AAAAAAUAAUA |
| HAO1_exon7 | + | **ATTG** | 457 | TGCACTGTCAGATCTTG GAAACGGCCAAAG | 912 | UGCACUGUCAGAUCUUGGA AACGGCCAAAG |
| HAO1_exon7 | + | **CTTG** | 458 | GAAACGGCCAAAGGATT TTTCCTCACCAAT | 913 | GAAACGGCCAAAGGAUUUU UCCUCACCAAU |
| HAO1_exon7 | + | **ATTT** | 459 | TTCCTCACCAATGTCTT GTCGATGACTTTC | 914 | UUCCUCACCAAUGUCUUGU CGAUGACUUUC |
| HAO1_exon7 | + | **TTTT** | 460 | TCCTCACCAATGTCTTG TCGATGACTTTCA | 915 | UCCUCACCAAUGUCUUGUC GAUGACUUUCA |
| HAO1_exon7 | + | **CTTT** | 461 | GTATTGAAGTGGGGAAT TACAGACTGTGGT | 916 | GUAUUGAAGUGGGGAAUUA CAGACUGUGGU |
| HAO1_exon7 | + | **ATTT** | 462 | CTTTCTAAAAGGTTCCT AGGACACCCATTG | 917 | CUUUCUAAAAGGUUCCUAG GACACCCAUUG |
| HAO1_exon7 | - | **CTTA** | 463 | GAGAGAAATAAAGCATT TTTGGGAAGAA | 918 | GAGAGAAAUAAAGCAUUUU UGGGAAGAA |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon7 | + | **ATTT** | 464 | AATATGAACTGAATGCA ATAATAATCA | 919 | AAUAUGAACUGAAUGCAAU AAUAAUCA |
| HAO1_exon7 | + | **TTTA** | 465 | ATATGAACTGAATGCAA TAATAATCA | 920 | AUAUGAACUGAAUGCAAUA AUAAUCA |

The 5'-TTN-3' 3-nucleotide PAM motif is in boldface.

The present disclosure includes all combinations of the direct repeats and spacers listed above, consistent with the disclosure herein.

In some embodiments, a spacer sequence described herein comprises an uracil (U). In some embodiments, a spacer sequence described herein comprises a thymine (T). In some embodiments, a spacer sequence according to Table 5 comprises a sequence comprising a thymine in one or more places indicated as uracil in Table 5.

(iii). Exemplary RNA Guides

The present disclosure provides RNA guides that comprise any and all combinations of the direct repeats and spacers described herein (e.g., as set forth in Table 5, above). In some embodiments, the sequence of an RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, an RNA guide has a sequence of any one of SEQ ID NOs: 967-1023.

In some embodiments, exemplary RNA guides provided herein may comprise a spacer sequence of any one of SEQ ID NOs: 1093-1097. In one example, the RNA guide may comprise a spacer of SEQ ID NO: 1096.

Any of the exemplary RNA guides disclosed herein may comprise a direct sequence of any one of SEQ ID NOs:1-10 or a fragment thereof that is at least 23-nucleotide in length. In one example, the direct sequence may comprise SEQ ID NO: 10.

In specific examples, the RNA guides provide herein may comprise the nucleotide sequence of SEQ ID NOs: 967, 968, 988, 989, or 994. In one example, the RNA guide provided herein comprise the nucleotide sequence of SEQ ID NO: 989.

(iv). Modifications

The RNA guide may include one or more covalent modifications with respect to a reference sequence, in particular the parent polyribonucleotide, which are included within the scope of the present disclosure.

Exemplary modifications can include any modification to the sugar, the nucleobase, the internucleoside linkage (e.g., to a linking phosphate/to a phosphodiester linkage/to the phosphodiester backbone), and any combination thereof. Some of the exemplary modifications provided herein are described in detail below.

The RNA guide may include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to RNA guide-protein interactions" from Nat Reviews Mol Cell Biol, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e., any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present disclosure, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotides (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

In some embodiments, one or more of the nucleotides of an RNA guide comprises a 2'-O-methyl phosphorothioate modification. In some embodiments, each of the first three nucleotides of the RNA guide comprises a 2'-O-methyl phosphorothioate modification. In some embodiments, each of the last four nucleotides of the RNA guide comprises a 2'-O-methyl phosphorothioate modification. In some embodiments, each of the first to last, second to last, and third to last nucleotides of the RNA guide comprises a 2'-O-methyl phosphorothioate modification, and wherein the last nucleotide of the RNA guide is unmodified. In some embodiments, each of the first three nucleotides of the RNA guide comprises a 2'-O-methyl phosphorothioate modification, and each of the first to last, second to last, and third to last nucleotides of the RNA guide comprises a 2'-O-methyl phosphorothioate modification.

When a gene editing system disclosed herein comprises nucleic acids encoding the Cas12i polypeptide disclosed herein, e.g., mRNA molecules, such nucleic acid molecules may contain any of the modifications disclosed herein, where applicable.

B. Cas12i Polypeptides

In some embodiments, the composition or system of the present disclosure includes a Cas12i polypeptide as described in WO/2019/178427, the relevant disclosures of which are incorporated by reference for the subject matter and purpose referenced herein.

In some embodiments, the genetic editing system disclosed herein includes a Cas12i2 polypeptide described herein (e.g., a polypeptide comprising SEQ ID NO: 922 and/or encoded by SEQ ID NO: 921). In some embodiments, the Cas12i2 polypeptide comprises at least one RuvC domain.

A nucleic acid sequence encoding the Cas12i2 polypeptide described herein may be substantially identical to a reference nucleic acid sequence, e.g., SEQ ID NO: 921. In some embodiments, the Cas12i2 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., SEQ ID NO: 921. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions of temperature and ionic strength (e.g., within a range of medium to high stringency). See, e.g., Tijssen, "Hybridization with Nucleic Acid Probes. Part I. Theory and Nucleic Acid Preparation" (Laboratory Techniques in Biochemistry and Molecular Biology, Vol 24).

In some embodiments, the Cas12i2 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., SEQ ID NO: 921.

In some embodiments, the Cas12i2 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 922.

In some embodiments, the present disclosure describes a Cas12i2 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 922. Homology or identity can be determined by amino acid sequence alignment, e.g., using a program such as BLAST, ALIGN, or CLUSTAL, as described herein.

Also provided is a Cas12i2 polypeptide of the present disclosure having enzymatic activity, e.g., nuclease or endonuclease activity, and comprising an amino acid sequence which differs from the amino acid sequences of SEQ ID NO: 922 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some examples, the Cas12i2 polypeptide may contain one or more mutations relative to SEQ ID NO: 922, for example, at position D581, G624, F626, P868, I926, V1030, E1035, S1046, or any combination thereof. In some instances, the one or more mutations are amino acid substitutions, for example, D581R, G624R, F626R, P868T, I926R, V1030G, E1035R, S1046G, or a combination thereof.

In some examples, the Cas12i2 polypeptide contains mutations at positions D581, D911, I926, and V1030. Such a Cas12i2 polypeptide may contain amino acid substitutions of D581R, D911R, I926R, and V1030G (e.g., SEQ ID NO: 923). In some examples, the Cas12i2 polypeptide contains mutations at positions D581, I926, and V1030. Such a Cas12i2 polypeptide may contain amino acid substitutions of D581R, I926R, and V1030G (e.g., SEQ ID NO: 924). In some examples, the Cas12i2 polypeptide may contain mutations at positions D581, I926, V1030, and S1046. Such a Cas12i2 polypeptide may contain amino acid substitutions of D581R, I926R, V1030G, and S1046G (e.g., SEQ ID NO: 925). In some examples, the Cas12i2 polypeptide may contain mutations at positions D581, G624, F626, I926, V1030, E1035, and S1046. Such a Cas12i2 polypeptide may contain amino acid substitutions of D581R, G624R, F626R, I926R, V1030G, E1035R, and S1046G (e.g., SEQ ID NO: 926). In some examples, the Cas12i2 polypeptide may contain mutations at positions D581, G624, F626, P868, I926, V1030, E1035, and S1046. Such a Cas12i2 polypeptide may contain amino acid substitutions of D581R, G624R, F626R, P868T, I926R, V1030G, E1035R, and S1046G (e.g., SEQ ID NO: 927).

In some embodiments, the Cas12i2 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 923, SEQ ID NO: 924, SEQ ID NO: 925, SEQ ID NO: 926, or SEQ ID NO: 927. In some embodiments, a Cas12i2 polypeptide having at least 50%, 60%, 65%, 70%, 75%, 80%, 85%, 90%, 91%, 92%, 93%, 94%, 95%, 96%, 97%, 98%, 99%, or 100% identity to SEQ ID NO: 923, SEQ ID NO: 924, SEQ ID NO: 925, SEQ ID NO: 926, or SEQ ID NO: 927 maintains the amino acid changes (or at least 1, 2, 3 etc. of these changes) that differentiate the polypeptide from its respective parent/reference sequence.

In some embodiments, the present disclosure describes a Cas12i2 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 923, SEQ ID NO: 924, SEQ ID NO: 925, SEQ ID NO: 926, or SEQ ID NO: 927. Homology or identity can be determined by amino acid sequence alignment, e.g., using a program such as BLAST, ALIGN, or CLUSTAL, as described herein.

Also provided is a Cas12i2 polypeptide of the present disclosure having enzymatic activity, e.g., nuclease or endonuclease activity, and comprising an amino acid sequence which differs from the amino acid sequences of SEQ ID NO: 923, SEQ ID NO: 924, SEQ ID NO: 925, SEQ ID NO: 926, or SEQ ID NO: 927 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i4 polypeptide described herein (e.g., a polypeptide comprising SEQ ID NO: 956 and/or encoded by SEQ ID NO: 955). In some embodiments, the Cas12i4 polypeptide comprises at least one RuvC domain.

A nucleic acid sequence encoding the Cas12i4 polypeptide described herein may be substantially identical to a reference nucleic acid sequence, e.g., SEQ ID NO: 955. In some embodiments, the Cas12i4 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., SEQ ID NO: 955. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions of temperature and ionic strength (e.g., within a range of medium to high stringency).

In some embodiments, the Cas12i4 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., SEQ ID NO: 955.

In some embodiments, the Cas12i4 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 956.

In some embodiments, the present disclosure describes a Cas12i4 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 956. Homology or identity can be determined by amino acid sequence alignment, e.g., using a program such as BLAST, ALIGN, or CLUSTAL, as described herein.

Also provided is a Cas12i4 polypeptide of the present disclosure having enzymatic activity, e.g., nuclease or endonuclease activity, and comprising an amino acid sequence which differs from the amino acid sequences of SEQ ID NO: 956 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the Cas12i4 polypeptide comprises a polypeptide having a sequence of SEQ ID NO: 957 or SEQ ID NO: 958.

In some embodiments, the Cas12i4 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 957 or SEQ ID NO: 958. In some embodiments, a Cas12i4 polypeptide having at least 50%, 60%, 65%, 70%, 75%, 80%, 85%, 90%, 91%, 92%, 93%, 94%, 95%, 96%, 97%, 98%, 99%, or 100% identity to SEQ ID NO: 957 or SEQ ID NO: 958 maintains the amino acid changes (or at least 1, 2, 3 etc. of these changes) that differentiate it from its respective parent/reference sequence.

In some embodiments, the present disclosure describes a Cas12i4 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 957 or SEQ ID NO: 958. Homology or identity can be determined by amino acid sequence alignment, e.g., using a program such as BLAST, ALIGN, or CLUSTAL, as described herein.

Also provided is a Cas12i4 polypeptide of the present disclosure having enzymatic activity, e.g., nuclease or endonuclease activity, and comprising an amino acid sequence which differs from the amino acid sequences of SEQ ID NO: 957 or SEQ ID NO: 958 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i1 polypeptide described herein (e.g., a polypeptide comprising SEQ ID NO: 965). In some embodiments, the Cas12i4 polypeptide comprises at least one RuvC domain.

In some embodiments, the Cas12i1 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 965.

In some embodiments, the present disclosure describes a Cas12i1 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 965. Homology or identity can be determined by amino acid sequence alignment, e.g., using a program such as BLAST, ALIGN, or CLUSTAL, as described herein.

Also provided is a Cas12i1 polypeptide of the present disclosure having enzymatic activity, e.g., nuclease or endonuclease activity, and comprising an amino acid sequence which differs from the amino acid sequences of SEQ ID NO: 965 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i3 polypeptide described herein (e.g., a polypeptide comprising SEQ ID NO: 966). In some embodiments, the Cas12i4 polypeptide comprises at least one RuvC domain.

In some embodiments, the Cas12i3 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 966.

In some embodiments, the present disclosure describes a Cas12i3 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 966. Homology or identity can be determined by amino acid sequence alignment, e.g., using a program such as BLAST, ALIGN, or CLUSTAL, as described herein.

Also provided is a Cas12i3 polypeptide of the present disclosure having enzymatic activity, e.g., nuclease or endonuclease activity, and comprising an amino acid sequence which differs from the amino acid sequences of SEQ ID NO: 966 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

Although the changes described herein may be one or more amino acid changes, changes to the Cas12i polypeptide may also be of a substantive nature, such as fusion of polypeptides as amino- and/or carboxyl-terminal extensions. For example, the Cas12i polypeptide may contain additional peptides, e.g., one or more peptides. Examples of additional peptides may include epitope peptides for labelling, such as a polyhistidine tag (His-tag), Myc, and FLAG. In some embodiments, the Cas12i polypeptide described herein can be fused to a detectable moiety such as a fluorescent protein (e.g., green fluorescent protein (GFP) or yellow fluorescent protein (YFP)).

In some embodiments, the Cas12i polypeptide comprises at least one (e.g., two, three, four, five, six, or more) nuclear localization signal (NLS). In some embodiments, the Cas12i polypeptide comprises at least one (e.g., two, three, four, five, six, or more) nuclear export signal (NES). In some embodiments, the Cas12i polypeptide comprises at least one (e.g., two, three, four, five, six, or more) NLS and at least one (e.g., two, three, four, five, six, or more) NES.

In some embodiments, the Cas12i polypeptide described herein can be self-inactivating. See, Epstein et al., "Engineering a Self-Inactivating CRISPR System for AAV Vectors," Mol. Ther., 24 (2016): S50, which is incorporated by reference in its entirety.

In some embodiments, the nucleotide sequence encoding the Cas12i polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA). In some examples, the nucleic acid encoding the Cas12i polypeptides such as Cas12i2 polypeptides as disclosed herein can be an mRNA molecule, which can be codon optimized.

Exemplary Cas12i polypeptide sequences and corresponding nucleotide sequences are listed in Table 6.

TABLE 6

Cas12i and HAO1 Sequences

| SEQ ID NO | Sequence | Description |
|---|---|---|
| 921 | ATGAGCAGCGCGATCAAAAGCTACAAGAGCGTTCTGCGTCCGAACGAGCGTAAGAA<br>CCAACTGCTGAAAAGCACCATTCAGTGCCTGGAAGACGGTAGCGCGTTCTTTTTCA<br>AGATGCTGCAAGGCCTGTTTGGTGGCATCACCCCGGAGATTGTTCGTTTCAGCACC<br>GAACAGGAGAAACAGCAACAGGATATCGCGCTGTGGTGCGCGGTTAACTGGTTCCG<br>TCCGGTGAGCCAAGACAGCCTGACCCACACCATTGCGAGCGATAACCTGGTGGAGA<br>AGTTTGAGGAATACTATGGTGGCACCGCGAGCGACGCGATCAAACAGTACTTCAGC<br>GCGAGCATTGGCGAAAGCTACTATTGGAACGACTGCCGTCAACAGTACTATGATCT<br>GTGCCGTGAGCTGGGTGTTGAGGTGAGCGACCTGACCCATGATCTGGAGATCCTGT<br>GCCGTGAAAAGTGCCTGGCGGTTGCGACCGAGAGCAACCAGAACAACAGCATCATT<br>AGCGTTCTGTTTGGCACCGGCGAAAAAGAGGACCGTAGCGTGAAACTGCGTATCAC<br>CAAGAAAATTCTGGAGGCGATCAGCAACCTGAAAGAAATCCCGAAGAACGTTGCGC<br>CGATTCAAGAGATCATTCTGAACGTGGCGAAAGCGACCAAGGAAACCTTCCGTCAG | Nucleotide sequence encoding parent Cas12i2 |

TABLE 6-continued

Cas12i and HAO1 Sequences

| SEQ ID NO | Sequence | Description |
|---|---|---|
| | GTGTATGCGGGTAACCTGGGTGCGCCGAGCACCCTGGAGAAATTTATCGCGAAGGA<br>CGGCCAAAAAGAGTTCGATCTGAAGAAACTGCAGACCGACCTGAAGAAAGTTATTC<br>GTGGTAAAAGCAAGGAGCGTGATTGGTGCTGCCAGGAAGAGCTGCGTAGCTACGTG<br>GAGCAAAACACCATCCAGTATGACCTGTGGGCGTGGGGCGAAATGTTCAACAAAGC<br>GCACACCGCGCTGAAAATCAAGAGCACCCGTAACTACAACTTTGCGAAGCAACGTC<br>TGGAACAGTTCAAAGAGATTCAGAGCCTGAACAACCTGCTGGTTGTGAAGAAGCTG<br>AACGACTTTTTCGATAGCGAATTTTTCAGCGGCGAGGAAACCTACACCATCTGCGT<br>TCACCATCTGGGTGGCAAGGACCTGAGCAAACTGTATAAGGCGTGGGAGGATGATC<br>CGGCGGACCCGGAAAACGCGATTGTGGTTCTGTGCGACGATCTGAAAAACAACTTT<br>AAGAAAGAGCCGATCCGTAACATTCTGCGTTACATCTTCACCATTCGTCAAGAATG<br>CAGCGCGCAGGACATCCTGGCGGCGGCGAAGTACAACCAACAGCTGGATCGTTATA<br>AAAGCCAAAAGGCGAACCCGAGCGTTCTGGGTAACCAGGGCTTTACCTGGACCAAC<br>GCGGTGATCCTGCCGGAGAAGGCGCAGCGTAACGACCGTCCGAACAGCCTGGATCT<br>GCGTATTTGGCTGTACCTGAAACTGCGTCACCCGGACGGTCGTTGGAAGAAACACC<br>ATATCCCGTTCTACGATACCCGTTTCTTCCAAGAAATTTATGCGGCGGGCAACAGC<br>CCGGTTGACACCTGCCAGTTTCGTACCCCGCGTTTCGGTTATCACCTGCCGAAACT<br>GACCGATCAGACCGCGATCCGTGTTAACAAGAAACATGTGAAAGCGGCGAAGACCG<br>AGGCGCGTATTCGTCTGGCGATCCAACAGGGCACCCTGCCGGTGAGCAACCTGAAG<br>ATCACCGAAATTAGCGCGACCATCAACAGCAAAGGTCAAGTGCGTATTCCGGTTAA<br>GTTTGACGTGGGTCGTCAAAAAGGCACCCTGCAGATCGGTGACCGTTTCTGCGGCT<br>ACGATCAAAACCAGACCGCGAGCCACGCGTATAGCCTGTGGGAAGTGGTTAAAGAG<br>GGTCAATACCATAAAGAGCTGGGCTGCTTTGTTCGTTTCATCAGCAGCGGTGACAT<br>CGTGAGCATTACCGAGAACCGTGGCAACCAATTTGATCAGCTGAGCTATGAAGGTC<br>TGGCGTACCCGCAATATGCGGACTGGCGTAAGAAAGCGAGCAAGTTCGTGAGCCTG<br>TGGCAGATCACCAAGAAAAACAAGAAAAAGGAAATCGTGACCGTTGAAGCGAAAGA<br>GAAGTTTGACGCGATCTGCAAGTACCAGCCGCGTCTGTATAAATTCAACAAGGAGT<br>ACGCGTATCTGCTGCGTGATATTGTTCGTGGCAAAAGCCTGGTGGAACTGCAACAG<br>ATTCGTCAAGAGATCTTTCGTTTCATTGAACAGGACTGCGGTGTTACCCGTCTGGG<br>CAGCCTGAGCCTGAGCACCCTGGAAACCGTGAAAGCGGTTAAGGGTATCATTTACA<br>GCTATTTTAGCACCGCGCTGAACGCGAGCAAGAACAACCCGATCAGCGACGAACAG<br>CGTAAAGAGTTTGATCCGGAACTGTTCGCGCTGCTGGAAAAGCTGGAGCTGATTCG<br>TACCCGTAAAAAGAAACAAAAAGTGGAACGTATCGCGAACAGCCTGATTCAGACCT<br>GCCTGGAGAACAACATCAAGTTCATTCGTGGTGAAGGCGACCTGAGCACCACCAAC<br>AACGCGACCAAGAAAAAGGCGAACAGCCGTAGCATGGATTGGTTGGCGCGTGGTGT<br>TTTTAACAAAATCCGTCAACTGGCGCCGATGCACAACATTACCCTGTTCGGTTGCG<br>GCAGCCTGTACACCAGCCACCAGGACCCGCTGGTGCATCGTAACCCGGATAAAGCG<br>ATGAAGTGCCGTTGGGCGGCGATCCCGGTTAAGGACATTGGCGATTGGGTGCTGCG<br>TAAGCTGAGCCAAAACCTGCGTGCGAAAAACATCGGCACCGGCGAGTACTATCACC<br>AAGGTGTTAAAGAGTTCCTGAGCCATTATGAACTGCAGGACCTGGAGGAAGAGCTG<br>CTGAAGTGGCGTAGCGATCGTAAAAGCAACATTCCGTGCTGGGTGCTGCAGAACCG<br>TCTGGCGGAGAAGCTGGGCAACAAAGAAGCGGTGGTTTACATCCCGGTTCGTGGTG<br>GCCGTATTTATTTTGCGACCCACAAGGTGGCGACCGGTGCGGTGAGCATCGTTTTC<br>GACCAAAAACAAGTGTGGGTTTGCAACGCGGATCATGTTGCGGCGGCGAACATCGC<br>GCTGACCGTGAAGGGTATTGGCGAACAAAGCAGCGACGAAGAGAACCCGGATGGTA<br>GCCGTATCAAACTGCAGCTGACCAGC | |
| 922 | MSSAIKSYKSVLRPNERKNQLLKSTIQCLEDGSAFFFKMLQGLFGGITPEIVRFST<br>EQEKQQQDIALWCAVNWFRPVSQDSLTHTIASDNLVEKFEEYYGGTASDAIKQYFS<br>ASIGESYYWNDCRQQYYDLCRELGVEVSDLTHDLEILCREKCLAVATESNQNNSII<br>SVLFGTGEKEDRSVKLRITKKILEAISNLKEIPKNVAPIQEIILNVAKATKETFRQ<br>VYAGNLGAPSTLEKFIAKDGQKEFDLKKLQTDLKKVIRGKSKERDWCCQEELRSYV<br>EQNTIQYDLWAWGEMFNKAHTALKIKSTRNYNFAKQRLEQFKEIQSLNNLLVVKKL<br>NDFFDSEFFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGNQGFTWTN<br>AVILPEKAQRNDRPNSLDLRIWLYLKLRHPDGRWKKHHIPFYDTRFFQEIYAAGNS<br>PVDTCQFRTPRFGYHLPKLTDQTAIRVNKKHVKAAKTEARIRLAIQQGTLPVSNLK<br>ITEISATINSKGQVRIPVKFDVGRQKGTLQIGDRFCGYDQNQTASHAYSLWEVVKE<br>GQYHKELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSLVELQQ<br>IRQEIFRFIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGEGDLSTTN<br>NATKKKANSRSMDWLARGVFNKIRQLAPMHNITLFGCGSLYTSHQDPLVHRNPDKA<br>MKCRWAAIPVKDIGDWVLRKLSQNLRAKNIGTGEYYHQGVKEFLSHYELQDLEEEL<br>LKWRSDRKSNIPCWVLQNRLAEKLGNKEAVVYIPVRGGRIYFATHKVATGAVSIVF<br>DQKQVWVCNADHVAAANIALTVKGIGEQSSDEENPDGSRIKLQLTS | Parent Cas12i2 amino acid sequence |
| 923 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV | Variant Cas12i2 of SEQ ID NO: 3 of PCT/US2021/ 025257 |

TABLE 6-continued

Cas12i and HAO1 Sequences

| SEQ ID NO | Sequence | Description |
| --- | --- | --- |
| | ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELGCFVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR WAAIPVKDIG RWVLRKLSQN LRAKNRGTGE YYHQGVKEFL SHYELQDLEE ELLKWRSDRK SNIPCWVLQN RLAEKLGNKE AVVYIPVRGG RIYFATHKVA TGAVSIVFDQ KQVWVCNADH VAAANIALTG KGIGEQSSDE ENPDGSRIKL QLTS | |
| 924 | MSSAIKSYKS VLRPNERKNQ LLKSTIQCLE DGSAFFFKML QGLFGGITPE IVRFSTEQEK QQQDIALWCA VNWFRPVSQD SLTHTIASDN LVEKFEEYYG GTASDAIKQY FSASIGESYY WNDCRQQYYD LCRELGVEVS DLTHDLEILC REKCLAVATE SNQNNSIISV LFGTGEKEDR SVKLRITKKI LEAISNLKEI PKNVAPIQEI ILNVAKATKE TFRQVYAGNL GAPSTLEKFI AKDGQKEFDL KKLQTDLKKV IRGKSKERDW CCQEELRSYV EQNTIQYDLW AWGEMFNKAH TALKIKSTRN YNFAKQRLEQ FKEIQSLNNL LVVKKLNDFF DSEFFSGEET YTICVHHLGG KDLSKLYKAW EDDPADPENA IVVLCDDLKN NFKKEPIRNI LRYIFTIRQE CSAQDILAAA KYNQQLDRYK SQKANPSVLG NQGFTWTNAV ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELGCFVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR WAAIPVKDIG DWVLRKLSQN LRAKNRGTGE YYHQGVKEFL SHYELQDLEE ELLKWRSDRK SNIPCWVLQN RLAEKLGNKE AVVYIPVRGG RIYFATHKVA TGAVSIVFDQ KQVWVCNADH VAAANIALTG KGIGEQSSDE ENPDGSRIKL QLTS | Variant Cas12i2 of SEQ ID NO: 4 of PCT/US2021/ 025257 |
| 925 | MSSAIKSYKS VLRPNERKNQ LLKSTIQCLE DGSAFFFKML QGLFGGITPE IVRFSTEQEK QQQDIALWCA VNWFRPVSQD SLTHTIASDN LVEKFEEYYG GTASDAIKQY FSASIGESYY WNDCRQQYYD LCRELGVEVS DLTHDLEILC REKCLAVATE SNQNNSIISV LFGTGEKEDR SVKLRITKKI LEAISNLKEI PKNVAPIQEI ILNVAKATKE TFRQVYAGNL GAPSTLEKFI AKDGQKEFDL KKLQTDLKKV IRGKSKERDW CCQEELRSYV EQNTIQYDLW AWGEMFNKAH TALKIKSTRN YNFAKQRLEQ FKEIQSLNNL LVVKKLNDFF DSEFFSGEET YTICVHHLGG KDLSKLYKAW EDDPADPENA IVVLCDDLKN NFKKEPIRNI LRYIFTIRQE CSAQDILAAA KYNQQLDRYK SQKANPSVLG NQGFTWTNAV ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELGCFVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS LSTLETVKAV KGIIYSYFST ALNASKNNPI SDEQRKEFDP ELFALLEKLE LIRTRKKKQK VERIANSLIQ TCLENNIKFI RGEGDLSTTN NATKKKANSR SMDWLARGVF NKIRQLAPMH NITLFGCGSL YTSHQDPLVH RNPDKAMKCR WAAIPVKDIG DWVLRKLSQN LRAKNRGTGE YYHQGVKEFL SHYELQDLEE ELLKWRSDRK SNIPCWVLQN RLAEKLGNKE AVVYIPVRGG RIYFATHKVA TGAVSIVFDQ KQVWVCNADH VAAANIALTG KGIGEQSSDE ENPDGGRIKL QLTS | Variant Cas12i2 of SEQ ID NO: 5 of PCT/US2021/ 025257 |
| 926 | MSSAIKSYKS VLRPNERKNQ LLKSTIQCLE DGSAFFFKML QGLFGGITPE IVRFSTEQEK QQQDIALWCA VNWFRPVSQD SLTHTIASDN LVEKFEEYYG GTASDAIKQY FSASIGESYY WNDCRQQYYD LCRELGVEVS DLTHDLEILC REKCLAVATE SNQNNSIISV LFGTGEKEDR SVKLRITKKI LEAISNLKEI PKNVAPIQEI ILNVAKATKE TFRQVYAGNL GAPSTLEKFI AKDGQKEFDL KKLQTDLKKV IRGKSKERDW CCQEELRSYV EQNTIQYDLW AWGEMFNKAH TALKIKSTRN YNFAKQRLEQ FKEIQSLNNL LVVKKLNDFF DSEFFSGEET YTICVHHLGG KDLSKLYKAW EDDPADPENA IVVLCDDLKN NFKKEPIRNI LRYIFTIRQE CSAQDILAAA KYNQQLDRYK SQKANPSVLG NQGFTWTNAV ILPEKAQRND RPNSLDLRIW LYLKLRHPDG RWKKHHIPFY DTRFFQEIYA AGNSPVDTCQ FRTPRFGYHL PKLTDQTAIR VNKKHVKAAK TEARIRLAIQ QGTLPVSNLK ITEISATINS KGQVRIPVKF RVGRQKGTLQ IGDRFCGYDQ NQTASHAYSL WEVVKEGQYH KELRCRVRFI SSGDIVSITE NRGNQFDQLS YEGLAYPQYA DWRKKASKFV SLWQITKKNK KKEIVTVEAK EKFDAICKYQ PRLYKFNKEY AYLLRDIVRG KSLVELQQIR QEIFRFIEQD CGVTRLGSLS | Variant Cas12i2 of SEQ ID NO: 495 of PCT/US2021/ 025257 |

TABLE 6-continued

Cas12i and HAO1 Sequences

| SEQ ID NO | Sequence | Description |
| --- | --- | --- |
| | LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLAPMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGRQSSDE ENPDGGRIKL<br>QLTS | |
| 927 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELRCRVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLATMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGRQSSDE ENPDGGRIKL<br>QLTS | Variant Cas12i2 of SEQ ID NO: 496 of PCT/US2021/025257 |
| 955 | ATGGCTTCCATCTCTAGGCCATACGGCACCAAGCTGCGACCGGACGCACGGAAGAA<br>GGAGATGCTCGATAAGTTCTTTAATACACTGACTAAGGGTCAGCGCGTGTTCGCAG<br>ACCTGGCCCTGTGCATCTATGGCTCCCTGACCCTGGAGATGGCCAAGTCTCTGGAG<br>CCAGAAAGTGATTCAGAACTGGTGTGCGCTATTGGGTGGTTTCGGCTGGTGGACAA<br>GACCATCTGGTCCAAGGATGGCATCAAGCAGGAGAATCTGGTGAAACAGTACGAAG<br>CCTATTCCGGAAAGGAGGCTTCTGAAGTGGTCAAAACATACCTGAACAGCCCCAGC<br>TCCGACAAGTACGTGTGGATCGATTGCAGGCAGAAATTCCTGAGGTTTCAGCGCGA<br>GCTCGGCACTCGCAACCTGTCCGAGGACTTCGAATGTATGCTCTTTGAACAGTACA<br>TTAGACTGACCAAGGGCGAGATCGAAGGGTATGCCGCTATTTCAAATATGTTCGGA<br>AACGGCGAGAAGGAAGACCGGAGCAAGAAAAGAATGTACGCTACACGGATGAAAGA<br>TTGGCTGGAGGCAAACGAAAATATCACTTGGGAGCAGTATAGAGAGGCCCTGAAGA<br>ACCAGCTGAATGCTAAAAACCTGGAGCAGGTTGTGGCCAATTACAAGGGGAACGCT<br>GGCGGGGCAGACCCCTTCTTTAAGTATAGCTTCTCCAAAGAGGGAATGGTGAGCAA<br>GAAAGAACATGCACAGCAGCTCGACAAGTTCAAAACCGTCCTGAAGAACAAAGCCC<br>GGGACCTGAATTTTCCAAACAAGGAGAAGCTGAAGCAGTACCTGGAGGCCGAAATC<br>GGCATTCCGGTCGACGCTAACGTGTACTCCCAGATGTTCTCTAACGGGGTGAGTGA<br>GGTCCAGCCTAAGACCACACGGAATATGTCTTTTAGTAACGAGAAACTGGATCTGC<br>TCACTGAACTGAAGGACCTGAACAAGGGCGATGGGTTCGAGTACGCCAGAGAAGTG<br>CTGAACGGGTTCTTTGACTCCGAGCTCCACACTACCGAGGATAAGTTTAATATCAC<br>CTCTAGGTACCTGGGAGGCGACAAATCAAACCGCCTGAGCAAACTCTATAAGATCT<br>GGAAGAAAGAGGGTGTGGACTGCGAGGAAGGCATTCAGCAGTTCTGTGAAGCCGTC<br>AAAGATAAGATGGGCCAGATCCCCATTCGAAATGTGCTGAAGTACCTGTGGCAGTT<br>CCGGGAGACAGTCAGTGCCGAGGATTTTGAAGCAGCCGCTAAGGCTAACCATCTGG<br>AGGAAAAGATCAGCCGGGTGAAAGCCCACCCAATCGTGATTAGCAATAGGTACTGG<br>GCTTTTGGGACTTCCGCACTGGTGGGAAACATTATGCCCGCAGACAAGAGGCATCA<br>GGGAGAGTATGCCGGTCAGAATTTCAAAATGTGGCTGGAGGCTGAACTGCACTACG<br>ATGGCAAGAAAGCAAAGCACCATCTGCCTTTTTATAACGCCCGCTTCTTTGAGGAA<br>GTGTACTGCTATCACCCCTCTGTCGCCGAGATCACTCCTTTCAAAACCAAGCAGTT<br>TGGCTGTGAAATCGGGAAGGACATTCCAGATTACGTGAGCGTCGCTCTGAAGGACA<br>ATCCGTATAAGAAAGCAACCAAACGAATCCTGCGTGCAATCTACAATCCCGTCGCC<br>AACACAACTGGCGTTGATAAGACCACAAACTGCAGCTTCATGATCAAACGCGAGAA<br>TGACGAATATAAGCTGGTCATCAACCGAAAAATTTCCGTGGATCGGCCTAAGAGAA<br>TCGAAGTGGGCAGGACAATTATGGGGTACGACCGCAATCAGACAGCTAGCGATACT<br>TATTGGATTGGCCGGCTGGTGCCACCTGGAACCCGGGGCGCATACCGCATCGGAGA<br>GTGGAGCGTCCAGTATATTAAGTCCGGGCCTGTCCTGTCTAGTACTCAGGGAGTTA<br>ACAATTCCACTACCGACCAGCTGGTGTACAACGGCATGCCATCAAGCTCCGAGCGG<br>TTCAAGGCCTGGAAGAGAAAGCCAGAATGGCTTTTATCCGAAAACTCATTCGTCAGCT<br>GAATGACGAGGGACTGGAATCTAAGGGTCAGGATTATATCCCCGAGAACCCTTCTA<br>GTTTCGATGTGCGGGGCGAAACCCTGTACGTCTTTAACAGTAATTATCTGAAGGCC<br>CTGGTGAGCAAACACAGAAAGGCCAAGAAACCTGTTGAGGGGATCCTGGACGAGAT<br>TGAAGCCTGGACATCTAAAGACAAGGATTCATGCAGCCTGATGCGGCTGAGCAGCC<br>TGAGCGATGCTTCCATGCAGGGAATCGCCAGCCTGAAGAGTCTGATTAACAGCTAC<br>TTCAACAAGAATGGCTGTAAAACCATCGAGGACAAAGAAAAGTTTAATCCCGTGCT<br>GTATGCCAAGCTGGTTGAGGTGGAACAGCGGAGAACAAACAAGCGGTCTGAGAAAG | Nucleotide sequence encoding parent Cas12i4 |

TABLE 6-continued

| Cas12i and HAO1 Sequences | | |
|---|---|---|
| SEQ ID NO | Sequence | Description |
| | TGGGAAGAATCGCAGGTAGTCTGGAGCAGCTGGCCCTGCTGAACGGGGTTGAGGTG<br>GTCATCGGCGAAGCTGACCTGGGGGAGGTCGAAAAAGGAAAGAGTAAGAAACAGAA<br>TTCACGGAACATGGATTGGTGCGCAAAGCAGGTGGCACAGCGGCTGGAGTACAAAC<br>TGGCCTTCCATGGAATCGGTTACTTTGGAGTGAACCCCATGTATACCAGCCACCAG<br>GACCCTTTCGAACATAGGCGCGTGGCTGATCACATCGTCATGCGAGCACGTTTTGA<br>GGAAGTCAACGTGGAGAACATTGCCGAATGGCACGTGCGAAATTTCTCAAACTACC<br>TGCGTGCAGACAGCGGCACTGGGCTGTACTATAAGCAGGCCACCATGGACTTCCTG<br>AAACATTACGGTCTGGAGGAACACGCTGAGGGCCTGGAAAATAAGAAAATCAAGTT<br>CTATGACTTTAGAAAGATCCTGGAGGATAAAAACCTGACAAGCGTGATCATTCCAA<br>AGAGGGGCGGGCGCATCTACATGGCCACCAACCCAGTGACATCCGACTCTACCCCG<br>ATTACATACGCCGGCAAGACTTATAATAGGTGTAACGCTGATGAGGTGGCAGCCGC<br>TAATATCGTTATTTCTGTGCTGGCTCCCCGCAGTAAGAAAAACGAGGAACAGGACG<br>ATATCCCTCTGATTACCAAGAAAGCCGAGAGTAAGTCACCACCGAAAGACCGGAAG<br>AGATCAAAAACAAGCCAGCTGCCTCAGAAA | |
| 956 | MASISRPYGTKLRPDARKKEMLDKFFNTLTKGQRVFADLALCIYGSLTLEMAKSLE<br>PESDSELVCAIGWFRLVDKTIWSKDGIKQENLVKQYEAYSGKEASEVVKTYLNSPS<br>SDKYVWIDCRQKFLRFQRELGTRNLSEDFECMLFEQYIRLTKGEIEGYAAISNMFG<br>NGEKEDRSKKRMYATRMKDWLEANENITWEQYREALKNQLNAKNLEQVVANYKGNA<br>GGADPFFKYSFSKEGMVSKKEHAQQLDKFKTVLKNKARDLNFPNKEKLKQYLEAEI<br>GIPVDANVYSQMFSNGVSEVQPKTTRNMSFSNEKLDLLTELKDLNKGDGFEYAREV<br>LNGFFDSELHTTEDKFNITSRYLGGDKSNRLSKLYKIWKKEGVDCEEGIQQFCEAV<br>KDKMGQIPIRNVLKYLWQFRETVSAEDFEAAAKANHLEEKISRVKAHPIVISNRYW<br>AFGTSALVGNIMPADKRHQGEYAGQNFKMWLEAELHYDGKKAKHHLPFYNARFFEE<br>VYCYHPSVAEITPFKTKQFGCEIGKDIPDYVSVALKDNPYKKATKRILRAIYNPVA<br>NTTGVDKTTNCSFMIKRENDEYKLVINRKISVDRPKRIEVGRTIMGYDRNQTASDT<br>YWIGRLVPPGTRGAYRIGEWSVQYIKSGPVLSSTQGVNNSTTDQLVYNGMPSSSER<br>FKAWKKARMAFIRKLIRQLNDEGLESKGQDYIPENPSSFDVRGETLYVFNSNYLKA<br>LVSKHRKAKKPVEGILDEIEAWTSKDKDSCSLMRLSSLSDASMQGIASLKSLINSY<br>FNKNGCKTIEDKEKFNPVLYAKLVEVEQRRTNKRSEKVGRIAGSLEQLALLNGVEV<br>VIGEADLGEVEKGKSKKQNSRNMDWCAKQVAQRLEYKLAFHGIGYFGVNPMYTSHQ<br>DPFEHRRVADHIVMRARFEEVNVENIAEWHVRNFSNYLRADSGTGLYYKQATMDFL<br>KHYGLEEHAEGLENKKIKFYDFRKILEDKNLTSVIIPKRGGRIYMATNPVTSDSTP<br>ITYAGKTYNRCNADEVAAANIVISVLAPRSKKNEEQDDIPLITKKAESKSPPKDRK<br>RSKTSQLPQK | Parent Cas12i4 amino acid sequence |
| 957 | MASISRPYGT KLRPDARKKE MLDKFFNTLT KGQRVFADLA LCIYGSLTLE<br>MAKSLEPESD SELVCAIGWF RLVDKTIWSK DGIKQENLVK QYEAYSGKEA<br>SEVVKTYLNS PSSDKYVWID CRQKFLRFQR ELGTRNLSED FECMLFEQYI<br>RLTKGEIEGY AAISNMFGNG EKEDRSKKRM YATRMKDWLE ANENITWEQY<br>REALKNQLNA KNLEQVVANY KGNAGGADPF FKYSFSKEGM VSKKEHAQQL<br>DKFKTVLKNK ARDLNFPNKE KLKQYLEAEI GIPVDANVYS QMFSNGVSEV<br>QPKTTRNMSF SNEKLDLLTE LKDLNKGDGF EYAREVLNGF FDSELHTTED<br>KFNITSRYLG GDKSNRLSKL YKIWKKEGVD CEEGIQQFCE AVKDKMGQIP<br>IRNVLKYLWQ FRETVSAEDF EAAAKANHLE EKISRVKAHP IVISNRYWAF<br>GTSALVGNIM PADKRHQGEY AGQNFKMWLE AELHYDGKKA KHHLPFYNAR<br>FFEEVYCYHP SVAEITPFKT KQFGCEIGKD IPDYVSVALK DNPYKKATKR<br>ILRAIYNPVA NTTGVDKTTN CSFMIKREND EYKLVINRKI SRDRPKRIEV<br>GRTIMGYDRN QTASDTYWIG RLVPPGTRGA YRIGEWSVQY IKSGPVLSST<br>QGVNNSTTDQ LVYNGMPSSS ERFKAWKKAR MAFIRKLIRQ LNDEGLESKG<br>QDYIPENPSS FDVRGETLYV FNSNYLKALV SKHRKAKKPV EGILDEIEAW<br>TSKDKDSCSL MRLSSLSDAS MQGIASLKSL INSYFNKNGC KTIEDKEKFN<br>PVLYAKLVEV EQRRTNKRSE KVGRIAGSLE QLALLNGVEV VIGEADLGEV<br>EKGKSKKQNS RNMDWCAKQV AQRLEYKLAF HGIGYFGVNP MYTSHQDPFE<br>HRRVADHIVM RARFEEVNVE NIAEWHVRNF SNYLRADSGT GLYYKQATMD<br>FLKHYGLEEH AEGLENKKIK FYDFRKILED KNLTSVIIPK RGGRIYMATN<br>PVTSDSTPIT YAGKTYNRCN ADEVAAANIV ISVLAPRSKK NREQDDIPLI<br>TKKAESKSPP KDRKRSKTSQ LPQK | Variant Cas12i4 A |
| 958 | MASISRPYGT KLRPDARKKE MLDKFFNTLT KGQRVFADLA LCIYGSLTLE<br>MAKSLEPESD SELVCAIGWF RLVDKTIWSK DGIKQENLVK QYEAYSGKEA<br>SEVVKTYLNS PSSDKYVWID CRQKFLRFQR ELGTRNLSED FECMLFEQYI<br>RLTKGEIEGY AAISNMFGNG EKEDRSKKRM YATRMKDWLE ANENITWEQY<br>REALKNQLNA KNLEQVVANY KGNAGGADPF FKYSFSKEGM VSKKEHAQQL<br>DKFKTVLKNK ARDLNFPNKE KLKQYLEAEI GIPVDANVYS QMFSNGVSEV<br>QPKTTRNMSF SNEKLDLLTE LKDLNKGDGF EYAREVLNGF FDSELHTTED<br>KFNITSRYLG GDKSNRLSKL YKIWKKEGVD CEEGIQQFCE AVKDKMGQIP<br>IRNVLKYLWQ FRETVSAEDF EAAAKANHLE EKISRVKAHP IVISNRYWAF<br>GTSALVGNIM PADKRHQGEY AGQNFKMWLR AELHYDGKKA KHHLPFYNAR<br>FFEEVYCYHP SVAEITPFKT KQFGCEIGKD IPDYVSVALK DNPYKKATKR<br>ILRAIYNPVA NTTRVDKTTN CSFMIKREND EYKLVINRKI SRDRPKRIEV<br>GRTIMGYDRN QTASDTYWIG RLVPPGTRGA YRIGEWSVQY IKSGPVLSST<br>QGVNNSTTDQ LVYNGMPSSS ERFKAWKKAR MAFIRKLIRQ LNDEGLESKG<br>QDYIPENPSS FDVRGETLYV FNSNYLKALV SKHRKAKKPV EGILDEIEAW<br>TSKDKDSCSL MRLSSLSDAS MQGIASLKSL INSYFNKNGC KTIEDKEKFN | Variant Cas12i4 B |

TABLE 6-continued

Cas12i and HAO1 Sequences

| SEQ ID NO | Sequence | Description |
|---|---|---|
| | PVLYAKLVEV EQRRTNKRSE KVGRIAGSLE QLALLNGVEV VIGEADLGEV<br>EKGKSKKQNS RNMDWCAKQV AQRLEYKLAF HGIGYFGVNP MYTSHQDPFE<br>HRRVADHIVM RARFEEVNVE NIAEWHVRNF SNYLRADSGT GLYYKQATMD<br>FLKHYGLEEH AEGLENKKIK FYDFRKILED KNLTSVIIPK RGGRIYMATN<br>PVTSDSTPIT YAGKTYNRCN ADEVAAANIV ISVLAPRSKK NREQDDIPLI<br>TKKAESKSPP KDRKRSKTSQ LPQK | |
| 928 | AACGAACTCCATCTGGGATAGCAATAACCTGTGAAAATGCTCCCCCGGCTAATTTG<br>TATCAATGATTATGAACAACATGCTAAATCAGTACTTCCAAAGTCTATATATGACT<br>ATTACAGGTCTGGGGCAAATGATGAAGAAACTTTGGCTGATAATATTGCAGCATTT<br>TCCAGGTAAGAAAATTTATTTTTAAAATCATGTTTTAAAATTACACAAAGACCGT<br>ACCAAAATAAGATCTCCTAGTTTTACGTTGGTGGTGTGTAATTATTTGTTCAGATT<br>TGTGCTTAGTAGAGAGGGAAAAGTTCTTGGGGCTGTAAGAAATCTTGGGCCTTTAA<br>ATTGTTAAAAAATATTCCAAGCCTGTGAATCTTGAGGAACTGACTGCAAAAGCCAA<br>ACCTATGTTACTTCACTTGGAAATATGACAACAATTAATTTAACTACATGTAAAAA<br>TAGCGATAAATTCGGATGACTTTTCTTTTTCTTAGTATGACAGTAAATGCTTATGT<br>TCATGGTGTAGGAAACAGCATTAAATGCCAGATAACCATCTTATCCGGATGAACCA<br>GACTGGATTGTTGGCTCAAATGTTTTCTTCCTGCTGGCTTTTCGTGTTATCATTCA<br>TTTTGATTACTGTTGTCTAAACTTTCACTTTAGATTTCAATTTGTCTATGCAGCAT<br>TAATCTTTCAACTTTGCTGTTTCATCTCTCCTTCAAAGCACTTCATCTCTCTTCCC<br>AAATTAGTTTTCCTTTGACTTTCATATTTCAAAGCACAAGATGGTGGGTGACATGG<br>TTTATGTTTTCTGTTTGTAATAAAAACAAGAAATAAAATCATTTCAAAGGGTTTTT<br>TTTTATAGCAGTTACAAAAATGGTTTATTTGCTGGAGCAAGAGAGGAGTGCCTTCA<br>CTACACTACACTCAGTCTCATCCATCTAACATTATGGCTGTTAGTAAAGGCAATCG<br>GTATTGTGGGTACTCATTGATGGTGATAAAGACAAAAAGGCAGAAAATATGCAGGG<br>GGAGAGAATTAGCCTTCCTCCCTGATTTCTTCTTTAGTCTACAACAAAATCACTCA<br>AAATCAGTTTTCCATATTTAAATTAGGAGAAATAAAATTATCCTGGCCAAGGTGGT<br>CTCTGGTAGGCAGCACTGATTCACCCACAAATCCATGTAGAAGACTGAAAATGGCA<br>ATGGGGTGAAGGATACGGCCTCTCCCCAACCCTTTCAAGCCTTGACTTTGTCTCAG<br>GTTTTGCCTGGAACCCAAATGAGCTCAACAAATGCCAGGGAAGTCATGGGAAGGGA<br>AGTTGACTGAGAGTAGAGGGGCTTAAAATTCTGCATCATTATTTACTATTTTGGAC<br>TCATTTAAAAGTTTCTGCTCTTGGAAGATGCCCCTTCTTGGGCCGATATTAACTTT<br>GTCCACCAAAATTTGCCTATGAGTGGTCTCTTGAAAACACTTTAACCCAAATAGGT<br>TATTACAACCAAGGAAATTTCAGACCCTTGACAGATTTATAGAGTTAGTGTCTCAG<br>CATTGCTAGACCTCCAATGCTCAAGTGATTATTTATTTCATTTGTATACAGCTTTC<br>CTTACTTCTTAATTCCCTTTGTCGCATGCTAGCTAATTAACTAGAGCTAATTAGGA<br>GTCTCCATGAGCTACACTGTGTACTACATGCTGAGGACAAAGCAGTGAGCCAGACA<br>AAGTTCCTGTCCCTAGGAACTTACATTCCCCTGGATGCATATCAGCCTCCATAATG<br>CTGTTGGGTTGAATTGATGCAAAATGGGCCCAAAATAGTTGGCCAAGTGGAGGTCT<br>CAGAGAGGATGCAAAGGGGCGCCCCAAAGCAGATGGATCACCTATGCAACCCTTTA<br>AAATGTAGAAACTTTGGGAGACATAGAAGGCTTGGTGACTTCTAAGTTATGAACTG<br>GAAAAGTGCCTCATGCCTTATGTGAATTACATGGTATTCAAGTGAGTATTCCCATC<br>CTATGTGTGTACCGAGTAACTTAGGGATAGGACACAGATAATGAAAATGAATTTGC<br>AGTGTCACCTTTTCCATGAACCTTGATCATTCTCTTTTGTTCAGCTTTAAATTAAA<br>AAAAAAAATCAATCAACTTTCTTTGGAGGACAGCTGATGCTATTTTATTATCAACT<br>AGTTGAGTTTTTATTGCAATACATTTTGCAATGTGTCCTCTTTTGCTGTATGACTC<br>GCTAGGTGAACCTTGATTCCTCACACTGCATCATGTAGCTGGTCACGTGAAACTAA<br>GAATAGAAATTCTGCCAGGGTTGTGGAGACTTTGGGTTGATGGCATGAAGGAAATC<br>AACCTGAAATTTCACATTCTGATTCTAATGAAAAGTGCAAAACAATCAAACCTCAG<br>ATAACCCATTGTGATACAAAGCCAGAGTATTTCAAACACATTTATGAAATTTATAC<br>ACCTCCCCATCTCGCAAGTACAACAAAAGGTCATTCACCGTGACAGCTTTTATTTC<br>TCTGTACTCAGCTCTGATAATCACATTTTGGAGTTCTGGGGACATGGACCACTCAT<br>GTGACCCAGCAGTTGCTTGGAGATATTTTTGGGTAAGACTTCAGACTAATATTACT<br>GTGGCAGTAGAAAAAAATGTTTAAAAGGACAAGTAAATGGAACCACCCAGAACAAA<br>ATTTCTTACGGTGGTTATAACAAAACAGGGTAAATGTCAACTTGCTACATTTTGCA<br>TGGCTGGAATTGATTGGGATTAATTCAACGAAGAACAGTAATTTGTTTCTCTTACA<br>CATTTATTCAAAGTAGCCTTCTCAACTATGGTCTTCACGTTGTTGTAGCTTTTTTT<br>TCTGAAATTATCAATGATGGAAGATGATTAAACAATTTCGACACTTAGAAGCCCTC<br>ATGATTTCAGAAAAGGAAACTCTTTTCTGCTGCGTTACCTATTGAGACTGAAGATG<br>GCATCATTTTCTTTTAAATAACAGATGGGTAAAAGTGATGTCATTCTTTCACTTTA<br>ATATTTGAGAAGTGATATGAAGTTACCAGTGACATTGTGTTCTCATAGGCATAAAT<br>GTCACAAAATAATTTATCTAGTATCCACAATAGGTGAATAAGGTGTTTTTGCTTTA<br>TATATTTTAACTGTTTAGAGTAAAAAATTAATGTGGAGAAAATTGGAATGCAGTAT<br>TATAGGATTACACAACTTACAAAACATGAATCCACTATGTCCAGTTAGTGTGATTC<br>AGAAACAGCATGCAGTTATAAAGCTGGGTGAGGCATGGGTGTCTTCCTTCAACAGG<br>GCAGCTACTTTGTGAGGAGTGTATATATCATTTGATTTTTTTATAAGTTAAATTTG<br>AGGCCCCTGTTAGATGTGAGGGTGGGCCAAAATTCCTGTGAACAGATTCTCCCCGT<br>TACCCCGCTTCCTTTACTCTGGCATCTCATTTTCTATCCTTTGAAAACGGTTTATT<br>ATTCAATTGGTTCAACTGTTTGCCAGTTGAACCAATTCTTTTTCCAAAGTGGAGGC<br>CCAGGAAAGCACAGTCCGAGAATATAGTGAGGTGCTATTTTATGTATGATTGTGGG<br>AAATTTACTTAAATTTGGAGTGGGGTTGGGCAAGGCTTGGAAAGCTAGTGAGCTAT<br>CTGACATAGTTGTTACTACTATTTGAAAAATATCAAAACATGGAGGACTCTTTAGA<br>TAACATGCCTGTTCCCATTCCATTGATTTTATCTAATTTTACGTAGCAATTACGTT<br>TTGTGCATTGGTTGACAAGCCTCTGTATTATCCTCAGAACAGAAAATACTGTTTAA<br>GGGAAATTAAGAGCCCGCAGTTACTAAAGTGACTGCGCCACCAAGTGGACAAGTGT | HAO1 |

TABLE 6-continued

| Cas12i and HAO1 Sequences | | |
|---|---|---|
| SEQ ID NO | Sequence | Description |
| | AAAGCCACTGTCTGGAGATGGAAGGATTCAGCTTTGCTTTATAAATGGGAATTTGA<br>CCTTTAAAAATGTCCCTTTTGGCACGCACGCGCGCGCGCGCGCGAACACACACA<br>CACACACACACACACACACACACACACACACACACGGCTGCTGCCCTGCAGATTTG<br>CTTGTTCTTGTCATAAAGCTTTCATTGTTTCTCTAGCTCTAAGTAAATATTAATGC<br>CTTCCAAGGCTGGCATGCCAATGGCTGCTATTAAGATCGTTTTCTCTCATTCTAAT<br>AACACACTTAGAGATGATTGGTAATAAAAACTCTCTTCAAGGCTTCTGCTTCTCCC<br>CCTTCAAAATGGAGATCAAAGAATCATGCTGTGAGGGTCCGTCAAGAAGAAAAGAC<br>TTTCAGCAACAGAGCATGTGGTGTGGCATAAAATAATGACAATTATAATGTTCAAA<br>GGAATAGCATAGAAATCACACAGTAAAACTTCTTTATTATGCTTTTCAGGGACTGG<br>ATGTTTTTACTTTATTATGTGAGGAAGGGTTAGATTACAGACCCTTAGCTATTCCA<br>CAAAGCAATAGAAGGCAGAATTTCTTCTTCCGCTACAGGAAGCACGCTTCGATTAA<br>GGGCTTTTTCTTTTTCTTCTTTTTTTTTCTTTAAGTTACTGCATTACTATATCATA<br>CTTCACTATATTTACTAAAAAGTCATGCTGTTTCTGGAAGTAGAGTTACATCTAGG<br>AAATACTAGGTGAATGCTGGTTAGATATGCATGTGTGCCTAAACAACACGTTTATT<br>ATACTCATGCATACTAGAAATAGGGCTGTATTTTCTTCAATTTTAATCAGTACTAA<br>TGAGAATAATAAATCAAAACAAATAGGAGAGATATATTTTGCCAGGAGGAAAGAGA<br>ACTAGTTCTTCTGTAAATTTTACTGGTGAATTTTTGGTTGCTGGTTTATTGGTAAT<br>TTTCATTCCAACACAGAAGAATCACAGAAACATTCATTTAAAATAATTTTCCGGAG<br>TCAAAAACTTTTTAACACCCAAATTTCAGTTTTTGTCAAATAACATTTTTGAGAAA<br>AGTGTTAAATTAAACTAATAAAAAACCTTCCCTCATCATTAGACTTTAATGAATAT<br>GGCATATAACTAAATAATTTTGAAGAAACCAAATTATAATTTTAAAAGTAATTGCC<br>TGAAGCTGCTGTTTATCACATAAAAAGAAGACAAACTAGACATAGCATATCTTCTT<br>AAACTCTAATCTAAACTCTATGCATTTGTATACCATCTTGATTTTCAAGATTGGGG<br>AAGTGAAACGAAAACTATGTTCACACAAGAACCTGTACGTGAATGTTTGTAGTGGC<br>TTTATTTAGAATTTCCCCCCAAACTGTAAGTATTCAAAATGTCTTTTAGCTTGGGA<br>ATGACTGGACAAATGATAGTACCCCTGTATGATGGAATATTATTCATCAACCAAAA<br>GGAACAAACTATTGACACGTACAACAACATGAGAAAATCTCTAATGCGTTATGTTA<br>AGTGAAAGAAGCCAAACTCAAAAGGCTACATACTGAATGATTTTGTTTACATGATA<br>TTCTTGCAAAGCAAAATTATCAGGACAAAGAAAAAATGCATCAGTGGTTGTCAGGG<br>GATTGAACTGGGGAGAGTTTCTCTGCAAAAGAAAATGGGGACTTTTTTGGGAATGA<br>TTGAACTTTTTCTAGATCTTGATTGTCATGGCAGTTACACCACTGTATGCATTTGT<br>CAAAATTCACAAAACTGCAGACTAAAATGAGTGAATACTATTATGTATTAGTTATA<br>CTTTAATAAATAATTGCTTGGGAAATTCATTATCCTCTAATTGTTAACTTTCTAAC<br>CAAACAAACAGTAAAATTGCCTCTTTTCCATTAGCTTTATGAAGTCATTTGCTTGT<br>TTGGAAAAAATCCAATTATATTTTTTCTTTTAACTAAAATGTAATGTCAAAGTTTT<br>GGTTATGATTCTGAAACTCTAAAGCCTTTTATTTTATTTTATTTTTTAATTCTAGA<br>TGGAAGCTGTATCCAAGGATGCTCCGGAATGTTGCTGAAACAGATCTGTCGACTTC<br>TGTTTTAGGACAGAGGGTCAGCATGCCAATATGTGTGGGGGCTACGGCCATGCAGC<br>GCATGGCTCATGTGGACGGCGAGCTTGCCACTGTGAGAGGTAGGAGGAAGATTGTC<br>ACCACAGGGACAGAAGGAGGCTAACGTTTATCGACCTCCTTCTCTGAATGCACCAA<br>GCAAATATGTTCCTTGATGTTTTTACACTCAGAAACATTAAGCTCATGGACTCTAT<br>CATCAAAATACTTGTTCTTGCATGTCCTGCTCCTCTTCTTTCCAGCTGTGTGACTG<br>GGCAAGATATCCTCTCTCTGCATTGGTTTCCTTGGCTGTAAAATAGGGACAAAAAT<br>TGTACCTGCCTCATTGGGTTATGGTGAGAATTGAATGAGTTCAGGTATACAAAGTT<br>CATGGCAGAGAGTAGGGGCTCAGTAACTGTTGGTTATATTATGGGTATTAATAGTA<br>CTGTCTCAGGAAATGGATCTCTGACAGGTAGACTTGCCCAAAGTCACAGCTAGGTA<br>GTTACAGAATTGGAATTCAGCCCTGTGGCTACCTTATCTCAAAACCCTCCTGCTTC<br>CCCCAAACCAAAGTGGTTCTCACAGCCAAATTGCAAATGGAGCAACGTGGTTGGTT<br>GTGTTTTCTTCCGTGGTTTTGGGTCATGATTCTTTTTTATGGATGAGTTATATTCC<br>CAATAGAGCAGTTCCAGCTGTCTTAGGAGGGAGTGATGAGAAAATCAAATATGATG<br>TAAAGAAATCTCTTATTAGGGCTAATTTATTAACTTTCCAGTTCTCTAGCAACTGT<br>GAACATTTGAAAGGCTGTGCAGAGTAAAAAATCTCCCCAAATTGTGCTCCAGAAAC<br>TAATATAAAAGTTGGAAATGAATTATTTTGATGCTAAGCAGAGCAGAAAAAGAACA<br>CGACTATATAATATTTTAAAACATTTTAGTTTTAAGAATTAAGGATCTTGTGAATT<br>CACTTCCCTTCTTGAAATGTCTGACATAAAATTCTGTCAGGGATATCAGAATGGCA<br>CAATGAGGTTTTGCTGGACAGACTTAGCAGCTTCCTTAATTCTAGGACCACATACA<br>AATAAGTGGCTTTGGGGCCTCAGCCTTTTGTCTATGGTAATCCTGAAACATAAGTA<br>GAGAGAAGAAAAAAAAAAGGGAAATACTAAATGGGTAAATATCTATACAAAATCAAG<br>ATAATAAAGGCCCTTTCAGGCTTGAAACTATAGGCAACAACCTTAGAACAAAAGAA<br>AACAAATGAACATCAAAAAACTAAAACTTTAGTGCTCTTAAATCTCAATGAAAATA<br>AAAAGTAAATGGTAAACTGAAAGAAATGGAAAAAAAATATGAGACTGTGAAGGGTT<br>AATGTCCTTTCCACGTAAAAAGCCCTTATATTTGAAGAAGAAAATAATATATTGCT<br>CAAAGGGAAAAAGAGAAATAAGTGAACAAAAGATATAAATAGGAAATTTACAAATG<br>GAGACATAAAAGTGACCAATAAACATATGAAAAATATTCAATTTCATTAATAAGCA<br>AAGACATGGAAATTATGACCATCTATTTTATTTTCCGTATATCGAATTTTTATTTT<br>AAGATCAGGCAGTATGATTAGGTTAGGGAGAAAATGTGCATTTCAAACAGTGTTGA<br>GAAAAGTATAAAGTGGAATAATCTTCCTAGAAAATAATCTGGCACTGTATATCAAA<br>GCTCTAAAAATGTAAATTCCATGTGATGTTAAAAATTCTCTTCTAGGAATTCCAAG<br>GAAATAATTATGATTTTTGAGGAAAAAAATCATTTCTGCAAGGATTTTCATGCTTC<br>TTATTTTTAGCAGGAAAATAATTTGAAAAAAATACCCAAACATCTTATAATTGGAG<br>ATAGTTTGCAAAAAATATGATGCATAAAAATGACATCAAATTTAAAAATTATACTA<br>TAGGAAGAGTGCAATAATGTAGAATGATATTTTAATTTAAAATTGTGAGAAATCAG<br>TTGCAAACAATAGTCAGGTCCTAAAATACATTTAGTTTCAAAGATCACAATTTACA<br>AATGTTTATTTATAAGTGATGAGATTACTCCTGACTTTATACTCTTCTGATTTTTG<br>GCTCAACCTTATAAACTCTTCTTTGAATTATTTTGTAAGGAGGAAATGATAACAAT | |

TABLE 6-continued

Cas12i and HAO1 Sequences

| SEQ ID NO | Sequence | Description |
|---|---|---|
| | TAGATTTAAAAGAGTAGAGATAAAGGGACAAGGGACCATGAAGAGAATGGAAATAA | |
| | AGAAAGGAAGCAGAGAAAGCAAAAAGCAGAGCTCACTTGGTAAGGCACCCTGGAGC | |
| | CAGCAAATTATTTTTACCACATGTATTAGTTCCTTCTCACACTGATTTAAAGATAC | |
| | TCTTCGAGACTGGGTAATTTATTAAGGAAAGAGGTTTAACTGACTCACAGTTCTAC | |
| | ATGGCTGGGGAGGCCTCAGGAAACTTACAATCATGGTGGAAGGCAAAGGGGAAGGA | |
| | ACGACCTTCTTCCCATGGTGGCAGGAGAGAGAAGTGCAAGCAGGGAAATGCCAGAT | |
| | ACTTATAAAACCATCTGATCTCATGAGAACTCACCCACTATCATGAGAACAGCATG | |
| | GGGGAAACCACCCCCATGATCCAATCACCTCCCACTAGGTCTTTCCCTCAACACCT | |
| | GGGATTATAATTCAAGATGAGATTTGGATGGAGAAACAAAGCCTAACCATACCAAC | |
| | ACATATTGCTTTATTTGATATTTGACAGGTGTTTCTGTCCCTGTTTTGTGGGCAAG | |
| | TAGCTAAAGTTCCAGAGAAAACAGTTTTTCATAGCTCGTCAATGACAGACTTATTC | |
| | TCCAAGTCACATTTGATGGTTCCAAGACCAGTCTTTATTCTTGGTGGAGTTGGGCT | |
| | GAGAAGAAAGAGGAGAAGAAAGAAGAAAAGAAAGCTTCCTTAGAAACTATGATTTG | |
| | ACAGTGTAAGTAGGACTATTTCCTCCAGAAGTAACCATAAGAAGATATTAAATGCC | |
| | TATTACAGTCTTATCCCCTTAGATTTATTTAACACTTATAAAGCAATTATCATGTT | |
| | CCAGACACTATTTTAAGTATATTACGAGTATTATAGCATTGAAGGCTCAGAGCGGC | |
| | CCAAATAAATCGATCATATTATTAAACCTATTTTACACAGGAGAAACTGAGGTACA | |
| | CGCCAGGTGAATAACCTTGCCTAGGGATGCACAATTCATAAGTGATAGAGATGGGA | |
| | TTCAGACAGAGGTATTCTGTCTCCAGAATCTGGGCTCCTCACCACTTTGCAAGAGC | |
| | TTTAATTTCAGAAACTCCTATGAAGTGTCATGAGGAGAAGCCCATTATGATCCCCT | |
| | AGAAGTAATTATAGTTTTAGGAGCATGCAAAGCAGACCCCTCAGGAAGATAAGTTA | |
| | CACAATAGACATTTGGATAAGGTGGATCCAGCAGAACAAAGAGAGGGTGGTGACAT | |
| | CGAGATTGCAGAGGAATTGGAGAAGGCAATGGAAGTGTACACATGTTGCCCTCAAA | |
| | AACATAGGGTCCTCCATTGGGTTCCTATCAGGGCAGCAACATCAGAGTTTCTATTC | |
| | TGTATTTATACTAGAAACCTCTCTCCAGGGTTTCTAAGTTTTCACCTATGTTTTAA | |
| | AGACTATCTATAGGTTATTAGTCTATTTAATATTTAGGTGTATCCAGAAAGCTGAT | |
| | GGTCATCAGCTCATAGCAGGTGTTCTTTGGCTGGTGTGTTTATGTTGTGGGACAGT | |
| | GGGTTACTTGCAAGGAAAGGATGAATGGCTGGAGTAGATGGTGCTTGTGCTCTGCA | |
| | TGTATTCCCTTCTTACTTCCCATTTCCATCAGACCTACCACTTTTTGCCTGACATT | |
| | ATCTGTTGCAACATGAGCCCATGGATAGGTGTGTTTGAAGTAGGGGAATGGGAGAG | |
| | AGGGTTCCCTAGCTAATGATGTACAGCAGTAGGTGGATAAATACCTCAGCTCTCTT | |
| | TGCTCAGGTAACTGAAGCATTTTCTAATATGGTCACCCAGTGTTCCTTGGAAGGAT | |
| | TGAGTCCCAGTTGCCCCCTGAGGTTGCCTGCCCATGAACACACCCTCTTTTATTGG | |
| | CTTCCTTCCCATTCTTTTCTCACTTCCCCATTCCTTCAATTCATTGAGATTGTTTC | |
| | CAAATAAGATGACTTGCTCTCACATCTCTGTGTCATTTTTGGCTTCTTGAAGTATG | |
| | CAAACCAGGATAATAGCTAACTGAAGGCTATAGATAGCCACAGGCAAATTTAAGTA | |
| | ACAGTGTAAGAATATTCATACTTGGCAGAGATTTATTTATAAAAACTCAGAAAATT | |
| | CACATGGAATTATGAAGTTATTATTGTATTTATTCCATCATTCCCAGAAAGAATAT | |
| | GGAAATCCTCTCAAGCAAGCCAGTCCTTGGGAATATTGGGAAATCTATGCAATTTG | |
| | TTGTGGAGTATTTTTTTTTTTGTTACCCTCCTAAATATCTGGCCGCTAAGCATTCC | |
| | TGTCTCCAGGGACTTAGACCCTAGCAAGGAAGAGAAGTTGGGGCCAGGTTCAGAAA | |
| | ACGGGTTAGTTATCAATCTCCCTGGAGAAGTGTCCCCCTCAGCAGGGTCAGTGAGA | |
| | GTAAGTGAAACCCATTGGTGCCCACAGGCAATGGTCTGGCCTGAGTAATTAGAATG | |
| | GGCCTCCAGAAAGTTCTGGGAATTGCTATGGTGCCATAGTCTCATTTTCCCCGTTG | |
| | ACTCTCCAGATTTATTCAGAGTCCAACTTCAAGGGCCTTTCTGCCCTTCCTCTCAC | |
| | AACTGTGGAATAATAATAATCCACCTTATTAACTGGGACCGAGAACTGAGCTCGAC | |
| | TCTTATTTTTTTGAGACAGAGTCTTGCTCTGTCACCAGACTGGAGTGCAGTGGCAC | |
| | TATCTCAGCTCACTGCAACCTCTGCCTCCCAGGTTCAAGCGATTCCCCTGCCTCAG | |
| | CCTCCTGGGTAGCTAGGACTATAGGCACGCACCGCGACGGCTGGCTAATTTTTTGT | |
| | ATTTTAGTATAGACAGGGTTTCACCATGTTGGCCAGGATGGTCTTGATCTCCTGAC | |
| | CTCATGATCTGCCTGCCTTGGCCTCCCAAAGTGCTGGGATTACATGCGTGAGCCAC | |
| | CGCGCCCTGTCTGAACTCTACTTTTTTACACTGCTGCATGTTTGTAGAGTGACCAA | |
| | TGAAGCTATACTTTTTTCATTTTCAAAATGATGATGAATACAAGGTTATCAAATAA | |
| | AACACAGAGGGCCCATTATGTTTGAATTTCAGATAAACAACAAATCATAGGTGTCC | |
| | TGTATGTTTGCTCAATCTGGCAACCCTGGATGAATAAGAGCTCTCACCTGAGGATT | |
| | TCTTGTGAGGATTCATGAAATAAATGCTAGAAATGCTTACACACTATCTTTATTTG | |
| | CCCCTCAGAGCCCAAAGTCTCTGAAATCTTTATCTTTCACACACAAAAACTCACTT | |
| | TCAGAAAAGTATATTCCATTTACATCTAGTGGAAATAAAAATTGTTCTTTTTCTTT | |
| | GTGAAAAATATTTTTATTTTAAGCTTTATGCAGAAACCTCAGGGAAAAAAAGGTAC | |
| | TTTTAGGAGCCAGGCTTGTAATGTAAATGTCCAAAAAAGATGAAATTGAAACAAAC | |
| | AAACAAACAAACAAACAAACAAACAAACAAAAAACAGTGCAAGCTCCTGTGTGGAG | |
| | ACTGCAGTGAGTCTGAGATTGCATGTTCCATCAGAAGGGGGCAGCCACATCTTAGC | |
| | TCTTGATGACCCAAGGGAGCAGGGATGTGGGGTTGCCAAATCTTCCAAAATTTTAA | |
| | GAAGCCAGAAATCTTGATTTCTATGTACAATCTCCTGGTTTTTAAATGTGGGCAAA | |
| | TAAATCAAAATTCCCTAAAACACTGTTTGGGGCAACAATGTGTGGGCCAAAGTAAA | |
| | TACTTTTGTGGGCTACAAGTGTCCCCTAGGCTGTACATCTGGGACATCTGATTTAT | |
| | GTGGAAATTTACCGAGAACTAGTTTTATTTCTGTGGCAGGTCATTTTCACTTTCTA | |
| | GGATTATGTTTCTTCATTGATAAAGTGAGCTACTTGAGCAAGACCAGTGGATTGAA | |
| | TGCCACGTCCCAAGGAGGCTGGGGTTGTTTCCAGGGATCTTACAGAACTTAGGTGT | |
| | GATACTGAGCATGAGCTACTTGTGTTGCATTTTGGTGTTCAAAAGAAAAGTTCTTT | |
| | AAATAGTTCTGCTGGAAAGACAAAAAAAAAAAAAAGAAAAAACTTTCACAACAAAA | |
| | ATCTCCAAAAACAAAAACCCAGAAAACTGGCATAGAAGTGGATGATCTTTGCAATT | |
| | TTTTTCAGTATATAAATAAATGATTTTGATCCCATTTAAAATTTTATCAAATGCAA | |
| | AAAGAAACAATTCAAAGTATAGAGCTACCTTTTCTTACTCTACTGAAATCTACACT | |
| | TTATGTCAGCCCTGGAGGGTTTAGACGCACTTTATGTCAGCCCACTTCTTTCGACT | |

TABLE 6-continued

Cas12i and HAO1 Sequences

| SEQ ID NO | Sequence | Description |
|---|---|---|
| | GCACTATGTCAGCCTTGGAGGGTTTAGATGAGGCAGTGAGCATTTGAATGCTTTTA | |
| | ATTTCCATTTTTCAAAGTACATTCTTGGTCTATAGGAGAGGAACAAGATATGTAAC | |
| | TATCTCTGACTATTGCTAAAAACACAAACGTCTTTAATAAATGTTGCATAAACTCA | |
| | GAAAGTGATACTTCAAAGTCTTGTGAAAAATGATGATCACCAGCATTTATACAGCA | |
| | ATTAGTATGTGCCACGCAATTTGACTTTATTATTTATTCATCTATCTTTACCACCA | |
| | TCTTAAAATATGTGAGTGCAAAACCCTGAGAAACTTTCTCCAACTCCTGTGGGTGT | |
| | GGAAATCGAGGCTTAGAGAGGTTAATGCTTTGCTCAGATTATTAATCACTTAGGCA | |
| | GTGCTACCTATAATATCCTGCTCTGTTACTGGTATTTCCAAACGTCATTAACTGTA | |
| | GCAAGAATCCTAAGGCAAGCACTATGCTATCATCTTAAAATATTTATTGCAAACAT | |
| | CCTATGTTTTATTGTTTTATCTTTTTAACTTTGAGAAGATAAAATAAGCCACAGAA | |
| | GTGAAATTAATTGGGAAATCATTCGCTTTTTGCAAAATTTGGGAGCATAAACAATG | |
| | GGTCATGAATTACAATCAAACAAAAGATAAAATTCTAAGAAGTCTTTTAAAGTGGA | |
| | AAAAAATAACTGAAAAATACTGAATGGAGGGCAGTTTTTCATGCACTGTGTTACGA | |
| | ATAAAAAATTTGATTCAATGGATTACTTAATCAACATTTTAATAGTTGTAAATCTT | |
| | ATAATATTTAAGCTGTTTTATAAGTGCCTCTACTTATAATGGCACATCCGTTTGAA | |
| | ACTCTAGCAGATCATTTTTATTTATTTTTTTGAATTTTTTTCTTTATATTCTTTAA | |
| | AGAAGGATACAAAATTATTTCTATGAATATTTAACATATGGAAGGAAATAGCAATA | |
| | ATAAACATAAATGCTAACACATATAAAATAGGTGGTATCATTAGGCTAAATTTTAG | |
| | TCTTCCAGGATAAGTAGAACATCTCTGACTTCTCAAATATCCAATTAATAAAATGC | |
| | TTACTATACCATTTGGTGCTTTAAGAACATTGCCATGGAAACCTCTCAGGTTTTAT | |
| | GCACAGTAGCTATAATAAAATTTTCCTTCATCTTTCATGGAGCTACTTGAGATTTT | |
| | TTTTCTCCCTTTAAACATGAGAAATCAAAAAGAAAGAGAAAAGAAGGATTAAATAT | |
| | TCATTTATCCTTTTGCTTCTGACTTGTTATGTGGGCAAGTGCCACATGAGGGAGTG | |
| | CTGGGACCTCATATCAAGAAAAATTAAAACCTACCTAATGCGTTCCAGGAATGTTC | |
| | AGCATATTAGCAAATTCTTATTAAACTGTCAAAAAAAAAAAAAAGTTTTAAAAGAAA | |
| | TTCCAGCCCCTGGATGCAATTAGAGGCTACCACACTGGATTTGATGGGCCATAAAA | |
| | CCATTAAATCTAAACACTTTCTTTTTGAGCCTAAAAGGCCAGAACATTCCAAAGTG | |
| | AAGTTTTGGGACTCAGCTATGACTTGACCACCTATTAAGATGCAGGTGGAACAGAT | |
| | TGCAGAGTAACACAAAGAGCCACACAGACCCCAGATGACTGCATTAGGGTGTAGGT | |
| | GAGAGTTTTAGCTGTTGAATTTTCTGGATTTTCCAAGATTAAGTGATCAACCTTAA | |
| | CAATGAGTGAAAGACCATTCAACAGGAAGAATTGTCATTTCCTTTGCTCTAAACCC | |
| | AAACGATGTATTTTTTGAAAGCTTTATTGATTTATATATTTATGTGTTGTGCTAGG | |
| | CGACCGACTAGATATATGTTTCAGCATACCTACTAGGAAAATATCCCCATTATTCT | |
| | CAATTTTACCTAATCCAGGCAAAGCACTGGACTTGCTTTAAGGAACATTTTTACTC | |
| | TTTCTGAAGTGGAGTGCCTGTCATGTATCAGGTGCAATGCTTGGACTTTACGTTCT | |
| | TGTGATTAATCCTTACAATAGGCCTGTGAAGTAATTCTCATTCTGTTTGACAGTAG | |
| | AGAAGAAGGAAGCCCTTGACCAAGGTCTAGTGCCAGTAATGGTGGTGATGGGGTTT | |
| | GAACCTAAGTCTGTTTCACTCTAAAGTGTAACCAAATTTTATGTTTTAGACTTGCT | |
| | TTTCTAACAATAAAAAGTCAGTGACATGCTCTTTCTGTGTGTAAGCACTCACACAC | |
| | ACACACACAAACACACATCCGTATTACATATGCTTATATATGTATTAAAAGATTAT | |
| | GGACATTTGATATATATACATATACTAAAATGTATAATTCATTGCTAAAGTATTTT | |
| | CATATAAATAGTGGCTTCAGTGTTAAAATCACTTTGCAATGAAACAAGATTGTTGA | |
| | TTAAAACACCTATTAAAAAATTAGAATCTAGCCATATTAAAGACAGTCATCGAATG | |
| | GAGTGATTTCTACGATTTTGCACCAAAATTTAAGCTATTGGGTGGCTTTCTTGAGA | |
| | GCATGAGATTGCTTCTTCTCAGAATTATTAATGTGCCTGATGACATTAAAATGTGA | |
| | CAGTGAAAAAAGTCAGAGGCTCACATGTGTATCCCAACACTGAAGTTGTTAAACAC | |
| | TGGGAGGTTGGTTGAAGTTGTTGTGTGCAAACTCAATACTCCTTAAAACCATTATT | |
| | TAAAGGCCTATCACTGTGTTATGGTCTCCATATGATCTGCCATTTATGCCAGGACT | |
| | TGACAATTCAGTAAAATGACAGAATAATAACACAGGAATCACTGCAGTAGAGCTAA | |
| | TGTTTTAGTCTGTTGCAGAGTTCTGCCCTAGAAATACAGTGAAAACAAGGAAGGGA | |
| | GAGCTAAGATGTCCCTGAGACTAATTGTTCCTTGAAAATATTTTCATAAGTAAAAA | |
| | AGAGGTCTAGAGGTGTAGTGGCAGTGTGATCACTCAAGATTATATAGCTCCGGATT | |
| | CGTTCAATGGGCCATGATGAAAGCACGGCAACGATTAAATCTGGTTTCTTGGTCTT | |
| | TCTTGGCAGTGTTTAAATTGGTTCAGTTCCATAAATTGTAAATTAAGATCTGTTTG | |
| | ACAACTTTTAAGTATTTCAAGCATAATTGTAGTTGAAGGTTTGTTCTTTTAGATCA | |
| | CTGACTTCAGAACTTTATTTTTCTGGTTAATCTCAATTGTAATTTTAGACATTCAT | |
| | AAAACAATGTTGACTGCGTCTATGTGATGGTAGATCCTCTGTGAAGACCTTTATGA | |
| | TGGTAGTTCCCCTGTGAAGATAGGATGACACACTCAATGGACATTATGGTGCACAG | |
| | TTATACAAACACTTCACTATGACAGGCCCTGAGTTTAGAACCACACAACTGCTTGG | |
| | TACTTGGTCATCGCATATTTTCCCCATTACGTAATGACTTCCTGTGCAGATGACAA | |
| | AATGCGTTTTCTCAACAAAATTATTTTCAGTGCAGCTGTTTTGATGACTAAGTTTT | |
| | GTAGGAGCTTTTTAATCAAATGCACCTAAGAAAACCCCAACACTTTAGGCCCTTTG | |
| | AACATATTACACTTTTTTGCTTCCTCTTTCCTCTTTTTCCTTAAAACCATAATTTG | |
| | GAAATTTGATTCTGCCTTCCCATAAAAGAGAATTATTTTCAAAGAAATTATTTGGG | |
| | TCTAAATTAACATGTTACTTAATTGTTCTGCTTGAATCTAGGTATATGATTAGTCC | |
| | CATATGAATTGATGTTCCAAATAATTTACTCTCATTGATAACTAATATTTTCTATT | |
| | TCCCTCTATTGTTTTGTGGTGGTGGTGGTGGCTGTGGATGAACATCATTCTCAAAT | |
| | ATATTATAATTCCCTTCCTCATCAAGCCCAGCATGATAAACTTCAGTTTTGCCTGA | |
| | TGGTTCATCATCTTATTTCTGTGTGTAAGATTGTTGGATTTGACATTAAACATTTG | |
| | GAAACTATTTTATAATTGATAACTTGTGCTTTCTCAGCTTTGAGTAAGCGCTCTCT | |
| | TCTTCATCTTATACCATTTTATTTTTATTTATTATTCACTTCTGCTTCTGATCTGA | |
| | GATCTAGGAAGCTGGACAAATCCCAGATAAGCAAGCTAAACAAACAAACAACAACA | |
| | ACAACAACAACAACAACAACAACACAACCCAAACTAAACCAAACCAAAATCATGGG | |
| | ATAATGGTTAAGTGTACTGAGGGGCCATTATGCGAACACAGTTTAATTCCTTGGCT | |
| | TTAAAACTAATAAGAGAAGAATACATAAACAAATGTGGCAAATGTACCTGTGACCC | |

TABLE 6-continued

Cas12i and HAO1 Sequences

| SEQ ID NO | Sequence | Description |
|---|---|---|
| | TCTCCAGAGGGTGCCAGGCTAGAAGAAAGGCAGATTTATCAGCAAGGCATGGCGGG | |
| | CCATTGGCAAACCATGGGACAACCACTACCAACTTCACTGCCATTGCTCCATATTT | |
| | CCCTCCCGTTTTCAATGAGCCCCAACTTTGCTCAGGACATCACACATATTCTACTA | |
| | ATTTGGATGAGTCCTTTTGAAAGAAAATATCTACCTCATGGTTCTCAAAGTATGGT | |
| | CCTTGGAACATCAGCGTCAGCAGGACTCTGGAGCTTGTTAGAAATGCAGATCTTAG | |
| | GTCGCACTACAGACCTACTGAGTCAGAATCTGAATTTTGTTAACATACCCATGTGA | |
| | TTCCTCAAAGATTGAGAAGCCCTGATCAGAGCCTGGGATGAAAGTTCCTGTTGGTT | |
| | CCAAGCCAAAGGCATAGTTCAGGTCTTCACACATGACACTATTAGATGTAGATGGA | |
| | TATTGTTCCCTTCTGAAGACCCTCAAGGTCTTCTGAGAGCCTATTAAGTTCAGAAT | |
| | GACTGCCTGAAATGAGTGAGAAGTCACAAGGAGACTCTAGATAATTAAGAGATGTG | |
| | TTCACAGTAGTCTTTGATAAAAACCTGGGACAGGCAGGCTTAGTATGCAGGCCCCT | |
| | AAAATTTATGTACACAATGGATTTCCTATTTTTGCTTCTTCACATCCAGATTACCT | |
| | GGATCAGAAATAAATGTTTTCATTAAGACTTGATGTGACAAACAAACAAAACAAAA | |
| | CTCTGCCAAGCTCTAGAAGAACAATTGCATTTCCCAGCCAGAGGGAGAACACTGCC | |
| | AGTTTTTGCTGTTTTCCAAAGCTGTTTACCTGTCCTAGCTCATTTAAATCACTGTA | |
| | CTTTGGAGTTCCGGATTAGCGTCCCCAGAGGTAGCTGCATTCATACTTGATGAGTT | |
| | CTTTTAAATCTCAGCCATTGATTGTAGGTTCCATAGTATAGGAAATTTAGCCAACC | |
| | CTCTATTGAATGGCAGTTTAGAAAGGTCGAGCTACACTTACCTTATGTCAGGTTAT | |
| | TGCAGACCCTTGTGGCATTTTTCCACCCTAGGACATGTGATTTAACTCTAATAGAA | |
| | ATCTTTATTATGGGTGGGTCTGAGATTAACTTTTATTCTATAAAACAGAAATCATG | |
| | CCACTGGCCGTAGCCCATTTTTTGAGATGGAGTGGGGGGAATGGATGATAGTAAAC | |
| | AAGGATATTAATCTCATTTATTTTTATATCATTATATTTATAGTTACATTGCAAAT | |
| | GGAAGAGTAGAGAAACCAAAAACTTACACTGGGAACTTTACAATTTTTCTTCCAAG | |
| | TATTACTGATTGATGTTTGGACTATGCAAGTGCTGCCAGCCCCTTAGACTCACTCT | |
| | GCAGCTCCCCCCATGGAAATTTGTGAACAGGTTAGGGTGGGGATAGGGAAAAGCAT | |
| | GTTCTTGTTTCACTTCTTGGATTATTTGTTCCAGGCTCTCCAAAGTAATGTGTACC | |
| | TTGGGAATGCAGAAATTATCTCCTTAGATATTCTCTCCCTATATATGTCCTCACAG | |
| | GGAATTCTTGGAATTGGAGAAGATTCCACTCTCCTTTAGGAGCTTTCTCCATAAAG | |
| | GTATTGAGCATTGGACACTATATTTGCAAGGGAAAAGAGGAATGGGTCTCTTGAGC | |
| | ATCAAAATCATTGTAGAAGAATCTCCAAACTGTTTTTCAAAATGTCTGTACTAACT | |
| | TACATTCCTGACATCAATGGGTTCCCTTTTCTCCACAAGGGTTCCCTTTTCTTTGC | |
| | ATCTTCACCAACACTTGTTATCATTGGTGTTTTTGATAATAACCATTCTAACAGTT | |
| | GGAGGTGATACTTCATTATGATTTTAATTTAAATTTCCCTGATAATTAGTGATACT | |
| | GAGCTTCTTTCATATATCTATTGGCCATTTATATCTCTTCTTTTGAGAAATGTCTG | |
| | TTCAGATCCTTTGCCAATTTTTTTTCTTTTTTCAACTTTTATTTTAGAATCAGGGA | |
| | GCCATGTGCAGGTTTGTTACAAAGGTATATTGCATGATGCTGAGGTTTGGAGTGCA | |
| | AATGAATCCATCACCTAGGTAGTGACCACAATTCCAAACAGGTAGTTTTTTTCAGC | |
| | CCTTTTCCCCCTCCCAACCCCACTGTTGTATTCCCCAGCATCTATTGTTACCATTT | |
| | TTTTGACCATGTGTATCCAATATTCAGCTTCCATTTATAAGTGACAACATGTGGTA | |
| | TTTGGTTTTTGGTTACTACATTAATTCACTTAGGTTATTGATTTCCAGCTGCATCC | |
| | ATGTTGGTGCAAAGGACATTATTTTGTTATTTTTTATGGCTACATAGTATTCCATG | |
| | GTGGATATGTACCACATTTTAAAAATTCAATCCACCATTGGTGGGCACCTGGATTG | |
| | ATTCCATGTCTTTGCTATTGTGAATAGTGCTGTGATGAACATGCAGGTGCACGTGT | |
| | CTCTTTGGTAGAATGACTTATTGTCCTTTGGGAATATACCCAGTTAGTGGGATTGC | |
| | TGGATCGAATGGTAGAAAAACTCTCAGGTCTTTGAGAAATCTCCAAACTGCTCTCT | |
| | ATAGTGGCTTATTTAATTTACATTCCCTACAGCAGTGTATCAGCCTTCTCTTTTCT | |
| | CCACAGACTCACCAACATAGTATTTTTTGACTTTTTAACAAAAGTAATTCTGACTG | |
| | GTATGAGATGGTATATCATTGTGGTTTTGATTTGCATTTCTTTGATGATTAGAGAT | |
| | GATGAGCATCATTTTCATATATTTATCAGCCTCTTTTATGCCTTTGTTTGAGAAGT | |
| | ATCTGCAAATGTCCTTTGCCCACTTTTTAATGGGGTTATCTGTTTTGTCATGTTGA | |
| | TTTGTTTAAGTTTCTTAAAGATTCTGGATATTAGACCTTTGTTGGATGCATAGTAT | |
| | GCAAATATTTTCTCCAATTTTGTAGGTTGCCTGTTTACTCCTTTGATTGTTTCTCT | |
| | TGCTGTCCTTTGCCTATTTTTTAATTGGGTTATTTGTTTTCTGGCTATTGAGTTGT | |
| | TTGAGTTCCTTATTTTTTTTTTTGGATATTAGCACTCATTAGATATACACTTTACA | |
| | AATATTTTCTCCCAATACCTGTGTTGTCTCTTGATTCTGTTAATTGTTTTCTTTGC | |
| | TGTGCAGAAACATTTTAGTTTCACACAATTCCTTAAAAAACTAAAAATAGAATTGC | |
| | CATATGATCCAGAAATTCTACTTCTGGATATTTATTGAGAGGAATTGAAATCAGCA | |
| | TGTTGAAGAGATATCTGCACTTCTATGTTCGTTATAGCATTATTCATAATAGTCAT | |
| | GATATGCCATCAACCTAAGTATCCATTGACAGATGAATGGATAAAGAATGAGGTGT | |
| | ATGTACACAAAGGAATACTATTCAGCCTTTAAAAAGTGGGAAATTCTGTAACAACA | |
| | TGGATAGACAGATACTATATGATCTTACTTATATGTGGAATCTAAAAAGGTAGGTC | |
| | TCACAGAAACAGATCATAAAAAGGTGGCTACCAGAGGCTGGGAGAGGAAGGAAAAG | |
| | AATGAGGAAAGTGACATATTGATCAAAGTTGTACAAAGTTTCAGTGCGACTGGAGT | |
| | AATAGGTTTTAGTGATCTATTGTACTGCATGGTGTCCACAGTTAATAGTAATGTAT | |
| | TGTATATCTTAAAATTACTAAACGATTAGGTATTTAATGTTCTCCCTACAAAAAAA | |
| | TGGTAAGTTGGTGTATTAGTCCACTTTCACACTGCTATAAGGAACTGCCCGAGACT | |
| | AAGTAATTTATAAAGAAAAGAGGTTTACTGGCTCACAGTTCTGTATGGCTGGGGAG | |
| | GCCTCAGGAAGCTTACAATCATGGTGAAAGGGAAAGCAGGTATGTCTTACATGGTG | |
| | GCAGGTAAGAGATCCTGTGTGTGAAGTGAAGGGGGAAGAGTCCCTTATAAAACCAT | |
| | CAGATCTCGTGTGAGCTCACTCACTAGCATGAAAACAGCATGGAGGAAATCACCCC | |
| | TATGATCCAATCACCTCTTTCCCTCAACACATGGGGATTACAGTTCCCTGCCTTGA | |
| | TGCGTGGGATTAAAATTTGAGATAAGATTTGGGTGGGGACACAAAGCCAAACCTTA | |
| | TCAGTTGGTGAGGTGATGAATATGGTCATTAGCTTGTCTAAATTTGTCTGCAATGT | |
| | ATACATAGATCAAAACATCACTTTGTACCCCATAAACATGTGCAATTACTATTTTC | |
| | CAATTAAAAATAAATATAAATAAATTAAAAATAATTGCAAAGGAAAGCTGGCTGTG | |

TABLE 6-continued

| Cas12i and HAO1 Sequences | | |
|---|---|---|
| SEQ ID NO | Sequence | Description |
| | GAGAAGATTAACAAATAATGACATTAAGAAATTCAGGTCCTTGGCAAAATTAGAAA<br>TACATACAAAGCTATCCAGAACTTATTTTTCCAAATGCATTAGGCGTCCTCTCACC<br>TTACCCTTTACAATTGCATGGCTTCAGAGATTACACAGAAAACGTTCAGAAACATT<br>GCCCCAGTAGATGATCTTGCAATGCTATGAAGTAGGCAGAACAGCTGTGGCTATAG<br>CAATTGTGCAGATAGAACGTACTTCATGGATGGCAAGACTGGGACTCTAGGACAGG<br>CTTTCAATCCATTCTACCCTGTTGTTGTTCTGAAATGAAAGTTTTATCTCCCAGTT<br>TATATAGGTAGCCTTATCTTTGATGCTTCAATACCTGAGACCTGGCCAGTGTCCCT<br>TTTAGTGATTGTATGTGTGTGTGTGTGTGTCATATGCAATTTCCTTATAGCAATGG<br>CACAGTGTATCACTGTTTAATTAAAGAAGAGAAAGAAATGCCAAACATACGAATAA<br>AGTCTGAATATATCTGTAACATTAAAAGTGTAGGTGTCTATCTTTGAAGATATGTC<br>TTAAGGACAATGAAAGAGTCAGTGAGTAAGAGAAGAGAGTCCTGGGATTTCATACA<br>AGATCAGTGTTACTTGATGGTGTAGGCTCCTAGGTATTTCATCTTTAGGATATACC<br>GTCTATTACAAAAGCCAAGATTTTTAGATTTGGATCAACATTAGGGAACTTCATTC<br>TAGGCAAGAGCCAGGTTTTGCCTTTATGTTAATATGACCTCAGCTGTGAGCTCCAT<br>TTTGCCAGGCATCTTAAAACTGCAACACATATCATTGGAATCTTCCGTTACAGTCT<br>AATACATAGCCACACATTGGGAGCAAGAATGAAATCCAACCCCTGTCCTTTGCAAA<br>ATGCAATGAGACAGTGTCTGCTTTGGGAGCAGGGAGTCAGAATTTCATTGTGGACA<br>ATGGATAAGGTGAGTAAAAGGGCTTAAAACATTTGTGCTTTCAAGCCATAGGCTAG<br>GATAACGATAGTCAGAACTTTTTGATGAAGTCTGACCATGCTACGCCATTTATAAA<br>ATTTTGAAGCTTGTAAGTATTACCCCAAAATGAGCAGTGTGAACTCAAAGGGTTTA<br>TCATTGTCTCTCAGGCAAAGGTAATATTTGAATTATTTAGCAAAGGACTTTGAGCA<br>ATTGGAAGAGATACTCAGCTGCTGGTCTCTAGCGCTCTAACAGGGTGGATGCCCCC<br>CGCTCTGCCGGCACTGATGTTTAAGTTGCTGGATTATGAGGAAGTCTGGGGATTCC<br>TTGGGGAGAAAAGGAAGTGATGACATATTGAAGCACAACGACATATTGAAGAGACT<br>CGGGGGCTGGGGTGATAAACTTCAGAGCCGTGGCTATTTACCAATTGGAGTGTAAG<br>TATTTTAATATTTTAACAAACATAATTGCCATTCTGGTATGTACCAACTTCATCTC<br>AGATCTGTCCTTAAGAAATAGGCAAATTCTTTATTGCCTCTCTGAATGGTTCATAT<br>AAATTCCCAGGCTCCCTTAGCTCATTCTAACATAAAACTGTATTAAAAATAATGAA<br>TGTAATTCATCAATAATTTTCCTTTGTCATAGCAAATAGTCACAAGTGGATTGAGA<br>TCAGAGTGATCACTCATATTTGTTCTGGGGAGAAGGGAGCCTGCTGTTTTGCTCCT<br>GTTTTCTCCTAGGACTAGTATTTTAGCTTCAAATGATAATACCTTAGCACAGACTC<br>TGATATTCCTCCTACATGCAGGAGCATTCTCTTGGAATAATTTTGGGGATGCCAAT<br>TCAAAATTTCAGCCATGTATGATTTACTTATTGGAAAATAATCACTGAGCAGCAAT<br>AACTCCAGCAGTTACTTGTATCAAGGTAGAATCAAGAAATAGATGGTATGGACCAA<br>ACTTGCTTCTCTCTAAATATGCATACCCAAGTGATTTGGGTAAAATGTTTGTGAAG<br>GGCTTACATTTCCTGCAAGTCAGATGGTTTAAGAGAAGTAGAAATTATGTGTGTTT<br>TGCAGCATTTTGGTAATCTGTGTGGAGTGTCTGTAGATATTTCTCATGAGTTCAAG<br>GGAATCCTTTTGTGGATTTTGATGTTCCTATTGGCAGAGCTGCTGCTTGACTACAT<br>GATGTCTTTGTATTAACTACAAAAACATGCCCTATCATCTGAGTGATTTTCTCTGC<br>CAGACCCCTTTGTGCATCCACACTCTGCACCTCCAGTGTACGGAGGACCTTCCCAC<br>TGGATTCTAAGATTCCATGCCTTCCCAATGCATGGCAGTGTCTCTCATGCACATGG<br>CAAACCTACTCTCTTGGATGTCACTGCCCTGAAATATTGAGGGAGTACATTTATCT<br>AGGCATGGTACCAGGGAGTCATTTAGACATGTAGGGAGTCTAGAAAGATCATTGCC<br>CTGGGAGAGTGCTCAGCCATGCTGAGTTCTCCTACTTTGTTGCTCATTTCTGTGTG<br>ACCTTAGGTAACATCCTCTTCAGGACTTTTTTTTTTTTTTTTTTTTTGACAGGGAG<br>TCTCATTCTGTCATCCAGGCTGGAGTACAGTGGTGTGATCTCAGCTCACTGCAATC<br>TCCGCCTCCTGGGTTCAAGCAATCCTAGTGCTTCAGTCGCCTGAGTAGCTGGGATT<br>ACAGGCATGCGCCACTACGCCCAGCTAATATTTGTATTTTCAGTAGAGATAGGGTT<br>TTATCATGTTGATCAGGCTGGTCTTGAACTCCTGACCTCAAGGGATCTGCCTACCT<br>TGGCCTCCCAAAGTGCTGGGATTACAGATGAGAGCCACCAACCCTGGCCAGGACAT<br>AATTTATTTCAGGTGAATTGATTGTTGGAGGATTTTGATCCAAGCAATCAATGTCC<br>CTTGGTGTTCCTTTCAAACAGCAGTAAGTGACCTGAATTTATTTTCCACATTTCCA<br>AATCTTAATGAAAATCAGACAATGGTCTATATGTTCATTTGTGTTCTTACTTAATA<br>AAATGTGGGTTTTAGACAATATTTTGCCAGTCATGAATTCCTATAGAAGGAACTCT<br>TTGGGAGAACAGACTAGTGATCTATAGACATGATGACCTCCAACTCAGATCTTCTG<br>TAGCTAACCACTGACCGGGAGAACATGTATGAAAAACATCTTCAAAGGCATTGAAA<br>AATTAACATTTATCAAAAACAAAATACATTTTATTTCATTTGAACTTAGACCTTTA<br>CTATCTAATGGCTATGGTACTATTTAAATGTCAAAGTGTGATCTAGCATCAGCCTA<br>ATCTGGTTAGAAATGCAAACTCTTGGGCCACATCTCAGACTTACTGGACCAGAAGC<br>TCTGTGGGTGGGACCCAGAAATCTGTGTTTCATTCACATGCCCTCCAGGGGATTGT<br>CCTGCTAAAGTTTGAGAATCATGGAAGCTTTTTAACCTCTCATTATAGCTTTATAA<br>GCAGCAACTCACTGGATTCCTATCAACATCCTGTGAGTGTCATTTGGACAAGTATA<br>TTTATACCCATTTGATGCATGGTAGGCACACAGATGAGTCAAATGACTTGAAGGAA<br>TAGAGTTTTACATAATATACTTTTATATATTTATACTTCTAATATATTTATACTTT<br>ATAACAGATTTGACTGTTTTATATATTGCATATAAACATTATATCAGTTTCTCCTC<br>CACTAAGGCTGACTCCAATTTTACTCCAATTTTACTACCAATTTTTGGAAGAAAGC<br>CTACCTATCACTCATGTTCTCTCAAGTACCCTCTAAAACTATTAGTTAGATGACTC<br>TATTTAATTTTCCATTTATTTGCCCGTTTCTTGCTACCTTTCCCCCCAAAATGTAA<br>CTGCTACCTTGCTCAAAAGGATGTGTCTACTTGGGATATCTAGCACACACATTTTA<br>TGAGATTTTAAAAGACAACATAAATGGTAAACTATATATTTAATACAATTTTGAAA<br>GACAAAATTTTAAAATTAAAAAGGAAGAAAAAAATTAAACTAACCCCATAATTCTC<br>CCACCCATCATTAGCATGTAGTTTGTTTAGATTCATCTACCAATAAGTAGAATTGT<br>ACAAATTTGATATCATGTAATACATGTCATTTTGTAAACTTTTTTCTTTCCTTAAT<br>ATATCTATATATCATAAACATTTTTCTATGTCTATATTATTTTAAAATTGTAATAC<br>CCAGAGTTCTCCAGAGAAACAGAATTAATAGGATCTCCCCCTTGGAGATTTCTCAT | |

TABLE 6-continued

| SEQ ID NO | Sequence | Description |
|---|---|---|
| | Cas12i and HAO1 Sequences | |
| | CTTTTTCTCTCTCGATAGATACAGATAGATACATACATAAGTCTATCTCTCTATCT<br>CTATCTTTATCTCTAAAACACCTATCCATAGATAGACATTTTTAGGAATTGGCTCA<br>TGTGTTTGTGGAAGCTTGCAAGTTCAAATGTGCAGAGTAGGTGGGCAAGCTACCAG<br>GGAAATGTTGATGTTGCAGTTCCAGTCTGAAGGCAGGCTCCTTGCAGAATTCTTCT<br>TTTTCTTAGCAGTCTTACTTCCCCTTCCTCTTCCCCTTCTCCTTCCCCTTTCCCTT<br>CTTCTTCTCCTTCCCCTTCTTCTTATTCTCCTTCACAGACTTATTTTTAAGGCCTT<br>GAGCTGATTAGATAAGACCCACTCACATTATGAGGGATAATCTGCTTTACCTGTAG<br>TCTACTAATTAAAATGTTAATCTCATCTAAAAAACACCTTCATAGCAGCATTCAGA<br>CATGTTTCACCAAATATCTGGGCACCATGGTTTAGCATATTGATGCAGAAAATTGA<br>TTATCATAATAATATTATTTTTTTTTGAGATGTAGTTTCACTCTTGTCACCCAGGC<br>TAGAGCGCAATGCTGCAATCTCAGCTCACTTCAACCTCTTCCTCCTAGGTTCAAGC<br>GATTCTCCTGCCTCAGCCTCCTGAGTAGCTGGGACTACAGGCGCCCATGACCACGC<br>CCGGTTAATTTTGTGTTTTTTTAGTAGAGATGGGGTTTCACCACGTTGGTCAGGCT<br>GGTCTCGAACTCCTGACCTCAGGTGATCCACCCGCCTCAGCCTCCCAAAGTGCTGG<br>GATTACAGGCGTGAGCCACTGTGCCCAGCAATAATATTAATTTTAATGGGTGTGTT<br>CATTTCATTTTATATATGACCTACAATTTAACCAATCCCCTAAGGCTGGATGTTCA<br>GGTTCTTAATATTTTTTGCCCGTATTTACAGACACCTTTGACTATTGGATTTATTT<br>TGTTCTTCAGGAACAATATACAAAGTGTGGAAAGAAATGTATATTTCTAATCATTG<br>GAAAATAAACACTGAGCAGAAATAACTCCAGTAGCCATTTGTATCAGAGGAGGTAG<br>AATCAGGAAATAGATGGTATGGGCCAGACTTTCTTCTCTCTTTAAGAGATTTGACT<br>TCATATTGCCAAATTGCCCTTCTAGATGTCTTTACTCATCCAACTACAATTCAAAG<br>GTTTGGGAGGGTAAGCAATGCCAGGCCCATCTTGATCATCCCCTTTCTTTCTCAGC<br>CTGTCAGTCCCTGGGAACGGGCATGATGTTGAGTTCCTGGGCCACCTCCTCAATTG<br>AAGAAGTGGCGGAAGCTGGTCCTGAGGCACTTCGTTGGCTGCAACTGTATATCTAC<br>AAGGACCGAGAAGTCACCAAGAAGCTAGTGCGGCAGGCAGAGAAGATGGGCTACAA<br>GGCCATATTTGTGACAGTGGACACACCTTACCTGGGCAACCGTCTGGATGATGTGC<br>GTAACAGATTCAAACTGCCGCCACAACTCAGGTAACCATGATCATGTGGGCCCCGA<br>GCTGAGGCGAAAGGGATCTTGACTGGGAATGTTAGGGTCTGGGTTCTACTGATAGC<br>AACGTTGCTAAACATCTAGTTAATCTTCAGCTAATCACATCCCTTTTGTAGACATC<br>ACTTTTTTTGAGATACACAATAGAAACAGAAATGGCCTCTATAAAAGTCCAATAAA<br>TTTTCAGACCAGAGTGCATTAAGGGCTTTGGCTTTGGGAAGTATGAATTGCTATAC<br>AGATGGAAGATACTGAATTTTGCCCAAGCAGCAGTTTATTATTATCATCCTGGTGC<br>CCTATTTCTTTGTTAAAGTCAAAGAGCCACCTTTACCTTTTATTTTTAATGGTACA<br>TGGGACAGCTAAGGCTAAGAAGATTGAAGAAAGAAAATAATGAAGGTTTAAAAAAG<br>CCACATCTTTGATCCCTCACTGTCTACTTCTTCTTTCAGCAATATTCCTTTCACTG<br>TGGTTCATCCATGGGTCAAGATTCATTGATTCATTCACTCAAATCATTCATCTTAG<br>CAAAAACAATATATCACATAATCTGATGTTGAACTATAAAGGTTTCATCAGGTCAT<br>TCATTCACCCTGTCCACAAGCTGTGAATTATTATCTCTTTCCTGGTTGTATTTTGG<br>GATTACAATCATCTTGAGTCAAAGCTGGAAACTGAGTGGAAGTCTCTGGGAAAGAC<br>TCAAACCTCCTTAAGCTATACACCTCTTTTCCCCATCAGATTTTCCTTCCTTCAGT<br>TTCCACCAAAATGTGCTCTTGGATTTTTCATATGAATGTATAATGTACCTCAGGCC<br>TATAAGTATTTTAAAAGGGATCAAAATCTTAGTTTTAATGGAGGACATTTTTATGA<br>TGGACTCCTACAGCATCCATCAGAATATGTAAGATGATGAGGAATGTCTTCCTGTG<br>TTCCCAGATCTCATGCCACAGAGGCCCTTGCTTACTCTATGTTTGAATTGTATTTG<br>GAAAAAAAAAAAAAAACAAAAAACTAGGGCTAGCAAAATTGAAAAAAGATAAAAGA<br>CGAAAGAAGCCACATGTAAACATACTGTGTTTACTCTTCTAAAATATTAAAAAATG<br>AAAAGATCCAAAATCAAATTAATATTCCCCTGGAATTTCATATCTATTTCAGTGAC<br>TGTGGAGTGAATCTCACCACGAAAGTTGCTGCAGTCTTGTATAAGTTTCACATAGT<br>TTTACTGTGTTTGTGCCTATGTGAGAATAAACTACTGTGCATAAAATCTTGCTGTT<br>GAGCCATGTGTGAATTAGCTGTGTGATGTTACCTCCCTGTTACTACCAGGCTGGTT<br>TAGGATATCATTTCTGTATGTGGCACCAGGATTAGACCAATGACAGAAAAAGAAAG<br>TGCTCTCCCTGCCAAACTGGCCAATAAAACTGTTCCACATATCCCAGACTCAGGGT<br>TACCTAAACAACCTGTGTTTAAAGAGAACAAAAACAAAAGCCTCTGACATAGTCTT<br>ACTCCTTGCCAAATTCGTCAGAAAGCTGATGGATTCAAATTCCCCCAATATGAATC<br>CCGTATTTACATTATTTCTCTATTTTGACTACTTTTTTTTTTTTTTAAAGACTTTC<br>TAAATAGTTTCCCACTATCGAGGCTTCTTAGAGGAAACATTTCTCATTATTTCCCC<br>TTGGCTATTTGAAAAGGAATTTGTTCTTCCTTTTCCTCCATCTCTTAACACTACTA<br>CTACTAACAATAGTAACAACAATAGTAAGTACAGTAGGGTTTTTTGTTTTGTTTTT<br>AACTTAAGACATACTTTCTTGTTCTGGATACCAAAATATGTTTCACAGAGGCATCT<br>ACTTAGATGGGGTGCAGATGACACAGTTGTTAATTCTGGCAGGTACCTCTTGCTTC<br>TTCACTGCTGGGGCTACTCAGTGAGTGGCAGGAAGGTTGATTTGCTTTCCCCCCTT<br>TTCTTTTGCTCCTGGGCTCCTTCCCAGATGATGTGACGGGCCATGAAACAAAGACT<br>CTTTTCAGCTGTCGGTGTGCATAGAACTGGCTGCGGCTTCCTAGCTTGTCACATCT<br>CCGGTCTGAAGATGATCAAATAATGAGCAACACATCCAGGTTATAGGGAACACGGG<br>AAACACCCCGCAGCTGGGTGTACCCCAGCCCCTCAGAGTGCACATTGGTGTTGTTT<br>GTCCTAGTGGACTTCGGAGTAGGCCAGTGCCTTCTGGTCAGTTCCTCAGTGGCCCA<br>CATTCAGCTCTTAAAGGCAGAGCATGCTAACGGGAGGTCCAGGCTTCCGCCTGAGG<br>CCAAATACACCCCAAAAGCTCATCTGTTATAGCCTGATATGAAATCGGTTTCTTTC<br>TGCAACTGACCTGACTCATAGAAAGTGAAGCCTGGCTTTTCATAAGTGAAGTTTGG<br>CAGGCAAGGGAGGCAGGAAATCCAGAGGAGAATGAGCCTGTAAAGCATGGCTCCTT<br>CCAGCCCTTGTTACTTCCTCTGCCCAAGTGTGGGGGAGGGTCCTGTCTCTTGGCAT<br>CTGGGCCCAGCAAGAGTTCAGAGGTTTGGTAGTCTCTGCTTGGTCCATATGCAAAA<br>CACATGTATGTGTATACATTATTAATGGCAAGGGGGTTCCTGAAACTGAGAGGGAG<br>TAAGGAGACTTCTCATCTGCTCTTGGAAGAAGCAAGGAATGAAGCCAGTTCAGTAG<br>ACTGATTCCTGAGGCTTTGGGGCAGGAACTTTTTCTTTCTCCATATCCCCATGGAG | |

TABLE 6-continued

| Cas12i and HAO1 Sequences | | |
|---|---|---|
| SEQ ID NO | Sequence | Description |
| | ATGGTTCATTTACCCTGAATTAAGATTTGGCCCTTCGGTGCAGTGCCAAGGCAGTT TAAAGAGAAGAAAAGTAATTTCTGATCATTGACTAAGATCAAGGTAAATCATGACA CTTATCCTTTCTATGATTTGCCAGTGACATGTTTTCTTAAGCCCAGAAATGATTTA TTGATCGCAGCAGCCAGAATATATCACACTAAAACAGATCAGCCTGCCACTGTCTT CTCAGGTCTCTCATGATTAAAGTGGCCTGCTTTAAAGTAGACTCAATGTGAATAGG TCTCCATGACCTCTGCCTCACTGCGTAGCACTCACATCCTCACCCACTCTTGCACT CTGGCTTCCCTGCGGTTCTTTCAATATGCCAGGCATGCTGGAACCCCGGAGCCTTT GCACTGGCTGTTCCCTCTGTCTGTAACAGTCATTCGCAGAATCAACGCATGACTAA TAGCCTCACTTCCATTGAGTCTTGACATTAGGAATGGATATACATGTCTATATTGG GAAACCACAATAAAAATTGATGGTAGAGATGCAAATATGAGCAAGATAACAGGGTG GGGGCAGGGGAGAGAGGTCAGTGGAGGACTTGGCACAGTAGCCTCTTAAATGGCAC AATAGCCTCTTAAATTTTTGGTTAAGAAATCATTCACATTGATAAGTATGGCAGGA TAAAGGTGTCCATGAGTGAATCCCGGGAACCTGTTACTTTATGTGGCAAAAGGGAC TTTGCAGATGTGATTAACTTAAGGGGCTTGAGATGGGAAGATTTTTCCTGTTTTTA TCAGTAGGCTTGATATAATTAAAAGGGTCCTTATAAGAGGGAAGCAAGAGTGTCAG AGTCAGAGAAAGAGATGAAATGACAGATGTAGAGGTTGGAATGATGTGGTCAGGAA CCAGGGAAAGCAGGGGGTATCTAGAAGCTGGAAAAGACAAGGGAATAGGGCTTCCC CTAGATTCTCCAGAAATACAGCCCTATTGATATCTTGAGTTTAGTCCAGTGAGACT TATTTTAGACTTCTGACATTTGGAACTGTAATATAATACCTTCATGTTATTTTTAT TGCTGTTGTAACAAATAACCACAAACACAGTTCTACTAATTTCTTTCTCAAGGTAG CTTCTCAATTTTGCCAACGCTGGTTACCATACATACTTAAAGTTTCATTTTGAGTC TCTGAAAACTCACATCTCTCTTAATCTGCTCTACTTTTTTCTTGGCTTTGTATAGT GCTTATGTTCTGCTACACTTTGTAATTTATTGATTATGCTTACCATGGGCAGGGAT TCTTAACTGTTTTATTTATTTATATATCTTAAACATTGAAAACACTGGCATGTAGT AGATGCTTAATAAGTAATTGTTGACTCAATCGATAAAATATACTAGAACATACAAG ATTTTCCCAATGTAACATAACTAGTAAGAGGCTGAACCGGGATTTGAACTCAAAAT TCATTCCCTGAACCTTCTTCTAGCAGCCACATTGAGGAAGAAATTACCAGGGCTGT GTTCTCAACACAAGTGTTTTCCGAACCACAGAATTAAAGGCTGGTGGCCCATGTAT CAGTGTCTGTATTTATGAGCCCCTCTTTCAATCTCTTTCTTTTCATATTGTGTTGA TGCTGTAGCTTCTACTGGTCATGTTATTTTTTTGTTTCCCAAGACGGAATTATGTG GCTTTATCTTTAATGTTGCATTATCAATACTTATAATAAATAATATTATGTATTAC TCAATATTCATGATTAATAGTGTTACTATTGGTTATTTAATAATGTTTAACTTACA TTAGCAGTTGTTACTATTTTTATGATGCTAAATTACTAACAGCTAAAACAACTTCT ATATTAAAAAGTATATTTGAGTGCCACTCAAGAGATAATGAGTACCTTACAAAGAA GAAATCTTGTTTCTCACCTTTGCGTCATTAAACAGATCAGGATTTGGAGAATTAAG CCCTAAGTAATAGTGTTATTATTTTGATCTCACCCCTTTTTTCTTATGAAATGGA ATACTTTGGTTATCAGAAGCCACTTTAAGCATATATATATATATATATATATATAC ATATATATATATATATATGTCATAATCCGAATAAAAATAGCATTCATGGAGGTTTC TTTTGGAGCCTTTGGTAAAACACTCCATCGTGGGTCTCTGTCAAGATATCTGAAAA CTTTTTCTTGGCTTCTGGCTTTGAACAAAGTTTCAGAGTAACAACAAGGCTTCATT GTGCACTGAAATTTCTGTAAGGCAACATTCATTCAAGTGTTGATTCGCATTTCACC ATCCAAGAATAACAACAGTTATTTATATAATTTTATCCACGTTTCTGTTTTTTCCT ATCCATTTCACCCTTTCACCCCACCCCCTGCTGAAACACTGGAGCTTGTTTGGGATG GGGGTGGGGTGCCATGCAGACTACATACACATACAGATGTTTTTCTTTTTCTTTTC CCGGTCTTGCTATGGGATAGACAGACTGGACTTTTTCTTATTAACAATATTATTTA AAAGCTTGGAATTTATTATCATTTAATCATTTGTATGTAATGAAATAGGTCTCCAT GGTAAAGATGTGTTTATTGACCAGCGGTTAGCTTTATTCAAATTAGGGTGACCATA GAAGACCAAGGACTATGATATAATGTACAATCCTAAGTGGTTTGATTTAAATAAAA AGAAAGACCAGGCATTTCAGCTAAAATCCCCACCAAAGCCCAATGACTAGATGGGC ATCCATATGACTCAATGAAATTTTCTATGATCTTAAATGGCCATCTGAGTCCGTGA AACTATAGGACTAACTATTCAATCCTTATTGAGAAAGCCTTGTTAATAGCTTGAAT TGAGTTATATGGGATAGGAATGTTCATATCTTTATGACAATATATGCCACCTAAGC TACATAACCAGCTGTGTTAGCTAAAATACTCTAAAGTGTAAAAAATCATAGTTTTC TATTAAAGGAAGTCATGATTGTTAAAAATAATTTTTAAATAGTGTGCCTAGATTCT TCTAGTATAATATATAATTTTTTTTTTTTTTTATTTGAGACAGAGTCTTGCTCT GTCACCCAGGCTGGAGTGCAGTGGCTGGAGTTGCTCACTGCAACCTCGCCTCCCGG GTTCAAGCGATTCTCGTGCCTCAGCCTCCCAAGTAGCTGAGATTACACGTGCCCAC CACTATGTCCGGCTAATTTTTTTGAATTTTTAGTAGAGACTGGGTTTCATCATGCT GGCCAGACTGGTCTTGAACTCCTGACCTCAGGTGATCTGCCCACCTCGGCCTCCCA AAGTGCTGGGATTACAGGCATGAGCCATTGCGCCCAGCCGATATATAAATTTTTAT ATGGCTCCATGATCTTCTCTACATTTAATGACAGAACTGGTGGAGGGGAAGAAAGA GATGGGACTAAGCCAGAGATCAATATACATACAACTATACTTTGACCAAAAAAAGG GAGATTGACTGGCAGGGGAATTAATAGTATGCAGAAGAGCAAGGTGAGTCCAGTCA CTGTCATTATTCAAAAACAGCCTTTCAGGAGAAGTTTGCAACTGAATTTGGGACTG TGGGCAGATAAGTCACAGGAATGATTCTATTGTGTATCCTGAAGTCATCCATCCAG CTAGGAGTCAGAGGTGCAGGCTGAAAAGACATTGCCCCTAGAGTGGGGAACTGCCA AAATCTAGCCAGGATATTAGGCCAAGAGAAAAGACCTCAGGCACAGGGGAAGCCAG CTTCAGA | |
| 929 | AACGAACTCCATCTGGGATAGCAATAACCTGTGAAAATGCTCCCCCGGCTAATTTG TATCAATGATTATGAACAACATGCTAAATCAGTACTTCCAAAGTCTATATATGACT ATTACAGGTCTGGGGCAAATGATGAAGAAACTTTGGCTGATAATATTGCAGCATTT TCCAGGTAAGAAAATTTATTTTTTAAAATCATGTTTTAAAATTACACAAAGACCG | HAO1 exon 1 |

TABLE 6-continued

Cas12i and HAO1 Sequences

| SEQ ID NO | Sequence | Description |
|---|---|---|
| 930 | TGATTCTGAAACTCTAAAGCCTTTTATTTTATTTTATTTTTTAATTCTAGATGGAAGCTGTATCCAAGGATGCTCCGGAATGTTGCTGAAACAGATCTGTCGACTTCTGTTTTAGGACAGAGGGTCAGCATGCCAATATGTGTGGGGGCTACGGCCATGCAGCGCATGGCTCATGTGGACGGCGAGCTTGCCACTGTGAGAGGTAGGAGGAAGATTGTCACCACAGGGACAGAAGGAGGCTAACGTTTATCG | HAO1 exon 2 |
| 931 | GGAGGGTAAGCAATGCCAGGCCCATCTTGATCATCCCCTTTCTTTCTCAGCCTGTCAGTCCCTGGGAACGGGCATGATGTTGAGTTCCTGGGCCACCTCCTCAATTGAAGAAGTGGCGGAAGCTGGTCCTGAGGCACTTCGTTGGCTGCAACTGTATATCTACAAGGACCGAGAAGTCACCAAGAAGCTAGTGCGGCAGGCAGAGAAGATGGGCTACAAGGCCATATTTGTGACAGTGGACACACCTTACCTGGGCAACCGTCTGGATGATGTGCGTAACAGATTCAAACTGCCGCCACAACTCAGGTAACCATGATCATGTGGGCCCCGAGCTGAGGCGAAAGGGATCTTGACTG | HAO1 exon 3 |
| 932 | ACGTATTTCTAATTTGGCAAATTTCTCATTTTATGCATTTCTTATTTTAGGATGAAAAATTTTGAAACCAGTACTTTATCATTTTCTCCTGAGGAAAATTTTGGAGACGACAGTGGACTTGCTGCATATGTGGCTAAAGCAATAGACCCATCTATCAGCTGGGAAGATATCAAATGGCTGAGAAGACTGACATCATTGCCAATTGTTGCAAAGGGCATTTTGAGAGGTTCGTTTATTTCTCTACTTGAATTCATACTGACTTTGTGATCCTTTGTG | HAO1 exon 4 |
| 933 | CTGCCTGTTAAGTTACAGTTTCCCTAAGGTGCTTGTTTTACTCTCTCCAGGTGATGATGCCAGGGAGGCTGTTAAACATGGCTTGAATGGGATCTTGGTGTCGAATCATGGGGCTCGACAACTCGATGGGGTGCCAGCCACTGTGAGTTTTGGCAGACGCTAAGATTTCCTTTTGGAGTTCCCATTTCCATC | HAO1 exon 5 |
| 934 | TAACAATTCAGTGTTAATAGAGTCACATTATTGAACTTTTCTTTCCCCAGATTGATGTTCTGCCAGAAATTGTGGAGGCTGTGGAAGGGAAGGTGGAAGTCTTCCTGGACGGGGGTGTGCGGAAAGGCACTGATGTTCTGAAAGCTCTGGCTCTTGGCGCCAAGGCTGTGTTTGTGGGGAGACCAATCGTTTGGGGCTTAGCTTTCCAGGTAACTGGACAAAGAAATGAATATATAAAATAGACAACTTGACAGTAAAACAAATGAATAAAACAAGTCAGACTGATTTAGTTCTGAATCACTCTGTATCTTTTCACTTGGTTAGGGGGAGAAAGGTGTTCAAGATGTCCTCGAGATACTAAAGGAAGAATTCCGGTTGGCCATGGCTCTGAGTGGTAAGACTCATTCTTGTTTACAACTTTCTTTTCTTTTATGATCTTTAAGT | HAO1 exon 6 |
| 935 | TGATTATTATTGCATTCAGTTCATATTAAATGTATGCATTATTTTTTCAGGGTGCCAGAATGTGAAAGTCATCGACAAGACATTGGTGAGGAAAAATCCTTTGGCCGTTTCCAAGATCTGACAGTGCACAATATTTTCCCATCTGTATTATTTTTTTCAGCATGTATTACTTGACAAAGAGACACTGTGCAGAGGGTGACCACAGTCTGTAATTCCCCACTTCAATACAAAGGGTGTCGTTCTTTTCCAACAAAATAGCAATCCCTTTTATTTCATTGCTTTTGACTTTTCAATGGGTGTCCTAGGAACCTTTTAGAAAGAAATGGACTTTCATCCTGGAAATATATTAACTGTTAAAAAGAAAACATTGAAAATGTGTTTAGACAACGTCATCCCCTGGCAGGCTAAAGTGCTGTATCCTTTAGTAAAATTGGAGGTAGCAAACACTAAGGTGAAAAGATAATGATCTCATTGTTTATTAACCTGTATTCTGTTTACATGTCTTTAAAACAGTGGTTCTTAAATTGTAAGCTCAGGTTCAAAGTGTTGGTAATGCCTGATTCACAACTTTGAGAAGGTAGCACTGGAGAGAATTGGAATGGGTGGCGGTAATTGGTGATACTTCTTTGAATGTAGATTTCCAATCACATCTTTAGTGTCTGAATATATCCAAATGTTTTAGGATGTATGTTACTTCTTAGAGAGAAATAAAGCATTTTTGGGAAGAA | HAO1 exon 7 |
| 965 | MSNKEKNASETRKAYTTKMIPRSHDRMKLLGNFMDYLMDGTPIFFELWNQFGGGIDRDIISGTANKDKISDDLLLAVNWFKVMPINSKPQGVSPSNLANLFQQYSGSEPDIQAQEYFASNFDTEKHQWKDMRVEYERLLAELQLSRSDMHHDLKLMYKEKCIGLSLSTAHYITSVMFGTGAKNNRQTKHQFYSKVIQLLEESTQINSVEQLASIILKAGDCDSYRKLRIRCSRKGATPSILKIVQDYELGTNHDDEVNVPSLIANLKEKLGRFEYECEWKCMEKIKAFLASKVGPYYLGSYSAMLENALSPIKGMTTKNCKFVLKQIDAKNDIKYENEPFGKIVEGFFDSPYFESDTNVKWVLHPHHIGESNIKTLWEDLNAIHSKYEEDIASLSEDKKEKRIKVYQGDVCQTINTYCEEVGKEAKTPLVQLLRYLYSRKDDIAVDKIIDGITFLSKKHKVEKQKINPVIQKYPSFNFGNNSKLLGKIISPKDKLKHNLKCNRNQVDNYIWIEIKVLNTKTMRWEKHHYALSSTRFLEEVYYPATSENPPDALAARFRTKTNGYEGKPALSAEQIEQIRSAPVGLRKVKKRQMRLEAARQQNLLPRYTWGKDFNINICKRGNNFEVTLATKVKKKKEKNYKVVLGYDANIVRKNTYAAIEAHANGDGVIDYNDLPVKPIESGFVTVESQVRDKSYDQLSYNGVKLLYCKPHVESRRSFLEKYRNGTMKDNRGNNIQIDFMKDFEAIADDETSLYYFNMKYCKLLQSSIRNHSSQAKEYREEIFELLRDGKLSVLKLSSLSNLSFVMFKVAKSLIGTYFGHLLKKPKNSKSDVKAPPITDEDKQKADPEMFALRLALEEKRLNKVKSKKEVIANKIVAKALELRDKYGPVLIKGENISDTTKKGKKSSTNSFLMDWLARGVANKVKEMVMMHQGLEFVEVNPNFTSHQDPFVHKNPENTFRARYSRCTPSELTEKNRKEILSFLSDKPSKRPTNAYYNEGAMAFLATYGLKKNDVLGVSLEKFKQIMANILHQRSEDQLLFPSRGGMFYLATYKLDADATSVNWNGKQFWVCNADLVAAYNVGLVDIQKDFKKK | (Cas12i1 of SEQ ID NO: 3 of U.S. Pat. No. 10,808,245) |

TABLE 6-continued

| Cas12i and HAO1 Sequences | | |
|---|---|---|
| SEQ ID NO | Sequence | Description |
| 966 | MSISNNNILPYNPKLLPDDRKHKMLVDTFNQLDLIRNNLHDMIIALYGALKYDNIK QFASKEKPHISADALCSINWFRLVKTNERKPAIESNQIISKFIQYSGHTPDKYALS HITGNHEPSHKWIDCREYAINYARIMHLSFSQFQDLATACLNCKILILNGTLTSSW AWGANSALFGGSDKENFSVKAKILNSFIENLKDEMNTTKFQVVEKVCQQIGSSDAA DLFDLYRSTVKDGNRGPATGRNPKVMNLFSQDGEISSEQREDFIESF QKVMQEKNSKQIIPHLDKLKYHLVKQSGLYDIYSWAAAIKNANSTIVASNSSNLNT ILNKTEKQQTFEELRKDEKIVACSKILLSVNDTLPEDLHYNPSTSNLGKNLDVFFD LLNENSVHTIENKEEKNKIVKECVNQYMEECKGLNKPPMPVLLTFISDYAHKHQAQ DFLSAAKMNFIDLKIKSIKVVPTVHGSSPYTWISNLSKKNKDGKMIRTPNSSLIGW IIPPEEIHDQKFAGQNPIIWAVLRVYCNNKWEMHHFPFSDSRFFTEVYAYKPNLPY LPGGENRSKRFGYRHSTNLSNESRQILLDKSKYAKANKSVLRCMENMTHNVVFDPK TSLNIRIKTDKNNSPVLDDKGRITFVMQINHRILEKYNNTKIEIGDRILAYDQNQS ENHTYAILQRTEEGSHAHQFNGWYVRVLETGKVTSIVQGLSGPIDQLNYDGMPVTS HKFNCWQADRSAFVSQFASLKISETETFDEAYQAINAQGAYTWNLFYLRILRKALR VCHMENINQFREEILAISKNRLSPMSLGSLSQNSLKMIRAFKSIINCYMSRMSFVD ELQKKEGDLELHTIMRLTDNKLNDKRVEKINRASSFLTNKAHSMGCKMIVGESDLP VADSKTSKKQNVDRMDWCARALSHKVEYACKLMGLAYRGIPAYMSSHQDPLVHLVE SKRSVLRPRFVVADKSDVKQHHLDNLRRMLNSKTKVGTAVYYREAVELMCEELGIH KTDMAKGKVSLSDFVDKFIGEKAIFPQRGGRFYMSTKRLTTGAKLICYSGSDVWLS DADEIAAINIGMFVVCDQTGAFKKKKKEKLDDEECDILPFRPM | (Cas12i3 of SEQ ID NO: 14 of U.S. Pat. No. 10,808,245) |
| 1024 | ATGCTCCCCCGGCTAATTTGTATCAATGATTATGAACAACATGCTAAATCAGTACT TCCAAAGTCTATATATGACTATTACAGGTCTGGGGCAAATGATGAAGAAACTTTGG CTGATAATATTGCAGCATTTTCCAGATGGAAGCTGTATCCAAGGATGCTCCGGAAT GTTGCTGAAACAGATCTGTCGACTTCTGTTTTAGGACAGAGGGTCAGCATGCCAAT ATGTGTGGGGGCTACGGCCATGCAGCGCATGGCTCATGTGGACGGCGAGCTTGCCA CTGTGAGAGCCTGTCAGTCCCTGGGAACGGGCATGATGTTGAGTTCCTGGGCCACC TCCTCAATTGAAGAAGTGGCGGAAGCTGGTCCTGAGGCACTTCGTTGGCTGCAACT GTATATCTACAAGGACCGAGAAGTCACCAAGAAGCTAGTGCGGCAGGCAGAGAAGA TGGGCTACAAGGCCATATTTGTGACAGTGGACACACCTTACCTGGGCAACCGTCTG GATGATGTGCGTAACAGATTCAAACTGCCGCCACAACTCAGGATGAAAAATTTTGA AACCAGTACTTTATCATTTTCTCCTGAGGAAAATTTTGGAGACGACAGTGGACTTG CTGCATATGTGGCTAAAGCAATAGACCCATCTATCAGCTGGGAAGATATCAAATGG CTGAGAAGACTGACATCATTGCCAATTGTTGCAAAGGGCATTTTGAGAGGTGATGA TGCCAGGGAGGCTGTTAAACATGGCTTGAATGGGATCTTGGTGTCGAATCATGGGG CTCGACAACTCGATGGGGTGCCAGCCACTATTGATGTTCTGCCAGAAATTGTGGAG GCTGTGGAAGGGAAGGTGGAAGTCTTCCTGGACGGGGGTGTGCGGAAAGGCACTGA TGTTCTGAAAGCTCTGGCTCTTGGCGCCAAGGCTGTGTTTGTGGGGAGACCAATCG TTTGGGGCTTAGCTTTCCAGGGGGAGAAAGGTGTTCAAGATGTCCTCGAGATACTA AAGGAAGAATTCCGGTTGGCCATGGCTCTGAGTGGGTGCCAGAATGTGAAAGTCAT CGACAAGACATTGGTGAGGAAAAATCCTTTGGCCGTTTCCAAGATCTGA | HAO1 cDNA |
| 1082 | rArGrArArArUrCrCrGrUrCrUrUrUrCrArUrUrGrArCrGrGrCrGrGrArG rCrArUrCrCrUrUrGrGrArUmA*mC*mA*rG | 3′ end modified RNA guide targeting HAO1 sequence of SEQ ID NO: 1047 |
| 1083 | mA*mG*mA*rArArUrCrCrGrUrCrUrUrUrCrArUrUrGrArCrGrGrCrGrGr ArGrCrArUrCrCrUrUrGrGrArUrmA*mC*mA*rG | 5′ and 3′ end modified RNA guide targeting HAO1 sequence of SEQ ID NO: 1047 |
| 1084 | rArGrArArArUrCrCrGrUrCrUrUrUrCrArUrUrGrArCrGrGrGrGrArArG rUrArCrUrGrArUrUrUrArGmC*mA*mU*rG | 3′ end modified RNA guide targeting HAO1 sequence of SEQ ID NO: 1026 |

TABLE 6-continued

Cas12i and HAO1 Sequences

| SEQ ID NO | Sequence | Description |
|---|---|---|
| 1085 | mA*mG*mA*rArArUrCrCrGrUrCrUrUrUrCrArUrUrGrArCrGrGrGrAr ArGrUrArCrUrGrArUrUrUrArGmC*mA*mU*rG | 5′ and 3′ end modified RNA guide targeting HAO1 sequence of SEQ ID NO: 1026 |
| 1086 | rArGrArArArUrCrCrGrUrCrUrUrUrCrArUrUrGrArCrGrGrCrArArArG rUrCrUrArUrArUrArUrGrAmC*mU*mA*rU | 3′ end modified RNA guide targeting HAO1 sequence of SEQ ID NO: 1025 |
| 1087 | mA*mG*mA*rArArUrCrCrGrUrCrUrUrUrCrArUrUrGrArCrGrGrCrArAr ArGrUrCrUrArUrArUrArUrGrAmC*mU*mA*rU | 5′ and 3′ end modified RNA guide targeting HAO1 sequence of SEQ ID NO: 1025 |

In some embodiments, the gene editing system disclosed herein may comprise a Cas12i polypeptide as disclosed herein. In other embodiments, the gene editing system may comprise a nucleic acid encoding the Cas12i polypeptide. For example, the gene editing system may comprise a vector (e.g., a viral vector such as an AAV vector, such as AAV1, AAV2, AAV3, AAV4, AAV5, AAV6, AAV7, AAV8, AAV9, AAVrh10, AAV11 and AAV12) encoding the Cas12i polypeptide. Alternatively, the gene editing system may comprise a mRNA molecule encoding the Cas12i polypeptide. In some instances, the mRNA molecule may be codon-optimized.

II. Preparation of Gene Editing System Components

The present disclosure provides methods for production of components of the gene editing systems disclosed herein, e.g., the RNA guide, methods for production of the Cas12i polypeptide, and methods for complexing the RNA guide and Cas12i polypeptide.

A. RNA Guide

In some embodiments, the RNA guide is made by in vitro transcription of a DNA template. Thus, for example, in some embodiments, the RNA guide is generated by in vitro transcription of a DNA template encoding the RNA guide using an upstream promoter sequence (e.g., a T7 polymerase promoter sequence). In some embodiments, the DNA template encodes multiple RNA guides or the in vitro transcription reaction includes multiple different DNA templates, each encoding a different RNA guide. In some embodiments, the RNA guide is made using chemical synthetic methods. In some embodiments, the RNA guide is made by expressing the RNA guide sequence in cells transfected with a plasmid including sequences that encode the RNA guide. In some embodiments, the plasmid encodes multiple different RNA guides. In some embodiments, multiple different plasmids, each encoding a different RNA guide, are transfected into the cells. In some embodiments, the RNA guide is expressed from a plasmid that encodes the RNA guide and also encodes a Cas12i polypeptide. In some embodiments, the RNA guide is expressed from a plasmid that expresses the RNA guide but not a Cas12i polypeptide. In some embodiments, the RNA guide is purchased from a commercial vendor. In some embodiments, the RNA guide is synthesized using one or more modified nucleotide, e.g., as described above.

B. Cas12i Polypeptide

In some embodiments, the Cas12i polypeptide of the present disclosure can be prepared by (a) culturing bacteria which produce the Cas12i polypeptide of the present disclosure, isolating the Cas12i polypeptide, optionally, purifying the Cas12i polypeptide, and complexing the Cas12i polypeptide with an RNA guide. The Cas12i polypeptide can be also prepared by (b) a known genetic engineering technique, specifically, by isolating a gene encoding the Cas12i polypeptide of the present disclosure from bacteria, constructing a recombinant expression vector, and then transferring the vector into an appropriate host cell that expresses the RNA guide for expression of a recombinant protein that complexes with the RNA guide in the host cell. Alternatively, the Cas12i polypeptide can be prepared by (c) an in vitro coupled transcription-translation system and then complexing with an RNA guide.

In some embodiments, a host cell is used to express the Cas12i polypeptide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electroporation, the calcium phosphate method, the liposome method and the DEAE dextran method can be used.

After a host is transformed with the expression vector, the host cells may be cultured, cultivated or bred, for production of the Cas12i polypeptide. After expression of the Cas12i polypeptide, the host cells can be collected and Cas12i polypeptide purified from the cultures etc. according to conventional methods (for example, filtration, centrifugation, cell disruption, gel filtration chromatography, ion exchange chromatography, etc.).

In some embodiments, the methods for Cas12i polypeptide expression comprises translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the Cas12i polypeptide. In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the Cas12i polypeptide.

A variety of methods can be used to determine the level of production of a Cas12i polypeptide in a host cell. Such methods include, but are not limited to, for example, methods that utilize either polyclonal or monoclonal antibodies specific for the Cas12i polypeptide or a labeling tag as described elsewhere herein. Exemplary methods include, but are not limited to, enzyme-linked immunosorbent assays (ELISA), radioimmunoassays (MA), fluorescent immunoassays (FIA), and fluorescent activated cell sorting (FACS). These and other assays are well known in the art (See, e.g., Maddox et al., J. Exp. Med. 158:1211 [1983]).

The present disclosure provides methods of in vivo expression of the Cas12i polypeptide in a cell, comprising providing a polyribonucleotide encoding the Cas12i polypeptide to a host cell wherein the polyribonucleotide encodes the Cas12i polypeptide, expressing the Cas12i polypeptide in the cell, and obtaining the Cas12i polypeptide from the cell.

The present disclosure further provides methods of in vivo expression of a Cas12i polypeptide in a cell, comprising providing a polyribonucleotide encoding the Cas12i polypeptide to a host cell wherein the polyribonucleotide encodes the Cas12i polypeptide and expressing the Cas12i polypeptide in the cell. In some embodiments, the polyribonucleotide encoding the Cas12i polypeptide is delivered to the cell with an RNA guide and, once expressed in the cell, the Cas12i polypeptide and the RNA guide form a complex. In some embodiments, the polyribonucleotide encoding the Cas12i polypeptide and the RNA guide are delivered to the cell within a single composition. In some embodiments, the polyribonucleotide encoding the Cas12i polypeptide and the RNA guide are comprised within separate compositions. In some embodiments, the host cell is present in a subject, e.g., a human patient.

C. Complexes

In some embodiments, an RNA guide targeting HAO1 is complexed with a Cas12i polypeptide to form a ribonucleoprotein. In some embodiments, complexation of the RNA guide and Cas12i polypeptide occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C.

In some embodiments, the RNA guide does not dissociate from the Cas12i polypeptide at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours.

In some embodiments, the RNA guide and Cas12i polypeptide are complexed in a complexation buffer. In some embodiments, the Cas12i polypeptide is stored in a buffer that is replaced with a complexation buffer to form a complex with the RNA guide. In some embodiments, the Cas12i polypeptide is stored in a complexation buffer.

In some embodiments, the complexation buffer has a pH in a range of about 7.3 to 8.6. In one embodiment, the pH of the complexation buffer is about 7.3. In one embodiment, the pH of the complexation buffer is about 7.4. In one embodiment, the pH of the complexation buffer is about 7.5. In one embodiment, the pH of the complexation buffer is about 7.6. In one embodiment, the pH of the complexation buffer is about 7.7. In one embodiment, the pH of the complexation buffer is about 7.8. In one embodiment, the pH of the complexation buffer is about 7.9. In one embodiment, the pH of the complexation buffer is about 8.0. In one embodiment, the pH of the complexation buffer is about 8.1. In one embodiment, the pH of the complexation buffer is about 8.2. In one embodiment, the pH of the complexation buffer is about 8.3. In one embodiment, the pH of the complexation buffer is about 8.4. In one embodiment, the pH of the complexation buffer is about 8.5. In one embodiment, the pH of the complexation buffer is about 8.6.

In some embodiments, the Cas12i polypeptide can be overexpressed and complexed with the RNA guide in a host cell prior to purification as described herein. In some embodiments, mRNA or DNA encoding the Cas12i polypeptide is introduced into a cell so that the Cas12i polypeptide is expressed in the cell. In some embodiments, the RNA guide is also introduced into the cell, whether simultaneously, separately, or sequentially from a single mRNA or DNA construct, such that the ribonucleoprotein complex is formed in the cell.

III. Genetic Editing Methods

The disclosure also provides methods of modifying a target site within the HAO1 gene. In some embodiments, the methods comprise introducing an HAO1-targeting RNA guide and a Cas12i polypeptide into a cell. The HAO1-targeting RNA guide and Cas12i polypeptide can be introduced as a ribonucleoprotein complex into a cell. The HAO1-targeting RNA guide and Cas12i polypeptide can be introduced on a nucleic acid vector. The Cas12i polypeptide can be introduced as an mRNA. The RNA guide can be introduced directly into the cell. In some embodiments, the composition described herein is delivered to a cell/tissue/liver/person to reduce HAO1 in the cell/tissue/liver/person. In some embodiments, the composition described herein is delivered to a cell/tissue/liver/person to reduce oxalate production in the cell/tissue/liver/person. In some embodiments, the composition described herein is delivered to a cell/tissue/liver/person to correct calcium oxalate crystal deposition in the cell/tissue/liver/person. In some embodiments, the composition described herein is delivered to a person with primary hyperoxaluria.

Any of the gene editing systems disclosed herein may be used to genetically engineered an HAO1 gene. The gene editing system may comprise an RNA guide and a Cas12i2 polypeptide. The RNA guide comprises a spacer sequence specific to a target sequence in the HAO1 gene, e.g., specific to a region in exon1 or exon 2 of the HAO1 gene.

A. Target Sequence

In some embodiments, an RNA guide as disclosed herein is designed to be complementary to a target sequence that is adjacent to a 5'-TTN-3' PAM sequence or 5'-NTTN-3' PAM sequence.

In some embodiments, the target sequence is within an HAO1 gene or a locus of an HAO1 gene (e.g., in exon1 or exon 2), to which the RNA guide can bind via base pairing. In some embodiments, a cell has only one copy of the target sequence. In some embodiments, a cell has more than one copy, such as at least about any one of 2, 3, 4, 5, 10, 100, or more copies of the target sequence.

In some embodiments, the HAO1 gene is a mammalian gene. In some embodiments, the HAO1 gene is a human gene. For example, in some embodiments, the target sequence is within the sequence of SEQ ID NO: 928 (or the reverse complement thereof). In some embodiments, the target sequence is within an exon of the HAO1 gene set forth in SEQ ID NO: 928, e.g., within a sequence of SEQ ID NO: 929, 930, 931, 932, 933, 934, or 935 (or a reverse complement thereof). Target sequences within an exon region of the HAO1 gene of SEQ ID NO: 928 are set forth in Table 5. In some embodiments, the target sequence is within an intron of the HAO1 gene set forth in SEQ ID NO: 928 (or the reverse complement thereof). In some embodiments, the target sequence is within a variant (e.g., a polymorphic variant) of the HAO1 gene sequence set forth in SEQ ID NO: 928 (or the reverse complement thereof). In some embodiments, the HAO1 gene sequence is a homolog of the sequence set forth in SEQ ID NO: 928 (or the reverse complement thereof). For examples, in some embodiments, the HAO1 gene sequence is a non-human HAO1 sequence. In some embodiments, the HAO1 gene sequence is a coding sequence set forth in SEQ ID NO: 1024 (or the reverse complement thereof). In some embodiments, the HAO1 gene sequence is a homolog of a coding sequence set forth in SEQ ID NO: 1024 (or the reverse complement thereof).

In some embodiments, the target sequence is adjacent to a 5'-TTN-3' PAM sequence or a 5'-NTTN-3' PAM sequence, wherein N is any nucleotide. The 5'-NTTN-3' sequence may be immediately adjacent to the target sequence or, for example, within a small number (e.g., 1, 2, 3, 4, or 5) of nucleotides of the target sequence. In some embodiments the 5'-NTTN-3' sequence is 5'-NTTY-3', 5'-NTTC-3', 5'-NTTT-3', 5'-NTTA-3', 5'-NTTB-3', 5'-NTTG-3', 5'-CTTY-3', 5'-DTTR-3', 5'-CTTR-3', 5'-DTTT-3', 5'-ATTN-3', or 5'-GTTN-3', wherein Y is C or T, B is any nucleotide except for A, D is any nucleotide except for C, and R is A or G. In some embodiments, the 5'-NTTN-3' sequence is 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'. The PAM sequence may be 5' to the target sequence.

The 5'-NTTN-3' sequence may be immediately adjacent to the target sequence or, for example, within a small number (e.g., 1, 2, 3, 4, or 5) of nucleotides of the target sequence. In some embodiments the 5'-NTTN-3' sequence is 5'-NTTY-3', 5'-NTTC-3', 5'-NTTT-3', 5'-NTTA-3', 5'-NTTB-3', 5'-NTTG-3', 5'-CTTY-3', 5'-DTTR-3', 5'-CTTR-3', 5'-DTTT-3', 5'-ATTN-3', or 5'-GTTN-3', wherein Y is C or T, B is any nucleotide except for A, D is any nucleotide except for C, and R is A or G. In some embodiments, the 5'-NTTN-3' sequence is 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'. In some embodiments, the RNA guide is designed to bind to a first strand of a double-stranded target nucleic acid (i.e., the non-PAM strand), and the 5'-NTTN-3' PAM sequence is present in the second, complementary strand (i.e., the PAM strand). In some embodiments, the RNA guide binds to a region on the non-PAM strand that is complementary to a target sequence on the PAM strand, which is adjacent to a 5'-NAAN-3' sequence.

In some embodiments, the target sequence is present in a cell. In some embodiments, the target sequence is present in the nucleus of the cell. In some embodiments, the target sequence is endogenous to the cell. In some embodiments, the target sequence is a genomic DNA. In some embodiments, the target sequence is a chromosomal DNA. In some embodiments, the target sequence is a protein-coding gene or a functional region thereof, such as a coding region, or a regulatory element, such as a promoter, enhancer, a 5' or 3' untranslated region, etc.

In some embodiments, the target sequence is present in a readily accessible region of the target sequence. In some embodiments, the target sequence is in an exon of a target gene. In some embodiments, the target sequence is across an exon-intron junction of a target gene. In some embodiments, the target sequence is present in a non-coding region, such as a regulatory region of a gene.

B. Gene Editing

In some embodiments, the Cas12i polypeptide has enzymatic activity (e.g., nuclease activity). In some embodiments, the Cas12i polypeptide induces one or more DNA double-stranded breaks in the cell. In some embodiments, the Cas12i polypeptide induces one or more DNA single-stranded breaks in the cell. In some embodiments, the Cas12i polypeptide induces one or more DNA nicks in the cell. In some embodiments, DNA breaks and/or nicks result in formation of one or more indels (e.g., one or more deletions).

In some embodiments, an RNA guide disclosed herein forms a complex with the Cas12i polypeptide and directs the Cas12i polypeptide to a target sequence adjacent to a 5'-NTTN-3' sequence. In some embodiments, the complex induces a deletion (e.g., a nucleotide deletion or DNA deletion) adjacent to the 5'-NTTN-3' sequence. In some embodiments, the complex induces a deletion adjacent to a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the complex induces a deletion adjacent to a T/C-rich sequence.

In some embodiments, the deletion is downstream of a 5'-NTTN-3' sequence. In some embodiments, the deletion is downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion is downstream of a T/C-rich sequence.

In some embodiments, the deletion alters expression of the HAO1 gene. In some embodiments, the deletion alters function of the HAO1 gene. In some embodiments, the deletion inactivates the HAO1 gene. In some embodiments, the deletion is a frameshifting deletion. In some embodiments, the deletion is a non-frameshifting deletion. In some embodiments, the deletion leads to cell toxicity or cell death (e.g., apoptosis).

In some embodiments, the deletion starts within about 5 to about 15 nucleotides (e.g., about 3, 4, 5, 6, 7, 8, 9, 10, 11, 12, 13, 14, 15, 16, or 17 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence.

In some embodiments, the deletion starts within about 5 to about 10 nucleotides (e.g., about 3, 4, 5, 6, 7, 8, 9, 10, 11, or 12 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence.

In some embodiments, the deletion starts within about 10 to about 15 nucleotides (e.g., about 8, 9, 10, 11, 12, 13, 14, 15, 16, or 17 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence.

In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of a T/C-rich sequence.

In some embodiments, the deletion ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion ends within about 20 to about 25 nucleotides (e.g., about 17, 18, 19, 20, 21, 22, 23, 24, 25, 26, 27, or 28 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 25 nucleotides (e.g., about 17, 18, 19, 20, 21, 22, 23, 24, 25, 26, 27, or 28 nucleotides) downstream of a T/C-rich sequence.

In some embodiments, the deletion ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion ends within about 25 to about 30 nucleotides (e.g., about 22, 23, 24, 25, 26, 27, 28, 29, 30, 31, 32, or 33 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 25 to about 30 nucleotides (e.g., about 22, 23, 24, 25, 26, 27, 28, 29, 30, 31, 32, or 33 nucleotides) downstream of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides and ends within about 20 to about 25 nucleotides (e.g., about 17, 18, 19, 20, 21, 22, 23, 24, 25, 26, 27, or 28 nucleotides) (e.g., about 3, 4, 5, 6, 7, 8, 9, 10, 11, or 12 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion is up to about 40 nucleotides in length (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides). In some embodiments, the deletion is between about 4 nucleotides and about 40 nucleotides in length (e.g., about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides). In some embodiments, the deletion is between about 4 nucleotides and about 25 nucleotides in length (e.g., about 3, 4, 5, 6, 7, 8, 9, 10, 11, 12, 13, 14, 15, 16, 17, 18, 19, 20, 21, 22, 23, 24, 25, 26, 27, or 28 nucleotides). In some embodiments, the deletion is between about 10 nucleotides and about 25 nucleotides in length (e.g., about 7, 8, 9, 10, 11, 12, 13, 14, 15, 16, 17, 18, 19, 20, 21, 22, 23, 24, 25, 26, 27, or 28 nucleotides). In some embodiments, the deletion is between about 10 nucleotides and about 15 nucleotides in length (e.g., about 7, 8, 9, 10, 11, 12, 13, 14, 15, 16, or 17 nucleotides).

In some embodiments, the methods described herein are used to engineer a cell comprising a deletion as described herein in an HAO1 gene. In some embodiments, the methods are carried out using a complex comprising a Cas12i enzyme as described herein and an RNA guide comprising a direct repeat and a spacer as described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, an RNA guide has a sequence of any one of SEQ ID NOs: 967-1023.

In some embodiments, the RNA guide targeting HAO1 is encoded in a plasmid. In some embodiments, the RNA guide targeting HAO1 is synthetic or purified RNA. In some embodiments, the Cas12i polypeptide is encoded in a plasmid. In some embodiments, the Cas12i polypeptide is encoded by an RNA that is synthetic or purified.

C. Delivery

Components of any of the gene editing systems disclosed herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, adeno-associated virus (AAV)), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, the method comprises delivering one or more nucleic acids (e.g., nucleic acids encoding the Cas12i polypeptide, RNA guide, donor DNA, etc.), one or more transcripts thereof, and/or a pre-formed RNA guide/Cas12i polypeptide complex to a cell, where a ternary complex is formed. In some embodiments, an RNA guide and an RNA encoding a Cas12i polypeptide are delivered together in a single composition. In some embodiments, an RNA guide and an RNA encoding a Cas12i polypeptide are delivered in separate compositions. In some embodiments, an RNA guide and an RNA encoding a Cas12i polypeptide delivered in separate compositions are delivered using the same delivery technology. In some embodiments, an RNA guide and an RNA encoding a Cas12i polypeptide delivered in separate compositions are delivered using different delivery technologies. Exemplary intracellular delivery methods, include, but are not limited to: viruses, such as AAV, or virus-like agents; chemical-based transfection methods, such as those using calcium phosphate, dendrimers, liposomes, lipid nanoparticles, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnectofection or magnet assisted transfection, particle bombardment; and hybrid methods, such as nucleofection. In some embodiments, a lipid nanoparticle comprises an mRNA encoding a Cas12i polypeptide, an RNA guide, or an mRNA encoding a Cas12i polypeptide and an RNA guide. In some embodiments, the mRNA encoding the Cas12i polypeptide is a transcript of the nucleotide sequence set forth in SEQ ID NO: 921 or SEQ ID NO: 955 or a variant thereof. In some embodiments, the present application further provides cells produced by such methods, and organisms (such as animals, plants, or fungi) comprising or produced from such cells.

D. Genetically Modified Cells

Any of the gene editing systems disclosed herein can be delivered to a variety of cells. In some embodiments, the cell is an isolated cell. In some embodiments, the cell is in cell culture or a co-culture of two or more cell types. In some embodiments, the cell is ex vivo. In some embodiments, the cell is obtained from a living organism and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the cell is an archaeal cell or derived from an archaeal cell.

In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, CHO, and transgenic varieties thereof. Cell lines are available from a variety of sources known to those with skill in the art (see, e.g., the American Type Culture Collection (ATCC) (Manassas, Va.)). In some embodiments, the cell is an immortal or immortalized cell.

In some embodiments, the cell is a primary cell. In some embodiments, the cell is a stem cell such as a totipotent stem cell (e.g., omnipotent), a pluripotent stem cell, a multipotent stem cell, an oligopotent stem cell, or an unipotent stem cell. In some embodiments, the cell is an induced pluripotent stem cell (iPSC) or derived from an iPSC. In some embodiments, the cell is a differentiated cell. For example, in some embodiments, the differentiated cell is a liver cell (e.g., a hepatocyte), a biliary cell (e.g., a cholangiocyte), a stellate cell, a Kupffer cell, a liver sinusoidal endothelial cell, a muscle cell (e.g., a myocyte), a fat cell (e.g., an adipocyte), a bone cell (e.g., an osteoblast, osteocyte, osteoclast), a blood cell (e.g., a monocyte, a lymphocyte, a neutrophil, an eosinophil, a basophil, a macrophage, a erythrocyte, or a platelet), a nerve cell (e.g., a neuron), an epithelial cell, an immune cell (e.g., a lymphocyte, a neutrophil, a monocyte, or a macrophage), a fibroblast, or a sex cell. In some embodiments, the cell is a terminally differentiated cell. For example, in some embodiments, the terminally differentiated cell is a neuronal cell, an adipocyte, a cardiomyocyte, a skeletal muscle cell, an epidermal cell, or a gut cell. In some embodiments, the cell is an immune cell. In some embodiments, the immune cell is a T cell. In some embodiments, the immune cell is a B cell. In some embodiments, the immune cell is a Natural Killer (NK) cell. In some embodiments, the immune cell is a Tumor Infiltrating Lymphocyte (TIL). In some embodiments, the cell is a mammalian cell, e.g., a human cell or a murine cell. In some embodiments, the murine cell is derived from a wild-type mouse, an immunosuppressed mouse, or a disease-specific mouse model. In some embodiments, the cell is a cell within a living tissue, organ, or organism.

Any of the genetically modified cells produced using any of the gene editing system disclosed herein is also within the scope of the present disclosure. Such modified cells may comprise a disrupted HAO1 gene.

Compositions, vectors, nucleic acids, RNA guides and cells disclosed herein may be used in therapy. Compositions, vectors, nucleic acids, RNA guides and cells disclosed herein may be used in methods of treating a disease or condition in a subject. In some embodiments, the disease or condition is Any suitable delivery or administration method known in the art may be used to deliver compositions, vectors, nucleic acids, RNA guides and cells disclosed herein. Such methods may involve contacting a target sequence with a composition, vector, nucleic acid, or RNA guide disclosed herein. Such methods may involve a method of editing an HAO1 sequence as disclosed herein. In some embodiments, a cell engineered using an RNA guide disclosed herein is used for ex vivo gene therapy.

IV. Therapeutic Applications

Any of the gene editing systems or modified cells generated using such a gene editing system as disclosed herein may be used for treating a disease that is associated with the HAO1 gene, for example, primary hyperoxaluria (PH). In some embodiments, the PH is PH1, PH2, or PH3. In specific examples, the target disease is PH1.

The gene editing system, pharmaceutical composition or kit comprising such, and any of the RNA guides disclosed herein may be used for treating primary hyperoxaluria (PH) in a subject. PH is a rare genetic disorder effecting subjects of all ages from infants to elderly. PH includes three subtypes involving genetic defects that alter the expression of three distinct proteins. PH1 involves alanine-glyoxylate aminotransferase, or AGT/AGT1. PH2 involves glyoxylate/hydroxypyruvate reductase, or GR/HPR, and PH3 involves 4-hydroxy-2-oxoglutarate aldolase, or HOGA.

In PH1, excess oxalate can also combine with calcium to form calcium oxalate in the kidney and other organs. Deposits of calcium oxalate can produce widespread deposition of calcium oxalate (nephrocalcinosis) or formation of kidney and bladder stones (urolithiasis) and lead to kidney damage. Common kidney complications in PH1 include blood in the urine (hematuria), urinary tract infections, kidney damage, and end-stage renal disease (ESRD). Over time, kidneys in patients with PH1 may begin to fail, and levels of oxalate may rise in the blood. Deposition of oxalate in tissues throughout the body, e.g., systemic oxalosis, may occur due to high blood levels of oxalate and can lead to complications in bone, skin, and eye. Patients with PH1 normally have kidney failure at an early age, with renal dialysis or dual kidney/liver organ transplant as the only treatment options.

In some embodiments, provided herein is a method for treating a target disease as disclosed herein (e.g., PH such as PH1) comprising administering to a subject (e.g., a human patient) in need of the treatment any of the gene editing systems disclosed herein. The gene editing system may be delivered to a specific tissue or specific type of cells where the gene edit is needed. The gene editing system may comprise LNPs encompassing one or more of the components, one or more vectors (e.g., viral vectors) encoding one or more of the components, or a combination thereof. Components of the gene editing system may be formulated to form a pharmaceutical composition, which may further comprise one or more pharmaceutically acceptable carriers.

In some embodiments, modified cells produced using any of the gene editing systems disclosed herein may be administered to a subject (e.g., a human patient) in need of the treatment. The modified cells may comprise a substitution, insertion, and/or deletion described herein. In some examples, the modified cells may include a cell line modified by a CRISPR nuclease, reverse transcriptase polypeptide, and editing template RNA (e.g., RNA guide and RT donor RNA). In some instances, the modified cells may be a heterogenous population comprising cells with different types of gene edits. Alternatively, the modified cells may comprise a substantially homogenous cell population (e.g., at least 80% of the cells in the whole population) comprising one particular gene edit in the HAO1 gene. In some examples, the cells can be suspended in a suitable media.

In some embodiments, provided herein is a composition comprising the gene editing system or components thereof. Such a composition can be a pharmaceutical composition. A pharmaceutical composition that is useful may be prepared, packaged, or sold in a formulation suitable for oral, rectal, vaginal, parenteral, topical, pulmonary, intranasal, intralesional, buccal, ophthalmic, intravenous, intra-organ or another route of administration. A pharmaceutical composition of the disclosure may be prepared, packaged, or sold in bulk, as a single unit dose, or as a plurality of single unit doses. As used herein, a “unit dose” is discrete amount of the pharmaceutical composition (e.g., the gene editing system or components thereof), which would be administered to a subject or a convenient fraction of such a dosage such as, for example, one-half or one-third of such a dosage.

In some embodiments, a pharmaceutical composition comprising the gene editing system or components thereof as described herein may be administered to a subject in need thereof, e.g., one who suffers from a liver disease associated with the HAO1 gene. In some instances, the gene editing system or components thereof may be delivered to specific cells or tissue (e.g., to liver cells), where the gene editing system could function to genetically modify the HAO1 gene in such cells.

A formulation of a pharmaceutical composition suitable for parenteral administration may comprise the active agent (e.g., the gene editing system or components thereof or the modified cells) combined with a pharmaceutically acceptable carrier, such as sterile water or sterile isotonic saline. Such a formulation may be prepared, packaged, or sold in a form suitable for bolus administration or for continuous administration. Some injectable formulations may be prepared, packaged, or sold in unit dosage form, such as in ampules or in multi-dose containers containing a preservative. Some formulations for parenteral administration include, but are not limited to, suspensions, solutions, emulsions in oily or aqueous vehicles, pastes, and implantable sustained-release or biodegradable formulations. Some formulations may further comprise one or more additional ingredients including, but not limited to, suspending, stabilizing, or dispersing agents.

The pharmaceutical composition may be in the form of a sterile injectable aqueous or oily suspension or solution. This suspension or solution may be formulated according to the known art, and may comprise, in addition to the cells, additional ingredients such as the dispersing agents, wetting agents, or suspending agents described herein. Such sterile injectable formulation may be prepared using a non-toxic parenterally-acceptable diluent or solvent, such as water or saline. Other acceptable diluents and solvents include, but are not limited to, Ringer's solution, isotonic sodium chloride solution, and fixed oils such as synthetic mono- or di-glycerides. Other parentally-administrable formulations which that are useful include those which may comprise the cells in a packaged form, in a liposomal preparation, or as a component of a biodegradable polymer system. Some compositions for sustained release or implantation may comprise pharmaceutically acceptable polymeric or hydrophobic materials such as an emulsion, an ion exchange resin, a sparingly soluble polymer, or a sparingly soluble salt.

V. Kits and Uses Thereof

The present disclosure also provides kits that can be used, for example, to carry out a method described herein for genetical modification of the HAO1 gene. In some embodiments, the kits include an RNA guide and a Cas12i polypeptide. In some embodiments, the kits include a polynucleotide that encodes such a Cas12i polypeptide, and optionally the polynucleotide is comprised within a vector, e.g., as described herein. The Cas12i polypeptide and the RNA guide (e.g., as a ribonucleoprotein) can be packaged within the same or other vessel within a kit or system or can be packaged in separate vials or other vessels, the contents of which can be mixed prior to use. The kits can additionally include, optionally, a buffer and/or instructions for use of the RNA guide and Cas12i polypeptide.

In some embodiments, the kit may be useful for research purposes. For example, in some embodiments, the kit may be useful to study gene function.

All references and publications cited herein are hereby incorporated by reference.

Additional Embodiments

Provided below are additional embodiments, which are also within the scope of the present disclosure.

Embodiment 1: A composition comprising an RNA guide, wherein the RNA guide comprises (i) a spacer sequence that is substantially complementary or completely complementary to a region on a non-PAM strand (the complementary sequence of a target sequence) within an HAO1 gene and (ii) a direct repeat sequence; wherein the target sequence is adjacent to a protospacer adjacent motif (PAM) comprising the sequence 5'-NTTN-3'.

In Embodiment 1, the target sequence may be within exon 1, exon 2, exon 3, exon 4, exon 5, exon 6, or exon 7 of the HAO1 gene. In some examples, the HAO1 gene comprises the sequence of SEQ ID NO: 928, the reverse complement of SEQ ID NO: 928, a variant of SEQ ID NO: 928, or the reverse complement of a variant of SEQ ID NO: 928.

In Embodiment 1, the spacer sequence may comprise: (a) nucleotide 1 through nucleotide 16 of a sequence that is at least 90% identical to a sequence of any one of SEQ ID NOs: 466-920; (b) nucleotide 1 through nucleotide 17 of a sequence that is at least 90% identical to a sequence of any one of SEQ ID NOs: 466-920; (c) nucleotide 1 through nucleotide 18 of a sequence that is at least 90% identical to a sequence of any one of SEQ ID NOs: 466-920; (d) nucleotide 1 through nucleotide 19 of a sequence that is at least 90% identical to a sequence of any one of SEQ ID NOs: 466-920; (e) nucleotide 1 through nucleotide 20 of a sequence that is at least 90% identical to a sequence of any one of SEQ ID NOs: 466-920; (f) nucleotide 1 through nucleotide 21 of a sequence that is at least 90% identical to a sequence of any one of SEQ ID NOs: 466-920; (g) nucleotide 1 through nucleotide 22 of a sequence that is at least 90% identical to a sequence of any one of SEQ ID NOs: 466-920; (h) nucleotide 1 through nucleotide 23 of a sequence that is at least 90% identical to a sequence of any one of SEQ ID NOs: 466-920; (i) nucleotide 1 through nucleotide 24 of a sequence that is at least 90% identical to a sequence of any one of SEQ ID NOs: 466-920; (j) nucleotide 1 through nucleotide 25 of a sequence that is at least 90% identical to a sequence of any one of SEQ ID NOs: 466-920; (k) nucleotide 1 through nucleotide 26 of a sequence that is at least 90% identical to a sequence of any one of SEQ ID NOs: 466-920; (l) nucleotide 1 through nucleotide 27 of a sequence that is at least 90% identical to a sequence of any one of SEQ ID NOs: 466-920; (m) nucleotide 1 through nucleotide 28 of a sequence that is at least 90% identical to a sequence of any one of SEQ ID NOs: 466-920; (n) nucleotide 1 through nucleotide 29 of a sequence that is at least 90% identical to a sequence of any one of SEQ ID NOs: 466-920; or (o) nucleotide 1 through nucleotide 30 of a sequence that is at least 90% identical to a sequence of any one of SEQ ID NOs: 466-920.

In any of the composition of Embodiment 1, the spacer sequence may comprise: (a) nucleotide 1 through nucleotide 16 of any one of SEQ ID NOs: 466-920; (b) nucleotide 1 through nucleotide 17 of any one of SEQ ID NOs: 466-920; (c) nucleotide 1 through nucleotide 18 of any one of SEQ ID NOs: 466-920; (d) nucleotide 1 through nucleotide 19 of any one of SEQ ID NOs: 466-920; (e) nucleotide 1 through nucleotide 20 of any one of SEQ ID NOs: 466-920; (f) nucleotide 1 through nucleotide 21 of any one of SEQ ID NOs: 466-920; (g) nucleotide 1 through nucleotide 22 of any one of SEQ ID NOs: 466-920; (h) nucleotide 1 through nucleotide 23 of any one of SEQ ID NOs: 466-920; (i) nucleotide 1 through nucleotide 24 of any one of SEQ ID NOs: 466-920; (j) nucleotide 1 through nucleotide 25 of any one of SEQ ID NOs: 466-920; (k) nucleotide 1 through nucleotide 26 of any one of SEQ ID NOs: 466-920; (l) nucleotide 1 through nucleotide 27 of any one of SEQ ID NOs: 466-920; (m) nucleotide 1 through nucleotide 28 of any one of SEQ ID NOs: 466-920; (n) nucleotide 1 through nucleotide 29 of any one of SEQ ID NOs: 466-920; or (o) nucleotide 1 through nucleotide 30 of any one of SEQ ID NOs: 466-920.

In any of the composition of Embodiment 1, the direct repeat sequence may comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; (or aa) SEQ ID NO: 10 or a portion thereof).

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof).

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; (or o) SEQ ID NO: 954 or a portion thereof.

In some examples, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof).

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof).

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof).

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof).

In some examples, the spacer sequence is substantially complementary or completely complementary to the complement of a sequence of any one of SEQ ID NOs: 11-465.

In any of the composition of Embodiment 1, the PAM may comprise the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence.

In some examples, the RNA guide has a sequence that is at least 90% identical to a sequence of any one of SEQ ID NOs: 967-1023.

In some examples, the RNA guide has the sequence of any one of SEQ ID NOs: 967-1023.

Embodiment 2: The composition of Embodiment 1 may further comprise a Cas12i polypeptide or a polyribonucleotide encoding a Cas12i polypeptide, which can be one of the following: (a) a Cas12i2 polypeptide comprising a sequence that is at least 90% identical to the sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence that is at least 90% identical to the sequence of SEQ ID NO: 956, SEQ ID NO: 957, or SEQ ID NO: 958; (c) a Cas12i1 polypeptide comprising a sequence that is at least 90% identical to the sequence of SEQ ID NO: 965; or (d) a Cas12i3 polypeptide comprising a sequence that is at least 90% identical to the sequence of SEQ ID NO: 966.

In specific examples, the Cas12i polypeptide is: (a) a Cas12i2 polypeptide comprising a sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence of SEQ ID NO: 956, SEQ ID NO: 957, or SEQ ID NO: 958; (c) a Cas12i1 polypeptide comprising a sequence of SEQ ID NO: 965; or (d) a Cas12i3 polypeptide comprising a sequence of SEQ ID NO: 966.

In any of the compositions of Embodiment 2, the RNA guide and the Cas12i polypeptide may form a ribonucleoprotein complex. In some examples, the ribonucleoprotein complex binds a target nucleic acid. In some examples, the composition is present within a cell.

In any of the compositions of Embodiment 2, the RNA guide and the Cas12i polypeptide may be encoded in a vector, e.g., expression vector. In some examples, the RNA guide and the Cas12i polypeptide are encoded in a single vector. In other examples, the RNA guide is encoded in a first vector and the Cas12i polypeptide is encoded in a second vector.

Embodiment 3: A vector system comprising one or more vectors encoding an RNA guide disclosed herein and a Cas12i polypeptide. In some examples, the vector system comprises a first vector encoding an RNA guide disclosed herein and a second vector encoding a Cas12i polypeptide. The vectors may be expression vectors.

Embodiment 4: A composition comprising an RNA guide and a Cas12i polypeptide, wherein the RNA guide comprises (i) a spacer sequence that is substantially complementary or completely complementary to a region on a non-PAM strand (the complementary sequence of a target sequence) within an HAO1 gene; and (ii) a direct repeat sequence.

In some examples, the target sequence is within exon 1, exon 2, exon 3, exon 4, exon 5, exon 6, or exon 7 of the HAO1 gene, which may comprise the sequence of SEQ ID NO: 928, the reverse complement of SEQ ID NO: 928, a variant of the sequence of SEQ ID NO: 928, or the reverse complement of a variant of SEQ ID NO: 928.

In some examples, the spacer sequence comprises: (a) nucleotide 1 through nucleotide 16 of a sequence that is at least 90% identical to a sequence of any one of SEQ ID NOs: 466-920; (b) nucleotide 1 through nucleotide 17 of a sequence that is at least 90% identical to a sequence of any one of SEQ ID NOs: 466-920; (c) nucleotide 1 through nucleotide 18 of a sequence that is at least 90% identical to a sequence of any one of SEQ ID NOs: 466-920; (d) nucleotide 1 through nucleotide 19 of a sequence that is at least 90% identical to a sequence of any one of SEQ ID NOs: 466-920; (e) nucleotide 1 through nucleotide 20 of a sequence that is at least 90% identical to a sequence of any one of SEQ ID NOs: 466-920; (f) nucleotide 1 through nucleotide 21 of a sequence that is at least 90% identical to a sequence of any one of SEQ ID NOs: 466-920; (g) nucleotide 1 through nucleotide 22 of a sequence that is at least 90% identical to a sequence of any one of SEQ ID NOs: 466-920; (h) nucleotide 1 through nucleotide 23 of a sequence that is at least 90% identical to a sequence of any one of SEQ ID NOs: 466-920; (i) nucleotide 1 through nucleotide 24 of a sequence that is at least 90% identical to a sequence of any one of SEQ ID NOs: 466-920; (j) nucleotide 1 through nucleotide 25 of a sequence that is at least 90% identical to a sequence of any one of SEQ ID NOs: 466-920; (k) nucleotide 1 through nucleotide 26 of a sequence that is at least 90% identical to a sequence of any one of SEQ ID NOs: 466-920; (l) nucleotide 1 through nucleotide 27 of a sequence that is at least 90% identical to a sequence of any one of SEQ ID NOs: 466-920; (m) nucleotide 1 through nucleotide 28 of a sequence that is at least 90% identical to a sequence of any one of SEQ ID NOs: 466-920; (n) nucleotide 1 through nucleotide 29 of a sequence that is at least 90% identical to a sequence of any one of SEQ ID NOs: 466-920; or (o) nucleotide 1 through nucleotide 30 of a sequence that is at least 90% identical to a sequence of any one of SEQ ID NOs: 466-920.

In some examples, the spacer sequence comprises: (a) nucleotide 1 through nucleotide 16 of any one of SEQ ID NOs: 466-920; (b) nucleotide 1 through nucleotide 17 of any one of SEQ ID NOs: 466-920; (c) nucleotide 1 through nucleotide 18 of any one of SEQ ID NOs: 466-920; (d) nucleotide 1 through nucleotide 19 of any one of SEQ ID NOs: 466-920; (e) nucleotide 1 through nucleotide 20 of any one of SEQ ID NOs: 466-920; (f) nucleotide 1 through nucleotide 21 of any one of SEQ ID NOs: 466-920; (g) nucleotide 1 through nucleotide 22 of any one of SEQ ID NOs: 466-920; (h) nucleotide 1 through nucleotide 23 of any one of SEQ ID NOs: 466-920; (i) nucleotide 1 through nucleotide 24 of any one of SEQ ID NOs: 466-920; (j) nucleotide 1 through nucleotide 25 of any one of SEQ ID NOs: 466-920; (k) nucleotide 1 through nucleotide 26 of any one of SEQ ID NOs: 466-920; (l) nucleotide 1 through nucleotide 27 of any one of SEQ ID NOs: 466-920; (m) nucleotide 1 through nucleotide 28 of any one of SEQ ID NOs: 466-920; (n) nucleotide 1 through nucleotide 29 of any one of SEQ ID NOs: 466-920; or (o) nucleotide 1 through nucleotide 30 of any one of SEQ ID NOs: 466-920.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof).

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof.

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; or (o) SEQ ID NO: 954 or a portion thereof.

In some embodiments, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof.

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof.

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof.

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof.

In any of the compositions of Embodiment 4, the spacer sequence may be substantially complementary or completely complementary to the complement of a sequence of any one of SEQ ID NOs: 11-465.

In some examples, the target sequence is adjacent to a protospacer adjacent motif (PAM) comprising the sequence 5'-NTTN-3'. In some examples, the PAM comprises the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence. In some examples, the target sequence is within 1, 2, 3, 4, or 5 nucleotides of the PAM sequence.

In any of the composition of Embodiment 4, the Cas12i polypeptide is: (a) a Cas12i2 polypeptide comprising a sequence that is at least 90% identical to the sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence that is at least 90% identical to the sequence of SEQ ID NO: 956, SEQ ID NO: 957, or SEQ ID NO: 958; (c) a Cas12i1 polypeptide comprising a sequence that is at least 90% identical to the sequence of SEQ ID NO: 965; (or (d) a Cas12i3 polypeptide comprising a sequence that is at least 90% identical to the sequence of SEQ ID NO: 966.

In some examples, the Cas12i polypeptide is: (a) a Cas12i2 polypeptide comprising a sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence of SEQ ID NO: 956, SEQ ID NO: 957, or SEQ ID NO: 958; (c) a Cas12i1 polypeptide comprising a sequence of SEQ ID NO: 965; or (d) a Cas12i3 polypeptide comprising a sequence of SEQ ID NO: 966.

In any of the composition of Embodiment 4, the RNA guide and the Cas12i polypeptide may form a ribonucleoprotein complex. In some examples, the ribonucleoprotein complex binds a target nucleic acid.

In any of the composition of Embodiment 4, the composition may be present within a cell.

In any of the composition of Embodiment 4, the RNA guide and the Cas12i polypeptide may be encoded in a vector, e.g., expression vector. In some examples, the RNA guide and the Cas12i polypeptide are encoded in a single vector. In other examples, the RNA guide is encoded in a first vector and the Cas12i polypeptide is encoded in a second vector.

Embodiment 5: A vector system comprising one or more vectors encoding an RNA guide disclosed herein and a Cas12i polypeptide. In some examples, the vector system comprises a first vector encoding an RNA guide disclosed herein and a second vector encoding a Cas12i polypeptide. In some examples, the vectors are expression vectors.

Embodiment 6: An RNA guide comprising (i) a spacer sequence that is substantially complementary or completely complementary to a region on a non-PAM strand (the complementary sequence of a target sequence) within an HAO1 gene, and (ii) a direct repeat sequence.

In some examples, the target sequence is within exon 1, exon 2, exon 3, exon 4, exon 5, exon 6, or exon 7 of the HAO1 gene, which may comprise the sequence of SEQ ID NO: 928, the reverse complement of SEQ ID NO: 928, a variant of the sequence of SEQ ID NO: 928, or the reverse complement of a variant of SEQ ID NO: 928.

In some examples, the spacer sequence comprises: (a) nucleotide 1 through nucleotide 16 of a sequence that is at least 90% identical to a sequence of any one of SEQ ID NOs: 466-920; (b) nucleotide 1 through nucleotide 17 of a sequence that is at least 90% identical to a sequence of any one of SEQ ID NOs: 466-920; (c) nucleotide 1 through nucleotide 18 of a sequence that is at least 90% identical to a sequence of any one of SEQ ID NOs: 466-920; (d) nucleotide 1 through nucleotide 19 of a sequence that is at least 90% identical to a sequence of any one of SEQ ID NOs: 466-920; (e) nucleotide 1 through nucleotide 20 of a sequence that is at least 90% identical to a sequence of any one of SEQ ID NOs: 466-920; (f) nucleotide 1 through nucleotide 21 of a sequence that is at least 90% identical to a sequence of any one of SEQ ID NOs: 466-920; (g) nucleotide 1 through nucleotide 22 of a sequence that is at least 90% identical to a sequence of any one of SEQ ID NOs: 466-920; (h) nucleotide 1 through nucleotide 23 of a sequence that is at least 90% identical to a sequence of any one of SEQ ID NOs: 466-920; (i) nucleotide 1 through nucleotide 24 of a sequence that is at least 90% identical to a sequence of any one of SEQ ID NOs: 466-920; (j) nucleotide 1 through nucleotide 25 of a sequence that is at least 90% identical to a sequence of any one of SEQ ID NOs: 466-920; (k) nucleotide 1 through nucleotide 26 of a sequence that is at least 90% identical to a sequence of any one of SEQ ID NOs: 466-920; (l) nucleotide 1 through nucleotide 27 of a sequence that is at least 90% identical to a sequence of any one of SEQ ID NOs: 466-920; (m) nucleotide 1 through nucleotide 28 of a sequence that is at least 90% identical to a sequence of any one of SEQ ID NOs: 466-920; (n) nucleotide 1 through nucleotide 29 of a sequence that is at least 90% identical to a sequence of any one of SEQ ID NOs: 466-920; or (o) nucleotide 1 through nucleotide 30 of a sequence that is at least 90% identical to a sequence of any one of SEQ ID NOs: 466-920.

In some examples, the spacer sequence comprises: (a) nucleotide 1 through nucleotide 16 of any one of SEQ ID NOs: 466-920; (b) nucleotide 1 through nucleotide 17 of any one of SEQ ID NOs: 466-920; (c) nucleotide 1 through nucleotide 18 of any one of SEQ ID NOs: 466-920; (d) nucleotide 1 through nucleotide 19 of any one of SEQ ID NOs: 466-920; (e) nucleotide 1 through nucleotide 20 of any one of SEQ ID NOs: 466-920; (f) nucleotide 1 through nucleotide 21 of any one of SEQ ID NOs: 466-920; (g) nucleotide 1 through nucleotide 22 of any one of SEQ ID NOs: 466-920; (h) nucleotide 1 through nucleotide 23 of any one of SEQ ID NOs: 466-920; (i) nucleotide 1 through nucleotide 24 of any one of SEQ ID NOs: 466-920; (j) nucleotide 1 through nucleotide 25 of any one of SEQ ID NOs: 466-920; (k) nucleotide 1 through nucleotide 26 of any one of SEQ ID NOs: 466-920; (l) nucleotide 1 through nucleotide 27 of any one of SEQ ID NOs: 466-920; (m) nucleotide 1 through nucleotide 28 of any one of SEQ ID NOs: 466-920; (n) nucleotide 1 through nucleotide 29 of any one of SEQ ID NOs: 466-920; or (o) nucleotide 1 through nucleotide 30 of any one of SEQ ID NOs: 466-920.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof.

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; or (o) SEQ ID NO: 954 or a portion thereof.

In some examples, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof.

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959;

(d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof.

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof.

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof.

In any of the RNA guide of Embodiment 6, the spacer sequence may be substantially complementary or completely complementary to the complement of a sequence of any one of SEQ ID NOs: 11-465.

In any of the RNA guide of Embodiment 6, the target sequence may be adjacent to a protospacer adjacent motif (PAM) comprising the sequence 5'-NTTN-3', wherein N is any nucleotide. In some examples, the PAM comprises the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence. In other examples, the target sequence is within 1, 2, 3, 4, or 5 nucleotides of the PAM sequence.

In some examples, the RNA guide has a sequence that is at least 90% identical to a sequence of any one of SEQ ID NOs: 967-1023. In some specific examples, the RNA guide has the sequence of any one of SEQ ID NOs: 967-1023.

Embodiment 7: A nucleic acid encoding an RNA guide as described herein.

Embodiment 8: A vector comprising an RNA guide as described herein.

Embodiment 9: A cell comprising a composition, an RNA guide, a nucleic acid, or a vector as described herein. In some examples, the cell is a eukaryotic cell, an animal cell, a mammalian cell, a human cell, a primary cell, a cell line, a stem cell, or a hepatocyte.

Embodiment 10: A kit comprising a composition, an RNA guide, a nucleic acid, or a vector as described herein.

Embodiment 11: A method of editing an HAO1 sequence, the method comprising contacting an HAO1 sequence with a composition or an RNA guide as described herein. In some examples, the method is carried out in vitro. In other examples, the method is carried out ex vivo.

In some examples, the HAO1 sequence is in a cell.

In some examples, the composition or the RNA guide induces a deletion in the HAO1 sequence. In some examples, the deletion is adjacent to a 5'-NTTN-3' sequence, wherein N is any nucleotide. In some specific examples, the deletion is downstream of the 5'-NTTN-3' sequence. In some specific examples, the deletion is up to about 40 nucleotides in length. In some instances, the deletion is from about 4 nucleotides to 40 nucleotides, about 4 nucleotides to 25 nucleotides, about 10 nucleotides to 25 nucleotides, or about 10 nucleotides to 15 nucleotides in length.

In some examples, the deletion starts within about 5 nucleotides to about 15 nucleotides, about 5 nucleotides to about 10 nucleotides, or about 10 nucleotides to about 15 nucleotides of the 5'-NTTN-3' sequence.

In some examples, the deletion starts within about 5 nucleotides to about 15 nucleotides, about 5 nucleotides to about 10 nucleotides, or about 10 nucleotides to about 15 nucleotides downstream of the 5'-NTTN-3' sequence.

In some examples, the deletion ends within about 20 nucleotides to about 30 nucleotides, about 20 nucleotides to about 25 nucleotides, or about 25 nucleotides to about 30 nucleotides of the 5'-NTTN-3' sequence.

In some examples, the deletion ends within about 20 nucleotides to about 30 nucleotides, about 20 nucleotides to about 25 nucleotides, about 25 nucleotides to about 30 nucleotides downstream of the 5'-NTTN-3' sequence.

In some examples, the deletion starts within about 5 nucleotides to about 15 nucleotides downstream of the 5'-NTTN-3' sequence and ends within about 20 nucleotides to about 30 nucleotides downstream of the 5'-NTTN-3' sequence.

In some examples, the deletion starts within about 5 nucleotides to about 15 nucleotides downstream of the 5'-NTTN-3' sequence and ends within about 20 nucleotides to about 25 nucleotides downstream of the 5'-NTTN-3' sequence.

In some examples, the deletion starts within about 5 nucleotides to about 15 nucleotides downstream of the 5'-NTTN-3' sequence and ends within about 25 nucleotides to about 30 nucleotides downstream of the 5'-NTTN-3' sequence.

In some examples, the deletion starts within about 5 nucleotides to about 10 nucleotides downstream of the 5'-NTTN-3' sequence and ends within about 20 nucleotides to about 30 nucleotides downstream of the 5'-NTTN-3' sequence.

In some examples, the deletion starts within about 5 nucleotides to about 10 nucleotides downstream of the 5'-NTTN-3' sequence and ends within about 20 nucleotides to about 25 nucleotides downstream of the 5'-NTTN-3' sequence.

In some examples, the deletion starts within about 5 nucleotides to about 10 nucleotides downstream of the 5'-NTTN-3' sequence and ends within about 25 nucleotides to about 30 nucleotides downstream of the 5'-NTTN-3' sequence.

In some examples, the deletion starts within about 10 nucleotides to about 15 nucleotides downstream of the 5'-NTTN-3' sequence and ends within about 20 nucleotides to about 30 nucleotides downstream of the 5'-NTTN-3' sequence.

In some examples, the deletion starts within about 10 nucleotides to about 15 nucleotides downstream of the 5'-NTTN-3' sequence and ends within about 20 nucleotides to about 25 nucleotides downstream of the 5'-NTTN-3' sequence.

In some examples, the deletion starts within about 10 nucleotides to about 15 nucleotides downstream of the 5'-NTTN-3' sequence and ends within about 25 nucleotides to about 30 nucleotides downstream of the 5'-NTTN-3' sequence.

In some examples, the 5'-NTTN-3' sequence is 5'-CTTT-3', 5'-CTTC-3', 5'-GTTT-3', 5'-GTTC-3', 5'-TTTC-3', 5'-GTTA-3', or 5'-GTTG-3'.

In some examples, the deletion overlaps with a mutation in the HAO1 sequence. In some instances, the deletion overlaps with an insertion in the HAO1 sequence. In some instances, the deletion removes a repeat expansion of the HAO1 sequence or a portion thereof. In some instances, the deletion disrupts one or both alleles of the HAO1 sequence.

In any of the compositions, RNA guides, nucleic acids, vectors, cells, kits, or methods of Embodiments 1-10 described herein, the RNA guide may comprise the sequence of any one of SEQ ID NOs: 967-1023.

Embodiment 12: A method of treating primary hyperoxaluria (PH), which optionally is PH1, PH2, or PH3, in a subject, the method comprising administering any of the compositions, RNAs, or cells as described herein to the subject.

In any of the compositions, RNA guides, cells, kits, or methods described herein, the RNA guide and/or the polyribonucleotide encoding the Cas12i polypeptide may be comprised within a lipid nanoparticle. In some examples, the RNA guide and the polyribonucleotide encoding the Cas12i polypeptide are comprised within the same lipid nanoparticle. In other examples, the RNA guide and the polyribonucleotide encoding the Cas12i polypeptide are comprised within separate lipid nanoparticles.

Embodiment 13: An RNA guide comprising (i) a spacer sequence that is complementary to a target site within an HAO1 gene (the target site being on the non-PAM strand and complementary to a target sequence), and (ii) a direct repeat sequence, wherein the target sequence is any one of SEQ ID NOs: 1047, 1026, or 1025 or the reverse complement thereof.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof.

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; or (o) SEQ ID NO: 954 or a portion thereof.

In some examples, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof.

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959;

(k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof.

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof.

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof.

In some examples, the RNA guide has a sequence that is at least 90% identical to a sequence of any one of SEQ ID NOs: 989, 968, or 967. In some specific examples, the RNA guide has the sequence of any one of SEQ ID NOs: 989, 968, or 967.

In some examples, each of the first three nucleotides of the RNA guide comprises a 2'-O-methyl phosphorothioate modification.

In some examples, each of the last four nucleotides of the RNA guide comprises a 2'-O-methyl phosphorothioate modification.

In some examples, each of the first to last, second to last, and third to last nucleotides of the RNA guide comprises a 2'-O-methyl phosphorothioate modification, and wherein the last nucleotide of the RNA guide is unmodified.

In some examples, the RNA guide has a sequence that is at least 90% identical to a sequence of any one of SEQ ID NOs: 1082-1087. In some specific examples, the RNA guide has a sequence of any one of SEQ ID NOs: 1082-1087.

In some embodiments, an HAO1-targeting RNA guide comprises at least 90% identity to any one of SEQ ID NOs: 1082-1087. In some embodiments, an HAO1-targeting RNA guide comprises any one of SEQ ID NOs: 1082-1087. In some embodiments, an HAO1-targeting RNA guide comprising at least 90% identity to SEQ ID NO: 1083 or SEQ ID NO: 1084 binds the complementary region of HAO1 target sequence of SEQ ID NO: 1047 via base-pairing. In some embodiments, the HAO1-targeting RNA guide of SEQ ID NO: 1083 or SEQ ID NO: 1084 binds the complementary region of HAO1 target sequence of SEQ ID NO: 1047 via base-pairing. In some embodiments, an HAO1-targeting RNA guide comprising at least 90% identity to SEQ ID NO: 1085 or SEQ ID NO: 1086 binds the complementary region of HAO1 target sequence of SEQ ID NO: 1026 via base-pairing. In some embodiments, the HAO1-targeting RNA guide of SEQ ID NO: 1085 or SEQ ID NO: 1086 binds the complementary region of HAO1 target sequence of SEQ ID NO: 1026 via base-pairing. In some embodiments, an HAO1-targeting RNA guide comprising at least 90% identity to SEQ ID NO: 1087 or SEQ ID NO: 2293 binds the complementary region of HAO1 target sequence of SEQ ID NO: 1025 via base-pairing. In some embodiments, the HAO1-targeting RNA guide of SEQ ID NO: 1087 or SEQ ID NO: 2293 binds the complementary region of HAO1 target sequence of SEQ ID NO: 1025 via base-pairing.

Embodiment 14: A nucleic acid encoding the RNA guide of Embodiment 13 as described herein.

Embodiment 15: A vector comprising the nucleic acid of Embodiment 14 as described herein.

Embodiment 16: A vector system comprising one or more vectors encoding (i) the RNA guide of Embodiment 13 as described herein, and (ii) a Cas12i polypeptide. In some examples, the vector system comprises a first vector encoding the RNA guide and a second vector encoding the Cas12i polypeptide.

Embodiment 17: A cell comprising the RNA guide, the nucleic acid, the vector, or the vector system of Embodiments 13-16 as described herein. In some examples, the cell is a eukaryotic cell, an animal cell, a mammalian cell, a human cell, a primary cell, a cell line, a stem cell, or a T cell.

Embodiment 18: A kit comprising the RNA guide, the nucleic acid, the vector, or the vector system of Embodiments 13-16 as described herein.

Embodiment 19: A method of editing an HAO1 sequence, the method comprising contacting an HAO1 sequence with the RNA guide of Embodiment 13 as described herein. In some examples, the HAO1 sequence is in a cell.

In some examples, the RNA guide induces an indel (e.g., an insertion or deletion) in the HAO1 sequence.

Embodiment 20: A method of treating primary hyperoxaluria (PH), which optionally is PH1, PH2, or PH3, in a subject, the method comprising administering the RNA guide of Embodiment 12 as described herein to the subject.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are provided to further illustrate some embodiments of the present invention but are not intended to limit the scope of the invention; it will be understood by their exemplary nature that other procedures, methodologies, or techniques known to those skilled in the art may alternatively be used.

Example 1—Cas12i2-Mediated Editing of HAO1 Target Sites in HEK293T Cells

This Example describes the genomic editing of the HAO1 gene using Cas12i2 introduced into HEK293T cells.

Cas12i2 RNA guides (crRNAs) were designed and ordered from Integrated DNA Technologies (IDT). For initial guide screening in HEK293T cells, target sequences were designed by tiling the coding exons of HAO1 for 5'-NTTN-3' PAM sequences, and then spacer sequences were designed for the 20-bp target sequences downstream of the PAM sequence. The HAO1-targeting RNA guide sequences are shown in Table 7. In the figures, “E #T #” can also be represented as “exon #target #.”

TABLE 7 crRNA Sequences for HAO1

| Guide Name | PAM* | Target strand (Non-PAM Strand) | crRNA Sequence | Target Sequences |
|---|---|---|---|---|
| HAO1_E1T2 | CTTC | BS | AGAAAUCCGUCUUUCAU UGACGGCAAAGUCUAUA UAUGACUAU (SEQ ID NO: 967) | CAAAGTCTATATATGA CTAT (SEQ ID NO: 1025) |
| HAO1_E1T3 | CTTT | TS | AGAAAUCCGUCUUUCAU UGACGGGGAAGUACUGA UUUAGCAUG (SEQ ID NO: 968) | GGAAGTACTGATTTAG CATG (SEQ ID NO: 1026) |
| HAO1_E1T4 | CTTC | TS | AGAAAUCCGUCUUUCAU UGACGGAUCAUUUGCCC CAGACCUGU (SEQ ID NO: 969) | ATCATTTGCCCCAGAC CTGT (SEQ ID NO: 1027) |
| HAO1_E1T5 | CTTT | BS | AGAAAUCCGUCUUUCAU UGACGGGGCUGAUAAUA UUGCAGCAU (SEQ ID NO: 970) | GGCTGATAATATTGCA GCAT (SEQ ID NO: 1028) |

TABLE 7-continued

| crRNA Sequences for HAO1 | | | | |
|---|---|---|---|---|
| Guide Name | PAM* | Target strand (Non-PAM Strand) | crRNA Sequence | Target Sequences |
| HAO1_E1T6 | ATTT | BS | AGAAAUCCGUCUUUCAUUGACGGGUAUCAAUGAUUAUGAACAA (SEQ ID NO: 971) | GTATCAATGATTATGAACAA (SEQ ID NO: 1029) |
| HAO1_E1T7 | TTTG | BS | AGAAAUCCGUCUUUCAUUGACGGUAUCAAUGAUUAUGAACAAC (SEQ ID NO: 972) | TATCAATGATTATGAACAAC (SEQ ID NO: 1030) |
| HAO1_E1T9 | ATTA | BS | AGAAAUCCGUCUUUCAUUGACGGUGAACAACAUGCUAAAUCAG (SEQ ID NO: 973) | TGAACAACATGCTAAATCAG (SEQ ID NO: 1031) |
| HAO1_E1T11 | TTTA | TS | AGAAAUCCGUCUUUCAUUGACGGGCAUGUUGUUCAUAAUCAUU (SEQ ID NO: 974) | GCATGTTGTTCATAATCATT (SEQ ID NO: 1032) |
| HAO1_E1T12 | ATTT | TS | AGAAAUCCGUCUUUCAUUGACGGAGCAUGUUGUUCAUAAUCAU (SEQ ID NO: 975) | AGCATGTTGTTCATAATCAT (SEQ ID NO: 1033) |
| HAO1_E1T13 | TTTG | TS | AGAAAUCCGUCUUUCAUUGACGGGAAGUACUGAUUUAGCAUGU (SEQ ID NO: 976) | GAAGTACTGATTTAGCATGT (SEQ ID NO: 1034) |
| HAO1_E1T14 | ATTA | BS | AGAAAUCCGUCUUUCAUUGACGGCAGGUCUGGGGCAAAUGAUG (SEQ ID NO: 977) | CAGGTCTGGGGCAAATGATG (SEQ ID NO: 1035) |
| HAO1_E1T15 | TTTG | TS | AGAAAUCCGUCUUUCAUUGACGGCCCCAGACCUGUAAUAGUCA (SEQ ID NO: 978) | CCCCAGACCTGTAATAGTCA (SEQ ID NO: 1036) |
| HAO1_E1T16 | ATTT | TS | AGAAAUCCGUCUUUCAUUGACGGGCCCCAGACCUGUAAUAGUC (SEQ ID NO: 979) | GCCCCAGACCTGTAATAGTC (SEQ ID NO: 1037) |
| HAO1_E1T17 | TTTC | TS | AGAAAUCCGUCUUUCAUUGACGGUUCAUCAUUUGCCCCAGACC (SEQ ID NO: 980) | TTCATCATTTGCCCCAGACC (SEQ ID NO: 1038) |
| HAO1_E1T18 | GTTT | TS | AGAAAUCCGUCUUUCAUUGACGGCUUCAUCAUUUGCCCCAGAC (SEQ ID NO: 981) | CTTCATCATTTGCCCCAGAC (SEQ ID NO: 1039) |
| HAO1_E1T19 | TTTG | BS | AGAAAUCCGUCUUUCAUUGACGGAAUGCUGCAAUAUUAUCAGC (SEQ ID NO: 982) | AATGCTGCAATATTATCAGC (SEQ ID NO: 1040) |
| HAO1_E1T23 | TTTT | TS | AGAAAUCCGUCUUUCAUUGACGGCUUACCUGGAAAAUGCUGCA (SEQ ID NO: 983) | CTTACCTGGAAAATGCTGCA (SEQ ID NO: 1041) |
| HAO1_E1T24 | ATTT | TS | AGAAAUCCGUCUUUCAUUGACGGUCUUACCUGGAAAAUGCUGC (SEQ ID NO: 984) | TCTTACCTGGAAAATGCTGC (SEQ ID NO: 1042) |

TABLE 7-continued

| crRNA Sequences for HAO1 | | | | |
|---|---|---|---|---|
| Guide Name | PAM* | Target strand (Non-PAM Strand) | crRNA Sequence | Target Sequences |
| HAO1_E2T1 | CTTC | BS | AGAAAUCCGUCUUUCAUUGACGGUGUUUUAGGACAGAGGGUCA (SEQ ID NO: 985) | TGTTTTAGGACAGAGGGTCA (SEQ ID NO: 1043) |
| HAO1_E2T2 | CTTC | TS | AGAAAUCCGUCUUUCAUUGACGGCUCCUACCUCUCACAGUGGC (SEQ ID NO: 986) | CTCCTACCTCTCACAGTGGC (SEQ ID NO: 1044) |
| HAO1_E2T3 | TTTA | BS | AGAAAUCCGUCUUUCAUUGACGGAUUCUAGAUGGAAGCUGUAU (SEQ ID NO: 987) | ATTCTAGATGGAAGCTGTAT (SEQ ID NO: 1045) |
| HAO1_E2T4 | ATTC | BS | AGAAAUCCGUCUUUCAUUGACGGUAGAUGGAAGCUGUAUCCAA (SEQ ID NO: 988) | TAGATGGAAGCTGTATCCAA (SEQ ID NO: 1046) |
| HAO1_E2T5 | ATTC | TS | AGAAAUCCGUCUUUCAUUGACGGCGGAGCAUCCUUGGAUACAG (SEQ ID NO: 989) | CGGAGCATCCTTGGATACAG (SEQ ID NO: 1047) |
| HAO1_E2T6 | GTTG | BS | AGAAAUCCGUCUUUCAUUGACGGCUGAAACAGAUCUGUCGACU (SEQ ID NO: 990) | CTGAAACAGATCTGTCGACT (SEQ ID NO: 1048) |
| HAO1_E2T7 | TTTC | TS | AGAAAUCCGUCUUUCAUUGACGGAGCAACAUUCCGGAGCAUCC (SEQ ID NO: 991) | AGCAACATTCCGGAGCATCC (SEQ ID NO: 1049) |
| HAO1_E2T8 | GTTT | TS | AGAAAUCCGUCUUUCAUUGACGGCAGCAACAUUCCGGAGCAUC (SEQ ID NO: 992) | CAGCAACATTCCGGAGCATC (SEQ ID NO: 1050) |
| HAO1_E2T9 | GTTT | BS | AGAAAUCCGUCUUUCAUUGACGGUAGGACAGAGGGUCAGCAUG (SEQ ID NO: 993) | TAGGACAGAGGGTCAGCATG (SEQ ID NO: 1051) |
| HAO1_E2T10 | TTTT | BS | AGAAAUCCGUCUUUCAUUGACGGAGGACAGAGGGUCAGCAUGC (SEQ ID NO: 994) | AGGACAGAGGGTCAGCATGC (SEQ ID NO: 1052) |
| HAO1_E2T11 | TTTA | BS | AGAAAUCCGUCUUUCAUUGACGGGGACAGAGGGUCAGCAUGCC (SEQ ID NO: 995) | GGACAGAGGGTCAGCATGCC (SEQ ID NO: 1053) |
| HAO1_E3T1 | CTTT | BS | AGAAAUCCGUCUUUCAUUGACGGCUUUCUCAGCCUGUCAGUCC (SEQ ID NO: 996) | CTTTCTCAGCCTGTCAGTCC (SEQ ID NO: 1054) |
| HAO1_E3T2 | CTTT | BS | AGAAAUCCGUCUUUCAUUGACGGCUCAGCCUGUCAGUCCCUGG (SEQ ID NO: 997) | CTCAGCCTGTCAGTCCCTGG (SEQ ID NO: 1055) |
| HAO1_E3T3 | GTTC | TS | AGAAAUCCGUCUUUCAUUGACGGCCAGGGACUGACAGGCUGAG (SEQ ID NO: 998) | CCAGGGACTGACAGGCTGAG (SEQ ID NO: 1056) |

TABLE 7-continued crRNA Sequences for HAO1

| Guide Name | PAM* | Target strand (Non-PAM Strand) | crRNA Sequence | Target Sequences |
|---|---|---|---|---|
| HAO1_E3T4 | GTTC | BS | AGAAAUCCGUCUUUCAUUGACGGCUGGGCCACCUCCUCAAUUG (SEQ ID NO: 999) | CTGGGCCACCTCCTCAATTG (SEQ ID NO: 1057) |
| HAO1_E3T5 | CTTC | TS | AGAAAUCCGUCUUUCAUUGACGGAAUUGAGGAGGUGGCCCAGG (SEQ ID NO: 1000) | AATTGAGGAGGTGGCCCAGG (SEQ ID NO: 1058) |
| HAO1_E3T6 | CTTC | TS | AGAAAUCCGUCUUUCAUUGACGGUUCAAUUGAGGAGGUGGCCC (SEQ ID NO: 1001) | TTCAATTGAGGAGGTGGCCC (SEQ ID NO: 1059) |
| HAO1_E3T7 | CTTC | TS | AGAAAUCCGUCUUUCAUUGACGGCGCCACUUCUUCAAUUGAGG (SEQ ID NO: 1002) | CGCCACTTCTTCAATTGAGG (SEQ ID NO: 1060) |
| HAO1_E3T8 | CTTC | BS | AGAAAUCCGUCUUUCAUUGACGGGUUGGCUGCAACUGUAUAUC (SEQ ID NO: 1003) | GTTGGCTGCAACTGTATATC (SEQ ID NO: 1061) |
| HAO1_E3T9 | CTTC | TS | AGAAAUCCGUCUUUCAUUGACGGUCGGUCCUUGUAGAUAUACA (SEQ ID NO: 1004) | TCGGTCCTTGTAGATATACA (SEQ ID NO: 1062) |
| HAO1_E3T11 | CTTC | TS | AGAAAUCCGUCUUUCAUUGACGGUCUGCCUGCCGCACUAGCUU (SEQ ID NO: 1005) | TCTGCCTGCCGCACTAGCTT (SEQ ID NO: 1063) |
| HAO1_E3T12 | TTTC | BS | AGAAAUCCGUCUUUCAUUGACGGUUUCUCAGCCUGUCAGUCCC (SEQ ID NO: 1006) | TTTCTCAGCCTGTCAGTCCC (SEQ ID NO: 1064) |
| HAO1_E3T13 | TTTC | BS | AGAAAUCCGUCUUUCAUUGACGGUCAGCCUGUCAGUCCCUGGG (SEQ ID NO: 1007) | TCAGCCTGTCAGTCCCTGGG (SEQ ID NO: 1065) |
| HAO1_E3T14 | GTTG | BS | AGAAAUCCGUCUUUCAUUGACGGAGUUCCUGGGCCACCUCCUC (SEQ ID NO: 1008) | AGTTCCTGGGCCACCTCCTC (SEQ ID NO: 1066) |
| HAO1_E3T15 | ATTG | TS | AGAAAUCCGUCUUUCAUUGACGGAGGAGGUGGCCCAGGAACUC (SEQ ID NO: 1009) | AGGAGGTGGCCCAGGAACTC (SEQ ID NO: 1067) |
| HAO1_E3T16 | ATTG | BS | AGAAAUCCGUCUUUCAUUGACGGAAGAAGUGGCGGAAGCUGGU (SEQ ID NO: 1010) | AAGAAGTGGCGGAAGCTGGT (SEQ ID NO: 1068) |
| HAO1_E3T17 | GTTG | BS | AGAAAUCCGUCUUUCAUUGACGGGCUGCAACUGUAUAUCUACA (SEQ ID NO: 1011) | GCTGCAACTGTATATCTACA (SEQ ID NO: 1069) |
| HAO1_E3T18 | GTTG | TS | AGAAAUCCGUCUUUCAUUGACGGCAGCCAACGAAGUGCCUCAG (SEQ ID NO: 1012) | CAGCCAACGAAGTGCCTCAG (SEQ ID NO: 1070) |

TABLE 7-continued crRNA Sequences for HAO1

| Guide Name | PAM* | Target strand (Non-PAM Strand) | crRNA Sequence | Target Sequences |
|---|---|---|---|---|
| HAO1_E3T19 | CTTG | TS | AGAAAUCCGUCUUUCAU UGACGGUAGAUAUACAG UUGCAGCCA (SEQ ID NO: 1013) | TAGATATACAGTTGCA GCCA (SEQ ID NO: 1071) |
| HAO1_E3T20 | CTTG | TS | AGAAAUCCGUCUUUCAU UGACGGGUGACUUCUCG GUCCUUGUA (SEQ ID NO: 1014) | GTGACTTCTCGGTCCTT GTA (SEQ ID NO: 1072) |
| HAO1_E3T22 | ATTT | BS | AGAAAUCCGUCUUUCAU UGACGGGUGACAGUGGA CACACCUUA (SEQ ID NO: 1015) | GTGACAGTGGACACAC CTTA (SEQ ID NO: 1073) |
| HAO1_E3T23 | TTTG | BS | AGAAAUCCGUCUUUCAU UGACGGUGACAGUGGAC ACACCUUAC (SEQ ID NO: 1016) | TGACAGTGGACACACC TTAC (SEQ ID NO: 1074) |
| HAO1_E3T24 | CTTA | BS | AGAAAUCCGUCUUUCAU UGACGGCCUGGGCAACC GUCUGGAUG (SEQ ID NO: 1017) | CCTGGGCAACCGTCTG GATG (SEQ ID NO: 1075) |
| HAO1_E3T25 | GTTG | TS | AGAAAUCCGUCUUUCAU UGACGGCCCAGGUAAGG UGUGUCCAC (SEQ ID NO: 1018) | CCCAGGTAAGGTGTGT CCAC (SEQ ID NO: 1076) |
| HAO1_E3T26 | GTTA | TS | AGAAAUCCGUCUUUCAU UGACGGCGCACAUCAUC CAGACGGUU (SEQ ID NO: 1019) | CGCACATCATCCAGAC GGTT (SEQ ID NO: 1077) |
| HAO1_E3T27 | TTTG | TS | AGAAAUCCGUCUUUCAU UGACGGAAUCUGUUACG CACAUCAUC (SEQ ID NO: 1020) | AATCTGTTACGCACAT CATC (SEQ ID NO: 1078) |
| HAO1_E3T28 | GTTT | TS | AGAAAUCCGUCUUUCAU UGACGGGAAUCUGUUAC GCACAUCAU (SEQ ID NO: 1021) | GAATCTGTTACGCACA TCAT (SEQ ID NO: 1079) |
| HAO1_E3T29 | GTTG | TS | AGAAAUCCGUCUUUCAU UGACGGUGGCGGCAGUU UGAAUCUGU (SEQ ID NO: 1022) | TGGCGGCAGTTTGAAT CTGT (SEQ ID NO: 1080) |
| HAO1_E3T30 | GTTA | TS | AGAAAUCCGUCUUUCAU UGACGGCCUGAGUUGUG GCGGCAGUU (SEQ ID NO: 1023) | CCTGAGTTGTGGCGGC AGTT(SEQID NO: 1081) |

*The 3' three nucleotides represent the 5'-TTN-3' motif.

Cas12i2 RNP complexation reactions were made by mixing purified Cas12i2 polypeptide of SEQ ID NO: 924 (400 μM) with an HAO1-targeting crRNA (1 mM in 250 mM NaCl) at a 1:1 (Cas12i2:crRNA) volume ratio (2.5:1 crRNA: Cas12i2 molar ratio). Complexations were incubated on ice for 30-60 min.

HEK293T cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032) at a concentration of 16,480 cells/pt. Resuspended cells were dispensed at $3\times10^5$ cells/reaction into Lonza 16-well NUCLEOCUVETTE® strips. Complexed Cas12i2 RNP was added to each reaction at a final concentration of 10 μM (Cas12i2), and transfection enhancer oligos were then added at a final concentration of 4 μM. The final volume of each electroporated reaction was 20 pt. Non-targeting guides were used as negative controls.

The strips were electroporated using an electroporation device (program CM-130, Lonza 4D-NUCLEOFECTOR™). Immediately following electroporation, 80 μL of pre-warmed DMEM+10% FBS was added to each well and mixed gently by pipetting. For each technical replicate plate, plated 10 μL (30,000 cells) of diluted nucleofected cells into pre-warmed 96-well plate with wells containing 100 μL DMEM+10% FBS. Editing plates were incubated for 3 days at 37° C. with 5% $CO_2$.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C.

Samples for Next Generation Sequencing (NGS) were prepared by rounds of PCR. The first round (PCR I) was used to amplify the genomic regions flanking the target site and add NGS adapters. The second round (PCR II) was used to add NGS indexes. Reactions were then pooled, purified by column purification, and quantified on a fluorometer (Qubit). Sequencing runs were done using a 150 cycle NGS instrument (NEXTSEQ™ v2.5) mid or high output kit (Illumina) and run on an NGS instrument (NEXTSEQ™ 550; Illumina).

For NGS analysis, the indel mapping function used a sample's fastq file, the amplicon reference sequence, and the forward primer sequence. For each read, a kmer-scanning algorithm was used to calculate the edit operations (match, mismatch, insertion, deletion) between the read and the reference sequence. In order to remove small amounts of primer dimer present in some samples, the first 30 nt of each read was required to match the reference and reads where over half of the mapping nucleotides are mismatches were filtered out as well. Up to 50,000 reads passing those filters were used for analysis, and reads were counted as an indel read if they contained an insertion or deletion. The % indels was calculated as the number of indel-containing reads divided by the number of reads analyzed (reads passing filters up to 50,000). The QC standard for the minimum number of reads passing filters was 10,000.

FIG. 1 shows HAO1 indels in HEK293T cells following RNP delivery. Error bars represent the average of three technical replicates across one biological replicate. Following delivery, indels were detected within and/or adjacent to each of the HAO1 target sites with each of the RNA guides. Delivery of E1T2, E1T3, E1T6, E1T7, E1T13, T1T17, E2T4, E2T5, E2T9, E2T10, E3T6, E3T19, E3T22, and E3T28 resulted in indels in over 70% of the NGS reads. Therefore, HAO1-targeting RNA guides induced indels in exon 1, exon 2, and exon 3 in HEK293T cells.

This Example thus shows that HAO1 can be individually targeted by Cas12i2 RNPs in mammalian cells such as HEK293T cells.

Example 2—Cas12i2-Mediated Editing of HAO1 Target Sites in HepG2 Cells

This Example describes the genomic editing of the HAO1 gene using Cas12i2 introduced into HepG2 cells by RNP.

RNP complexation reactions were performed as described in Example 1 with various RNA guides of Table 7. HepG2 cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032) at a concentration of 13,889 cells/pt. Resuspended cells were dispensed at 2.5e5 cells/reaction into Lonza 16-well NUCLEOCUVETTE® strips. Complexed Cas12i2 RNP was added to each reaction at a final concentration of 20 μM (Cas12i2), with no transfection enhancer oligo. The final volume of each electroporated reaction was 20 pt. Non-targeting guides were used as negative controls.

The strips were electroporated using an electroporation device (program DJ-100, Lonza 4D-NUCLEOFECTOR™). Immediately following electroporation, 80 μL of pre-warmed EMEM+10% FBS was added to each well and mixed gently by pipetting. For each technical replicate plate, plated 10 μL (25,000 cells) of diluted nucleofected cells into pre-warmed 96-well plate with wells containing 100 μL EMEM+10% FBS. Editing plates were incubated for 3 days at 37° C. with 5% $CO_2$.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C. Samples were analyzed by NGS as described in Example 1.

Figure 2:
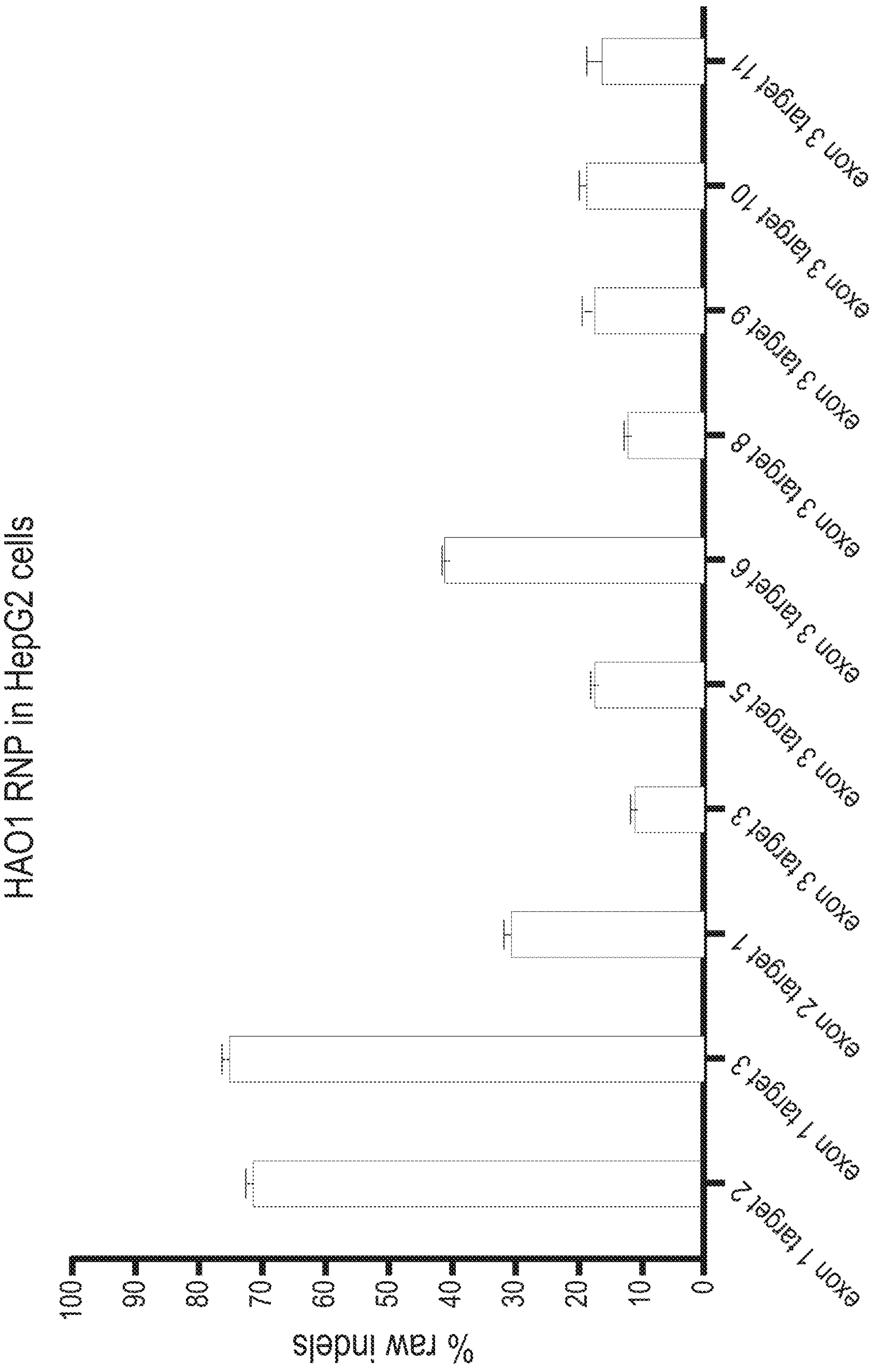
FIG. 2 is a graph showing the ability of RNPs prepared with a Cas12i2 polypeptide and a crRNA to edit the HAO1 gene in HepG2 cells.

FIG. 2 shows HAO1 indels in HepG2 cells following RNP delivery. Error bars represent the average of three technical replicates across one biological replicate. Following delivery, indels were detected within and/or adjacent to each of the HAO1 target sites with each of the RNA guides. Therefore, HAO1-targeting RNA guides induced indels in exon 1, exon 2, and exon 3 in HepG2 cells.

This Example thus shows that HAO1 can be targeted by Cas12i2 RNPs in mammalian cells such as HepG2 cells.

Example 3—Cas12i2-Mediated Editing of HAO1 Target Sites in Primary Hepatocytes This Example describes the genomic editing of the HAO1 using Cas12i2 introduced into primary hepatocytes cells by RNP.

RNP complexation reactions were performed as described in Example 1 with RNA guides of Table 7. Primary hepatocyte cells from human donors were thawed from liquid nitrogen very quickly in a 37° C. water bath. The cells were added to pre-warmed hepatocyte recovery media (Thermofisher, CM7000) and centrifuged at 100 g for 10 minutes. The cell pellet was resuspended in appropriate volume of hepatocyte plating Medium (Williams' Medium E, Thermofisher A1217601 supplemented with Hepatocyte Plating Supplement Pack (serum-containing), Thermofisher CM3000). The cells were subjected to trypan blue viability count with an INCUCYTE® disposable hemocytometer (Fisher scientific, 22-600-100). The cells were then washed in PBS and resuspended in P3 buffer+supplement (P3 PRIMARY CELL 4D-NUCLEOFECTOR™ X Kit; Lonza, VXP-3032) at a concentration of ~7,500 cells/μL. Resuspended cells were dispensed at 150,000 cells/reaction into the 16 well Lonza NUCLEOCUVETTE strips or 500,000 cells/reaction into the single Lonza NUCLEOCUVETTES® for the mRNA readout. Complexed Cas12i2 RNP was added to each reaction at a final concentration of 20 μM (Cas12i2), and transfection enhancer oligos were then added at a final concentration of 4 The final volume of each electroporated reaction was either 20 μL in the 16 well nucleocuvette strip format or 100 μL in the single nucleocuvette format. Non-targeting guides were used as negative controls.

The strips were electroporated using DS-150 program, while the single nucleocuvettes were electroporated using CA137 program (Lonza 4D-NUCLEOFECTOR™). Immediately following electroporation, pre-warmed Hepatocyte plating medium was added to each well and mixed very gently by pipetting. For each technical replicate plate, plated all the cell suspension of diluted nucleofected cells into a pre-warmed collagen-coated 96-well plate or 24-well plate (Thermofisher) with wells containing Hepatocyte plating medium. The cells were then incubated in a 37° C. incubator. The media was changed to hepatocyte maintenance media (Williams' Medium E, Thermofisher A1217601 supplemented with William's E medium Cell Maintenance Cocktail, Thermofisher CM 4000) after the cells attached after 4 hours. Fresh hepatocyte maintenance media was replaced after 2 days.

After 4-5 days post RNP electroporation, media was aspirated and the cells were harvested by shaking (500 rpm) in a 37° C. incubator with 2 mg/ml collagenase IV (Thermofisher, 17104019) dissolved in PBS containing Ca/Mg (Thermofisher). After cells were dissociated from the plate, they were transferred to 96-well TWIN.TEC® PCR plates (Eppendorf) and centrifuged. Media was flicked off and cell pellets for the NGS readout were resuspended in 20 μL QUICKEXTRACT™ (DNA extraction buffer; Lucigen). Samples were then cycled in a PCR machine at 65° C. for 15 min, 68° C. for 15 min, 98° C. for 10 min and analyzed by NGS as described in Example 1.

For the mRNA readout, cell pellets were frozen at −80° C. and subsequently resuspended in lysis buffer and DNA/RNA extracted with the RNeasy kit (Qiagen) following manufacturer's instructions. The DNA extracted from the samples were analyzed by NGS. The RNA isolated was checked for quantity and purity using nanodrop, and subsequently used for cDNA synthesis using 5× iScript reverse transcription reaction mix (Bio-Rad laboratories), following manufacturer's recommendations. cDNA templated was appropriately diluted to be in linear range of the subsequent analysis. Diluted cDNA was used to set up a 20 μL Digital Droplet PCR (ddPCR-BioRad laboratories) reaction using target-specific primer and probe for HAO1, ATTGTGC ACTGTCAGATCTTGGAAACGGCCAAAGGATTTTT CCTCACCAATGTCTTG TCGATGACTTTCACATTCT GGCACCCACTCAGAGCCATGGCCAACCGGAAT-TCTTCC TTTAGTAT (SEQ ID NO: 1088), and 2×ddPCR Supermix for Probes No dUTP (BioRad laboratories) following manufacturer's instructions. The reaction was used to generate droplets using Automated Droplet Generator (BioRad Laboratories), following manufacture's recommendations. The plate was sealed using PX1 PCR Plate Sealer (BioRad Laboratories) generated droplets were subjected to PCR amplification using C1000 Touch Thermal Cycler (BioRad Laboratories) using conditions recommended by the manufacturer. The PCR amplified droplets were read on QX200 Droplet Reader (BioRad Laboratories) and the acquired data was analyzed using QX Manager version 1.2 (BioRad Laboratories) to determine presence of absolute copy number of mRNA present in each reaction for the appropriate targets.

Figure 3:
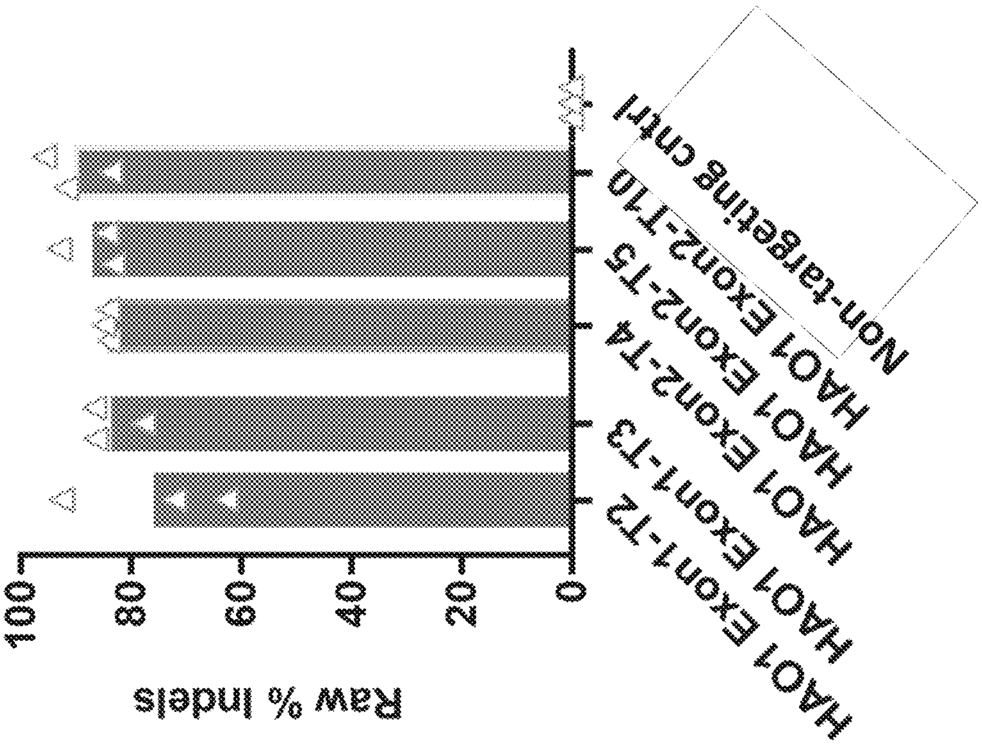
FIG. 3 is a graph showing the ability of RNPs prepared with a Cas12i2 polypeptide and a crRNA to edit the HAO1 gene in primary hepatocytes.
Figure 4:
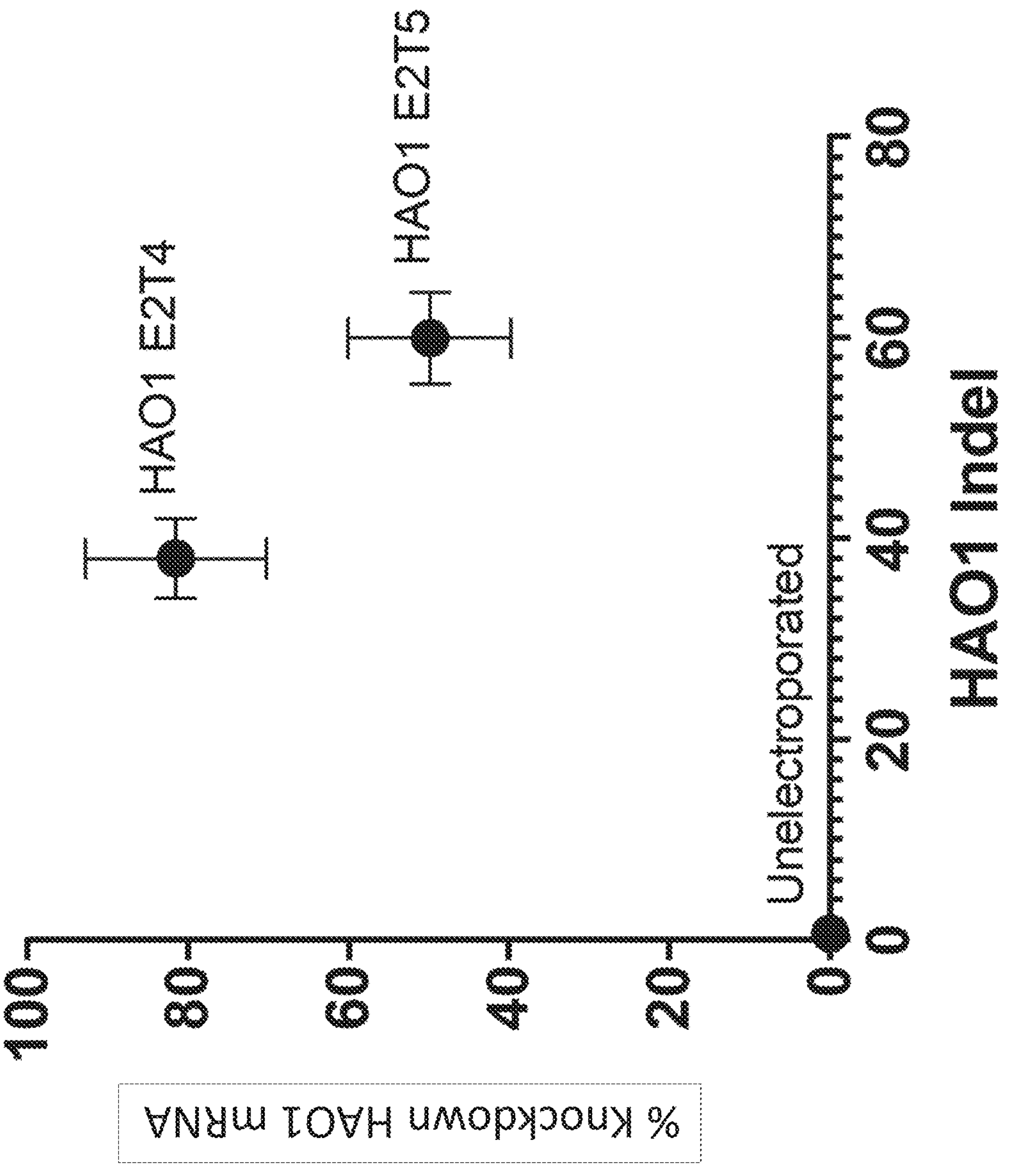
FIG. 4 is a graph showing knockdown of HAO1 mRNA in primary human hepatocytes with a Cas12i2 polypeptide and an HAO1-targeting crRNA.

As shown in FIG. 3, each RNA guide tested induced indels within and/or adjacent to the HAO1 target sites. Indels were not induced with the non-targeting control. Therefore, HAO1-targeting RNA guides induced indels in primary hepatocytes. Indels were then correlated with mRNA levels for each target to determine whether indels lead to mRNA knockdown and subsequent protein knockdown. FIG. 4 shows % mRNA knockdown of HAO1 in edited cells compared to unedited control cells. Although a higher percentage of NGS reads comprised indels using HAO1 E2T5 (SEQ ID NO: 989) compared to HAO1 E2T4 (SEQ ID NO: 988), HAO1 E2T4 resulted in a greater knockdown of HAO1 mRNA.

This Example thus shows that HAO1 can be targeted by Cas12i2 RNPs in mammalian cells such as primary human hepatocytes.

Example 4—Editing of HAO1 Target Sites in HepG2 Cells with Cas12i2 Variants

This Example describes indel assessment on HAO1 targets using variants introduced into HepG2 cells by transient transfection.

The Cas12i2 variants of SEQ ID NO: 924 and SEQ ID NO: 927 were individually cloned into a pcda3.1 backbone (Invitrogen). Nucleic acids encoding RNA guides E1T2 (SEQ ID NO: 967), E1T3 (SEQ ID NO: 968), E2T4 (SEQ ID NO: 988), E2T5 (SEQ ID NO: 989), E2T10 (SEQ ID NO: 994) were cloned into a pUC19 backbone (New England Biolabs). The plasmids were then maxi-prepped and diluted.

HepG2 cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032).

Approximately 16 hours prior to transfection, 25,000 HepG2 cells in EMEM/10% FBS were plated into each well of a 96-well plate. On the day of transfection, the cells were 70-90% confluent. For each well to be transfected, a mixture of Lipofectamine™ 3000 and Opti-MEM® was prepared and then incubated at room temperature for 5 minutes (Solution 1). After incubation, the Lipofectamine™:OptiMEM® mixture was added to a separate mixture containing nuclease plasmid and RNA guide plasmid and P3000 reagent (Solution 2). In the case of negative controls, the crRNA was not included in Solution 2. The Solution 1 and Solution 2 were mixed by pipetting up and down and then incubated at room temperature for 15 minutes. Following incubation, the Solution 1 and Solution 2 mixture was added dropwise to each well of a 96 well plate containing the cells.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C. and analyzed by NGS as described in Example 1.

Figure 5A:
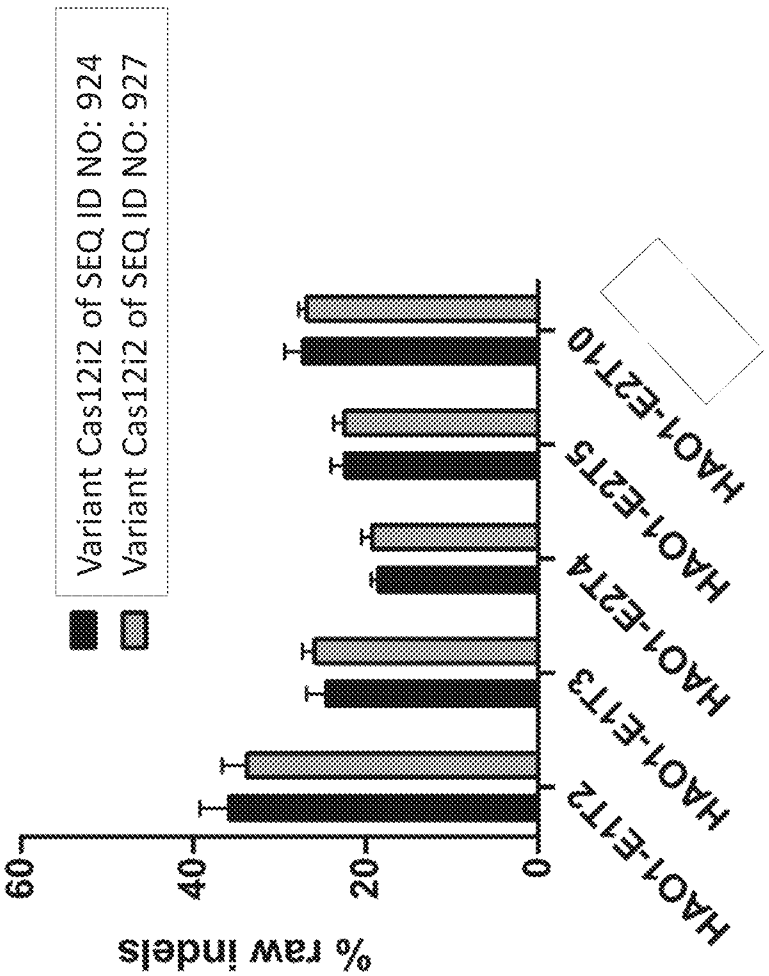
FIG. 5A is a graph showing % indels induced by an HAO1-targeting crRNA and the variant Cas12i2 polypeptide of SEQ ID NO: 924 or SEQ ID NO: 927 in HepG2 cells.
Figure 5B:
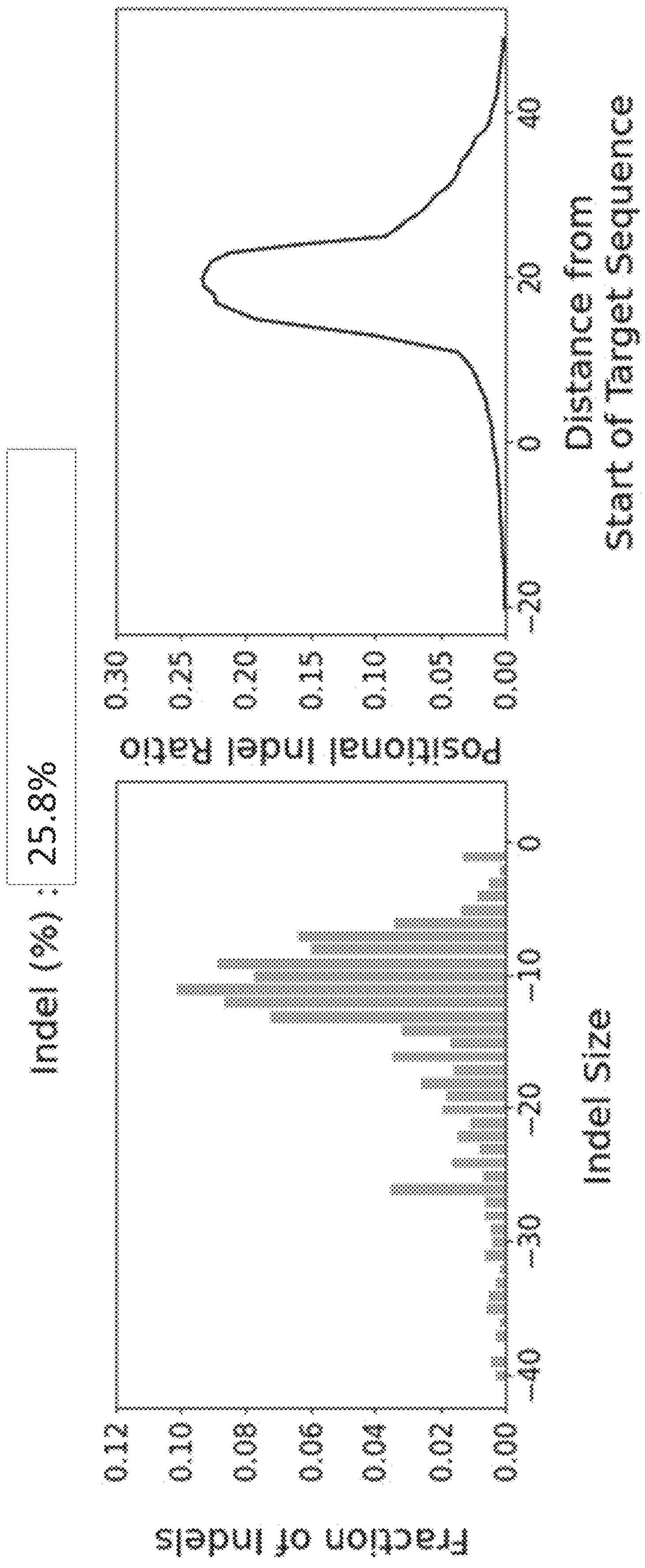
FIG. 5B shows the size (left) and start position (right) of indels induced in HepG2 cells by the variant Cas12i2 of SEQ ID NO: 924 and the HAO1-targeting RNA guide of E1T3 (SEQ ID NO: 968).

As shown in FIG. 5A, comparable indel activity with the two Cas12i2 variants was observed for E1T2, E1T3, E2T4, E2T5, E2T10. FIG. 5B shows the indel size frequency (left) and indel start position relative to the PAM for E1T3 and the variant Cas12i2 of SEQ ID NO: 924. As shown on the left, deletions ranged in size from 1 nucleotide to about 40 nucleotides. The majority of the deletions were about 6 nucleotides to about 27 nucleotides in length. As shown on the right, the target sequence is represented as starting at position 0 and ending at position 20. Indels started within about 10 nucleotides and about 35 nucleotides downstream of the PAM sequence. The majority of indels started near the end of the target sequence, e.g., about 18 nucleotides to about 25 nucleotides downstream of the PAM sequence.

Thus, this Example shows that HAO1 is capable of being targeted by multiple Cas12i2 polypeptides.

Example 5—Editing of HAO1 in Primary Human Hepatocytes Using Cas12i2 mRNA Constructs This Example describes indel assessment on HAO1 target sites via delivery of Cas12i2 mRNA and chemically modified HAO1-targeting RNA guides.

mRNA sequences corresponding to the variant Cas12i2 sequence of SEQ ID NO: 924 and the variant Cas12i2 sequence of SEQ ID NO: 927 were synthesized by Aldeveron with 1-pseudo-U modified nucleotides and using CleanCap® Reagent AG (TriLink Biotechnologies). The Cas12i2 mRNA sequences, shown in Table 8, further comprised a C-terminal NLS.

TABLE 8

| Cas12i2 mRNA Sequences | |
|---|---|
| Description | mRNA Sequence |
| mRNA corresponding to variant Cas12i2 of SEQ ID NO: 924 | AUGAGCUCCGCCAUCAAGUCCUACAAGUCUGUGCUGCGGCCAAACGAGAGAAAGAAUCAGC<br>UGCUGAAGUCCACCAUCCAGUGCCUGGAGGACGGCUCCGCCUUCUUUUUCAAGAUGCUGCA<br>GGGCCUGUUUGGCGGCAUCACCCCCGAGAUCGUGAGAUUCAGCACAGAGCAGGAGAAGCAG<br>CAGCAGGAUAUCGCCCUGUGGUGUGCCGUGAAUUGGUUCAGGCCUGUGAGCCAGGACUCCC<br>UGACCCACACAAUCGCCUCCGAUAACCUGGUGGAGAAGUUUGAGGAGUACUAUGGCGGCAC<br>AGCCAGCGACGCCAUCAAGCAGUACUUCAGCGCCUCCAUCGGCGAGUCCUACUAUUGGAAU<br>GACUGCCGCCAGCAGUACUAUGAUCUGUGUCGGGAGCUGGGCGUGGAGGUGUCUGACCUGA<br>CCCACGAUCUGGAGAUCCUGUGCCGGGAGAAGUGUCUGGCCGUGGCCACAGAGAGCAACCA<br>GAACAAUUCUAUCAUCAGCGUGCUGUUUGGCACCGGCGAGAAGGAGGAUAGGUCUGUGAAG<br>CUGCGCAUCACAAAGAAGAUCCUGGAGGCCAUCAGCAACCUGAAGGAGAUCCCAAAGAAUG<br>UGGCCCCCAUCCAGGAGAUCAUCCUGAAUGUGGCCAAGGCCACCAAGGAGACAUUCAGACA<br>GGUGUACGCAGGAAACCUGGGAGCACCAUCCACCCUGGAGAAGUUUAUCGCCAAGGACGGC<br>CAGAAGGAGUUCGAUCUGAAGAAGCUGCAGACAGACCUGAAGAAAGUGAUCCGGGGCAAGU<br>CUAAGGAGAGAGAUUGGUGCUGUCAGGAGGAGCUGAGGAGCUACGUGGAGCAGAAUACCAU<br>CCAGUAUGACCUGUGGGCCUGGGGCGAGAUGUUCAACAAGGCCCACACCGCCCUGAAGAUC<br>AAGUCCACAAGAAACUACAAUUUUGCCAAGCAGAGGCUGGAGCAGUUCAAGGAGAUCCAGU<br>CUCUGAACAAUCUGCUGGUGGUGAAGAAGCUGAACGACUUUUUCGAUAGCGAGUUUUUCUC<br>CGGCGAGGAGACCUACACAAUCUGCGUGCACCACCUGGGCGGCAAGGACCUGUCCAAGCUG<br>UAUAAGGCCUGGGAGGACGAUCCCGCCGAUCCUGAGAAUGCCAUCGUGGUGCUGUGCGACG<br>AUCUGAAGAACAAUUUUAAGAAGGAGCCUAUCAGGAACAUCCUGCGCUACAUCUUCACCAU<br>CCGCCAGGAGUGUAGCGCACAGGACAUCCUGGCAGCAGCAAAGUACAAUCAGCAGCUGGAU<br>CGGUAUAAGAGCCAGAAGGCCAACCCAUCCGUGCUGGGCAAUCAGGGCUUUACCUGGACAA<br>ACGCCGUGAUCCUGCCAGAGAAGGCCCAGCGGAACGACAGACCCAAUUCUCUGGAUCUGCG<br>CAUCUGGCUGUACCUGAAGCUGCGGCACCCUGACGGCAGAUGGAAGAAGCACCACAUCCCA<br>UUCUACGAUACCCGGUUUUUCCAGGAGAUCUAUGCCGCCGGCAAUAGCCCUGUGGACACCU<br>GUCAGUUUAGGACACCCCGCUUCGGCUAUCACCUGCCUAAGCUGACCGAUCAGACAGCCAU<br>CCGCGUGAACAAGAAGCACGUGAAGGCAGCAAAGACCGAGGCACGGAUCAGACUGGCCAUC<br>CAGCAGGGCACACUGCCAGUGUCCAAUCUGAAGAUCACCGAGAUCUCCGCCACAAUCAACU<br>CUAAGGGCCAGGUGCGCAUCCCCGUGAAGUUUCGGGUGGGAAGGCAGAAGGGAACCCUGCA<br>GAUCGGCGACCGGUUCUGCGGCUACGAUCAGAACCAGACAGCCUCUCACGCCUAUAGCCUG<br>UGGGAGGUGGUGAAGGAGGGCCAGUACCACAAGGAGCUGGGCUGUUUUGUGCGCUUCAUCU<br>CUAGCGGCGACAUCGUGUCCAUCACCGAGAACCGGGGCAAUCAGUUUGAUCAGCUGUCUUA<br>UGAGGGCCUGGCCUACCCCCAGUAUGCCGACUGGAGAAAGAAGGCCUCCAAGUUCGUGUCU<br>CUGUGGCAGAUCACCAAGAAGAACAAGAAGAAGGAGAUCGUGACAGUGGAGGCCAAGGAGA<br>AGUUUGACGCCAUCUGCAAGUACCAGCCUAGGCUGUAUAAGUUCAACAAGGAGUACGCCUA<br>UCUGCUGCGGGAUAUCGUGAGAGGCAAGAGCCUGGUGGAGCUGCAGCAGAUCAGGCAGGAG<br>AUCUUUCGCUUCAUCGAGCAGGACUGUGGAGUGACCCGCCUGGGAUCUCUGAGCCUGUCCA<br>CCCUGGAGACAGUGAAGGCCGUGAAGGGCAUCAUCUACUCCUAUUUUUCUACAGCCCUGAA<br>UGCCUCUAAGAACAAUCCCAUCAGCGACGAGCAGCGGAAGGAGUUUGAUCCUGAGCUGUUC<br>GCCCUGCUGGAGAAGCUGGAGCUGAUCAGGACUCGGAAGAAGAAGCAGAAGGUGGAGAGAA<br>UCGCCAAUAGCCUGAUCCAGACAUGCCUGGAGAACAAUAUCAAGUUCAUCAGGGGCGAGGG<br>CGACCUGUCCACCACAAACAAUGCCACCAAGAAGAAGGCCAACUCUAGGAGCAUGGAUUGG<br>CUGGCCAGAGGCGUGUUUAAUAAGAUCCGGCAGCUGGCCCCAAUGCACAACAUCACCCUGU<br>UCGGCUGCGGCAGCCUGUACACAUCCCACCAGGACCCUCUGGUGCACAGAAACCCAGAUAA<br>GGCCAUGAAGUGUAGAUGGGCAGCAAUCCCAGUGAAGGACAUCGGCGAUUGGGUGCUGAGA<br>AAGCUGUCCCAGAACCUGAGGGCCAAGAAUCGGGGCACCGGCGAGUACUAUCACCAGGGCG<br>UGAAGGAGUUCCUGUCUCACUAUGAGCUGCAGGACCUGGAGGAGGAGCUGCUGAAGUGGCG<br>GUCUGAUAGAAAGAGCAACAUCCCUUGCUGGGUGCUGCAGAAUAGACUGGCCGAGAAGCUG<br>GGCAACAAGGAGGCCGUGGUGUACAUCCCAGUGAGGGGCGGCCGCAUCUAUUUUGCAACCC<br>ACAAGGUGGCAACAGGAGCCGUGAGCAUCGUGUUCGACCAGAAGCAAGUGUGGGUGUGUAA<br>UGCAGAUCACGUGGCAGCAGCAAACAUCGCACUGACCGGCAAGGGCAUCGGCGAGCAGUCC<br>UCUGACGAGGAGAACCCCGAUGGCUCCAGGAUCAAGCUGCAGCUGACAUCUAAAAGGCCGG<br>CGGCCACGAAAAAGGCCGGCCAGGCAAAAAAGAAAAAGUAA (SEQ ID NO: 1089) |
| mRNA corresponding to variant Cas12i2 of SEQ ID NO: 927 | AUGAGCUCCGCCAUCAAGUCCUACAAGUCUGUGCUGCGGCCAAACGAGAGAAAGAAUCAGC<br>UGCUGAAGUCCACCAUCCAGUGCCUGGAGGACGGCUCCGCCUUCUUUUUCAAGAUGCUGCA<br>GGGCCUGUUUGGCGGCAUCACCCCCGAGAUCGUGAGAUUCAGCACAGAGCAGGAGAAGCAG<br>CAGCAGGAUAUCGCCCUGUGGUGUGCCGUGAAUUGGUUCAGGCCUGUGAGCCAGGACUCCC<br>UGACCCACACAAUCGCCUCCGAUAACCUGGUGGAGAAGUUUGAGGAGUACUAUGGCGGCAC<br>AGCCAGCGACGCCAUCAAGCAGUACUUCAGCGCCUCCAUCGGCGAGUCCUACUAUUGGAAU<br>GACUGCCGCCAGCAGUACUAUGAUCUGUGUCGGGAGCUGGGCGUGGAGGUGUCUGACCUGA<br>CCCACGAUCUGGAGAUCCUGUGCCGGGAGAAGUGUCUGGCCGUGGCCACAGAGAGCAACCA<br>GAACAAUUCUAUCAUCAGCGUGCUGUUUGGCACCGGCGAGAAGGAGGAUAGGUCUGUGAAG<br>CUGCGCAUCACAAAGAAGAUCCUGGAGGCCAUCAGCAACCUGAAGGAGAUCCCAAAGAAUG<br>UGGCCCCCAUCCAGGAGAUCAUCCUGAAUGUGGCCAAGGCCACCAAGGAGACAUUCAGACA<br>GGUGUACGCAGGAAACCUGGGAGCACCAUCCACCCUGGAGAAGUUUAUCGCCAAGGACGGC<br>CAGAAGGAGUUCGAUCUGAAGAAGCUGCAGACAGACCUGAAGAAAGUGAUCCGGGGCAAGU<br>CUAAGGAGAGAGAUUGGUGCUGUCAGGAGGAGCUGAGGAGCUACGUGGAGCAGAAUACCAU<br>CCAGUAUGACCUGUGGGCCUGGGGCGAGAUGUUCAACAAGGCCCACACCGCCCUGAAGAUC<br>AAGUCCACAAGAAACUACAAUUUUGCCAAGCAGAGGCUGGAGCAGUUCAAGGAGAUCCAGU<br>CUCUGAACAAUCUGCUGGUGGUGAAGAAGCUGAACGACUUUUUCGAUAGCGAGUUUUUCUC<br>CGGCGAGGAGACCUACACAAUCUGCGUGCACCACCUGGGCGGCAAGGACCUGUCCAAGCUG<br>UAUAAGGCCUGGGAGGACGAUCCCGCCGAUCCUGAGAAUGCCAUCGUGGUGCUGUGCGACG<br>AUCUGAAGAACAAUUUUAAGAAGGAGCCUAUCAGGAACAUCCUGCGCUACAUCUUCACCAU<br>CCGCCAGGAGUGUAGCGCACAGGACAUCCUGGCAGCAGCAAAGUACAAUCAGCAGCUGGAU<br>CGGUAUAAGAGCCAGAAGGCCAACCCAUCCGUGCUGGGCAAUCAGGGCUUUACCUGGACAA |

TABLE 8-continued

| Cas12i2 mRNA Sequences | |
|---|---|
| Description | mRNA Sequence |
| | ACGCCGUGAUCCUGCCAGAGAAGGCCCAGCGGAACGACAGACCCAAUUCUCUGGAUCUGCG CAUCUGGCUGUACCUGAAGCUGCGGCACCCUGACGGCAGAUGGAAGAAGCACCACAUCCCA UUCUACGAUACCCGGUUUUUCCAGGAGAUCUAUGCCGCCGGCAAUAGCCCUGUGGACACCU GUCAGUUUAGGACACCCCGCUUCGGCUAUCACCUGCCUAAGCUGACCGAUCAGACAGCCAU CCGCGUGAACAAGAAGCACGUGAAGGCAGCAAAGACCGAGGCACGGAUCAGACUGGCCAUC CAGCAGGGCACACUGCCAGUGUCCAAUCUGAAGAUCACCGAGAUCUCCGCCACAAUCAACU CUAAGGGCCAGGUGCGCAUCCCCGUGAAGUUUCGGGUGGGAAGGCAGAAGGGAACCCUGCA GAUCGGCGACCGGUUCUGCGGCUACGAUCAGAACCAGACAGCCUCUCACGCCUAUAGCCUG UGGGAGGUGGUGAAGGAGGGCCAGUACCACAAGGAGCUGCGGUGUCGGGUGCGCUUCAUCU CUAGCGGCGACAUCGUGUCCAUCACCGAGAACCGGGGCAAUCAGUUUGAUCAGCUGUCUUA UGAGGGCCUGGCCUACCCCCAGUAUGCCGACUGGAGAAAGAAGGCCUCCAAGUUCGUGUCU CUGUGGCAGAUCACCAAGAAGAACAAGAAGAAGGAGAUCGUGACAGUGGAGGCCAAGGAGA AGUUUGACGCCAUCUGCAAGUACCAGCCUAGGCUGUAUAAGUUCAACAAGGAGUACGCCUA UCUGCUGCGGGAUAUCGUGAGAGGCAAGAGCCUGGUGGAGCUGCAGCAGAUCAGGCAGGAG AUCUUUCGCUUCAUCGAGCAGGACUGUGGAGUGACCCGCCUGGGAUCUCUGAGCCUGUCCA CCCUGGAGACAGUGAAGGCCGUGAAGGGCAUCAUCUACUCCUAUUUUUCUACAGCCCUGAA UGCCUCUAAGAACAAUCCCAUCAGCGACGAGCAGCGGAAGGAGUUUGAUCCUGAGCUGUUC GCCCUGCUGGAGAAGCUGGAGCUGAUCAGGACUCGGAAGAAGAAGCAGAAGGUGGAGAGAA UCGCCAAUAGCCUGAUCCAGACAUGCCUGGAGAACAAUAUCAAGUUCAUCAGGGGCGAGGG CGACCUGUCCACCACAAACAAUGCCACCAAGAAGAAGGCCAACUCUAGGAGCAUGGAUUGG CUGGCCAGAGGCGUGUUUAAUAAGAUCCGGCAGCUGGCCACCAUGCACAACAUCACCCUGU UCGGCUGCGGCAGCCUGUACACAUCCCACCAGGACCCUCUGGUGCACAGAAACCCAGAUAA GGCCAUGAAGUGUAGAUGGGCAGCAAUCCCAGUGAAGGACAUCGGCGAUUGGGUGCUGAGA AAGCUGUCCCAGAACCUGAGGGCCAAGAAUCGGGGCACCGGCGAGUACUAUCACCAGGGCG UGAAGGAGUUCCUGUCUCACUAUGAGCUGCAGGACCUGGAGGAGGAGCUGCUGAAGUGGCG GUCUGAUAGAAAGAGCAACAUCCCUUGCUGGGUGCUGCAGAAUAGACUGGCCGAGAAGCUG GGCAACAAGGAGGCCGUGGUGUACAUCCCAGUGAGGGGCGGCCGCAUCUAUUUUGCAACCC ACAAGGUGGCAACAGGAGCCGUGAGCAUCGUGUUCGACCAGAAGCAAGUGUGGGUGUGUAA UGCAGAUCACGUGGCAGCAGCAAACAUCGCACUGACCGGCAAGGGCAUCGGCCGGCAGUCC UCUGACGAGGAGAACCCCGAUGGCGGCAGGAUCAAGCUGCAGCUGACAUCUAAAAGGCCGG CGGCCACGAAAAAGGCCGGCCAGGCAAAAAAGAAAAAGUAA (SEQ ID NO: 1090) |

Cas12i2 RNA guides were designed and ordered from Integrated DNA Technologies (IDT) as having 3' end modified phosphorothioated 2' O-methyl bases or 5' end and 3' end modified phosphorothioated 2' O-methyl bases guides, as specified in Table 9. Each variant Cas12i2 mRNA was mixed with a crRNA at a 1:1 (Cas12i2:crRNA) volume ratio (1050:1 crRNA:Cas12i2 molar ratio). The mRNA and crRNA were mixed immediately before electroporation. The primary human hepatocyte cells were cultured and electroporated as described in Example 3.

TABLE 9

| Chemically modified RNA guide sequences | |
|---|---|
| RNA guide | Sequence |
| 3'end modified E2T5 | AGAAAUCCGUCUUUCAUUGACGGCGGAGCAUCC UUGGAUA*mC*mA*mG(SEQID NO: 1091) |
| 5' and 3' end modified E2T5 | mA*mG*mA*AAUCCGUCUUUCAUUGACGGCGGA GCAUCCUUGGAUA*mC*mA*mG (SEQ ID NO: 1092) |

Figure 6:
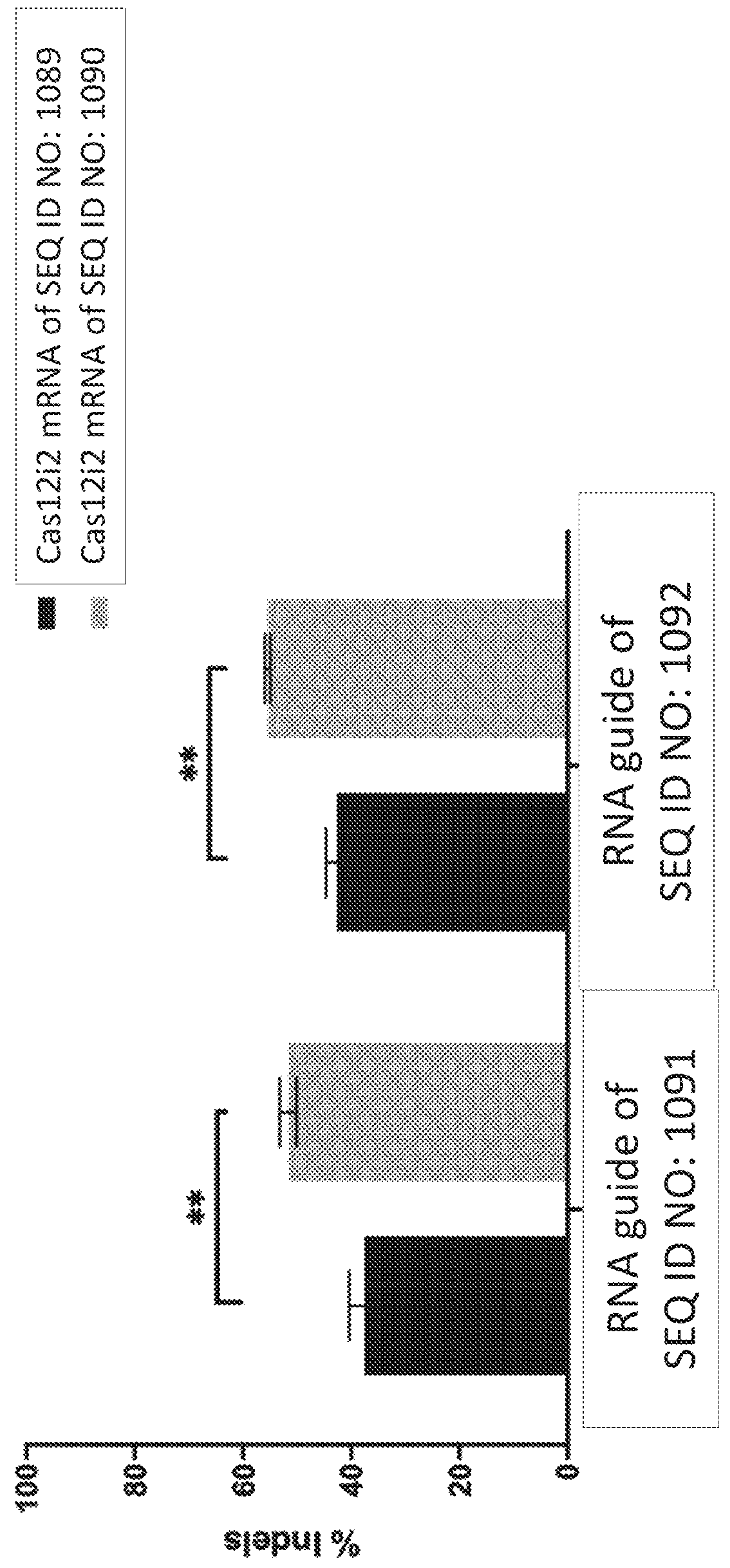
FIG. 6 is a graph showing % indels induced by chemically modified HAO1-targeting crRNAs of SEQ ID NO: 1091 and SEQ ID NO: 1092 and the variant Cas12i2 mRNA of SEQ ID NO: 1089 or SEQ ID NO: 1090.

FIG. 6 shows editing of an HAO1 target site by a variant Cas12i2 mRNA and 3' end modified E2T5 (SEQ ID NO: 1091) or 5' and 3' end modified E2T5 (SEQ ID NO: 1092). Indels in the HAO1 target site were introduced following electroporation of the Cas12i2 mRNA of SEQ ID NO: 1089 or SEQ ID NO: 1090 and either the RNA guide of SEQ ID NO: 1091 or SEQ ID NO: 1092. Approximately 50% NGS reads comprised an indel following electroporation of the Cas12i2 mRNA of SEQ ID NO: 1090 and the RNA guide of SEQ ID NO: 1091 or SEQ ID NO: 1092. Statistically significant higher % indels were observed using variant Cas12i2 mRNA of SEQ ID NO: 1090 compared to variant Cas12i2 mRNA of SEQ ID NO: 1089. No statistical difference was observed using 5' and 3' versus 3' only modifications to RNA guide E2T5.

This Example thus shows that HAO1 can be targeted by Cas12i2 mRNA constructs and chemically modified RNA guides in mammalian cells.

Example 6—Off-Target Analysis of Cas12i2 and HAO1-Targeting RNA Guides

This Example describes on-target versus off-target assessment of a Cas12i2 variant and an HAO1-targeting RNA guide.

HEK293T cells were transfected with a plasmid encoding the variant Cas12i2 of SEQ ID NO: 924 or the variant Cas12i2 of SEQ ID NO: 927 and a plasmid encoding E2T5 (SEQ ID NO: 989), E1T2 (SEQ ID NO: 967), E1T3 (SEQ ID NO: 968), and E2T10 (SEQ ID NO: 994) according to the method described in Example 16 of PCT/US21/25257. The tagmentation-based tag integration site sequencing (TTISS) method described in Example 16 of PCT/US21/25257 was then carried out.

Figure 7A:
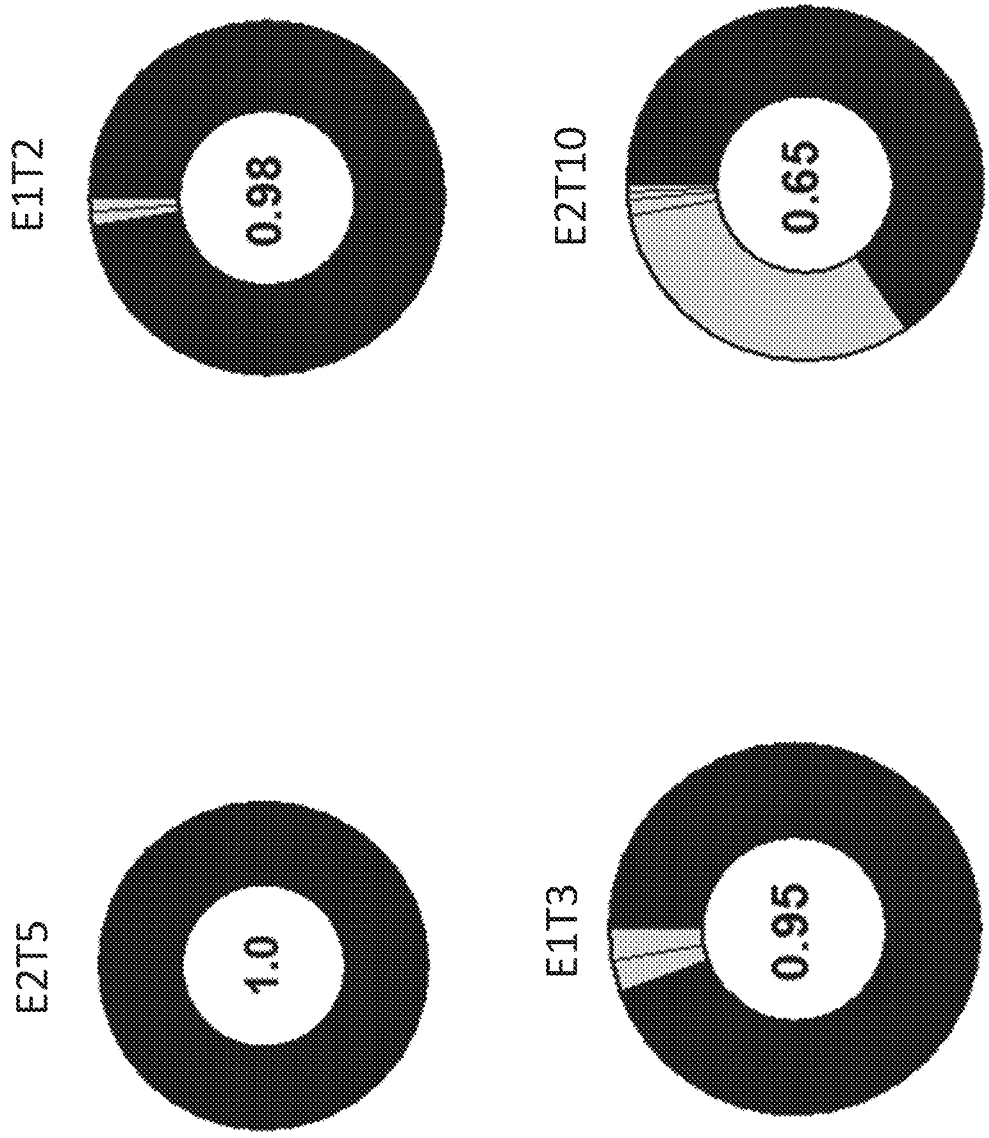
FIG. 7A shows plots depicting tagmentation-based tag integration site sequencing (TTISS) reads for variant Cas12i2 of SEQ ID NO: 924 and HAO1-targeting RNA guides E2T5 (SEQ ID NO: 989), E1T2 (SEQ ID NO: 967), E1T3 (SEQ ID NO: 968), and E2T10 (SEQ ID NO: 994). The black wedge and centered number represent the fraction of on-target TTISS reads. Each gray wedge represents a unique off-target site identified by TTISS. The size of each gray wedge represents the fraction of TTISS reads mapping to a given off-target.
Figure 7B:
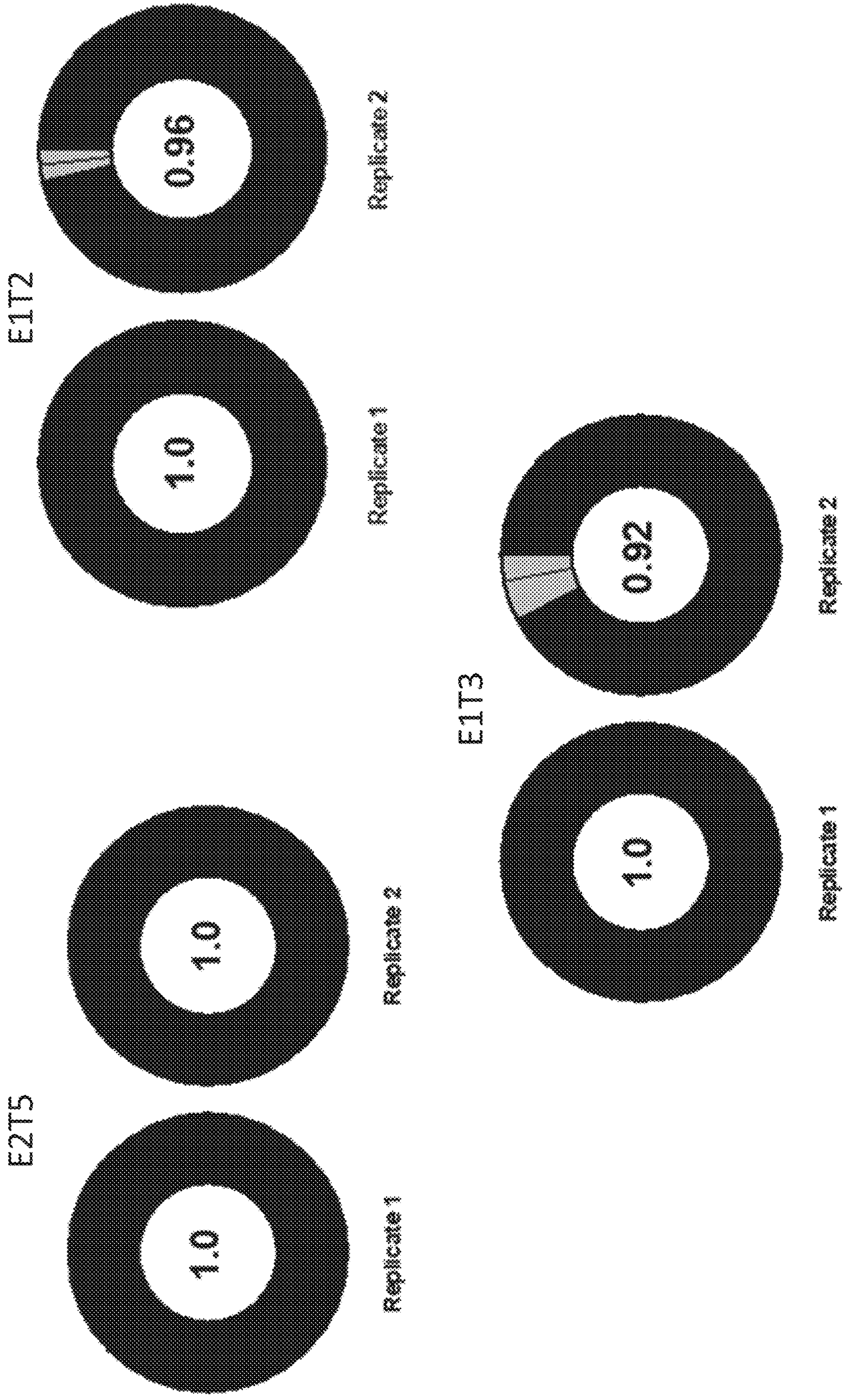
FIG. 7B shows plots depicting two replicates of TTISS reads for variant Cas12i2 of SEQ ID NO: 927 and HAO1-targeting RNA guides E2T5 (SEQ ID NO: 989), E1T2 (SEQ ID NO: 967), and E1T3 (SEQ ID NO: 968). The black wedge and centered number represent the fraction of on-target TTISS reads. Each gray wedge represents a unique off-target site identified by TTISS. The size of each gray wedge represents the fraction of TTISS reads mapping to a given off-target.

FIG. 7A and FIG. 7B show plots depicting on-target and off-target TTISS reads. The black wedge and centered number represent the fraction of on-target TTISS reads. Each grey wedge represents a unique off-target site identified by TTISS. The size of each grey wedge represents the fraction of TTISS reads mapping to a given off-target site. FIG. 7A shows TTISS reads for variant Cas12i2 of SEQ ID NO: 924, and FIG. 7B shows TTISS reads for variant Cas12i2 of SEQ ID NO: 927.

As shown in FIG. 7A, variant Cas12i2 of SEQ ID NO: 924 paired with E2T5 demonstrated a low likelihood of off-target editing, as 100% of TTISS reads mapped to the on-target. No TTISS reads mapped to potential off-target sites. E1T2 also showed a low likelihood of off-target editing. For E1T2, 98% of TTISS reads mapped to the on-target, and two potential off-target sites represented a combined 2% of TTISS reads. For E5T10, 95% of TTISS reads mapped to the on-target, and two potential off-target sites represented a combined 5% of TTISS reads. E2T10 demonstrated a higher likelihood of off-target editing using the TTISS method. For E2T10, only 65% of TTISS reads mapped to the on-target and 4 potential off-target sites represented the remaining combined 35% of TTISS reads. One potential off-target represented the majority of potential off-target TTISS reads for E2T10.

As shown in FIG. 7B, variant Cas12i2 of SEQ ID NO: 927 paired with E2T5 demonstrated a low likelihood of off-target editing, as 100% of TTISS reads mapped to the on-target. No TTISS reads mapped to potential off-target sites. Variant Cas12i2 of SEQ ID NO: 927 paired with the E1T2 or E1T3 also demonstrated a low likelihood of off-target editing. For E1T2, 100% of TTISS reads in replicate 1 and 96% of TTISS reads in replicate 2 mapped to the on-target; two potential off-target sites represented the remaining 4% of TTISS reads in replicate 2. For E1T3, 100% of TTISS reads in replicate 1 and 92% of TTISS reads in replicate 2 mapped to the on-target; two potential off-target sites represented the remaining 8% of TTISS reads in replicate 2.

Therefore, this Example shows that compositions comprising Cas12i2 and HAO1-targeting RNA guides comprise different off-target activity profiles.

Example 7—HAO1 Protein Knockdown with Cas12i2 and HAO1-Targeting RNA Guides

This Example describes use of a Western Blot to identify knockdown of HAO1 protein using variant Cas12i2 of SEQ ID NO: 924 and HAO1-targeting RNA guides.

Primary hepatocyte cells from human donors were thawed from liquid nitrogen very quickly in a 37° C. water bath. The cells were added to pre-warmed hepatocyte recovery media (Thermo Fisher, CM7000) and centrifuged at 100 g for 10 minutes. The cell pellet was resuspended in appropriate volume of hepatocyte plating Medium (Williams' Medium E, Thermo Fisher A1217601 supplemented with Hepatocyte Plating Supplement Pack (serum-containing), Thermo Fisher CM3000). The cells were subjected to trypan blue viability count with an Inucyte disposable hemocytometer (Fisher scientific, 22-600-100). The cells were then washed in PBS and resuspended in P3 buffer+supplement (Lonza, VXP-3032) at a concentration of ~5000 cells/μL. Resuspended cells were dispensed at 500,000 cells/reaction into Lonza electroporation cuvettes For the RNP reactions, E2T5 (SEQ ID NO: 989) was used as the HAO1-targeting RNA guides. RNPs were added to each reaction at a final concentration of 20 μM (Cas12i2), and transfection enhancer oligos were then added at a final concentration of 4 Unelectroporated cells and cells electroporated without cargo were used as negative controls.

The strips were electroporated using an electroporation device (program CA137, Lonza 4D-nucleofector). Immediately following electroporation, pre-warmed Hepatocyte plating medium was added to each well and mixed very gently by pipetting. For each technical replicate plate, 500,000 cells of diluted nucleofected cells were plated into a pre-warmed collagen-coated 24-well plate (Thermo Fisher) with wells containing Hepatocyte plating medium. The cells were then incubated at 37° C. The media was changed to hepatocyte maintenance media (Williams' Medium E, Thermo Fisher A1217601 supplemented with William's E medium Cell Maintenance Cocktail, Thermo Fisher CM 4000) after the cells attached after 24 hours. Fresh hepatocyte maintenance media was replaced every 48 hours.

16 days post RNP electroporation, the media was aspirated, and the cells were washed gently with PBS. Cells were then lysed with RIPA Lysis and Extraction buffer (Thermo Fisher 89901)+1× protease inhibitors (Thermo Fisher 78440) for 30 minutes on ice, mixing the samples every 5 minutes. Cell lysate was quantified via Pierce BCA Protein Assay Kit (Thermo Fisher 23227). 15 μg of total protein per sample was prepared for SDS-PAGE in 1× Laemmlli Sample buffer (BioRad 1610747) and 100 mM DTT, then heated at 95 C for 10 minutes. Samples were run on a 4-15% TGX gel (BioRad 5671084) at 200V for 45 minutes. Samples were transferred to a 0.2 um nitrocellulose membrane (BioRad 1704159) using the Trans Blot Turbo System. The membrane was blocked in Intercept TBS Blocking Buffer (Li-cor 927-60001) for 30 minutes at room temperature. The blot was then incubated in a 1:1000 dilution of primary anti-HAO1 antibody (Genetex GTX81144) and 1:2500 dilution of primary anti-vinculin antibody (Sigma V9131) in blocking buffer at 4 C overnight. The blot was washed three times with TBST (ThermoFisher 28360) for 5 minutes each, then incubated with a 1:12500 dilution of IR680 anti-mouse (ThermoFisher PI35518) and IR800 anti-rabbit secondary antibodies (ThermoFisher PISA535571) in TBST for 1 hour at room temperature. The blot was then washed three times with TBST for 5 minutes each and visualized on the Li-cor Odyssey CLX.

Figure 8:
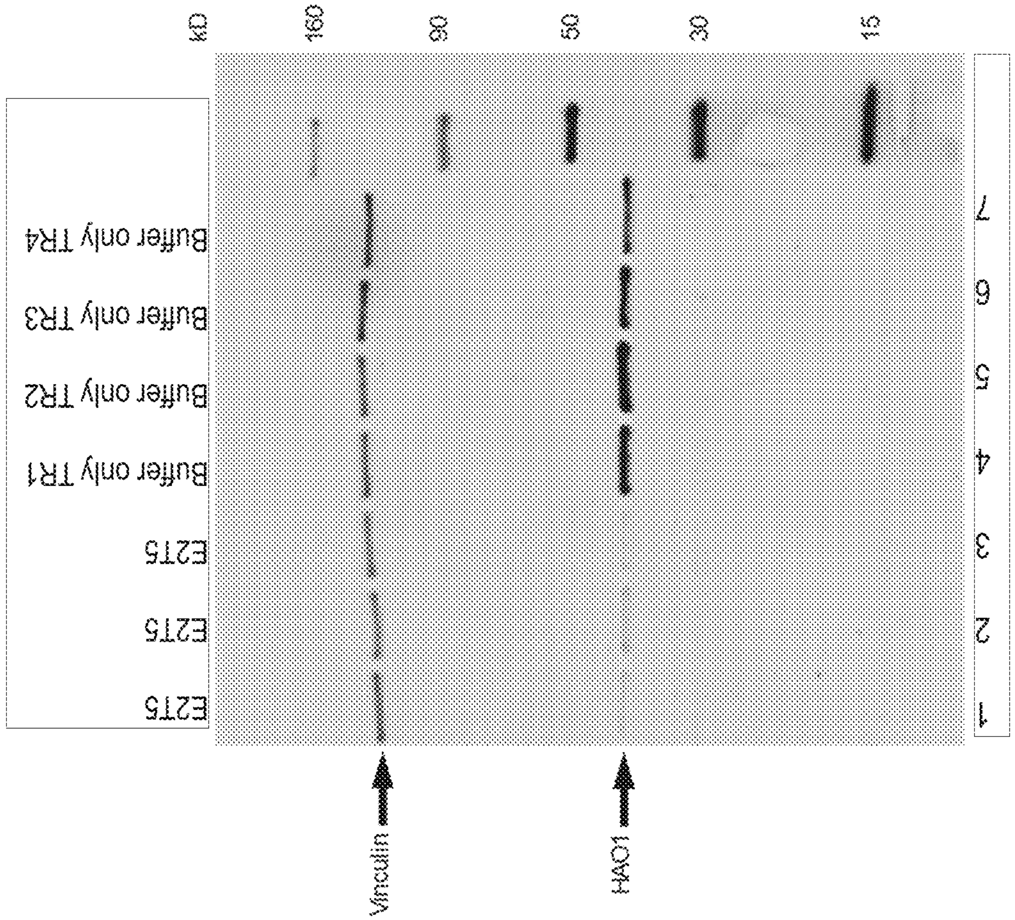
FIG. 8 is a Western Blot showing knockdown of HAO1 protein following electroporation of primary human hepatocytes with variant Cas12i2 of SEQ ID NO: 924 and RNA guide E2T5 (SEQ ID NO: 989).

Knockdown of HAO1 protein was observed in primary human hepatocytes at Day 7 post editing by Cas12i2 RNPs targeting the HAO1 gene with E2T5 (lanes 1-3 of FIG. 8). HAO1 knockdown was not observed for the buffer only controls (lanes 4-7).

This Example thus shows that HAO1 protein levels were decreased following editing with Cas12i2 and HAO1-targeting RNA guides.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A gene editing system for genetic editing of a hydroxy-acid oxidase 1 (HAO1) gene, comprising (i) a Cas12i2 polypeptide or a first nucleic acid encoding the Cas12i2 polypeptide, wherein the Cas12i2 polypeptide is a variant of SEQ ID NO: 922, and wherein, relative to SEQ ID NO:922, the Cas12i2 polypeptide comprises mutations at positions D581, I926, and V1030;

(ii) an RNA guide or a second nucleic acid encoding the RNA guide, wherein the RNA guide comprises a spacer sequence specific to a target sequence within an HAO1 gene, the target sequence being adjacent to a protospacer adjacent motif (PAM) comprising the motif of 5'-TTN-3', which is located 5' to the target sequence.

2. The gene editing system of claim 1, wherein the mutations at D581, I926, and V1030 in SEQ ID NO: 922 are amino acid substitutions of D581R, I926R, and V1030G, respectively.

3. The gene editing system of claim 1, wherein the Cas12i2 polypeptide further comprises mutations at positions G624, F626, P868, E1035, and S1046 in SEQ ID NO: 922.

4. The gene editing system of claim 3, wherein the mutations at G624, F626, P868, E1035, and S1046 in SEQ ID NO: 922 are amino acid substitutions G624R, F626R, P868T, E1035R, and S1046G, respectively.

5. The gene editing system of claim 1, wherein Cas12i2 polypeptide consists of the following mutations:

(i) D581R, I926R, and V1030G in SEQ ID NO: 922; or (ii) D581R, I926R, V1030G, G624R, F626R, P868T, E1035R, and S1046G in SEQ ID NO: 922.

6. The gene editing system of claim 1, wherein the Cas12i2 polypeptide comprises the amino acid sequence of SEQ ID NO: 924 or SEQ ID NO: 927.

7. The gene editing system of claim 1, which comprises the first nucleic acid encoding the Cas12i2 polypeptide.

8. The gene editing system of claim 7, wherein the first nucleic acid is a messenger RNA (mRNA).

9. The gene editing system of claim 1, wherein the target sequence is within exon 1 or exon 2 of the HAO1 gene.

10. The gene editing system of claim 1, wherein the RNA guide comprises the spacer sequence and a direct repeat sequence.

11. The gene editing system of claim 10, wherein the direct repeat sequence comprises the nucleotide sequence of any one of SEQ ID NOs: 1-10, or a fragment thereof that is at least 23 nucleotides in length.

12. The gene editing system of claim 11, wherein the direct repeat sequence is 5'-AGAAAUCCGUCUUUCAUUGACGG-3' (SEQ ID NO: 10).

13. The gene editing system of claim 1, which comprises the second nucleic acid encoding the RNA guide.

14. The gene editing system of claim 1, wherein the system comprises the first nucleic acid encoding the Cas12i2 polypeptide, which is an mRNA, and wherein the system comprises the RNA guide.

15. The gene editing system of claim 14, wherein the RNA guide is chemically modified.

16. The gene editing system of claim 1, wherein the system further comprises lipid nanoparticles (LNPs).

17. The gene editing system of claim 16, wherein at least a portion of the LNPs encompasses the first nucleic acid encoding the Cas12i2 polypeptide, the RNA guide, or both.

18. The gene editing system of claim 17, wherein the first nucleic acid is an mRNA.

19. The gene editing system of claim 17, wherein the RNA guide is chemically modified.

20. A pharmaceutical composition comprising the gene editing system of claim 1.

21. The pharmaceutical composition of claim 20, which further comprises lipid nanoparticles (LNPs).

22. A kit comprising the elements (i) and (ii) set forth in claim 1.

* * * * *

SEQUENCE LISTING

```
Sequence total quantity: 1097
SEQ ID NO: 1            moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 1
gttgcaaaac ccaagaaatc cgtctttcat tgacgg                          36

SEQ ID NO: 2            moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 2
```

```
aatagcggcc ctaagaaatc cgtctttcat tgacgg                        36

SEQ ID NO: 3           moltype = RNA  length = 36
FEATURE                Location/Qualifiers
misc_feature           1..36
                       note = Synthetic
source                 1..36
                       mol_type = other RNA
                       organism = synthetic construct
SEQUENCE: 3
attggaactg gcgagaaatc cgtctttcat tgacgg                        36

SEQ ID NO: 4           moltype = RNA  length = 36
FEATURE                Location/Qualifiers
misc_feature           1..36
                       note = Synthetic
source                 1..36
                       mol_type = other RNA
                       organism = synthetic construct
SEQUENCE: 4
ccagcaacac ctaagaaatc cgtctttcat tgacgg                        36

SEQ ID NO: 5           moltype = RNA  length = 36
FEATURE                Location/Qualifiers
misc_feature           1..36
                       note = Synthetic
source                 1..36
                       mol_type = other RNA
                       organism = synthetic construct
SEQUENCE: 5
cggcgctcga ataggaaatc cgtctttcat tgacgg                        36

SEQ ID NO: 6           moltype = RNA  length = 36
FEATURE                Location/Qualifiers
misc_feature           1..36
                       note = Synthetic
source                 1..36
                       mol_type = other RNA
                       organism = synthetic construct
SEQUENCE: 6
gtggcaacac ctaagaaatc cgtctttcat tgacgg                        36

SEQ ID NO: 7           moltype = RNA  length = 36
FEATURE                Location/Qualifiers
misc_feature           1..36
                       note = Synthetic
source                 1..36
                       mol_type = other RNA
                       organism = synthetic construct
SEQUENCE: 7
gttgcaacac ctaagaaatc cgtctttcat tgacgg                        36

SEQ ID NO: 8           moltype = RNA  length = 36
FEATURE                Location/Qualifiers
misc_feature           1..36
                       note = Synthetic
source                 1..36
                       mol_type = other RNA
                       organism = synthetic construct
SEQUENCE: 8
gttgcaatgc ctaagaaatc cgtctttcat tgacgg                        36

SEQ ID NO: 9           moltype = RNA  length = 34
FEATURE                Location/Qualifiers
misc_feature           1..34
                       note = Synthetic
source                 1..34
                       mol_type = other RNA
                       organism = synthetic construct
SEQUENCE: 9
gcaacaccta agaaatccgt ctttcattga cggg                          34

SEQ ID NO: 10          moltype = RNA  length = 23
FEATURE                Location/Qualifiers
misc_feature           1..23
                       note = Synthetic
source                 1..23
                       mol_type = other RNA
                       organism = synthetic construct
```

```
SEQUENCE: 10
agaaatccgt ctttcattga cgg                                          23

SEQ ID NO: 11          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 11
cctggaaaat gctgcaatat tatcagccaa                                   30

SEQ ID NO: 12          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 12
tcttacctgg aaaatgctgc aatattatca                                   30

SEQ ID NO: 13          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 13
cttacctgga aaatgctgca atattatcag                                   30

SEQ ID NO: 14          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 14
ttacctggaa aatgctgcaa tattatcagc                                   30

SEQ ID NO: 15          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 15
tcagccaaag tttcttcatc atttgcccca                                   30

SEQ ID NO: 16          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 16
cttcatcatt tgccccagac ctgtaatagt                                   30

SEQ ID NO: 17          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 17
ttcatcattt gccccagacc tgtaatagtc                                   30

SEQ ID NO: 18          moltype = DNA  length = 30
FEATURE                Location/Qualifiers
misc_feature           1..30
                       note = Synthetic
source                 1..30
                       mol_type = other DNA
```

```
                         organism = synthetic construct
SEQUENCE: 18
atcatttgcc ccagacctgt aatagtcata                                  30

SEQ ID NO: 19            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 19
gccccagacc tgtaatagtc atatatagac                                  30

SEQ ID NO: 20            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 20
ccccagacct gtaatagtca tatatagact                                  30

SEQ ID NO: 21            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 21
aaaaaataaa ttttcttacc tggaaaatgc                                  30

SEQ ID NO: 22            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 22
ggaagtactg atttagcatg ttgttcataa                                  30

SEQ ID NO: 23            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 23
agcatgttgt tcataatcat tgatacaaat                                  30

SEQ ID NO: 24            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 24
gcatgttgtt cataatcatt gatacaaatt                                  30

SEQ ID NO: 25            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 25
ttcataatca ttgatacaaa ttagccgggg                                  30

SEQ ID NO: 26            moltype = DNA  length = 30
FEATURE                  Location/Qualifiers
misc_feature             1..30
                         note = Synthetic
source                   1..30
```

```
                        mol_type = other DNA
                        organism = synthetic construct
SEQUENCE: 26
ataatcattg atacaaatta gccgggggag                                      30

SEQ ID NO: 27           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 27
atacaaatta gccgggggag cattttcaca                                      30

SEQ ID NO: 28           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 28
gccgggggag cattttcaca ggttattgct                                      30

SEQ ID NO: 29           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 29
tcacaggtta ttgctatccc agatggagtt                                      30

SEQ ID NO: 30           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 30
cacaggttat tgctatccca gatggagttc                                      30

SEQ ID NO: 31           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 31
acaggttatt gctatcccag atggagttcg                                      30

SEQ ID NO: 32           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 32
gaagtactga tttagcatgt tgttcataat                                      30

SEQ ID NO: 33           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 33
taaaaaataa attttcttac ctggaaaatg                                      30

SEQ ID NO: 34           moltype = DNA  length = 30
FEATURE                 Location/Qualifiers
misc_feature            1..30
                        note = Synthetic
```

```
source                  1..30
                        mol_type = other DNA
                        organism = synthetic construct
SEQUENCE: 34
aaaaataaat tttcttacct ggaaaatgct                                  30

SEQ ID NO: 35           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 35
aaaacatgat tttaaaaaat aaattttctt                                  30

SEQ ID NO: 36           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 36
tatcaatgat tatgaacaac atgctaaatc                                  30

SEQ ID NO: 37           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 37
tgaacaacat gctaaatcag tacttccaaa                                  30

SEQ ID NO: 38           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 38
caaagtctat atatgactat tacaggtctg                                  30

SEQ ID NO: 39           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 39
caggtctggg gcaaatgatg aagaaacttt                                  30

SEQ ID NO: 40           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 40
ggctgataat attgcagcat tttccaggta                                  30

SEQ ID NO: 41           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 41
gctgataata ttgcagcatt ttccaggtaa                                  30

SEQ ID NO: 42           moltype = DNA  length = 30
FEATURE                 Location/Qualifiers
misc_feature            1..30
```

-continued

```
                         note = Synthetic
source                   1..30
                         mol_type = other DNA
                         organism = synthetic construct
SEQUENCE: 42
cagcattttc caggtaagaa aatttatttt                                    30

SEQ ID NO: 43            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 43
tccaggtaag aaaatttatt ttttaaaatc                                    30

SEQ ID NO: 44            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 44
ccaggtaaga aaatttattt tttaaaatca                                    30

SEQ ID NO: 45            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 45
aaacatgatt ttaaaaaata aattttctta                                    30

SEQ ID NO: 46            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 46
attttttaaa atcatgtttt aaaattacac                                    30

SEQ ID NO: 47            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 47
caggtaagaa aatttatttt ttaaaatcat                                    30

SEQ ID NO: 48            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 48
tttaaaatca tgttttaaaa ttacacaaag                                    30

SEQ ID NO: 49            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 49
ttaaaatcat gttttaaaat tacacaaaga                                    30

SEQ ID NO: 50            moltype = DNA  length = 30
FEATURE                  Location/Qualifiers
```

```
misc_feature           1..30
                       note = Synthetic
source                 1..30
                       mol_type = other DNA
                       organism = synthetic construct
SEQUENCE: 50
taaaatcatg ttttaaaatt acacaaagac                                   30

SEQ ID NO: 51          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 51
aaaatcatgt tttaaaatta cacaaagacc                                   30

SEQ ID NO: 52          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 52
aaatcatgtt ttaaaattac acaaagaccg                                   30

SEQ ID NO: 53          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 53
gtgtaatttt aaaacatgat tttaaaaaat                                   30

SEQ ID NO: 54          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 54
tgtaatttta aaacatgatt ttaaaaaata                                   30

SEQ ID NO: 55          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 55
taaaacatga ttttaaaaaa taaattttct                                   30

SEQ ID NO: 56          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 56
ttttttaaaa tcatgtttta aaattacaca                                   30

SEQ ID NO: 57          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 57
gtatcaatga ttatgaacaa catgctaaat                                   30

SEQ ID NO: 58          moltype = DNA  length = 24
```

-continued

```
FEATURE                 Location/Qualifiers
misc_feature            1..24
                        note = Synthetic
source                  1..24
                        mol_type = other DNA
                        organism = synthetic construct
SEQUENCE: 58
ttgctatccc agatggagtt cgtt                                        24

SEQ ID NO: 59           moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 59
ctatcccaga tggagttcgt t                                           21

SEQ ID NO: 60           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 60
ttttttaatt ctagatggaa gctgtatcca                                  30

SEQ ID NO: 61           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 61
attttatttt ttaattctag atggaagctg                                  30

SEQ ID NO: 62           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 62
attttttaat tctagatgga agctgtatcc                                  30

SEQ ID NO: 63           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 63
tattttttaa ttctagatgg aagctgtatc                                  30

SEQ ID NO: 64           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 64
ttttattttt taattctaga tggaagctgt                                  30

SEQ ID NO: 65           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 65
aaaaataaaa taaaataaaa ggctttagag                                  30
```

```
SEQ ID NO: 66          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 66
attttatttt attttttaat tctagatgga                                   30

SEQ ID NO: 67          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 67
tattttattt tattttttaa ttctagatgg                                   30

SEQ ID NO: 68          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 68
tgaaactcta aagcctttta ttttatttta                                   30

SEQ ID NO: 69          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 69
tttaattcta gatggaagct gtatccaagg                                   30

SEQ ID NO: 70          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 70
ttttatttta ttttttaatt ctagatggaa                                   30

SEQ ID NO: 71          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 71
ttaattctag atggaagctg tatccaagga                                   30

SEQ ID NO: 72          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 72
tattttattt tttaattcta gatggaagct                                   30

SEQ ID NO: 73          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 73
catctagaat taaaaaataa aataaaataa                                   30
```

```
SEQ ID NO: 74          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 74
taattctaga tggaagctgt atccaaggat                                   30

SEQ ID NO: 75          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 75
aattctagat ggaagctgta tccaaggatg                                   30

SEQ ID NO: 76          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 76
attctagatg gaagctgtat ccaaggatgc                                   30

SEQ ID NO: 77          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 77
tagatggaag ctgtatccaa ggatgctccg                                   30

SEQ ID NO: 78          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 78
ctgaaacaga tctgtcgact tctgttttag                                   30

SEQ ID NO: 79          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 79
taggacagag ggtcagcatg ccaatatgtg                                   30

SEQ ID NO: 80          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 80
aggacagagg gtcagcatgc caatatgtgt                                   30

SEQ ID NO: 81          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 81
```

```
ggacagaggg tcagcatgcc aatatgtgtg                                  30

SEQ ID NO: 82           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 82
ccactgtgag aggtaggagg aagattgtca                                  30

SEQ ID NO: 83           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 83
tgttttagga cagagggtca gcatgccaat                                  30

SEQ ID NO: 84           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 84
gcctccttct gtccctgtgg tgacaatctt                                  30

SEQ ID NO: 85           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 85
tcaccacagg gacagaagga ggctaacgtt                                  30

SEQ ID NO: 86           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 86
cggagcatcc ttggatacag cttccatcta                                  30

SEQ ID NO: 87           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 87
agcaacattc cggagcatcc ttggatacag                                  30

SEQ ID NO: 88           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 88
cagcaacatt ccggagcatc cttggataca                                  30

SEQ ID NO: 89           moltype = DNA  length = 30
FEATURE                 Location/Qualifiers
misc_feature            1..30
                        note = Synthetic
source                  1..30
                        mol_type = other DNA
                        organism = synthetic construct
```

```
SEQUENCE: 89
gatacagctt ccatctagaa ttaaaaaata                                    30

SEQ ID NO: 90           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 90
ctcctacctc tcacagtggc aagctcgccg                                    30

SEQ ID NO: 91           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 91
tgtccctgtg gtgacaatct tcctcctacc                                    30

SEQ ID NO: 92           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 92
gcatgctgac cctctgtcct aaaacagaag                                    30

SEQ ID NO: 93           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 93
cctgggcaac cgtctggatg atgtgcgtaa                                    30

SEQ ID NO: 94           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 94
aatctgttac gcacatcatc cagacggttg                                    30

SEQ ID NO: 95           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 95
gaatctgtta cgcacatcat ccagacggtt                                    30

SEQ ID NO: 96           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 96
tggcggcagt ttgaatctgt tacgcacatc                                    30

SEQ ID NO: 97           moltype = DNA  length = 30
FEATURE                 Location/Qualifiers
misc_feature            1..30
                        note = Synthetic
source                  1..30
                        mol_type = other DNA
```

```
                        organism = synthetic construct
SEQUENCE: 97
cctgagttgt ggcggcagtt tgaatctgtt                                    30

SEQ ID NO: 98           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 98
gcctcagctc ggggcccaca tgatcatggt                                    30

SEQ ID NO: 99           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 99
cgcctcagct cggggcccac atgatcatgg                                    30

SEQ ID NO: 100          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 100
aaactgccgc cacaactcag gtaaccatga                                    30

SEQ ID NO: 101          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 101
tgacagtgga cacaccttac ctgggcaacc                                    30

SEQ ID NO: 102          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 102
atcatcccct ttctttctca gcctgtcagt                                    30

SEQ ID NO: 103          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 103
gctgcaactg tatatctaca aggaccgaga                                    30

SEQ ID NO: 104          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 104
aagaagtggc ggaagctggt cctgaggcac                                    30

SEQ ID NO: 105          moltype = DNA  length = 30
FEATURE                 Location/Qualifiers
misc_feature            1..30
                        note = Synthetic
source                  1..30
```

```
                        mol_type = other DNA
                        organism = synthetic construct
SEQUENCE: 105
ctgggccacc tcctcaattg aagaagtggc                                       30

SEQ ID NO: 106          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 106
agttcctggg ccacctcctc aattgaagaa                                       30

SEQ ID NO: 107          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 107
tcagcctgtc agtccctggg aacgggcatg                                       30

SEQ ID NO: 108          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 108
ctcagcctgt cagtccctgg gaacgggcat                                       30

SEQ ID NO: 109          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 109
tttctcagcc tgtcagtccc tgggaacggg                                       30

SEQ ID NO: 110          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 110
ctttctcagc ctgtcagtcc ctgggaacgg                                       30

SEQ ID NO: 111          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 111
cgcacatcat ccagacggtt gcccaggtaa                                       30

SEQ ID NO: 112          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 112
gtgacagtgg acacacctta cctgggcaac                                       30

SEQ ID NO: 113          moltype = DNA  length = 30
FEATURE                 Location/Qualifiers
misc_feature            1..30
                        note = Synthetic
```

```
source                  1..30
                        mol_type = other DNA
                        organism = synthetic construct
SEQUENCE: 113
cccaggtaag gtgtgtccac tgtcacaaat                                    30

SEQ ID NO: 114          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 114
gttggctgca actgtatatc tacaaggacc                                    30

SEQ ID NO: 115          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 115
tctgcctgcc gcactagctt cttggtgact                                    30

SEQ ID NO: 116          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 116
tagcccatct tctctgcctg ccgcactagc                                    30

SEQ ID NO: 117          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 117
ccagggactg acaggctgag aaagaaaggg                                    30

SEQ ID NO: 118          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 118
aggaggtggc ccaggaactc aacatcatgc                                    30

SEQ ID NO: 119          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 119
ttcaattgag gaggtggccc aggaactcaa                                    30

SEQ ID NO: 120          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 120
cgccacttct tcaattgagg aggtggccca                                    30

SEQ ID NO: 121          moltype = DNA  length = 30
FEATURE                 Location/Qualifiers
misc_feature            1..30
```

```
                       note = Synthetic
source                 1..30
                       mol_type = other DNA
                       organism = synthetic construct
SEQUENCE: 121
aattgaggag gtggcccagg aactcaacat                                   30

SEQ ID NO: 122         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 122
tagatataca gttgcagcca acgaagtgcc                                   30

SEQ ID NO: 123         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 123
tcggtccttg tagatataca gttgcagcca                                   30

SEQ ID NO: 124         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 124
gtgacttctc ggtccttgta gatatacagt                                   30

SEQ ID NO: 125         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 125
ttggtgactt ctcggtcctt gtagatatac                                   30

SEQ ID NO: 126         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 126
cagccaacga agtgcctcag gaccagcttc                                   30

SEQ ID NO: 127         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 127
ctaatttggc aaatttctca ttttatgcat                                   30

SEQ ID NO: 128         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 128
atcctaaaat aagaaatgca taaaatgaga                                   30

SEQ ID NO: 129         moltype = DNA  length = 30
FEATURE                Location/Qualifiers
```

```
misc_feature          1..30
                      note = Synthetic
source                1..30
                      mol_type = other DNA
                      organism = synthetic construct
SEQUENCE: 129
aagtagagaa ataaacgaac ctctcaaaat                                   30

SEQ ID NO: 130        moltype = DNA  length = 30
FEATURE               Location/Qualifiers
misc_feature          1..30
                      note = Synthetic
source                1..30
                      mol_type = other DNA
                      organism = synthetic construct
SEQUENCE: 130
tctacttgaa ttcatactga ctttgtgatc                                   30

SEQ ID NO: 131        moltype = DNA  length = 30
FEATURE               Location/Qualifiers
misc_feature          1..30
                      note = Synthetic
source                1..30
                      mol_type = other DNA
                      organism = synthetic construct
SEQUENCE: 131
taatttggca aatttctcat tttatgcatt                                   30

SEQ ID NO: 132        moltype = DNA  length = 30
FEATURE               Location/Qualifiers
misc_feature          1..30
                      note = Synthetic
source                1..30
                      mol_type = other DNA
                      organism = synthetic construct
SEQUENCE: 132
tatgcatttc ttattttagg atgaaaaatt                                   30

SEQ ID NO: 133        moltype = DNA  length = 30
FEATURE               Location/Qualifiers
misc_feature          1..30
                      note = Synthetic
source                1..30
                      mol_type = other DNA
                      organism = synthetic construct
SEQUENCE: 133
gcaaatttct cattttatgc atttcttatt                                   30

SEQ ID NO: 134        moltype = DNA  length = 30
FEATURE               Location/Qualifiers
misc_feature          1..30
                      note = Synthetic
source                1..30
                      mol_type = other DNA
                      organism = synthetic construct
SEQUENCE: 134
ctcattttat gcatttctta ttttaggatg                                   30

SEQ ID NO: 135        moltype = DNA  length = 30
FEATURE               Location/Qualifiers
misc_feature          1..30
                      note = Synthetic
source                1..30
                      mol_type = other DNA
                      organism = synthetic construct
SEQUENCE: 135
tcattttatg catttcttat tttaggatga                                   30

SEQ ID NO: 136        moltype = DNA  length = 30
FEATURE               Location/Qualifiers
misc_feature          1..30
                      note = Synthetic
source                1..30
                      mol_type = other DNA
                      organism = synthetic construct
SEQUENCE: 136
catcctaaaa taagaaatgc ataaaatgag                                   30

SEQ ID NO: 137        moltype = DNA  length = 30
```

```
FEATURE                Location/Qualifiers
misc_feature           1..30
                       note = Synthetic
source                 1..30
                       mol_type = other DNA
                       organism = synthetic construct
SEQUENCE: 137
ggcaaatttc tcattttatg catttcttat                                   30

SEQ ID NO: 138         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 138
tcatcctaaa ataagaaatg cataaaatga                                   30

SEQ ID NO: 139         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 139
tcctcaggag aaaatgataa agtactggtt                                   30

SEQ ID NO: 140         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 140
aaaattttc atcctaaaat aagaaatgca                                    30

SEQ ID NO: 141         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 141
caaaattttt catcctaaaa taagaaatgc                                   30

SEQ ID NO: 142         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 142
ctcaggagaa aatgataaag tactggtttc                                   30

SEQ ID NO: 143         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 143
cctcaggaga aaatgataaa gtactggttt                                   30

SEQ ID NO: 144         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 144
atgcatttct tattttagga tgaaaaattt                                   30
```

```
SEQ ID NO: 145          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 145
gccacatatg cagcaagtcc actgtcgtct                                   30

SEQ ID NO: 146          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 146
agccacatat gcagcaagtc cactgtcgtc                                   30

SEQ ID NO: 147          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 147
ctttagccac atatgcagca agtccactgt                                   30

SEQ ID NO: 148          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 148
ccagctgata gatgggtcta ttgctttagc                                   30

SEQ ID NO: 149          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 149
atatcttccc agctgataga tgggtctatt                                   30

SEQ ID NO: 150          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 150
gatatcttcc cagctgatag atgggtctat                                   30

SEQ ID NO: 151          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 151
tcagccattt gatatcttcc cagctgatag                                   30

SEQ ID NO: 152          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 152
gcaatgatgt cagtcttctc agccatttga                                   30
```

```
SEQ ID NO: 153          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 153
ttcatcctaa aataagaaat gcataaaatg                                     30

SEQ ID NO: 154          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 154
tgcatttctt attttaggat gaaaaatttt                                     30

SEQ ID NO: 155          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 155
ggatgaaaaa ttttgaaacc agtactttat                                     30

SEQ ID NO: 156          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 156
ttattttagg atgaaaaatt ttgaaaccag                                     30

SEQ ID NO: 157          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 157
ccaattgttg caaagggcat tttgagaggt                                     30

SEQ ID NO: 158          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 158
ttgcaaaggg cattttgaga ggttcgttta                                     30

SEQ ID NO: 159          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 159
gcaacaattg gcaatgatgt cagtcttctc                                     30

SEQ ID NO: 160          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 160
```

```
caaagggcat tttgagaggt tcgtttattt                                    30

SEQ ID NO: 161          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 161
tgagaggttc gtttatttct ctacttgaat                                    30

SEQ ID NO: 162          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 162
gagaggttcg tttatttctc tacttgaatt                                    30

SEQ ID NO: 163          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 163
agaggttcgt ttatttctct acttgaattc                                    30

SEQ ID NO: 164          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 164
gtttatttct ctacttgaat tcatactgac                                    30

SEQ ID NO: 165          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 165
atttctctac ttgaattcat actgactttg                                    30

SEQ ID NO: 166          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 166
tttctctact tgaattcata ctgactttgt                                    30

SEQ ID NO: 167          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 167
ctctacttga attcatactg actttgtgat                                    30

SEQ ID NO: 168          moltype = DNA  length = 30
FEATURE                 Location/Qualifiers
misc_feature            1..30
                        note = Synthetic
source                  1..30
                        mol_type = other DNA
                        organism = synthetic construct
```

```
SEQUENCE: 168
ctgcatatgt ggctaaagca atagacccat                                   30

SEQ ID NO: 169         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 169
cttattttag gatgaaaaat tttgaaacca                                   30

SEQ ID NO: 170         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 170
gagacgacag tggacttgct gcatatgtgg                                   30

SEQ ID NO: 171         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 171
tggagacgac agtggacttg ctgcatatgt                                   30

SEQ ID NO: 172         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 172
tcctgaggaa aattttggag acgacagtgg                                   30

SEQ ID NO: 173         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 173
ctcctgagga aaattttgga gacgacagtg                                   30

SEQ ID NO: 174         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 174
tctcctgagg aaaattttgg agacgacagt                                   30

SEQ ID NO: 175         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 175
tcattttctc ctgaggaaaa ttttggagac                                   30

SEQ ID NO: 176         moltype = DNA  length = 30
FEATURE                Location/Qualifiers
misc_feature           1..30
                       note = Synthetic
source                 1..30
                       mol_type = other DNA
```

```
                        organism = synthetic construct
SEQUENCE: 176
atcattttct cctgaggaaa attttggaga                                   30

SEQ ID NO: 177          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 177
aaaccagtac tttatcattt tctcctgagg                                   30

SEQ ID NO: 178          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 178
gaaaccagta ctttatcatt ttctcctgag                                   30

SEQ ID NO: 179          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 179
tgaaaccagt actttatcat tttctcctga                                   30

SEQ ID NO: 180          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 180
aggatgaaaa attttgaaac cagtacttta                                   30

SEQ ID NO: 181          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 181
taggatgaaa aattttgaaa ccagtacttt                                   30

SEQ ID NO: 182          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 182
ttttaggatg aaaaattttg aaaccagtac                                   30

SEQ ID NO: 183          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 183
ggagacgaca gtggacttgc tgcatatgtg                                   30

SEQ ID NO: 184          moltype = DNA  length = 30
FEATURE                 Location/Qualifiers
misc_feature            1..30
                        note = Synthetic
source                  1..30
```

```
                        mol_type = other DNA
                        organism = synthetic construct
SEQUENCE: 184
caacaattgg caatgatgtc agtcttctca                                    30

SEQ ID NO: 185          moltype = DNA  length = 29
FEATURE                 Location/Qualifiers
misc_feature            1..29
                        note = Synthetic
source                  1..29
                        mol_type = other DNA
                        organism = synthetic construct
SEQUENCE: 185
aattcatact gactttgtga tcctttgtg                                     29

SEQ ID NO: 186          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 186
atactgactt tgtgatcctt tgtg                                          24

SEQ ID NO: 187          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 187
agttacagtt tccctaaggt gcttgtttta                                    30

SEQ ID NO: 188          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 188
aagccatgtt taacagcctc cctggcatca                                    30

SEQ ID NO: 189          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 189
acagcctccc tggcatcatc acctggagag                                    30

SEQ ID NO: 190          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 190
aacagcctcc ctggcatcat cacctggaga                                    30

SEQ ID NO: 191          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 191
gacaccaaga tcccattcaa gccatgttta                                    30

SEQ ID NO: 192          moltype = DNA  length = 30
FEATURE                 Location/Qualifiers
misc_feature            1..30
                        note = Synthetic
```

```
source                1..30
                      mol_type = other DNA
                      organism = synthetic construct
SEQUENCE: 192
tcgagcccca tgattcgaca ccaagatccc                                  30

SEQ ID NO: 193        moltype = DNA  length = 30
FEATURE               Location/Qualifiers
misc_feature          1..30
                      note = Synthetic
source                1..30
                      mol_type = other DNA
                      organism = synthetic construct
SEQUENCE: 193
gcgtctgcca aaactcacag tggctggcac                                  30

SEQ ID NO: 194        moltype = DNA  length = 30
FEATURE               Location/Qualifiers
misc_feature          1..30
                      note = Synthetic
source                1..30
                      mol_type = other DNA
                      organism = synthetic construct
SEQUENCE: 194
gcagacgcta agatttcctt ttggagttcc                                  30

SEQ ID NO: 195        moltype = DNA  length = 30
FEATURE               Location/Qualifiers
misc_feature          1..30
                      note = Synthetic
source                1..30
                      mol_type = other DNA
                      organism = synthetic construct
SEQUENCE: 195
tggcagacgc taagatttcc ttttggagtt                                  30

SEQ ID NO: 196        moltype = DNA  length = 30
FEATURE               Location/Qualifiers
misc_feature          1..30
                      note = Synthetic
source                1..30
                      mol_type = other DNA
                      organism = synthetic construct
SEQUENCE: 196
gtgtcgaatc atggggctcg acaactcgat                                  30

SEQ ID NO: 197        moltype = DNA  length = 30
FEATURE               Location/Qualifiers
misc_feature          1..30
                      note = Synthetic
source                1..30
                      mol_type = other DNA
                      organism = synthetic construct
SEQUENCE: 197
ggcagacgct aagatttcct tttggagttc                                  30

SEQ ID NO: 198        moltype = DNA  length = 30
FEATURE               Location/Qualifiers
misc_feature          1..30
                      note = Synthetic
source                1..30
                      mol_type = other DNA
                      organism = synthetic construct
SEQUENCE: 198
aacatggctt gaatgggatc ttggtgtcga                                  30

SEQ ID NO: 199        moltype = DNA  length = 30
FEATURE               Location/Qualifiers
misc_feature          1..30
                      note = Synthetic
source                1..30
                      mol_type = other DNA
                      organism = synthetic construct
SEQUENCE: 199
ctctctccag gtgatgatgc cagggaggct                                  30

SEQ ID NO: 200        moltype = DNA  length = 30
FEATURE               Location/Qualifiers
misc_feature          1..30
```

```
                        note = Synthetic
source                  1..30
                        mol_type = other DNA
                        organism = synthetic construct
SEQUENCE: 200
actctctcca ggtgatgatg ccagggaggc                                   30

SEQ ID NO: 201          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 201
tactctctcc aggtgatgat gccagggagg                                   30

SEQ ID NO: 202          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 202
ttttactctc tccaggtgat gatgccaggg                                   30

SEQ ID NO: 203          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 203
cctaaggtgc ttgttttact ctctccaggt                                   30

SEQ ID NO: 204          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 204
ccctaaggtg cttgttttac tctctccagg                                   30

SEQ ID NO: 205          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 205
cagtttccct aaggtgcttg ttttactctc                                   30

SEQ ID NO: 206          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 206
aatgggatct tggtgtcgaa tcatggggct                                   30

SEQ ID NO: 207          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 207
ccttttggag ttcccatttc catc                                         24

SEQ ID NO: 208          moltype = DNA  length = 23
FEATURE                 Location/Qualifiers
```

```
misc_feature          1..23
                      note = Synthetic
source                1..23
                      mol_type = other DNA
                      organism = synthetic construct
SEQUENCE: 208
cttttggagt tcccatttcc atc                                          23

SEQ ID NO: 209        moltype = DNA  length = 24
FEATURE               Location/Qualifiers
misc_feature          1..24
                      note = Synthetic
source                1..24
                      mol_type = other DNA
                      organism = synthetic construct
SEQUENCE: 209
gggaaactgt aacttaacag gcag                                         24

SEQ ID NO: 210        moltype = DNA  length = 30
FEATURE               Location/Qualifiers
misc_feature          1..30
                      note = Synthetic
source                1..30
                      mol_type = other DNA
                      organism = synthetic construct
SEQUENCE: 210
caactttctt ttcttttatg atctttaagt                                   30

SEQ ID NO: 211        moltype = DNA  length = 30
FEATURE               Location/Qualifiers
misc_feature          1..30
                      note = Synthetic
source                1..30
                      mol_type = other DNA
                      organism = synthetic construct
SEQUENCE: 211
cggttggcca tggctctgag tggtaagact                                   30

SEQ ID NO: 212        moltype = DNA  length = 30
FEATURE               Location/Qualifiers
misc_feature          1..30
                      note = Synthetic
source                1..30
                      mol_type = other DNA
                      organism = synthetic construct
SEQUENCE: 212
gccatggctc tgagtggtaa gactcattct                                   30

SEQ ID NO: 213        moltype = DNA  length = 30
FEATURE               Location/Qualifiers
misc_feature          1..30
                      note = Synthetic
source                1..30
                      mol_type = other DNA
                      organism = synthetic construct
SEQUENCE: 213
ttgtttacaa ctttcttttc ttttatgatc                                   30

SEQ ID NO: 214        moltype = DNA  length = 30
FEATURE               Location/Qualifiers
misc_feature          1..30
                      note = Synthetic
source                1..30
                      mol_type = other DNA
                      organism = synthetic construct
SEQUENCE: 214
tttacaactt tcttttcttt tatgatcttt                                   30

SEQ ID NO: 215        moltype = DNA  length = 30
FEATURE               Location/Qualifiers
misc_feature          1..30
                      note = Synthetic
source                1..30
                      mol_type = other DNA
                      organism = synthetic construct
SEQUENCE: 215
acaactttct tttcttttat gatctttaag                                   30

SEQ ID NO: 216        moltype = DNA  length = 30
```

```
FEATURE                Location/Qualifiers
misc_feature           1..30
                       note = Synthetic
source                 1..30
                       mol_type = other DNA
                       organism = synthetic construct
SEQUENCE: 216
aagatcataa aagaaaagaa agttgtaaac                                   30

SEQ ID NO: 217         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 217
tctattttat atattcattt ctttgtccag                                   30

SEQ ID NO: 218         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 218
ccactcagag ccatggccaa ccggaattct                                   30

SEQ ID NO: 219         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 219
ttcctttagt atctcgagga catcttgaac                                   30

SEQ ID NO: 220         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 220
ctttagtatc tcgaggacat cttgaacacc                                   30

SEQ ID NO: 221         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 221
agtatctcga ggacatcttg aacacctttc                                   30

SEQ ID NO: 222         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 222
gtatctcgag gacatcttga acacctttct                                   30

SEQ ID NO: 223         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 223
aagatgtcct cgagatacta aaggaagaat                                   30
```

```
SEQ ID NO: 224         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 224
taaacaagaa tgagtcttac cactcagagc                                   30

SEQ ID NO: 225         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 225
gggggagaaa ggtgttcaag atgtcctcga                                   30

SEQ ID NO: 226         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 226
ccaggtaact ggacaaagaa atgaatatat                                   30

SEQ ID NO: 227         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 227
acttggttag ggggagaaag gtgttcaaga                                   30

SEQ ID NO: 228         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 228
cacttggtta gggggagaaa ggtgttcaag                                   30

SEQ ID NO: 229         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 229
tcacttggtt agggggagaa aggtgttcaa                                   30

SEQ ID NO: 230         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 230
tgaatcactc tgtatctttt cacttggtta                                   30

SEQ ID NO: 231         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 231
gttctgaatc actctgtatc ttttcacttg                                   30
```

```
SEQ ID NO: 232          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 232
agttctgaat cactctgtat cttttcactt                                   30

SEQ ID NO: 233          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 233
acagtaaaac aaatgaataa aacaagtcag                                   30

SEQ ID NO: 234          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 234
caggtaactg gacaaagaaa tgaatatata                                   30

SEQ ID NO: 235          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 235
aacacctttc tccccctaac caagtgaaaa                                   30

SEQ ID NO: 236          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 236
gctttccagg taactggaca aagaaatgaa                                   30

SEQ ID NO: 237          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 237
gggcttagct ttccaggtaa ctggacaaag                                   30

SEQ ID NO: 238          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 238
ggggcttagc tttccaggta actggacaaa                                   30

SEQ ID NO: 239          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 239
```

```
tggggagacc aatcgtttgg ggcttagctt                                    30

SEQ ID NO: 240          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 240
gtggggagac caatcgtttg gggcttagct                                    30

SEQ ID NO: 241          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 241
gttaggggga gaaaggtgtt caagatgtcc                                    30

SEQ ID NO: 242          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 242
ctccccctaa ccaagtgaaa agatacagag                                    30

SEQ ID NO: 243          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 243
tactgtcaag ttgtctattt tatatattca                                    30

SEQ ID NO: 244          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 244
agaactaaat cagtctgact tgttttattc                                    30

SEQ ID NO: 245          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 245
aataatgtga ctctattaac actgaattgt                                    30

SEQ ID NO: 246          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 246
tggcagaaca tcaatctggg gaaagaaaag                                    30

SEQ ID NO: 247          moltype = DNA  length = 30
FEATURE                 Location/Qualifiers
misc_feature            1..30
                        note = Synthetic
source                  1..30
                        mol_type = other DNA
                        organism = synthetic construct
```

```
SEQUENCE: 247
ctggcagaac atcaatctgg ggaaagaaaa                                  30

SEQ ID NO: 248          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 248
cacagcctcc acaatttctg gcagaacatc                                  30

SEQ ID NO: 249          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 249
ccttccacag cctccacaat ttctggcaga                                  30

SEQ ID NO: 250          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 250
caccttccct tccacagcct ccacaatttc                                  30

SEQ ID NO: 251          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 251
cgcacacccc cgtccaggaa gacttccacc                                  30

SEQ ID NO: 252          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 252
ccgcacaccc ccgtccagga agacttccac                                  30

SEQ ID NO: 253          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 253
agaacatcag tgcctttccg cacacccccg                                  30

SEQ ID NO: 254          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 254
cagaacatca gtgcctttcc gcacaccccc                                  30

SEQ ID NO: 255          moltype = DNA  length = 30
FEATURE                 Location/Qualifiers
misc_feature            1..30
                        note = Synthetic
source                  1..30
                        mol_type = other DNA
```

```
                       organism = synthetic construct
SEQUENCE: 255
gcgccaagag ccagagcttt cagaacatca                                   30

SEQ ID NO: 256         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 256
gtctccccac aaacacagcc ttggcgccaa                                   30

SEQ ID NO: 257         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 257
cctggaaagc taagccccaa acgattggtc                                   30

SEQ ID NO: 258         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 258
tccagttacc tggaaagcta agccccaaac                                   30

SEQ ID NO: 259         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 259
gtccagttac ctggaaagct aagccccaaa                                   30

SEQ ID NO: 260         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 260
tttgtccagt tacctggaaa gctaagcccc                                   30

SEQ ID NO: 261         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 261
ctttgtccag ttacctggaa agctaagccc                                   30

SEQ ID NO: 262         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 262
ttttattcat ttgttttact gtcaagttgt                                   30

SEQ ID NO: 263         moltype = DNA  length = 30
FEATURE                Location/Qualifiers
misc_feature           1..30
                       note = Synthetic
source                 1..30
```

```
                        mol_type = other DNA
                        organism = synthetic construct
SEQUENCE: 263
tattcatttg ttttactgtc aagttgtcta                                     30

SEQ ID NO: 264          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 264
attcatttgt tttactgtca agttgtctat                                     30

SEQ ID NO: 265          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 265
ttcatttgtt ttactgtcaa gttgtctatt                                     30

SEQ ID NO: 266          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 266
atttgtttta ctgtcaagtt gtctatttta                                     30

SEQ ID NO: 267          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 267
gttttactgt caagttgtct attttatata                                     30

SEQ ID NO: 268          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 268
tccccctaac caagtgaaaa gatacagagt                                     30

SEQ ID NO: 269          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 269
ttttactgtc aagttgtcta ttttatatat                                     30

SEQ ID NO: 270          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 270
actgtcaagt tgtctatttt atatattcat                                     30

SEQ ID NO: 271          moltype = DNA  length = 30
FEATURE                 Location/Qualifiers
misc_feature            1..30
                        note = Synthetic
```

-continued

```
source                  1..30
                        mol_type = other DNA
                        organism = synthetic construct
SEQUENCE: 271
ctgtcaagtt gtctatttta tatattcatt                                   30

SEQ ID NO: 272          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 272
tatatattca tttctttgtc cagttacctg                                   30

SEQ ID NO: 273          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 273
atatattcat ttctttgtcc agttacctgg                                   30

SEQ ID NO: 274          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 274
tatattcatt tctttgtcca gttacctgga                                   30

SEQ ID NO: 275          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 275
atttctttgt ccagttacct ggaaagctaa                                   30

SEQ ID NO: 276          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 276
gcgccaaggc tgtgtttgtg gggagaccaa                                   30

SEQ ID NO: 277          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 277
tgaaagctct ggctcttggc gccaaggctg                                   30

SEQ ID NO: 278          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 278
tggaggctgt ggaagggaag gtggaagtct                                   30

SEQ ID NO: 279          moltype = DNA  length = 30
FEATURE                 Location/Qualifiers
misc_feature            1..30
```

```
                        note = Synthetic
source                  1..30
                        mol_type = other DNA
                        organism = synthetic construct
SEQUENCE: 279
ttgaactttt ctttccccag attgatgttc                                   30

SEQ ID NO: 280          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 280
tgccagaaat tgtggaggct gtggaaggga                                   30

SEQ ID NO: 281          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 281
atgttctgcc agaaattgtg gaggctgtgg                                   30

SEQ ID NO: 282          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 282
cccagattga tgttctgcca gaaattgtgg                                   30

SEQ ID NO: 283          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 283
ccccagattg atgttctgcc agaaattgtg                                   30

SEQ ID NO: 284          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 284
tttccccaga ttgatgttct gccagaaatt                                   30

SEQ ID NO: 285          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 285
ctttccccag attgatgttc tgccagaaat                                   30

SEQ ID NO: 286          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 286
tctttcccca gattgatgtt ctgccagaaa                                   30

SEQ ID NO: 287          moltype = DNA  length = 30
FEATURE                 Location/Qualifiers
```

```
misc_feature           1..30
                       note = Synthetic
source                 1..30
                       mol_type = other DNA
                       organism = synthetic construct
SEQUENCE: 287
aacttttctt tccccagatt gatgttctgc                                   30

SEQ ID NO: 288         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 288
atagagtcac attattgaac ttttctttcc                                   30

SEQ ID NO: 289         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 289
agtgttaata gagtcacatt attgaacttt                                   30

SEQ ID NO: 290         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 290
ctggacgggg gtgtgcggaa aggcactgat                                   30

SEQ ID NO: 291         moltype = DNA  length = 23
FEATURE                Location/Qualifiers
misc_feature           1..23
                       note = Synthetic
source                 1..23
                       mol_type = other DNA
                       organism = synthetic construct
SEQUENCE: 291
cttttctttt atgatcttta agt                                          23

SEQ ID NO: 292         moltype = DNA  length = 22
FEATURE                Location/Qualifiers
misc_feature           1..22
                       note = Synthetic
source                 1..22
                       mol_type = other DNA
                       organism = synthetic construct
SEQUENCE: 292
ttttctttta tgatctttaa gt                                           22

SEQ ID NO: 293         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 293
tttcagggtg ccagaatgtg aaagtcatcg                                   30

SEQ ID NO: 294         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 294
ttttttcagg gtgccagaat gtgaaagtca                                   30

SEQ ID NO: 295         moltype = DNA  length = 30
```

```
FEATURE                Location/Qualifiers
misc_feature           1..30
                       note = Synthetic
source                 1..30
                       mol_type = other DNA
                       organism = synthetic construct
SEQUENCE: 295
taagctcagg ttcaaagtgt tggtaatgcc                                   30

SEQ ID NO: 296         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 296
atattaaatg tatgcattat tttttcaggg                                   30

SEQ ID NO: 297         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 297
agttcatatt aaatgtatgc attatttttt                                   30

SEQ ID NO: 298         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 298
ttcagggtgc cagaatgtga aagtcatcga                                   30

SEQ ID NO: 299         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 299
aatgtatgca ttattttttc agggtgccag                                   30

SEQ ID NO: 300         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 300
tcagggtgcc agaatgtgaa agtcatcgac                                   30

SEQ ID NO: 301         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 301
gccgtttcca agatctgaca gtgcacaata                                   30

SEQ ID NO: 302         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 302
agggtgccag aatgtgaaag tcatcgacaa                                   30
```

-continued

```
SEQ ID NO: 303         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 303
gtgaggaaaa atcctttggc cgtttccaag                                   30

SEQ ID NO: 304         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 304
ggccgtttcc aagatctgac agtgcacaat                                   30

SEQ ID NO: 305         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 305
cattcagttc atattaaatg tatgcattat                                   30

SEQ ID NO: 306         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 306
ccaagatctg acagtgcaca atattttccc                                   30

SEQ ID NO: 307         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 307
caagatctga cagtgcacaa tattttccca                                   30

SEQ ID NO: 308         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 308
cagggtgcca gaatgtgaaa gtcatcgaca                                   30

SEQ ID NO: 309         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 309
ttgcattcag ttcatattaa atgtatgcat                                   30

SEQ ID NO: 310         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 310
gaggtagcaa acactaaggt gaaaagataa                                   30
```

```
SEQ ID NO: 311          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 311
agacaacgtc atcccctggc aggctaaagt                                    30

SEQ ID NO: 312          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 312
aattgtaagc tcaggttcaa agtgttggta                                    30

SEQ ID NO: 313          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 313
ttaaattgta agctcaggtt caaagtgttg                                    30

SEQ ID NO: 314          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 314
aaacagtggt tcttaaattg taagctcagg                                    30

SEQ ID NO: 315          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 315
aaaacagtgg ttcttaaatt gtaagctcag                                    30

SEQ ID NO: 316          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 316
catgtcttta aaacagtggt tcttaaattg                                    30

SEQ ID NO: 317          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 317
acatgtcttt aaaacagtgg ttcttaaatt                                    30

SEQ ID NO: 318          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 318
```

```
tgtttacatg tctttaaaac agtggttctt                                              30

SEQ ID NO: 319          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 319
acctgtattc tgtttacatg tctttaaaac                                              30

SEQ ID NO: 320          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 320
ttaacctgta ttctgtttac atgtctttaa                                              30

SEQ ID NO: 321          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 321
attaacctgt attctgttta catgtcttta                                              30

SEQ ID NO: 322          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 322
tttattaacc tgtattctgt ttacatgtct                                              30

SEQ ID NO: 323          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 323
tcccatctgt attatttttt ttcagcatgt                                              30

SEQ ID NO: 324          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 324
gtaaaattgg aggtagcaaa cactaaggtg                                              30

SEQ ID NO: 325          moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 325
agtaaaattg gaggtagcaa acactaaggt                                              30

SEQ ID NO: 326          moltype = DNA   length = 30
FEATURE                 Location/Qualifiers
misc_feature            1..30
                        note = Synthetic
source                  1..30
                        mol_type = other DNA
                        organism = synthetic construct
```

```
SEQUENCE: 326
gacaacgtca tcccctggca ggctaaagtg                                    30

SEQ ID NO: 327          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 327
ttattgcatt cagttcatat taaatgtatg                                    30

SEQ ID NO: 328          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 328
cccatctgta ttattttttt tcagcatgta                                    30

SEQ ID NO: 329          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 329
ttcagcatgt attacttgac aaagagacac                                    30

SEQ ID NO: 330          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 330
ttttttttca gcatgtatta cttgacaaag                                    30

SEQ ID NO: 331          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 331
attgcttttg acttttcaat gggtgtccta                                    30

SEQ ID NO: 332          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 332
cttttgactt ttcaatgggt gtcctaggaa                                    30

SEQ ID NO: 333          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 333
tgacttttca atgggtgtcc taggaacctt                                    30

SEQ ID NO: 334          moltype = DNA  length = 30
FEATURE                 Location/Qualifiers
misc_feature            1..30
                        note = Synthetic
source                  1..30
                        mol_type = other DNA
```

```
                         organism = synthetic construct
SEQUENCE: 334
gacttttcaa tgggtgtcct aggaaccttt                                       30

SEQ ID NO: 335           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 335
acttttcaat gggtgtccta ggaacctttt                                       30

SEQ ID NO: 336           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 336
tcaatgggtg tcctaggaac cttttagaaa                                       30

SEQ ID NO: 337           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 337
caatgggtgt cctaggaacc ttttagaaag                                       30

SEQ ID NO: 338           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 338
aatgggtgtc ctaggaacct tttagaaaga                                       30

SEQ ID NO: 339           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 339
tagaaagaaa tggactttca tcctggaaat                                       30

SEQ ID NO: 340           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 340
agaaagaaat ggactttcat cctggaaata                                       30

SEQ ID NO: 341           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 341
gaaagaaatg gactttcatc ctggaaatat                                       30

SEQ ID NO: 342           moltype = DNA  length = 30
FEATURE                  Location/Qualifiers
misc_feature             1..30
                         note = Synthetic
source                   1..30
```

```
                        mol_type = other DNA
                        organism = synthetic construct
SEQUENCE: 342
catcctggaa atatattaac tgttaaaaag                                      30

SEQ ID NO: 343          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 343
atcctggaaa tatattaact gttaaaaaga                                      30

SEQ ID NO: 344          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 344
actgttaaaa agaaaacatt gaaaatgtgt                                      30

SEQ ID NO: 345          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 345
aaaagaaaac attgaaaatg tgtttagaca                                      30

SEQ ID NO: 346          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 346
cattgctttt gacttttcaa tgggtgtcct                                      30

SEQ ID NO: 347          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 347
ccatctgtat tatttttttt cagcatgtat                                      30

SEQ ID NO: 348          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 348
tttcattgct tttgactttt caatgggtgt                                      30

SEQ ID NO: 349          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 349
tatttcattg cttttgactt ttcaatgggt                                      30

SEQ ID NO: 350          moltype = DNA  length = 30
FEATURE                 Location/Qualifiers
misc_feature            1..30
                        note = Synthetic
```

```
source                  1..30
                        mol_type = other DNA
                        organism = synthetic construct
SEQUENCE: 350
aaaatgtgtt tagacaacgt catcccctgg                                    30

SEQ ID NO: 351          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 351
tttttcagca tgtattactt gacaaagaga                                    30

SEQ ID NO: 352          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 352
ttttcagcat gtattacttg acaaagagac                                    30

SEQ ID NO: 353          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 353
tttcagcatg tattacttga caaagagaca                                    30

SEQ ID NO: 354          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 354
tcagcatgta ttacttgaca aagagacact                                    30

SEQ ID NO: 355          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 355
cagcatgtat tacttgacaa agagacactg                                    30

SEQ ID NO: 356          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 356
agcatgtatt acttgacaaa gagacactgt                                    30

SEQ ID NO: 357          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 357
cttgacaaag agacactgtg cagagggtga                                    30

SEQ ID NO: 358          moltype = DNA  length = 30
FEATURE                 Location/Qualifiers
misc_feature            1..30
```

```
                        note = Synthetic
source                  1..30
                        mol_type = other DNA
                        organism = synthetic construct
SEQUENCE: 358
acaaagagac actgtgcaga gggtgaccac                                    30

SEQ ID NO: 359          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 359
cccacttcaa tacaaagggt gtcgttcttt                                    30

SEQ ID NO: 360          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 360
aatacaaagg gtgtcgttct tttccaacaa                                    30

SEQ ID NO: 361          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 361
ttttccaaca aaatagcaat cccttttatt                                    30

SEQ ID NO: 362          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 362
tccaacaaaa tagcaatccc ttttatttca                                    30

SEQ ID NO: 363          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 363
ccaacaaaat agcaatccct tttatttcat                                    30

SEQ ID NO: 364          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 364
caacaaaata gcaatccctt ttatttcatt                                    30

SEQ ID NO: 365          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 365
atttcattgc ttttgacttt tcaatgggtg                                    30

SEQ ID NO: 366          moltype = DNA  length = 30
FEATURE                 Location/Qualifiers
```

```
misc_feature          1..30
                      note = Synthetic
source                1..30
                      mol_type = other DNA
                      organism = synthetic construct
SEQUENCE: 366
aaagtgttgg taatgcctga ttcacaactt                                   30

SEQ ID NO: 367        moltype = DNA  length = 30
FEATURE               Location/Qualifiers
misc_feature          1..30
                      note = Synthetic
source                1..30
                      mol_type = other DNA
                      organism = synthetic construct
SEQUENCE: 367
ctctctaaga agtaacatac atcctaaaac                                   30

SEQ ID NO: 368        moltype = DNA  length = 30
FEATURE               Location/Qualifiers
misc_feature          1..30
                      note = Synthetic
source                1..30
                      mol_type = other DNA
                      organism = synthetic construct
SEQUENCE: 368
acaactttga gaaggtagca ctggagagaa                                   30

SEQ ID NO: 369        moltype = DNA  length = 30
FEATURE               Location/Qualifiers
misc_feature          1..30
                      note = Synthetic
source                1..30
                      mol_type = other DNA
                      organism = synthetic construct
SEQUENCE: 369
accttagtgt ttgctacctc caattttact                                   30

SEQ ID NO: 370        moltype = DNA  length = 30
FEATURE               Location/Qualifiers
misc_feature          1..30
                      note = Synthetic
source                1..30
                      mol_type = other DNA
                      organism = synthetic construct
SEQUENCE: 370
gtgtttgcta cctccaattt tactaaagga                                   30

SEQ ID NO: 371        moltype = DNA  length = 30
FEATURE               Location/Qualifiers
misc_feature          1..30
                      note = Synthetic
source                1..30
                      mol_type = other DNA
                      organism = synthetic construct
SEQUENCE: 371
gctacctcca attttactaa aggatacagc                                   30

SEQ ID NO: 372        moltype = DNA  length = 30
FEATURE               Location/Qualifiers
misc_feature          1..30
                      note = Synthetic
source                1..30
                      mol_type = other DNA
                      organism = synthetic construct
SEQUENCE: 372
ctacctccaa ttttactaaa ggatacagca                                   30

SEQ ID NO: 373        moltype = DNA  length = 30
FEATURE               Location/Qualifiers
misc_feature          1..30
                      note = Synthetic
source                1..30
                      mol_type = other DNA
                      organism = synthetic construct
SEQUENCE: 373
tactaaagga tacagcactt tagcctgcca                                   30

SEQ ID NO: 374        moltype = DNA  length = 30
```

```
FEATURE                Location/Qualifiers
misc_feature           1..30
                       note = Synthetic
source                 1..30
                       mol_type = other DNA
                       organism = synthetic construct
SEQUENCE: 374
actaaaggat acagcacttt agcctgccag                                   30

SEQ ID NO: 375         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 375
ctaaaggata cagcacttta gcctgccagg                                   30

SEQ ID NO: 376         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 376
agcctgccag gggatgacgt tgtctaaaca                                   30

SEQ ID NO: 377         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 377
gcctgccagg ggatgacgtt gtctaaacac                                   30

SEQ ID NO: 378         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 378
caccttagtg tttgctacct ccaattttac                                   30

SEQ ID NO: 379         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 379
tctaaacaca ttttcaatgt tttcttttta                                   30

SEQ ID NO: 380         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 380
caatgttttc tttttaacag ttaatatatt                                   30

SEQ ID NO: 381         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 381
aatgttttct ttttaacagt taatatattt                                   30
```

```
SEQ ID NO: 382         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 382
tctttttaac agttaatata tttccaggat                                   30

SEQ ID NO: 383         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 383
ctttttaaca gttaatatat ttccaggatg                                   30

SEQ ID NO: 384         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 384
tttttaacag ttaatatatt tccaggatga                                   30

SEQ ID NO: 385         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 385
ttaacagtta atatatttcc aggatgaaag                                   30

SEQ ID NO: 386         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 386
taacagttaa tatatttcca ggatgaaagt                                   30

SEQ ID NO: 387         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 387
aacagttaat atatttccag gatgaaagtc                                   30

SEQ ID NO: 388         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 388
acagttaata tatttccagg atgaaagtcc                                   30

SEQ ID NO: 389         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 389
tcaatgtttt ctttttaaca gttaatatat                                   30
```

```
SEQ ID NO: 390          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 390
atatatttcc aggatgaaag tccatttctt                                   30

SEQ ID NO: 391          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 391
tcaccttagt gtttgctacc tccaatttta                                   30

SEQ ID NO: 392          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 392
ataaacaatg agatcattat cttttcacct                                   30

SEQ ID NO: 393          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 393
tctctaagaa gtaacataca tcctaaaaca                                   30

SEQ ID NO: 394          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 394
ggatatattc agacactaaa gatgtgattg                                   30

SEQ ID NO: 395          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 395
gatatattca gacactaaag atgtgattgg                                   30

SEQ ID NO: 396          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 396
agacactaaa gatgtgattg gaaatctaca                                   30

SEQ ID NO: 397          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 397
```

```
gaaatctaca ttcaaagaag tatcaccaat                                   30

SEQ ID NO: 398         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 398
aaagaagtat caccaattac cgccacccat                                   30

SEQ ID NO: 399         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 399
ccgccaccca ttccaattct ctccagtgct                                   30

SEQ ID NO: 400         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 400
caattctctc cagtgctacc ttctcaaagt                                   30

SEQ ID NO: 401         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 401
tctccagtgc taccttctca aagttgtgaa                                   30

SEQ ID NO: 402         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 402
tcttttcacc ttagtgtttg ctacctccaa                                   30

SEQ ID NO: 403         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 403
tcaaagttgt gaatcaggca ttaccaacac                                   30

SEQ ID NO: 404         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 404
ccaacacttt gaacctgagc ttacaattta                                   30

SEQ ID NO: 405         moltype = DNA  length = 30
FEATURE                Location/Qualifiers
misc_feature           1..30
                       note = Synthetic
source                 1..30
                       mol_type = other DNA
                       organism = synthetic construct
```

```
SEQUENCE: 405
gaacctgagc ttacaattta agaaccactg                                   30

SEQ ID NO: 406          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 406
aacctgagct tacaatttaa gaaccactgt                                   30

SEQ ID NO: 407          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 407
caatttaaga accactgttt taaagacatg                                   30

SEQ ID NO: 408          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 408
aagaaccact gttttaaaga catgtaaaca                                   30

SEQ ID NO: 409          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 409
agaaccactg ttttaaagac atgtaaacag                                   30

SEQ ID NO: 410          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 410
taaagacatg taaacagaat acaggttaat                                   30

SEQ ID NO: 411          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 411
aaagacatgt aaacagaata caggttaata                                   30

SEQ ID NO: 412          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 412
aagacatgta aacagaatac aggttaataa                                   30

SEQ ID NO: 413          moltype = DNA  length = 30
FEATURE                 Location/Qualifiers
misc_feature            1..30
                        note = Synthetic
source                  1..30
                        mol_type = other DNA
```

```
                         organism = synthetic construct
SEQUENCE: 413
tgaatcaggc attaccaaca ctttgaacct                                   30

SEQ ID NO: 414           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 414
gtaatgcctg attcacaact ttgagaaggt                                   30

SEQ ID NO: 415           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 415
ccaggatgaa agtccatttc tttctaaaag                                   30

SEQ ID NO: 416           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 416
atttctctct aagaagtaac atacatccta                                   30

SEQ ID NO: 417           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 417
acattctggc accctgaaaa aataatgcat                                   30

SEQ ID NO: 418           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 418
tggcaccctg aaaaaataat gcatacattt                                   30

SEQ ID NO: 419           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 419
tttctctcta agaagtaaca tacatcctaa                                   30

SEQ ID NO: 420           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 420
ccaaaaatgc tttatttctc tctaagaagt                                   30

SEQ ID NO: 421           moltype = DNA  length = 30
FEATURE                  Location/Qualifiers
misc_feature             1..30
                         note = Synthetic
source                   1..30
```

```
                         mol_type = other DNA
                         organism = synthetic construct
SEQUENCE: 421
ttagagagaa ataaagcatt tttgggaaga                                      30

SEQ ID NO: 422           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 422
cttcttagag agaaataaag catttttggg                                      30

SEQ ID NO: 423           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 423
ggatgtatgt tacttcttag agagaaataa                                      30

SEQ ID NO: 424           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 424
aggatgtatg ttacttctta gagagaaata                                      30

SEQ ID NO: 425           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 425
taggatgtat gttacttctt agagagaaat                                      30

SEQ ID NO: 426           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 426
cacattctgg caccctgaaa aaataatgca                                      30

SEQ ID NO: 427           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 427
gtgtctgaat atatccaaat gttttaggat                                      30

SEQ ID NO: 428           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 428
caatcacatc tttagtgtct gaatatatcc                                      30

SEQ ID NO: 429           moltype = DNA  length = 30
FEATURE                  Location/Qualifiers
misc_feature             1..30
                         note = Synthetic
```

```
source                 1..30
                       mol_type = other DNA
                       organism = synthetic construct
SEQUENCE: 429
ccaatcacat ctttagtgtc tgaatatatc                                   30

SEQ ID NO: 430         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 430
aatgtagatt tccaatcaca tctttagtgt                                   30

SEQ ID NO: 431         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 431
gaatgtagat ttccaatcac atctttagtg                                   30

SEQ ID NO: 432         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 432
tttgaatgta gatttccaat cacatcttta                                   30

SEQ ID NO: 433         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 433
gtgatacttc tttgaatgta gatttccaat                                   30

SEQ ID NO: 434         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 434
gaatgggtgg cggtaattgg tgatacttct                                   30

SEQ ID NO: 435         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 435
agaaggtagc actggagaga attggaatgg                                   30

SEQ ID NO: 436         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 436
gagaaggtag cactggagag aattggaatg                                   30

SEQ ID NO: 437         moltype = DNA  length = 30
FEATURE                Location/Qualifiers
misc_feature           1..30
```

```
                         note = Synthetic
source                   1..30
                         mol_type = other DNA
                         organism = synthetic construct
SEQUENCE: 437
agtgtctgaa tatatccaaa tgttttagga                                    30

SEQ ID NO: 438           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 438
caggatgaaa gtccatttct ttctaaaagg                                    30

SEQ ID NO: 439           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 439
tcgatgactt tcacattctg gcaccctgaa                                    30

SEQ ID NO: 440           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 440
cctcaccaat gtcttgtcga tgactttcac                                    30

SEQ ID NO: 441           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 441
tttctaaaag gttcctagga cacccattga                                    30

SEQ ID NO: 442           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 442
ctaaaaggtt cctaggacac ccattgaaaa                                    30

SEQ ID NO: 443           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 443
taaaaggttc ctaggacacc cattgaaaag                                    30

SEQ ID NO: 444           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 444
ctaggacacc cattgaaaag tcaaaagcaa                                    30

SEQ ID NO: 445           moltype = DNA  length = 30
FEATURE                  Location/Qualifiers
```

```
misc_feature           1..30
                       note = Synthetic
source                 1..30
                       mol_type = other DNA
                       organism = synthetic construct
SEQUENCE: 445
aaaagtcaaa agcaatgaaa taaaagggat                                  30

SEQ ID NO: 446         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 446
ctattttgtt ggaaaagaac gacacccttt                                  30

SEQ ID NO: 447         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 447
tgttggaaaa gaacgacacc ctttgtattg                                  30

SEQ ID NO: 448         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 448
gttggaaaag aacgacaccc tttgtattga                                  30

SEQ ID NO: 449         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 449
ttggaaaaga acgacaccct ttgtattgaa                                  30

SEQ ID NO: 450         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 450
ctcaccaatg tcttgtcgat gactttcaca                                  30

SEQ ID NO: 451         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 451
gaaaagaacg acaccctttg tattgaagtg                                  30

SEQ ID NO: 452         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 452
tattgaagtg gggaattaca gactgtggtc                                  30

SEQ ID NO: 453         moltype = DNA  length = 30
```

```
FEATURE                Location/Qualifiers
misc_feature           1..30
                       note = Synthetic
source                 1..30
                       mol_type = other DNA
                       organism = synthetic construct
SEQUENCE: 453
aagtggggaa ttacagactg tggtcaccct                                   30

SEQ ID NO: 454         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 454
cagactgtgg tcaccctctg cacagtgtct                                   30

SEQ ID NO: 455         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 455
gtcaagtaat acatgctgaa aaaaaataat                                   30

SEQ ID NO: 456         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 456
tcaagtaata catgctgaaa aaaaataata                                   30

SEQ ID NO: 457         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 457
tgcactgtca gatcttggaa acggccaaag                                   30

SEQ ID NO: 458         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 458
gaaacggcca aaggattttt cctcaccaat                                   30

SEQ ID NO: 459         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 459
ttcctcacca atgtcttgtc gatgactttc                                   30

SEQ ID NO: 460         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 460
tcctcaccaa tgtcttgtcg atgactttca                                   30
```

```
SEQ ID NO: 461         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 461
gtattgaagt ggggaattac agactgtggt                                   30

SEQ ID NO: 462         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 462
ctttctaaaa ggttcctagg acacccattg                                   30

SEQ ID NO: 463         moltype = DNA  length = 28
FEATURE                Location/Qualifiers
misc_feature           1..28
                       note = Synthetic
source                 1..28
                       mol_type = other DNA
                       organism = synthetic construct
SEQUENCE: 463
gagagaaata aagcattttt gggaagaa                                     28

SEQ ID NO: 464         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 464
aatatgaact gaatgcaata ataatca                                      27

SEQ ID NO: 465         moltype = DNA  length = 26
FEATURE                Location/Qualifiers
misc_feature           1..26
                       note = Synthetic
source                 1..26
                       mol_type = other DNA
                       organism = synthetic construct
SEQUENCE: 465
atatgaactg aatgcaataa taatca                                       26

SEQ ID NO: 466         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 466
cctggaaaat gctgcaatat tatcagccaa                                   30

SEQ ID NO: 467         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 467
tcttacctgg aaaatgctgc aatattatca                                   30

SEQ ID NO: 468         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 468
cttacctgga aaatgctgca atattatcag                                   30
```

```
SEQ ID NO: 469         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 469
ttacctggaa aatgctgcaa tattatcagc                                   30

SEQ ID NO: 470         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 470
tcagccaaag tttcttcatc atttgcccca                                   30

SEQ ID NO: 471         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 471
cttcatcatt tgccccagac ctgtaatagt                                   30

SEQ ID NO: 472         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 472
ttcatcattt gccccagacc tgtaatagtc                                   30

SEQ ID NO: 473         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 473
atcatttgcc ccagacctgt aatagtcata                                   30

SEQ ID NO: 474         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 474
gccccagacc tgtaatagtc atatatagac                                   30

SEQ ID NO: 475         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 475
ccccagacct gtaatagtca tatatagact                                   30

SEQ ID NO: 476         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 476
```

```
aaaaaataaa ttttcttacc tggaaaatgc                                   30

SEQ ID NO: 477         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 477
ggaagtactg atttagcatg ttgttcataa                                   30

SEQ ID NO: 478         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 478
agcatgttgt tcataatcat tgatacaaat                                   30

SEQ ID NO: 479         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 479
gcatgttgtt cataatcatt gatacaaatt                                   30

SEQ ID NO: 480         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 480
ttcataatca ttgatacaaa ttagccgggg                                   30

SEQ ID NO: 481         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 481
ataatcattg atacaaatta gccgggggag                                   30

SEQ ID NO: 482         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 482
atacaaatta gccgggggag cattttcaca                                   30

SEQ ID NO: 483         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 483
gccgggggag cattttcaca ggttattgct                                   30

SEQ ID NO: 484         moltype = RNA  length = 30
FEATURE                Location/Qualifiers
misc_feature           1..30
                       note = Synthetic
source                 1..30
                       mol_type = other RNA
                       organism = synthetic construct
```

```
SEQUENCE: 484
tcacaggtta ttgctatccc agatggagtt                                          30

SEQ ID NO: 485        moltype = RNA  length = 30
FEATURE               Location/Qualifiers
misc_feature          1..30
                      note = Synthetic
source                1..30
                      mol_type = other RNA
                      organism = synthetic construct
SEQUENCE: 485
cacaggttat tgctatccca gatggagttc                                          30

SEQ ID NO: 486        moltype = RNA  length = 30
FEATURE               Location/Qualifiers
misc_feature          1..30
                      note = Synthetic
source                1..30
                      mol_type = other RNA
                      organism = synthetic construct
SEQUENCE: 486
acaggttatt gctatcccag atggagttcg                                          30

SEQ ID NO: 487        moltype = RNA  length = 30
FEATURE               Location/Qualifiers
misc_feature          1..30
                      note = Synthetic
source                1..30
                      mol_type = other RNA
                      organism = synthetic construct
SEQUENCE: 487
gaagtactga tttagcatgt tgttcataat                                          30

SEQ ID NO: 488        moltype = RNA  length = 30
FEATURE               Location/Qualifiers
misc_feature          1..30
                      note = Synthetic
source                1..30
                      mol_type = other RNA
                      organism = synthetic construct
SEQUENCE: 488
taaaaaataa attttcttac ctggaaaatg                                          30

SEQ ID NO: 489        moltype = RNA  length = 30
FEATURE               Location/Qualifiers
misc_feature          1..30
                      note = Synthetic
source                1..30
                      mol_type = other RNA
                      organism = synthetic construct
SEQUENCE: 489
aaaaataaat tttcttacct ggaaaatgct                                          30

SEQ ID NO: 490        moltype = RNA  length = 30
FEATURE               Location/Qualifiers
misc_feature          1..30
                      note = Synthetic
source                1..30
                      mol_type = other RNA
                      organism = synthetic construct
SEQUENCE: 490
aaaacatgat tttaaaaaat aaattttctt                                          30

SEQ ID NO: 491        moltype = RNA  length = 30
FEATURE               Location/Qualifiers
misc_feature          1..30
                      note = Synthetic
source                1..30
                      mol_type = other RNA
                      organism = synthetic construct
SEQUENCE: 491
tatcaatgat tatgaacaac atgctaaatc                                          30

SEQ ID NO: 492        moltype = RNA  length = 30
FEATURE               Location/Qualifiers
misc_feature          1..30
                      note = Synthetic
source                1..30
                      mol_type = other RNA
```

```
                        organism = synthetic construct
SEQUENCE: 492
tgaacaacat gctaaatcag tacttccaaa                                        30

SEQ ID NO: 493          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 493
caaagtctat atatgactat tacaggtctg                                        30

SEQ ID NO: 494          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 494
caggtctggg gcaaatgatg aagaaacttt                                        30

SEQ ID NO: 495          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 495
ggctgataat attgcagcat tttccaggta                                        30

SEQ ID NO: 496          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 496
gctgataata ttgcagcatt ttccaggtaa                                        30

SEQ ID NO: 497          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 497
cagcattttc caggtaagaa aatttatttt                                        30

SEQ ID NO: 498          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 498
tccaggtaag aaaatttatt ttttaaaatc                                        30

SEQ ID NO: 499          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 499
ccaggtaaga aaatttattt tttaaaatca                                        30

SEQ ID NO: 500          moltype = RNA  length = 30
FEATURE                 Location/Qualifiers
misc_feature            1..30
                        note = Synthetic
source                  1..30
```

```
                        mol_type = other RNA
                        organism = synthetic construct
SEQUENCE: 500
aaacatgatt ttaaaaaata aatttctta                                     30

SEQ ID NO: 501          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 501
attttttaaa atcatgtttt aaaattacac                                    30

SEQ ID NO: 502          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 502
caggtaagaa aatttatttt ttaaaatcat                                    30

SEQ ID NO: 503          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 503
tttaaaatca tgttttaaaa ttacacaaag                                    30

SEQ ID NO: 504          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 504
ttaaaatcat gttttaaaat tacacaaaga                                    30

SEQ ID NO: 505          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 505
taaaatcatg ttttaaaatt acacaaagac                                    30

SEQ ID NO: 506          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 506
aaaatcatgt tttaaaatta cacaaagacc                                    30

SEQ ID NO: 507          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 507
aaatcatgtt ttaaaattac acaaagaccg                                    30

SEQ ID NO: 508          moltype = RNA  length = 30
FEATURE                 Location/Qualifiers
misc_feature            1..30
                        note = Synthetic
```

```
source                  1..30
                        mol_type = other RNA
                        organism = synthetic construct
SEQUENCE: 508
gtgtaatttt aaaacatgat tttaaaaaat                                     30

SEQ ID NO: 509          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 509
tgtaatttta aaacatgatt ttaaaaaata                                     30

SEQ ID NO: 510          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 510
taaaacatga ttttaaaaaa taaattttct                                     30

SEQ ID NO: 511          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 511
ttttttaaaa tcatgtttta aaattacaca                                     30

SEQ ID NO: 512          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 512
gtatcaatga ttatgaacaa catgctaaat                                     30

SEQ ID NO: 513          moltype = RNA  length = 24
FEATURE                 Location/Qualifiers
misc_feature            1..24
                        note = Synthetic
source                  1..24
                        mol_type = other RNA
                        organism = synthetic construct
SEQUENCE: 513
ttgctatccc agatggagtt cgtt                                           24

SEQ ID NO: 514          moltype = RNA  length = 21
FEATURE                 Location/Qualifiers
misc_feature            1..21
                        note = Synthetic
source                  1..21
                        mol_type = other RNA
                        organism = synthetic construct
SEQUENCE: 514
ctatcccaga tggagttcgt t                                              21

SEQ ID NO: 515          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 515
ttttttaatt ctagatggaa gctgtatcca                                     30

SEQ ID NO: 516          moltype = RNA  length = 30
FEATURE                 Location/Qualifiers
misc_feature            1..30
```

```
                        note = Synthetic
source                  1..30
                        mol_type = other RNA
                        organism = synthetic construct
SEQUENCE: 516
attttatttt ttaattctag atggaagctg                                    30

SEQ ID NO: 517          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 517
attttttaat tctagatgga agctgtatcc                                    30

SEQ ID NO: 518          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 518
tatttttaa ttctagatgg aagctgtatc                                     30

SEQ ID NO: 519          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 519
ttttattttt taattctaga tggaagctgt                                    30

SEQ ID NO: 520          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 520
aaaaataaaa taaaataaaa ggctttagag                                    30

SEQ ID NO: 521          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 521
attttatttt atttttaat tctagatgga                                     30

SEQ ID NO: 522          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 522
tattttattt tattttttaa ttctagatgg                                    30

SEQ ID NO: 523          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 523
tgaaactcta aagcctttta ttttatttta                                    30

SEQ ID NO: 524          moltype = RNA  length = 30
FEATURE                 Location/Qualifiers
```

```
misc_feature           1..30
                       note = Synthetic
source                 1..30
                       mol_type = other RNA
                       organism = synthetic construct
SEQUENCE: 524
tttaattcta gatggaagct gtatccaagg                                   30

SEQ ID NO: 525         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 525
ttttatttta ttttttaatt ctagatggaa                                   30

SEQ ID NO: 526         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 526
ttaattctag atggaagctg tatccaagga                                   30

SEQ ID NO: 527         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 527
tattttattt tttaattcta gatggaagct                                   30

SEQ ID NO: 528         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 528
catctagaat taaaaaataa aataaaataa                                   30

SEQ ID NO: 529         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 529
taattctaga tggaagctgt atccaaggat                                   30

SEQ ID NO: 530         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 530
aattctagat ggaagctgta tccaaggatg                                   30

SEQ ID NO: 531         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 531
attctagatg gaagctgtat ccaaggatgc                                   30

SEQ ID NO: 532         moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 532
tagatggaag ctgtatccaa ggatgctccg                                   30

SEQ ID NO: 533          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 533
ctgaaacaga tctgtcgact tctgttttag                                   30

SEQ ID NO: 534          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 534
taggacagag ggtcagcatg ccaatatgtg                                   30

SEQ ID NO: 535          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 535
aggacagagg gtcagcatgc caatatgtgt                                   30

SEQ ID NO: 536          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 536
ggacagaggg tcagcatgcc aatatgtgtg                                   30

SEQ ID NO: 537          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 537
ccactgtgag aggtaggagg aagattgtca                                   30

SEQ ID NO: 538          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 538
tgttttagga cagagggtca gcatgccaat                                   30

SEQ ID NO: 539          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 539
gcctccttct gtccctgtgg tgacaatctt                                   30
```

```
SEQ ID NO: 540         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 540
tcaccacagg gacagaagga ggctaacgtt                                   30

SEQ ID NO: 541         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 541
cggagcatcc ttggatacag cttccatcta                                   30

SEQ ID NO: 542         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 542
agcaacattc cggagcatcc ttggatacag                                   30

SEQ ID NO: 543         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 543
cagcaacatt ccggagcatc cttggataca                                   30

SEQ ID NO: 544         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 544
gatacagctt ccatctagaa ttaaaaaata                                   30

SEQ ID NO: 545         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 545
ctcctacctc tcacagtggc aagctcgccg                                   30

SEQ ID NO: 546         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 546
tgtccctgtg gtgacaatct tcctcctacc                                   30

SEQ ID NO: 547         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 547
gcatgctgac cctctgtcct aaaacagaag                                   30
```

```
SEQ ID NO: 548          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 548
cctgggcaac cgtctggatg atgtgcgtaa                                   30

SEQ ID NO: 549          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 549
aatctgttac gcacatcatc cagacggttg                                   30

SEQ ID NO: 550          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 550
gaatctgtta cgcacatcat ccagacggtt                                   30

SEQ ID NO: 551          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 551
tggcggcagt ttgaatctgt tacgcacatc                                   30

SEQ ID NO: 552          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 552
cctgagttgt ggcggcagtt tgaatctgtt                                   30

SEQ ID NO: 553          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 553
gcctcagctc ggggcccaca tgatcatggt                                   30

SEQ ID NO: 554          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 554
cgcctcagct cggggcccac atgatcatgg                                   30

SEQ ID NO: 555          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 555
```

```
aaactgccgc cacaactcag gtaaccatga                                    30

SEQ ID NO: 556          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 556
tgacagtgga cacaccttac ctgggcaacc                                    30

SEQ ID NO: 557          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 557
atcatcccct ttctttctca gcctgtcagt                                    30

SEQ ID NO: 558          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 558
gctgcaactg tatatctaca aggaccgaga                                    30

SEQ ID NO: 559          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 559
aagaagtggc ggaagctggt cctgaggcac                                    30

SEQ ID NO: 560          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 560
ctgggccacc tcctcaattg aagaagtggc                                    30

SEQ ID NO: 561          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 561
agttcctggg ccacctcctc aattgaagaa                                    30

SEQ ID NO: 562          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 562
tcagcctgtc agtccctggg aacgggcatg                                    30

SEQ ID NO: 563          moltype = RNA  length = 30
FEATURE                 Location/Qualifiers
misc_feature            1..30
                        note = Synthetic
source                  1..30
                        mol_type = other RNA
                        organism = synthetic construct
```

```
SEQUENCE: 563
ctcagcctgt cagtccctgg gaacgggcat                                 30

SEQ ID NO: 564          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 564
tttctcagcc tgtcagtccc tgggaacggg                                 30

SEQ ID NO: 565          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 565
ctttctcagc ctgtcagtcc ctgggaacgg                                 30

SEQ ID NO: 566          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 566
cgcacatcat ccagacggtt gcccaggtaa                                 30

SEQ ID NO: 567          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 567
gtgacagtgg acacacctta cctgggcaac                                 30

SEQ ID NO: 568          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 568
cccaggtaag gtgtgtccac tgtcacaaat                                 30

SEQ ID NO: 569          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 569
gttggctgca actgtatatc tacaaggacc                                 30

SEQ ID NO: 570          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 570
tctgcctgcc gcactagctt cttggtgact                                 30

SEQ ID NO: 571          moltype = RNA  length = 30
FEATURE                 Location/Qualifiers
misc_feature            1..30
                        note = Synthetic
source                  1..30
                        mol_type = other RNA
```

```
                        organism = synthetic construct
SEQUENCE: 571
tagcccatct tctctgcctg ccgcactagc                                    30

SEQ ID NO: 572          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 572
ccagggactg acaggctgag aaagaaaggg                                    30

SEQ ID NO: 573          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 573
aggaggtggc ccaggaactc aacatcatgc                                    30

SEQ ID NO: 574          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 574
ttcaattgag gaggtggccc aggaactcaa                                    30

SEQ ID NO: 575          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 575
cgccacttct tcaattgagg aggtggccca                                    30

SEQ ID NO: 576          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 576
aattgaggag gtggcccagg aactcaacat                                    30

SEQ ID NO: 577          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 577
tagatataca gttgcagcca acgaagtgcc                                    30

SEQ ID NO: 578          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 578
tcggtccttg tagatataca gttgcagcca                                    30

SEQ ID NO: 579          moltype = RNA  length = 30
FEATURE                 Location/Qualifiers
misc_feature            1..30
                        note = Synthetic
source                  1..30
```

```
                         mol_type = other RNA
                         organism = synthetic construct
SEQUENCE: 579
gtgacttctc ggtccttgta gatatacagt                                       30

SEQ ID NO: 580           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 580
ttggtgactt ctcggtcctt gtagatatac                                       30

SEQ ID NO: 581           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 581
cagccaacga agtgcctcag gaccagcttc                                       30

SEQ ID NO: 582           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 582
ctaatttggc aaatttctca ttttatgcat                                       30

SEQ ID NO: 583           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 583
atcctaaaat aagaaatgca taaaatgaga                                       30

SEQ ID NO: 584           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 584
aagtagagaa ataaacgaac ctctcaaaat                                       30

SEQ ID NO: 585           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 585
tctacttgaa ttcatactga ctttgtgatc                                       30

SEQ ID NO: 586           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 586
taatttggca aatttctcat tttatgcatt                                       30

SEQ ID NO: 587           moltype = RNA  length = 30
FEATURE                  Location/Qualifiers
misc_feature             1..30
                         note = Synthetic
```

```
source                  1..30
                        mol_type = other RNA
                        organism = synthetic construct
SEQUENCE: 587
tatgcatttc ttattttagg atgaaaaatt                                30

SEQ ID NO: 588          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 588
gcaaatttct cattttatgc atttcttatt                                30

SEQ ID NO: 589          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 589
ctcattttat gcatttctta ttttaggatg                                30

SEQ ID NO: 590          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 590
tcattttatg catttcttat tttaggatga                                30

SEQ ID NO: 591          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 591
catcctaaaa taagaaatgc ataaaatgag                                30

SEQ ID NO: 592          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 592
ggcaaatttc tcattttatg catttcttat                                30

SEQ ID NO: 593          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 593
tcatcctaaa ataagaaatg cataaaatga                                30

SEQ ID NO: 594          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 594
tcctcaggag aaaatgataa agtactggtt                                30

SEQ ID NO: 595          moltype = RNA  length = 30
FEATURE                 Location/Qualifiers
misc_feature            1..30
```

```
                        note = Synthetic
source                  1..30
                        mol_type = other RNA
                        organism = synthetic construct
SEQUENCE: 595
aaaattttc atcctaaaat aagaaatgca                                    30

SEQ ID NO: 596          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 596
caaaattttt catcctaaaa taagaaatgc                                   30

SEQ ID NO: 597          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 597
ctcaggagaa aatgataaag tactggtttc                                   30

SEQ ID NO: 598          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 598
cctcaggaga aaatgataaa gtactggttt                                   30

SEQ ID NO: 599          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 599
atgcatttct tattttagga tgaaaaattt                                   30

SEQ ID NO: 600          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 600
gccacatatg cagcaagtcc actgtcgtct                                   30

SEQ ID NO: 601          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 601
agccacatat gcagcaagtc cactgtcgtc                                   30

SEQ ID NO: 602          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 602
ctttagccac atatgcagca agtccactgt                                   30

SEQ ID NO: 603          moltype = RNA  length = 30
FEATURE                 Location/Qualifiers
```

```
misc_feature            1..30
                        note = Synthetic
source                  1..30
                        mol_type = other RNA
                        organism = synthetic construct
SEQUENCE: 603
ccagctgata gatgggtcta ttgctttagc                                    30

SEQ ID NO: 604          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 604
atatcttccc agctgataga tgggtctatt                                    30

SEQ ID NO: 605          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 605
gatatcttcc cagctgatag atgggtctat                                    30

SEQ ID NO: 606          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 606
tcagccattt gatatcttcc cagctgatag                                    30

SEQ ID NO: 607          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 607
gcaatgatgt cagtcttctc agccatttga                                    30

SEQ ID NO: 608          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 608
ttcatcctaa aataagaaat gcataaaatg                                    30

SEQ ID NO: 609          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 609
tgcatttctt attttaggat gaaaaatttt                                    30

SEQ ID NO: 610          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 610
ggatgaaaaa ttttgaaacc agtactttat                                    30

SEQ ID NO: 611          moltype = RNA  length = 30
```

```
FEATURE                Location/Qualifiers
misc_feature           1..30
                       note = Synthetic
source                 1..30
                       mol_type = other RNA
                       organism = synthetic construct
SEQUENCE: 611
ttattttagg atgaaaaatt ttgaaaccag                                   30

SEQ ID NO: 612         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 612
ccaattgttg caaagggcat tttgagaggt                                   30

SEQ ID NO: 613         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 613
ttgcaaaggg cattttgaga ggttcgttta                                   30

SEQ ID NO: 614         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 614
gcaacaattg gcaatgatgt cagtcttctc                                   30

SEQ ID NO: 615         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 615
caaagggcat tttgagaggt tcgtttattt                                   30

SEQ ID NO: 616         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 616
tgagaggttc gtttatttct ctacttgaat                                   30

SEQ ID NO: 617         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 617
gagaggttcg tttatttctc tacttgaatt                                   30

SEQ ID NO: 618         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 618
agaggttcgt ttatttctct acttgaattc                                   30
```

```
SEQ ID NO: 619          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 619
gtttatttct ctacttgaat tcatactgac                                   30

SEQ ID NO: 620          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 620
atttctctac ttgaattcat actgactttg                                   30

SEQ ID NO: 621          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 621
tttctctact tgaattcata ctgactttgt                                   30

SEQ ID NO: 622          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 622
ctctacttga attcatactg actttgtgat                                   30

SEQ ID NO: 623          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 623
ctgcatatgt ggctaaagca atagacccat                                   30

SEQ ID NO: 624          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 624
cttattttag gatgaaaaat tttgaaacca                                   30

SEQ ID NO: 625          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 625
gagacgacag tggacttgct gcatatgtgg                                   30

SEQ ID NO: 626          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 626
tggagacgac agtggacttg ctgcatatgt                                   30
```

```
SEQ ID NO: 627          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 627
tcctgaggaa aattttggag acgacagtgg                                   30

SEQ ID NO: 628          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 628
ctcctgagga aaattttgga gacgacagtg                                   30

SEQ ID NO: 629          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 629
tctcctgagg aaaattttgg agacgacagt                                   30

SEQ ID NO: 630          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 630
tcattttctc ctgaggaaaa ttttggagac                                   30

SEQ ID NO: 631          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 631
atcattttct cctgaggaaa attttggaga                                   30

SEQ ID NO: 632          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 632
aaaccagtac tttatcattt tctcctgagg                                   30

SEQ ID NO: 633          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 633
gaaaccagta ctttatcatt ttctcctgag                                   30

SEQ ID NO: 634          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 634
```

```
tgaaaccagt actttatcat tttctcctga                                  30

SEQ ID NO: 635          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 635
aggatgaaaa attttgaaac cagtacttta                                  30

SEQ ID NO: 636          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 636
taggatgaaa aattttgaaa ccagtacttt                                  30

SEQ ID NO: 637          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 637
ttttaggatg aaaaattttg aaaccagtac                                  30

SEQ ID NO: 638          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 638
ggagacgaca gtggacttgc tgcatatgtg                                  30

SEQ ID NO: 639          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 639
caacaattgg caatgatgtc agtcttctca                                  30

SEQ ID NO: 640          moltype = RNA  length = 29
FEATURE                 Location/Qualifiers
misc_feature            1..29
                        note = Synthetic
source                  1..29
                        mol_type = other RNA
                        organism = synthetic construct
SEQUENCE: 640
aattcatact gactttgtga tcctttgtg                                   29

SEQ ID NO: 641          moltype = RNA  length = 24
FEATURE                 Location/Qualifiers
misc_feature            1..24
                        note = Synthetic
source                  1..24
                        mol_type = other RNA
                        organism = synthetic construct
SEQUENCE: 641
atactgactt tgtgatcctt tgtg                                        24

SEQ ID NO: 642          moltype = RNA  length = 30
FEATURE                 Location/Qualifiers
misc_feature            1..30
                        note = Synthetic
source                  1..30
                        mol_type = other RNA
                        organism = synthetic construct
```

```
SEQUENCE: 642
agttacagtt tccctaaggt gcttgtttta                                  30

SEQ ID NO: 643          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 643
aagccatgtt taacagcctc cctggcatca                                  30

SEQ ID NO: 644          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 644
acagcctccc tggcatcatc acctggagag                                  30

SEQ ID NO: 645          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 645
aacagcctcc ctggcatcat cacctggaga                                  30

SEQ ID NO: 646          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 646
gacaccaaga tcccattcaa gccatgttta                                  30

SEQ ID NO: 647          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 647
tcgagcccca tgattcgaca ccaagatccc                                  30

SEQ ID NO: 648          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 648
gcgtctgcca aaactcacag tggctggcac                                  30

SEQ ID NO: 649          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 649
gcagacgcta agatttcctt ttggagttcc                                  30

SEQ ID NO: 650          moltype = RNA  length = 30
FEATURE                 Location/Qualifiers
misc_feature            1..30
                        note = Synthetic
source                  1..30
                        mol_type = other RNA
```

-continued

```
                       organism = synthetic construct
SEQUENCE: 650
tggcagacgc taagatttcc ttttggagtt                                   30

SEQ ID NO: 651         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 651
gtgtcgaatc atggggctcg acaactcgat                                   30

SEQ ID NO: 652         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 652
ggcagacgct aagatttcct tttggagttc                                   30

SEQ ID NO: 653         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 653
aacatggctt gaatgggatc ttggtgtcga                                   30

SEQ ID NO: 654         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 654
ctctctccag gtgatgatgc cagggaggct                                   30

SEQ ID NO: 655         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 655
actctctcca ggtgatgatg ccagggaggc                                   30

SEQ ID NO: 656         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 656
tactctctcc aggtgatgat gccagggagg                                   30

SEQ ID NO: 657         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 657
ttttactctc tccaggtgat gatgccaggg                                   30

SEQ ID NO: 658         moltype = RNA  length = 30
FEATURE                Location/Qualifiers
misc_feature           1..30
                       note = Synthetic
source                 1..30
```

```
                        mol_type = other RNA
                        organism = synthetic construct
SEQUENCE: 658
cctaaggtgc ttgttttact ctctccaggt                                30

SEQ ID NO: 659          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 659
ccctaaggtg cttgttttac tctctccagg                                30

SEQ ID NO: 660          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 660
cagtttccct aaggtgcttg ttttactctc                                30

SEQ ID NO: 661          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 661
aatgggatct tggtgtcgaa tcatggggct                                30

SEQ ID NO: 662          moltype = RNA  length = 24
FEATURE                 Location/Qualifiers
misc_feature            1..24
                        note = Synthetic
source                  1..24
                        mol_type = other RNA
                        organism = synthetic construct
SEQUENCE: 662
ccttttggag ttcccatttc catc                                      24

SEQ ID NO: 663          moltype = RNA  length = 23
FEATURE                 Location/Qualifiers
misc_feature            1..23
                        note = Synthetic
source                  1..23
                        mol_type = other RNA
                        organism = synthetic construct
SEQUENCE: 663
cttttggagt tcccatttcc atc                                       23

SEQ ID NO: 664          moltype = RNA  length = 24
FEATURE                 Location/Qualifiers
misc_feature            1..24
                        note = Synthetic
source                  1..24
                        mol_type = other RNA
                        organism = synthetic construct
SEQUENCE: 664
gggaaactgt aacttaacag gcag                                      24

SEQ ID NO: 665          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 665
caactttctt ttcttttatg atctttaagt                                30

SEQ ID NO: 666          moltype = RNA  length = 30
FEATURE                 Location/Qualifiers
misc_feature            1..30
                        note = Synthetic
```

```
source                  1..30
                        mol_type = other RNA
                        organism = synthetic construct
SEQUENCE: 666
cggttggcca tggctctgag tggtaagact                                   30

SEQ ID NO: 667          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 667
gccatggctc tgagtggtaa gactcattct                                   30

SEQ ID NO: 668          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 668
ttgtttacaa ctttcttttc ttttatgatc                                   30

SEQ ID NO: 669          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 669
tttacaactt tcttttcttt tatgatcttt                                   30

SEQ ID NO: 670          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 670
acaactttct tttcttttat gatctttaag                                   30

SEQ ID NO: 671          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 671
aagatcataa aagaaaagaa agttgtaaac                                   30

SEQ ID NO: 672          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 672
tctattttat atattcattt ctttgtccag                                   30

SEQ ID NO: 673          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 673
ccactcagag ccatggccaa ccggaattct                                   30

SEQ ID NO: 674          moltype = RNA  length = 30
FEATURE                 Location/Qualifiers
misc_feature            1..30
```

-continued

```
                        note = Synthetic
source                  1..30
                        mol_type = other RNA
                        organism = synthetic construct
SEQUENCE: 674
ttcctttagt atctcgagga catcttgaac                                   30

SEQ ID NO: 675          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 675
ctttagtatc tcgaggacat cttgaacacc                                   30

SEQ ID NO: 676          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 676
agtatctcga ggacatcttg aacacctttc                                   30

SEQ ID NO: 677          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 677
gtatctcgag gacatcttga acacctttct                                   30

SEQ ID NO: 678          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 678
aagatgtcct cgagatacta aaggaagaat                                   30

SEQ ID NO: 679          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 679
taaacaagaa tgagtcttac cactcagagc                                   30

SEQ ID NO: 680          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 680
gggggagaaa ggtgttcaag atgtcctcga                                   30

SEQ ID NO: 681          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 681
ccaggtaact ggacaaagaa atgaatatat                                   30

SEQ ID NO: 682          moltype = RNA  length = 30
FEATURE                 Location/Qualifiers
```

```
misc_feature           1..30
                       note = Synthetic
source                 1..30
                       mol_type = other RNA
                       organism = synthetic construct
SEQUENCE: 682
acttggttag ggggagaaag gtgttcaaga                                  30

SEQ ID NO: 683         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 683
cacttggtta gggggagaaa ggtgttcaag                                  30

SEQ ID NO: 684         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 684
tcacttggtt agggggagaa aggtgttcaa                                  30

SEQ ID NO: 685         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 685
tgaatcactc tgtatctttt cacttggtta                                  30

SEQ ID NO: 686         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 686
gttctgaatc actctgtatc ttttcacttg                                  30

SEQ ID NO: 687         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 687
agttctgaat cactctgtat cttttcactt                                  30

SEQ ID NO: 688         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 688
acagtaaaac aaatgaataa aacaagtcag                                  30

SEQ ID NO: 689         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 689
caggtaactg gacaaagaaa tgaatatata                                  30

SEQ ID NO: 690         moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 690
aacacctttc tccccctaac caagtgaaaa                                   30

SEQ ID NO: 691          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 691
gctttccagg taactggaca aagaaatgaa                                   30

SEQ ID NO: 692          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 692
gggcttagct ttccaggtaa ctggacaaag                                   30

SEQ ID NO: 693          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 693
ggggcttagc tttccaggta actggacaaa                                   30

SEQ ID NO: 694          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 694
tggggagacc aatcgtttgg ggcttagctt                                   30

SEQ ID NO: 695          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 695
gtggggagac caatcgtttg gggcttagct                                   30

SEQ ID NO: 696          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 696
gttaggggga gaaaggtgtt caagatgtcc                                   30

SEQ ID NO: 697          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 697
ctccccctaa ccaagtgaaa agatacagag                                   30
```

```
SEQ ID NO: 698          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 698
tactgtcaag ttgtctattt tatatattca                                   30

SEQ ID NO: 699          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 699
agaactaaat cagtctgact tgttttattc                                   30

SEQ ID NO: 700          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 700
aataatgtga ctctattaac actgaattgt                                   30

SEQ ID NO: 701          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 701
tggcagaaca tcaatctggg gaaagaaaag                                   30

SEQ ID NO: 702          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 702
ctggcagaac atcaatctgg ggaaagaaaa                                   30

SEQ ID NO: 703          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 703
cacagcctcc acaatttctg gcagaacatc                                   30

SEQ ID NO: 704          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 704
ccttccacag cctccacaat ttctggcaga                                   30

SEQ ID NO: 705          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 705
caccttccct tccacagcct ccacaatttc                                   30
```

```
SEQ ID NO: 706          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 706
cgcacacccc cgtccaggaa gacttccacc                                   30

SEQ ID NO: 707          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 707
ccgcacaccc ccgtccagga agacttccac                                   30

SEQ ID NO: 708          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 708
agaacatcag tgcctttccg cacacccccg                                   30

SEQ ID NO: 709          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 709
cagaacatca gtgcctttcc gcacaccccc                                   30

SEQ ID NO: 710          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 710
gcgccaagag ccagagcttt cagaacatca                                   30

SEQ ID NO: 711          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 711
gtctccccac aaacacagcc ttggcgccaa                                   30

SEQ ID NO: 712          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 712
cctggaaagc taagccccaa acgattggtc                                   30

SEQ ID NO: 713          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 713
```

```
tccagttacc tggaaagcta agccccaaac                              30

SEQ ID NO: 714          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 714
gtccagttac ctggaaagct aagccccaaa                              30

SEQ ID NO: 715          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 715
tttgtccagt tacctggaaa gctaagcccc                              30

SEQ ID NO: 716          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 716
ctttgtccag ttacctggaa agctaagccc                              30

SEQ ID NO: 717          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 717
ttttattcat ttgttttact gtcaagttgt                              30

SEQ ID NO: 718          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 718
tattcatttg ttttactgtc aagttgtcta                              30

SEQ ID NO: 719          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 719
attcatttgt tttactgtca agttgtctat                              30

SEQ ID NO: 720          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 720
ttcatttgtt ttactgtcaa gttgtctatt                              30

SEQ ID NO: 721          moltype = RNA  length = 30
FEATURE                 Location/Qualifiers
misc_feature            1..30
                        note = Synthetic
source                  1..30
                        mol_type = other RNA
                        organism = synthetic construct
```

```
SEQUENCE: 721
atttgtttta ctgtcaagtt gtctatttta                                   30

SEQ ID NO: 722          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 722
gttttactgt caagttgtct attttatata                                   30

SEQ ID NO: 723          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 723
tccccctaac caagtgaaaa gatacagagt                                   30

SEQ ID NO: 724          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 724
ttttactgtc aagttgtcta ttttatatat                                   30

SEQ ID NO: 725          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 725
actgtcaagt tgtctatttt atatattcat                                   30

SEQ ID NO: 726          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 726
ctgtcaagtt gtctatttta tatattcatt                                   30

SEQ ID NO: 727          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 727
tatatattca tttctttgtc cagttacctg                                   30

SEQ ID NO: 728          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 728
atatattcat ttctttgtcc agttacctgg                                   30

SEQ ID NO: 729          moltype = RNA  length = 30
FEATURE                 Location/Qualifiers
misc_feature            1..30
                        note = Synthetic
source                  1..30
                        mol_type = other RNA
```

```
                        organism = synthetic construct
SEQUENCE: 729
tatattcatt tctttgtcca gttacctgga                                   30

SEQ ID NO: 730          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 730
atttctttgt ccagttacct ggaaagctaa                                   30

SEQ ID NO: 731          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 731
gcgccaaggc tgtgtttgtg gggagaccaa                                   30

SEQ ID NO: 732          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 732
tgaaagctct ggctcttggc gccaaggctg                                   30

SEQ ID NO: 733          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 733
tggaggctgt ggaagggaag gtggaagtct                                   30

SEQ ID NO: 734          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 734
ttgaactttt ctttccccag attgatgttc                                   30

SEQ ID NO: 735          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 735
tgccagaaat tgtggaggct gtggaaggga                                   30

SEQ ID NO: 736          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 736
atgttctgcc agaaattgtg gaggctgtgg                                   30

SEQ ID NO: 737          moltype = RNA  length = 30
FEATURE                 Location/Qualifiers
misc_feature            1..30
                        note = Synthetic
source                  1..30
```

```
                        mol_type = other RNA
                        organism = synthetic construct
SEQUENCE: 737
cccagattga tgttctgcca gaaattgtgg                                      30

SEQ ID NO: 738          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 738
ccccagattg atgttctgcc agaaattgtg                                      30

SEQ ID NO: 739          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 739
tttccccaga ttgatgttct gccagaaatt                                      30

SEQ ID NO: 740          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 740
ctttccccag attgatgttc tgccagaaat                                      30

SEQ ID NO: 741          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 741
tctttcccca gattgatgtt ctgccagaaa                                      30

SEQ ID NO: 742          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 742
aacttttctt tccccagatt gatgttctgc                                      30

SEQ ID NO: 743          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 743
atagagtcac attattgaac ttttctttcc                                      30

SEQ ID NO: 744          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 744
agtgttaata gagtcacatt attgaacttt                                      30

SEQ ID NO: 745          moltype = RNA  length = 30
FEATURE                 Location/Qualifiers
misc_feature            1..30
                        note = Synthetic
```

```
source                  1..30
                        mol_type = other RNA
                        organism = synthetic construct
SEQUENCE: 745
ctggacgggg gtgtgcggaa aggcactgat                                  30

SEQ ID NO: 746          moltype = RNA  length = 23
FEATURE                 Location/Qualifiers
misc_feature            1..23
                        note = Synthetic
source                  1..23
                        mol_type = other RNA
                        organism = synthetic construct
SEQUENCE: 746
cttttctttt atgatcttta agt                                         23

SEQ ID NO: 747          moltype = RNA  length = 22
FEATURE                 Location/Qualifiers
misc_feature            1..22
                        note = Synthetic
source                  1..22
                        mol_type = other RNA
                        organism = synthetic construct
SEQUENCE: 747
ttttctttta tgatctttaa gt                                          22

SEQ ID NO: 748          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 748
tttcagggtg ccagaatgtg aaagtcatcg                                  30

SEQ ID NO: 749          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 749
ttttttcagg gtgccagaat gtgaaagtca                                  30

SEQ ID NO: 750          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 750
taagctcagg ttcaaagtgt tggtaatgcc                                  30

SEQ ID NO: 751          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 751
atattaaatg tatgcattat tttttcaggg                                  30

SEQ ID NO: 752          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 752
agttcatatt aaatgtatgc attatttttt                                  30

SEQ ID NO: 753          moltype = RNA  length = 30
FEATURE                 Location/Qualifiers
misc_feature            1..30
```

-continued

```
                        note = Synthetic
source                  1..30
                        mol_type = other RNA
                        organism = synthetic construct
SEQUENCE: 753
ttcagggtgc cagaatgtga aagtcatcga                                    30

SEQ ID NO: 754          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 754
aatgtatgca ttatttttc agggtgccag                                    30

SEQ ID NO: 755          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 755
tcagggtgcc agaatgtgaa agtcatcgac                                    30

SEQ ID NO: 756          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 756
gccgtttcca agatctgaca gtgcacaata                                    30

SEQ ID NO: 757          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 757
agggtgccag aatgtgaaag tcatcgacaa                                    30

SEQ ID NO: 758          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 758
gtgaggaaaa atcctttggc cgtttccaag                                    30

SEQ ID NO: 759          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 759
ggccgtttcc aagatctgac agtgcacaat                                    30

SEQ ID NO: 760          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 760
cattcagttc atattaaatg tatgcattat                                    30

SEQ ID NO: 761          moltype = RNA  length = 30
FEATURE                 Location/Qualifiers
```

```
misc_feature          1..30
                      note = Synthetic
source                1..30
                      mol_type = other RNA
                      organism = synthetic construct
SEQUENCE: 761
ccaagatctg acagtgcaca atattttccc                                   30

SEQ ID NO: 762        moltype = RNA  length = 30
FEATURE               Location/Qualifiers
misc_feature          1..30
                      note = Synthetic
source                1..30
                      mol_type = other RNA
                      organism = synthetic construct
SEQUENCE: 762
caagatctga cagtgcacaa tattttccca                                   30

SEQ ID NO: 763        moltype = RNA  length = 30
FEATURE               Location/Qualifiers
misc_feature          1..30
                      note = Synthetic
source                1..30
                      mol_type = other RNA
                      organism = synthetic construct
SEQUENCE: 763
cagggtgcca gaatgtgaaa gtcatcgaca                                   30

SEQ ID NO: 764        moltype = RNA  length = 30
FEATURE               Location/Qualifiers
misc_feature          1..30
                      note = Synthetic
source                1..30
                      mol_type = other RNA
                      organism = synthetic construct
SEQUENCE: 764
ttgcattcag ttcatattaa atgtatgcat                                   30

SEQ ID NO: 765        moltype = RNA  length = 30
FEATURE               Location/Qualifiers
misc_feature          1..30
                      note = Synthetic
source                1..30
                      mol_type = other RNA
                      organism = synthetic construct
SEQUENCE: 765
gaggtagcaa acactaaggt gaaaagataa                                   30

SEQ ID NO: 766        moltype = RNA  length = 30
FEATURE               Location/Qualifiers
misc_feature          1..30
                      note = Synthetic
source                1..30
                      mol_type = other RNA
                      organism = synthetic construct
SEQUENCE: 766
agacaacgtc atcccctggc aggctaaagt                                   30

SEQ ID NO: 767        moltype = RNA  length = 30
FEATURE               Location/Qualifiers
misc_feature          1..30
                      note = Synthetic
source                1..30
                      mol_type = other RNA
                      organism = synthetic construct
SEQUENCE: 767
aattgtaagc tcaggttcaa agtgttggta                                   30

SEQ ID NO: 768        moltype = RNA  length = 30
FEATURE               Location/Qualifiers
misc_feature          1..30
                      note = Synthetic
source                1..30
                      mol_type = other RNA
                      organism = synthetic construct
SEQUENCE: 768
ttaaattgta agctcaggtt caaagtgttg                                   30

SEQ ID NO: 769        moltype = RNA  length = 30
```

```
FEATURE                 Location/Qualifiers
misc_feature            1..30
                        note = Synthetic
source                  1..30
                        mol_type = other RNA
                        organism = synthetic construct
SEQUENCE: 769
aaacagtggt tcttaaattg taagctcagg                                   30

SEQ ID NO: 770          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 770
aaaacagtgg ttcttaaatt gtaagctcag                                   30

SEQ ID NO: 771          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 771
catgtcttta aaacagtggt tcttaaattg                                   30

SEQ ID NO: 772          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 772
acatgtcttt aaaacagtgg ttcttaaatt                                   30

SEQ ID NO: 773          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 773
tgtttacatg tctttaaaac agtggttctt                                   30

SEQ ID NO: 774          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 774
acctgtattc tgtttacatg tctttaaaac                                   30

SEQ ID NO: 775          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 775
ttaacctgta ttctgtttac atgtctttaa                                   30

SEQ ID NO: 776          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 776
attaacctgt attctgttta catgtcttta                                   30
```

```
SEQ ID NO: 777          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 777
tttattaacc tgtattctgt ttacatgtct                                   30

SEQ ID NO: 778          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 778
tcccatctgt attatttttt ttcagcatgt                                   30

SEQ ID NO: 779          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 779
gtaaaattgg aggtagcaaa cactaaggtg                                   30

SEQ ID NO: 780          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 780
agtaaaattg gaggtagcaa acactaaggt                                   30

SEQ ID NO: 781          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 781
gacaacgtca tcccctggca ggctaaagtg                                   30

SEQ ID NO: 782          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 782
ttattgcatt cagttcatat taaatgtatg                                   30

SEQ ID NO: 783          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 783
cccatctgta ttattttttt tcagcatgta                                   30

SEQ ID NO: 784          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 784
ttcagcatgt attacttgac aaagagacac                                   30
```

```
SEQ ID NO: 785          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 785
tttttttca gcatgtatta cttgacaaag                                   30

SEQ ID NO: 786          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 786
attgcttttg acttttcaat gggtgtccta                                   30

SEQ ID NO: 787          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 787
cttttgactt ttcaatgggt gtcctaggaa                                   30

SEQ ID NO: 788          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 788
tgacttttca atgggtgtcc taggaacctt                                   30

SEQ ID NO: 789          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 789
gacttttcaa tgggtgtcct aggaaccttt                                   30

SEQ ID NO: 790          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 790
acttttcaat gggtgtccta ggaacctttt                                   30

SEQ ID NO: 791          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 791
tcaatgggtg tcctaggaac cttttagaaa                                   30

SEQ ID NO: 792          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 792
```

```
caatgggtgt cctaggaacc ttttagaaag                                   30

SEQ ID NO: 793          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 793
aatgggtgtc ctaggaacct tttagaaaga                                   30

SEQ ID NO: 794          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 794
tagaaagaaa tggactttca tcctggaaat                                   30

SEQ ID NO: 795          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 795
agaaagaaat ggactttcat cctggaaata                                   30

SEQ ID NO: 796          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 796
gaaagaaatg gactttcatc ctggaaatat                                   30

SEQ ID NO: 797          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 797
catcctggaa atatattaac tgttaaaaag                                   30

SEQ ID NO: 798          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 798
atcctggaaa tatattaact gttaaaaaga                                   30

SEQ ID NO: 799          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 799
actgttaaaa agaaaacatt gaaaatgtgt                                   30

SEQ ID NO: 800          moltype = RNA  length = 30
FEATURE                 Location/Qualifiers
misc_feature            1..30
                        note = Synthetic
source                  1..30
                        mol_type = other RNA
                        organism = synthetic construct
```

```
SEQUENCE: 800
aaaagaaaac attgaaaatg tgtttagaca                                    30

SEQ ID NO: 801          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 801
cattgctttt gacttttcaa tgggtgtcct                                    30

SEQ ID NO: 802          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 802
ccatctgtat tatttttttt cagcatgtat                                    30

SEQ ID NO: 803          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 803
tttcattgct tttgactttt caatgggtgt                                    30

SEQ ID NO: 804          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 804
tatttcattg cttttgactt ttcaatgggt                                    30

SEQ ID NO: 805          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 805
aaaatgtgtt tagacaacgt catcccctgg                                    30

SEQ ID NO: 806          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 806
tttttcagca tgtattactt gacaaagaga                                    30

SEQ ID NO: 807          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 807
ttttcagcat gtattacttg acaaagagac                                    30

SEQ ID NO: 808          moltype = RNA  length = 30
FEATURE                 Location/Qualifiers
misc_feature            1..30
                        note = Synthetic
source                  1..30
                        mol_type = other RNA
```

```
                         organism = synthetic construct
SEQUENCE: 808
tttcagcatg tattacttga caaagagaca                                      30

SEQ ID NO: 809           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 809
tcagcatgta ttacttgaca aagagacact                                      30

SEQ ID NO: 810           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 810
cagcatgtat tacttgacaa agagacactg                                      30

SEQ ID NO: 811           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 811
agcatgtatt acttgacaaa gagacactgt                                      30

SEQ ID NO: 812           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 812
cttgacaaag agacactgtg cagagggtga                                      30

SEQ ID NO: 813           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 813
acaaagagac actgtgcaga gggtgaccac                                      30

SEQ ID NO: 814           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 814
cccacttcaa tacaaagggt gtcgttcttt                                      30

SEQ ID NO: 815           moltype = RNA  length = 30
FEATURE                  Location/Qualifiers
misc_feature             1..30
                         note = Synthetic
source                   1..30
                         mol_type = other RNA
                         organism = synthetic construct
SEQUENCE: 815
aatacaaagg gtgtcgttct tttccaacaa                                      30

SEQ ID NO: 816           moltype = RNA  length = 30
FEATURE                  Location/Qualifiers
misc_feature             1..30
                         note = Synthetic
source                   1..30
```

```
                        mol_type = other RNA
                        organism = synthetic construct
SEQUENCE: 816
ttttccaaca aaatagcaat cccttttatt                                   30

SEQ ID NO: 817          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 817
tccaacaaaa tagcaatccc ttttatttca                                   30

SEQ ID NO: 818          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 818
ccaacaaaat agcaatccct tttatttcat                                   30

SEQ ID NO: 819          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 819
caacaaaata gcaatccctt ttatttcatt                                   30

SEQ ID NO: 820          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 820
atttcattgc ttttgacttt tcaatgggtg                                   30

SEQ ID NO: 821          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 821
aaagtgttgg taatgcctga ttcacaactt                                   30

SEQ ID NO: 822          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 822
ctctctaaga agtaacatac atcctaaaac                                   30

SEQ ID NO: 823          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 823
acaactttga gaaggtagca ctggagagaa                                   30

SEQ ID NO: 824          moltype = RNA  length = 30
FEATURE                 Location/Qualifiers
misc_feature            1..30
                        note = Synthetic
```

```
source                  1..30
                        mol_type = other RNA
                        organism = synthetic construct
SEQUENCE: 824
accttagtgt ttgctacctc caattttact                                    30

SEQ ID NO: 825          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 825
gtgtttgcta cctccaattt tactaaagga                                    30

SEQ ID NO: 826          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 826
gctacctcca attttactaa aggatacagc                                    30

SEQ ID NO: 827          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 827
ctacctccaa ttttactaaa ggatacagca                                    30

SEQ ID NO: 828          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 828
tactaaagga tacagcactt tagcctgcca                                    30

SEQ ID NO: 829          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 829
actaaaggat acagcacttt agcctgccag                                    30

SEQ ID NO: 830          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 830
ctaaaggata cagcacttta gcctgccagg                                    30

SEQ ID NO: 831          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 831
agcctgccag ggatgacgt tgtctaaaca                                     30

SEQ ID NO: 832          moltype = RNA  length = 30
FEATURE                 Location/Qualifiers
misc_feature            1..30
```

```
                        note = Synthetic
source                  1..30
                        mol_type = other RNA
                        organism = synthetic construct
SEQUENCE: 832
gcctgccagg ggatgacgtt gtctaaacac                                   30

SEQ ID NO: 833          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 833
caccttagtg tttgctacct ccaattttac                                   30

SEQ ID NO: 834          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 834
tctaaacaca ttttcaatgt tttcttttta                                   30

SEQ ID NO: 835          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 835
caatgttttc tttttaacag ttaatatatt                                   30

SEQ ID NO: 836          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 836
aatgttttct ttttaacagt taatatattt                                   30

SEQ ID NO: 837          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 837
tctttttaac agttaatata tttccaggat                                   30

SEQ ID NO: 838          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 838
ctttttaaca gttaatatat ttccaggatg                                   30

SEQ ID NO: 839          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 839
tttttaacag ttaatatatt tccaggatga                                   30

SEQ ID NO: 840          moltype = RNA  length = 30
FEATURE                 Location/Qualifiers
```

```
misc_feature            1..30
                        note = Synthetic
source                  1..30
                        mol_type = other RNA
                        organism = synthetic construct
SEQUENCE: 840
ttaacagtta atatatttcc aggatgaaag                                   30

SEQ ID NO: 841          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 841
taacagttaa tatatttcca ggatgaaagt                                   30

SEQ ID NO: 842          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 842
aacagttaat atatttccag gatgaaagtc                                   30

SEQ ID NO: 843          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 843
acagttaata tatttccagg atgaaagtcc                                   30

SEQ ID NO: 844          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 844
tcaatgtttt ctttttaaca gttaatatat                                   30

SEQ ID NO: 845          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 845
atatatttcc aggatgaaag tccatttctt                                   30

SEQ ID NO: 846          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 846
tcaccttagt gtttgctacc tccaatttta                                   30

SEQ ID NO: 847          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 847
ataaacaatg agatcattat cttttcacct                                   30

SEQ ID NO: 848          moltype = RNA  length = 30
```

```
FEATURE                Location/Qualifiers
misc_feature           1..30
                       note = Synthetic
source                 1..30
                       mol_type = other RNA
                       organism = synthetic construct
SEQUENCE: 848
tctctaagaa gtaacataca tcctaaaaca                                   30

SEQ ID NO: 849         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 849
ggatatattc agacactaaa gatgtgattg                                   30

SEQ ID NO: 850         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 850
gatatattca gacactaaag atgtgattgg                                   30

SEQ ID NO: 851         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 851
agacactaaa gatgtgattg gaaatctaca                                   30

SEQ ID NO: 852         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 852
gaaatctaca ttcaaagaag tatcaccaat                                   30

SEQ ID NO: 853         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 853
aaagaagtat caccaattac cgccacccat                                   30

SEQ ID NO: 854         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 854
ccgccaccca ttccaattct ctccagtgct                                   30

SEQ ID NO: 855         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 855
caattctctc cagtgctacc ttctcaaagt                                   30
```

```
SEQ ID NO: 856          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 856
tctccagtgc taccttctca aagttgtgaa                                    30

SEQ ID NO: 857          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 857
tcttttcacc ttagtgtttg ctacctccaa                                    30

SEQ ID NO: 858          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 858
tcaaagttgt gaatcaggca ttaccaacac                                    30

SEQ ID NO: 859          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 859
ccaacacttt gaacctgagc ttacaattta                                    30

SEQ ID NO: 860          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 860
gaacctgagc ttacaattta agaaccactg                                    30

SEQ ID NO: 861          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 861
aacctgagct tacaatttaa gaaccactgt                                    30

SEQ ID NO: 862          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 862
caatttaaga accactgttt taaagacatg                                    30

SEQ ID NO: 863          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 863
aagaaccact gttttaaaga catgtaaaca                                    30
```

```
SEQ ID NO: 864         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 864
agaaccactg ttttaaagac atgtaaacag                                   30

SEQ ID NO: 865         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 865
taaagacatg taaacagaat acaggttaat                                   30

SEQ ID NO: 866         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 866
aaagacatgt aaacagaata caggttaata                                   30

SEQ ID NO: 867         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 867
aagacatgta aacagaatac aggttaataa                                   30

SEQ ID NO: 868         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 868
tgaatcaggc attaccaaca ctttgaacct                                   30

SEQ ID NO: 869         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 869
gtaatgcctg attcacaact ttgagaaggt                                   30

SEQ ID NO: 870         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 870
ccaggatgaa agtccatttc tttctaaaag                                   30

SEQ ID NO: 871         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 871
```

```
atttctctct aagaagtaac atacatccta                                   30

SEQ ID NO: 872          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 872
acattctggc accctgaaaa aataatgcat                                   30

SEQ ID NO: 873          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 873
tggcaccctg aaaaaataat gcatacattt                                   30

SEQ ID NO: 874          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 874
tttctctcta agaagtaaca tacatcctaa                                   30

SEQ ID NO: 875          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 875
ccaaaaatgc tttatttctc tctaagaagt                                   30

SEQ ID NO: 876          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 876
ttagagagaa ataaagcatt tttgggaaga                                   30

SEQ ID NO: 877          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 877
cttcttagag agaaataaag catttttggg                                   30

SEQ ID NO: 878          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 878
ggatgtatgt tacttcttag agagaaataa                                   30

SEQ ID NO: 879          moltype = RNA  length = 30
FEATURE                 Location/Qualifiers
misc_feature            1..30
                        note = Synthetic
source                  1..30
                        mol_type = other RNA
                        organism = synthetic construct
```

```
SEQUENCE: 879
aggatgtatg ttacttctta gagagaaata                                    30

SEQ ID NO: 880         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 880
taggatgtat gttacttctt agagagaaat                                    30

SEQ ID NO: 881         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 881
cacattctgg caccctgaaa aaataatgca                                    30

SEQ ID NO: 882         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 882
gtgtctgaat atatccaaat gttttaggat                                    30

SEQ ID NO: 883         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 883
caatcacatc tttagtgtct gaatatatcc                                    30

SEQ ID NO: 884         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 884
ccaatcacat ctttagtgtc tgaatatatc                                    30

SEQ ID NO: 885         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 885
aatgtagatt tccaatcaca tctttagtgt                                    30

SEQ ID NO: 886         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 886
gaatgtagat ttccaatcac atctttagtg                                    30

SEQ ID NO: 887         moltype = RNA  length = 30
FEATURE                Location/Qualifiers
misc_feature           1..30
                       note = Synthetic
source                 1..30
                       mol_type = other RNA
```

```
                        organism = synthetic construct
SEQUENCE: 887
tttgaatgta gatttccaat cacatcttta                                    30

SEQ ID NO: 888          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 888
gtgatacttc tttgaatgta gatttccaat                                    30

SEQ ID NO: 889          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 889
gaatgggtgg cggtaattgg tgatacttct                                    30

SEQ ID NO: 890          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 890
agaaggtagc actggagaga attggaatgg                                    30

SEQ ID NO: 891          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 891
gagaaggtag cactggagag aattggaatg                                    30

SEQ ID NO: 892          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 892
agtgtctgaa tatatccaaa tgttttagga                                    30

SEQ ID NO: 893          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 893
caggatgaaa gtccatttct ttctaaaagg                                    30

SEQ ID NO: 894          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 894
tcgatgactt tcacattctg gcaccctgaa                                    30

SEQ ID NO: 895          moltype = RNA  length = 30
FEATURE                 Location/Qualifiers
misc_feature            1..30
                        note = Synthetic
source                  1..30
```

```
                        mol_type = other RNA
                        organism = synthetic construct
SEQUENCE: 895
cctcaccaat gtcttgtcga tgactttcac                                       30

SEQ ID NO: 896          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 896
tttctaaaag gttcctagga cacccattga                                       30

SEQ ID NO: 897          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 897
ctaaaaggtt cctaggacac ccattgaaaa                                       30

SEQ ID NO: 898          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 898
taaaaggttc ctaggacacc cattgaaaag                                       30

SEQ ID NO: 899          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 899
ctaggacacc cattgaaaag tcaaaagcaa                                       30

SEQ ID NO: 900          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 900
aaaagtcaaa agcaatgaaa taaaagggat                                       30

SEQ ID NO: 901          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 901
ctattttgtt ggaaaagaac gacacccttt                                       30

SEQ ID NO: 902          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 902
tgttggaaaa gaacgacacc ctttgtattg                                       30

SEQ ID NO: 903          moltype = RNA  length = 30
FEATURE                 Location/Qualifiers
misc_feature            1..30
                        note = Synthetic
```

```
source                  1..30
                        mol_type = other RNA
                        organism = synthetic construct
SEQUENCE: 903
gttggaaaag aacgacaccc tttgtattga                                    30

SEQ ID NO: 904          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 904
ttggaaaaga acgacaccct ttgtattgaa                                    30

SEQ ID NO: 905          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 905
ctcaccaatg tcttgtcgat gactttcaca                                    30

SEQ ID NO: 906          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 906
gaaaagaacg acaccctttg tattgaagtg                                    30

SEQ ID NO: 907          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 907
tattgaagtg gggaattaca gactgtggtc                                    30

SEQ ID NO: 908          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 908
aagtggggaa ttacagactg tggtcaccct                                    30

SEQ ID NO: 909          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 909
cagactgtgg tcaccctctg cacagtgtct                                    30

SEQ ID NO: 910          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 910
gtcaagtaat acatgctgaa aaaaaataat                                    30

SEQ ID NO: 911          moltype = RNA  length = 30
FEATURE                 Location/Qualifiers
misc_feature            1..30
```

```
                        note = Synthetic
source                  1..30
                        mol_type = other RNA
                        organism = synthetic construct
SEQUENCE: 911
tcaagtaata catgctgaaa aaaaataata                                      30

SEQ ID NO: 912          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 912
tgcactgtca gatcttggaa acggccaaag                                      30

SEQ ID NO: 913          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 913
gaaacggcca aaggattttt cctcaccaat                                      30

SEQ ID NO: 914          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 914
ttcctcacca atgtcttgtc gatgactttc                                      30

SEQ ID NO: 915          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 915
tcctcaccaa tgtcttgtcg atgactttca                                      30

SEQ ID NO: 916          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 916
gtattgaagt ggggaattac agactgtggt                                      30

SEQ ID NO: 917          moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 917
ctttctaaaa ggttcctagg acacccattg                                      30

SEQ ID NO: 918          moltype = RNA  length = 28
FEATURE                 Location/Qualifiers
misc_feature            1..28
                        note = Synthetic
source                  1..28
                        mol_type = other RNA
                        organism = synthetic construct
SEQUENCE: 918
gagagaaata aagcattttt gggaagaa                                        28

SEQ ID NO: 919          moltype = RNA  length = 27
FEATURE                 Location/Qualifiers
```

```
misc_feature            1..27
                        note = Synthetic
source                  1..27
                        mol_type = other RNA
                        organism = synthetic construct
SEQUENCE: 919
aatatgaact gaatgcaata ataatca                                   27

SEQ ID NO: 920          moltype = RNA  length = 26
FEATURE                 Location/Qualifiers
misc_feature            1..26
                        note = Synthetic
source                  1..26
                        mol_type = other RNA
                        organism = synthetic construct
SEQUENCE: 920
atatgaactg aatgcaataa taatca                                    26

SEQ ID NO: 921          moltype = DNA  length = 3162
FEATURE                 Location/Qualifiers
misc_feature            1..3162
                        note = Synthetic
source                  1..3162
                        mol_type = other DNA
                        organism = synthetic construct
SEQUENCE: 921
atgagcagcg cgatcaaaag ctacaagagc gttctgcgtc cgaacgagcg taagaaccaa  60
ctgctgaaaa gcaccattca gtgcctggaa gacggtagcg cgttcttttt caagatgctg  120
caaggcctgt ttggtggcat caccccggag attgttcgtt tcagcaccga acaggagaaa  180
cagcaacagg atatcgcgct gtggtgcgcg gttaactggt tccgtccggt gagccaagac  240
agcctgaccc acaccattgc gagcgataac ctggtggaga agtttgagga atactatggt  300
ggcaccgcga gcgacgcgat caaacagtac ttcagcgcga gcattggcga aagctactat  360
tggaacgact gccgtcaaca gtactatgat ctgtgccgtg agctgggtgt tgaggtgagc  420
gacctgaccc atgatctgga gatcctgtgc cgtgaaaagt gcctggcggt tgcgaccgag  480
agcaaccaga acaacagcat cattagcgtt ctgtttggca ccggcgaaaa agaggaccgt  540
agcgtgaaac tgcgtatcac caagaaaatt ctggaggcga tcagcaacct gaaagaaatc  600
ccgaagaacg ttgcgccgat tcaagagatc attctgaacg tggcgaaagc gaccaaggaa  660
accttccgtc aggtgtatgc gggtaacctg ggtgcgccga gcaccctgga gaaatttatc  720
gcgaaggacg gccaaaaaga gttcgatctg aagaaactgc agaccgacct gaagaaagtt  780
attcgtggta aaagcaagga gcgtgattgg tgctgccagg aagagctgcg tagctacgtg  840
gagcaaaaca ccatccagta tgacctgtgg gcgtggggcg aaatgttcaa caaagcgcac  900
accgcgctga aatcaagag cacccgtaac tacaactttg cgaagcaacg tctggaacag  960
ttcaaagaga ttcagagcct gaacaacctg ctggttgtga agaagctgaa cgactttttc  1020
gatagcgaat ttttcagcgg cgaggaaacc tacaccatct gcgttcacca tctgggtggc  1080
aaggacctga gcaaactgta taaggcgtgg gaggatgatc cggcggaccc ggaaaacgcg  1140
attgtggttc tgtgcgacga tctgaaaaac aactttaaga aagagccgat ccgtaacatt  1200
ctgcgttaca tcttcaccat tcgtcaagaa tgcagcgcgc aggacatcct ggcggcggcg  1260
aagtacaacc aacagctgga tcgttataaa agccaaaagg cgaacccgag cgttctgggt  1320
aaccagggct ttacctggac caacgcggtg atcctgccgg agaaggcgca gcgtaacgac  1380
cgtccgaaca gcctggatct gcgtatttgg ctgtacctga aactgcgtca cccggacggt  1440
cgttggaaga aacaccatat cccgttctac gatacccgtt tcttccaaga aatttatgcg  1500
gcgggcaaca gcccggttga cacctgccag tttcgtaccc cgcgtttcgg ttatcacctg  1560
ccgaaactga ccgatcagac cgcgatccgt gttaacaaga aacatgtgaa agcggcgaag  1620
accgaggcgc gtattcgtct ggcgatccaa cagggcaccc tgccggtgag caacctgaag  1680
atcaccgaaa ttagcgcgac catcaacagc aaaggtcaag tgcgtattcc ggttaagttt  1740
gacgtgggtc gtcaaaaagg caccctgcag atcggtgacc gtttctgcgg ctacgatcaa  1800
aaccagaccg cgagccacgc gtatagcctg tgggaagtgg ttaaagaggg tcaataccat  1860
aaagagctgg gctgctttgt tcgtttcatc agcagcggtg acatcgtgag cattaccgag  1920
aaccgtggca accaatttga tcagctgagc tatgaaggtc tggcgtaccc gcaatatgcg  1980
gactggcgta agaaagcgag caagttcgtg agcctgtggc agatcaccaa gaaaaacaag  2040
aaaaaggaaa tcgtgaccgt tgaagcgaaa gagaagtttg acgcgatctg caagtaccag  2100
ccgcgtctgt ataaattcaa caaggagtac gcgtatctgc tgcgtgatat tgttcgtggc  2160
aaaagcctgg tggaactgca acagattcgt caagagatct ttcgtttcat tgaacaggac  2220
tgcggtgtta cccgtctggg cagcctgagc ctgagcaccc tggaaaccgt gaaagcggtt  2280
aagggtatca tttacagcta ttttagcacc gcgctgaacg cgagcaagaa caacccgatc  2340
agcgacgaac agcgtaaaga gtttgatccg gaactgttcg cgctgctgga aaagctggag  2400
ctgattcgta cccgtaaaaa gaaacaaaaa gtggaacgta tcgcgaacag cctgattcag  2460
acctgcctgg agaacaacat caagttcatt cgtggtgaag gcgacctgag caccaccaac  2520
aacgcgacca agaaaaaggc gaacagccgt agcatggatt ggttggcgcg tggtgttttt  2580
aacaaaatcc gtcaactggc gccgatgcac aacattaccc tgttcggttg cggcagcctg  2640
tacaccagcc accaggaccc gctggtgcat cgtaacccgg ataaagcgat gaagtgccgt  2700
tgggcggcga tcccggttaa ggacattggc gattgggtgc tgcgtaagct gagccaaaac  2760
ctgcgtgcga aaaacatcgg caccggcgag tactatcacc aaggtgttaa agagttcctg  2820
agccattatg aactgcagga cctggaggaa gagctgctga agtggcgtag cgatcgtaaa  2880
agcaacattc cgtgctgggt gctgcagaac cgtctggcgg agaagctggg caacaaagaa  2940
gcggtggttt acatcccggt tcgtggtggc cgtatttatt ttgcgaccca caaggtggcg  3000
accggtgcgg tgagcatcgt tttcgaccaa aaacaagtgt gggtttgcaa cgcggatcat  3060
gttgcggcgg cgaacatcgc gctgaccgtg aagggtattg gcgaacaaag cagcgacgaa  3120
gagaacccgg atggtagccg tatcaaactg cagctgacca gc                  3162
```

SEQ ID NO: 922 moltype = AA length = 1054
FEATURE Location/Qualifiers
REGION 1..1054
note = Synthetic
source 1..1054
mol_type = protein
organism = synthetic construct
SEQUENCE: 922
MSSAIKSYKS VLRPNERKNQ LLKSTIQCLE DGSAFFFKML QGLFGGITPE IVRFSTEQEK 60
QQQDIALWCA VNWFRPVSQD SLTHTIASDN LVEKFEEYYG GTASDAIKQY FSASIGESYY 120
WNDCRQQYYD LCRELGVEVS DLTHDLEILC REKCLAVATE SNQNNSIISV LFGTGEKEDR 180
SVKLRITKKI LEAISNLKEI PKNVAPIQEI ILNVAKATKE TFRQVYAGNL GAPSTLEKFI 240
AKDGQKEFDL KKLQTDLKKV IRGKSKERDW CCQEELRSYV EQNTIQYDLW AWGEMFNKAH 300
TALKIKSTRN YNFAKQRLEQ FKEIQSLNNL LVVKKLNDFF DSEFFSGEET YTICVHHLGG 360
KDLSKLYKAW EDDPADPENA IVVLCDDLKN NFKKEPIRNI LRYIFTIRQE CSAQDILAAA 420
KYNQQLDRYK SQKANPSVLG NQGFTWTNAV ILPEKAQRND RPNSLDLRIW LYLKLRHPDG 480
RWKKHHIPFY DTRFFQEIYA AGNSPVDTCQ FRTPRFGYHL PKLTDQTAIR VNKKHVKAAK 540
TEARIRLAIQ QGTLPVSNLK ITEISATINS KGQVRIPVKF DVGRQKGTLQ IGDRFCGYDQ 600
NQTASHAYSL WEVVKEGQYH KELGCFVRFI SSGDIVSITE NRGNQFDQLS YEGLAYPQYA 660
DWRKKASKFV SLWQITKKNK KKEIVTVEAK EKFDAICKYQ PRLYKFNKEY AYLLRDIVRG 720
KSLVELQQIR QEIFRFIEQD CGVTRLGSLS LSTLETVKAV KGIIYSYFST ALNASKNNPI 780
SDEQRKEFDP ELFALLEKLE LIRTRKKKQK VERIANSLIQ TCLENNIKFI RGEGDLSTTN 840
NATKKKANSR SMDWLARGVF NKIRQLAPMH NITLFGCGSL YTSHQDPLVH RNPDKAMKCR 900
WAAIPVKDIG DWVLRKLSQN LRAKNIGTGE YYHQGVKEFL SHYELQDLEE ELLKWRSDRK 960
SNIPCWVLQN RLAEKLGNKE AVVYIPVRGG RIYFATHKVA TGAVSIVFDQ KQVWVCNADH 1020
VAAANIALTV KGIGEQSSDE ENPDGSRIKL QLTS 1054

SEQ ID NO: 923 moltype = AA length = 1054
FEATURE Location/Qualifiers
REGION 1..1054
note = Synthetic
source 1..1054
mol_type = protein
organism = synthetic construct
SEQUENCE: 923
MSSAIKSYKS VLRPNERKNQ LLKSTIQCLE DGSAFFFKML QGLFGGITPE IVRFSTEQEK 60
QQQDIALWCA VNWFRPVSQD SLTHTIASDN LVEKFEEYYG GTASDAIKQY FSASIGESYY 120
WNDCRQQYYD LCRELGVEVS DLTHDLEILC REKCLAVATE SNQNNSIISV LFGTGEKEDR 180
SVKLRITKKI LEAISNLKEI PKNVAPIQEI ILNVAKATKE TFRQVYAGNL GAPSTLEKFI 240
AKDGQKEFDL KKLQTDLKKV IRGKSKERDW CCQEELRSYV EQNTIQYDLW AWGEMFNKAH 300
TALKIKSTRN YNFAKQRLEQ FKEIQSLNNL LVVKKLNDFF DSEFFSGEET YTICVHHLGG 360
KDLSKLYKAW EDDPADPENA IVVLCDDLKN NFKKEPIRNI LRYIFTIRQE CSAQDILAAA 420
KYNQQLDRYK SQKANPSVLG NQGFTWTNAV ILPEKAQRND RPNSLDLRIW LYLKLRHPDG 480
RWKKHHIPFY DTRFFQEIYA AGNSPVDTCQ FRTPRFGYHL PKLTDQTAIR VNKKHVKAAK 540
TEARIRLAIQ QGTLPVSNLK ITEISATINS KGQVRIPVKF RVGRQKGTLQ IGDRFCGYDQ 600
NQTASHAYSL WEVVKEGQYH KELGCFVRFI SSGDIVSITE NRGNQFDQLS YEGLAYPQYA 660
DWRKKASKFV SLWQITKKNK KKEIVTVEAK EKFDAICKYQ PRLYKFNKEY AYLLRDIVRG 720
KSLVELQQIR QEIFRFIEQD CGVTRLGSLS LSTLETVKAV KGIIYSYFST ALNASKNNPI 780
SDEQRKEFDP ELFALLEKLE LIRTRKKKQK VERIANSLIQ TCLENNIKFI RGEGDLSTTN 840
NATKKKANSR SMDWLARGVF NKIRQLAPMH NITLFGCGSL YTSHQDPLVH RNPDKAMKCR 900
WAAIPVKDIG RWVLRKLSQN LRAKNRGTGE YYHQGVKEFL SHYELQDLEE ELLKWRSDRK 960
SNIPCWVLQN RLAEKLGNKE AVVYIPVRGG RIYFATHKVA TGAVSIVFDQ KQVWVCNADH 1020
VAAANIALTG KGIGEQSSDE ENPDGSRIKL QLTS 1054

SEQ ID NO: 924 moltype = AA length = 1054
FEATURE Location/Qualifiers
REGION 1..1054
note = Synthetic
source 1..1054
mol_type = protein
organism = synthetic construct
SEQUENCE: 924
MSSAIKSYKS VLRPNERKNQ LLKSTIQCLE DGSAFFFKML QGLFGGITPE IVRFSTEQEK 60
QQQDIALWCA VNWFRPVSQD SLTHTIASDN LVEKFEEYYG GTASDAIKQY FSASIGESYY 120
WNDCRQQYYD LCRELGVEVS DLTHDLEILC REKCLAVATE SNQNNSIISV LFGTGEKEDR 180
SVKLRITKKI LEAISNLKEI PKNVAPIQEI ILNVAKATKE TFRQVYAGNL GAPSTLEKFI 240
AKDGQKEFDL KKLQTDLKKV IRGKSKERDW CCQEELRSYV EQNTIQYDLW AWGEMFNKAH 300
TALKIKSTRN YNFAKQRLEQ FKEIQSLNNL LVVKKLNDFF DSEFFSGEET YTICVHHLGG 360
KDLSKLYKAW EDDPADPENA IVVLCDDLKN NFKKEPIRNI LRYIFTIRQE CSAQDILAAA 420
KYNQQLDRYK SQKANPSVLG NQGFTWTNAV ILPEKAQRND RPNSLDLRIW LYLKLRHPDG 480
RWKKHHIPFY DTRFFQEIYA AGNSPVDTCQ FRTPRFGYHL PKLTDQTAIR VNKKHVKAAK 540
TEARIRLAIQ QGTLPVSNLK ITEISATINS KGQVRIPVKF RVGRQKGTLQ IGDRFCGYDQ 600
NQTASHAYSL WEVVKEGQYH KELGCFVRFI SSGDIVSITE NRGNQFDQLS YEGLAYPQYA 660
DWRKKASKFV SLWQITKKNK KKEIVTVEAK EKFDAICKYQ PRLYKFNKEY AYLLRDIVRG 720
KSLVELQQIR QEIFRFIEQD CGVTRLGSLS LSTLETVKAV KGIIYSYFST ALNASKNNPI 780
SDEQRKEFDP ELFALLEKLE LIRTRKKKQK VERIANSLIQ TCLENNIKFI RGEGDLSTTN 840
NATKKKANSR SMDWLARGVF NKIRQLAPMH NITLFGCGSL YTSHQDPLVH RNPDKAMKCR 900
WAAIPVKDIG DWVLRKLSQN LRAKNRGTGE YYHQGVKEFL SHYELQDLEE ELLKWRSDRK 960

```
SNIPCWVLQN RLAEKLGNKE AVVYIPVRGG RIYFATHKVA TGAVSIVFDQ KQVWVCNADH  1020
VAAANIALTG KGIGEQSSDE ENPDGSRIKL QLTS                              1054

SEQ ID NO: 925          moltype = AA  length = 1054
FEATURE                 Location/Qualifiers
REGION                  1..1054
                        note = Synthetic
source                  1..1054
                        mol_type = protein
                        organism = synthetic construct
SEQUENCE: 925
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELGCFVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGEQSSDE ENPDGGRIKL QLTS                              1054

SEQ ID NO: 926          moltype = AA  length = 1054
FEATURE                 Location/Qualifiers
REGION                  1..1054
                        note = Synthetic
source                  1..1054
                        mol_type = protein
                        organism = synthetic construct
SEQUENCE: 926
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELRCRVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
NATKKKANSR SMDWLARGVF NKIRQLAPMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGRQSSDE ENPDGGRIKL QLTS                              1054

SEQ ID NO: 927          moltype = AA  length = 1054
FEATURE                 Location/Qualifiers
REGION                  1..1054
                        note = Synthetic
source                  1..1054
                        mol_type = protein
                        organism = synthetic construct
SEQUENCE: 927
MSSAIKSYKS VLRPNERKNQ LLKSTIQCLE DGSAFFFKML QGLFGGITPE IVRFSTEQEK  60
QQQDIALWCA VNWFRPVSQD SLTHTIASDN LVEKFEEYYG GTASDAIKQY FSASIGESYY  120
WNDCRQQYYD LCRELGVEVS DLTHDLEILC REKCLAVATE SNQNNSIISV LFGTGEKEDR  180
SVKLRITKKI LEAISNLKEI PKNVAPIQEI ILNVAKATKE TFRQVYAGNL GAPSTLEKFI  240
AKDGQKEFDL KKLQTDLKKV IRGKSKERDW CCQEELRSYV EQNTIQYDLW AWGEMFNKAH  300
TALKIKSTRN YNFAKQRLEQ FKEIQSLNNL LVVKKLNDFF DSEFFSGEET YTICVHHLGG  360
KDLSKLYKAW EDDPADPENA IVVLCDDLKN NFKKEPIRNI LRYIFTIRQE CSAQDILAAA  420
KYNQQLDRYK SQKANPSVLG NQGFTWTNAV ILPEKAQRND RPNSLDLRIW LYLKLRHPDG  480
RWKKHHIPFY DTRFFQEIYA AGNSPVDTCQ FRTPRFGYHL PKLTDQTAIR VNKKHVKAAK  540
TEARIRLAIQ QGTLPVSNLK ITEISATINS KGQVRIPVKF RVGRQKGTLQ IGDRFCGYDQ  600
NQTASHAYSL WEVVKEGQYH KELRCRVRFI SSGDIVSITE NRGNQFDQLS YEGLAYPQYA  660
DWRKKASKFV SLWQITKKNK KKEIVTVEAK EKFDAICKYQ PRLYKFNKEY AYLLRDIVRG  720
KSLVELQQIR QEIFRFIEQD CGVTRLGSLS LSTLETVKAV KGIIYSYFST ALNASKNNPI  780
SDEQRKEFDP ELFALLEKLE LIRTRKKKQK VERIANSLIQ TCLENNIKFI RGEGDLSTTN  840
```

```
NATKKKANSR SMDWLARGVF NKIRQLATMH NITLFGCGSL YTSHQDPLVH RNPDKAMKCR  900
WAAIPVKDIG DWVLRKLSQN LRAKNRGTGE YYHQGVKEFL SHYELQDLEE ELLKWRSDRK  960
SNIPCWVLQN RLAEKLGNKE AVVYIPVRGG RIYFATHKVA TGAVSIVFDQ KQVWVCNADH  1020
VAAANIALTG KGIGRQSSDE ENPDGGRIKL QLTS                             1054

SEQ ID NO: 928          moltype = DNA  length = 32767
FEATURE                 Location/Qualifiers
misc_feature            1..32767
                        note = Synthetic
source                  1..32767
                        mol_type = other DNA
                        organism = synthetic construct
SEQUENCE: 928
aacgaactcc atctgggata gcaataacct gtgaaaatgc tcccccggct aatttgtatc  60
aatgattatg aacaacatgc taaatcagta cttccaaagt ctatatatga ctattacagg  120
tctggggcaa atgatgaaga aactttggct gataatattg cagcattttc caggtaagaa  180
aatttatttt ttaaaatcat gttttaaaat tacacaaaga ccgtaccaaa ataagatctc  240
ctagttttac gttggtggtg tgtaattatt tgttcagatt tgtgcttagt agagagggaa  300
aagttcttgg ggctgtaaga aatcttgggc ctttaaattg ttaaaaaata ttccaagcct  360
gtgaatcttg aggaactgac tgcaaaagcc aaacctatgt tacttcactt ggaaatatga  420
caacaattaa tttaactaca tgtaaaaata gcgataaatt cggatgactt ttctttttct  480
tagtatgaca gtaaatgctt atgttcatgg tgtaggaaac agcattaaat gccagataac  540
catcttatcc ggatgaacca gactggattg ttggctcaaa tgttttcttc ctgctggctt  600
ttcgtgttat cattcatttt gattactgtt gtctaaactt tcactttaga tttcaatttg  660
tctatgcagc attaatcttt caactttgct gtttcatctc tccttcaaag cacttcatct  720
ctcttcccaa attagtttc ctttgacttt catatttcaa agcacaagat ggtgggtgac  780
atggtttatg ttttctgttt gtaataaaaa caagaaataa aatcatttca aagggttttt  840
ttttatagca gttacaaaaa tggtttattt gctggagcaa gagaggagtg ccttcactac  900
actacactca gtctcatcca tctaacatta tggctgttag taaaggcaat cggtattgtg  960
ggtactcatt gatggtgata aagacaaaaa ggcagaaaat atgcaggggg agagaattag  1020
ccttcctccc tgatttcttc tttagtctac aacaaaatca ctcaaaatca gttttccata  1080
tttaaattag gagaaataaa attatcctgg ccaaggtggt ctctggtagg cagcactgat  1140
tcacccacaa atccatgtag aagactgaaa atggcaatgg ggtgaaggat acggcctctc  1200
cccaaccctt tcaagccttg actttgtctc aggttttgcc tggaacccaa atgagctcaa  1260
caaatgccag ggaagtcatg ggaagggaag ttgactgaga gtagaggggc ttaaaattct  1320
gcatcattat ttactatttt ggactcattt aaaagtttct gctcttggaa gatgcccctt  1380
cttgggccga tattaacttt gtccaccaaa atttgcctat gagtggtctc ttgaaaacac  1440
tttaacccaa ataggttatt acaaccaagg aaatttcaga cccttgacag atttatagag  1500
ttagtgtctc agcattgcta gacctccaat gctcaagtga ttatttattt catttgtata  1560
cagctttcct tacttcttaa ttccctttgt cgcatgctag ctaattaact agagctaatt  1620
aggagtctcc atgagctaca ctgtgtacta catgctgagg acaaagcagt gagccagaca  1680
aagttcctgt ccctaggaac ttacattccc ctggatgcat atcagcctcc ataatgctgt  1740
tgggttgaat tgatgcaaaa tgggcccaaa atagttggcc aagtggaggt ctcagagagg  1800
atgcaaaggg gcgccccaaa gcagatggat cacctatgca accctttaaa atgtagaaac  1860
tttgggagac atagaaggct tggtgacttc taagttatga actggaaaag tgcctcatgc  1920
cttatgtgaa ttacatggta ttcaagtgag tattcccatc ctatgtgtgt accgagtaac  1980
ttagggatag gacacagata atgaaaatga atttgcagtg tcaccttttc catgaacctt  2040
gatcattctc ttttgttcag ctttaaatta aaaaaaaaaa tcaatcaact ttctttggag  2100
gacagctgat gctattttat tatcaactag ttgagttttt attgcaatac attttgcaat  2160
gtgtcctctt ttgctgtatg actcgctagg tgaaccttga ttcctcacac tgcatcatgt  2220
agctggtcac gtgaaactaa gaatagaaat tctgccaggg ttgtggagac tttgggttga  2280
tggcatgaag gaaatcaacc tgaaatttca cattctgatt ctaatgaaaa gtgcaaaaca  2340
atcaaacctc agataaccca ttgtgataca aagccagagt atttcaaaca catttatgaa  2400
atttatacac ctccccatct cgcaagtaca acaaaaggtc attcaccgtg acagctttta  2460
tttctctgta ctcagctctg ataatcacat tttggagttc tggggacatg gaccactcat  2520
gtgacccagc agttgcttgg agatattttt gggtaagact tcagactaat attactgtgg  2580
cagtagaaaa aaatgtttaa aaggacaagt aaatggaacc acccagaaca aaatttctta  2640
cggtggttat aacaaaacag ggtaaatgtc aacttgctac attttgcatg gctggaattg  2700
attgggatta attcaacgaa gaacagtaat ttgtttctct tacacattta ttcaaagtag  2760
ccttctcaac tatggtcttc acgttgttgt agctttttt tctgaaatta tcaatgatgg  2820
aagatgatta aacaatttcg acacttagaa gccctcatga tttcagaaaa ggaaactctt  2880
ttctgctgcg ttacctattg agactgaaga tggcatcatt ttcttttaaa taacagatgg  2940
gtaaaagtga tgtcattctt tcactttaat atttgagaag tgatatgaag ttaccagtga  3000
cattgtgttc tcataggcat aaatgtcaca aaataattta tctagtatcc acaataggtg  3060
aataaggtgt ttttgcttta tatattttaa ctgtttagag taaaaaaatta atgtggagaa  3120
aattggaatg cagtattata ggattacaca acttacaaaa catgaatcca ctatgtccag  3180
ttagtgtgat tcagaaacag catgcagtta taaagctggg tgaggcatgg gtgtcttcct  3240
tcaacagggc agctactttg tgaggagtgt atatatcatt tgattttttt ataagttaaa  3300
tttgaggccc ctgttagatg tgagggtggg ccaaaattcc tgtgaacaga ttctccccgt  3360
taccccgctt cctttactct ggcatctcat tttctatcct ttgaaaacgg tttattattc  3420
aattggttca actgtttgcc agttgaacca attctttttc caaagtggag gcccaggaaa  3480
gcacagtccg agaatatagt gaggtgctat tttatgtatg attgtgggaa atttacttaa  3540
atttggagtg gggttgggca aggcttggaa agctagtgag ctatctgaca tagttgttac  3600
tactatttga aaaatatcaa aacatggagg actctttaga taacatgcct gttcccattc  3660
cattgatttt atctaatttt acgtagcaat tacgttttgt gcattggttg acaagcctct  3720
gtattatcct cagaacagaa aatactgttt aagggaaatt aagagcccgc agttactaaa  3780
gtgactgcgc caccaagtgg acaagtgtaa agccactgtc tggagatgga aggattcagc  3840
tttgctttat aaatgggaat ttgaccttta aaaatgtccc ttttggcacg cacgcgcgcg  3900
cgcgcgcgcg aacacacaca cacacacaca cacacacaca cacacacaca cacacggctg  3960
```

-continued

```
ctgccctgca gatttgcttg ttcttgtcat aaagctttca ttgtttctct agctctaagt  4020
aaatattaat gccttccaag gctggcatgc caatggctgc tattaagatc gttttctctc  4080
attctaataa cacacttaga gatgattggt aataaaaact ctcttcaagg cttctgcttc  4140
tccccccttca aaatggagat caaagaatca tgctgtgagg gtccgtcaag aagaaaagac  4200
tttcagcaac agagcatgtg gtgtggcata aaataatgac aattataatg ttcaaaggaa  4260
tagcatagaa atcacacagt aaaacttctt tattatgctt ttcagggact ggatgttttt  4320
actttattat gtgaggaagg gttagattac agaccccttag ctattccaca aagcaataga  4380
aggcagaatt tcttcttccg ctacaggaag cacgcttcga ttaagggctt tttctttttc  4440
ttcttttttt ttctttaagt tactgcatta ctatatcata cttcactata tttactaaaa  4500
agtcatgctg tttctggaag tagagttaca tctaggaaat actaggtgaa tgctggttag  4560
atatgcatgt gtgcctaaac aacacgttta ttatactcat gcatactaga aatagggctg  4620
tattttcttc aattttaatc agtactaatg agaataataa atcaaaacaa ataggagaga  4680
tatattttgc caggaggaaa gagaactagt tcttctgtaa attttactgg tgaatttttg  4740
gttgctggtt tattggtaat tttcattcca acacagaaga atcacagaaa cattcattta  4800
aaataatttt ccggagtcaa aaacttttta acacccaaat ttcagttttt gtcaaataac  4860
atttttgaga aaagtgttaa attaaactaa taaaaaacct tccctcatca ttagacttta  4920
atgaatatgg catataacta aataatttg aagaaaccaa attataattt taaaagtaat  4980
tgcctgaagc tgctgtttat cacataaaaa gaagacaaac tagacatagc atatcttctt  5040
aaactctaat ctaaactcta tgcatttgta taccatcttg attttcaaga ttggggaagt  5100
gaaacgaaaa ctatgttcac acaagaacct gtacgtgaat gtttgtagtg gctttattta  5160
gaatttcccc ccaaactgta agtattcaaa atgtctttta gcttgggaat gactggacaa  5220
atgatagtac ccctgtatga tggaatatta ttcatcaacc aaaaggaaca aactattgac  5280
acgtacaaca acatgagaaa atctctaatg cgttatgtta agtgaaagaa gccaaactca  5340
aaaggctaca tactgaatga ttttgtttac atgatattct tgcaaagcaa aattatcagg  5400
acaaagaaaa aatgcatcag tggttgtcag gggattgaac tggggagagt ttctctgcaa  5460
aagaaaatgg ggacttttt gggaatgatt gaacttttc tagatcttga ttgtcatggc  5520
agttacacca ctgtatgcat ttgtcaaaat tcacaaaact gcagactaaa atgagtgaat  5580
actattatgt attagttata ctttaataaa taattgcttg ggaaattcat tatcctctaa  5640
ttgttaactt tctaaccaaa caaacagtaa aattgcctct tttccattag ctttatgaag  5700
tcatttgctt gtttggaaaa aatccaatta tattttttct tttaactaaa atgtaatgtc  5760
aaagttttgg ttatgattct gaaactctaa agccttttat tttattttat tttttaattc  5820
tagatggaag ctgtatccaa ggatgctccg gaatgttgct gaaacagatc tgtcgacttc  5880
tgttttagga cagagggtca gcatgccaat atgtgtgggg gctacggcca tgcagcgcat  5940
ggctcatgtg gacggcgagc ttgccactgt gagaggtagg aggaagattg tcaccacagg  6000
gacagaagga ggctaacgtt tatcgacctc cttctctgaa tgcaccaagc aaatatgttc  6060
cttgatgttt ttacactcag aaacattaag ctcatggact ctatcatcaa aatacttgtt  6120
cttgcatgtc ctgctcctct tctttccagc tgtgtgactg ggcaagatat cctctctctg  6180
cattggtttc cttggctgta aaatagggac aaaaattgta cctgcctcat tgggttatgg  6240
tgagaattga atgagttcag gtatacaaag ttcatggcag agagtagggg ctcagtaact  6300
gttggttata ttatgggtat taatagtact gtctcaggaa atggatctct gacaggtaga  6360
cttgcccaaa gtcacagcta ggtagttaca gaattggaat tcagccctgt ggctacctta  6420
tctcaaaacc ctcctgcttc ccccaaacca aagtggttct cacagccaaa ttgcaaatgg  6480
agcaacgtgg ttggttgtgt tttcttccgt ggttttgggt catgattctt ttttatggat  6540
gagttatatt cccaatagag cagttccagc tgtcttagga gggagtgatg agaaaatcaa  6600
atatgatgta aagaaatctc ttattagggc taatttatta actttccagt tctctagcaa  6660
ctgtgaacat ttgaaaggct gtgcagagta aaaaatctcc ccaaattgtg ctccagaaac  6720
taatataaaa gttggaaatg aattattttg atgctaagca gagcagaaaa agaacacgac  6780
tatataatat tttaaaacat tttagtttta agaattaagg atcttgtgaa ttcacttccc  6840
ttcttgaaat gtctgacata aaattctgtc agggatatca gaatggcaca atgaggtttt  6900
gctggacaga cttagcagct tccttaattc taggaccaca tacaaataag tggctttggg  6960
gcctcagcct tttgtctatg gtaatcctga aacataagta gagagaagaa aaaaaaaggg  7020
aaatactaaa tgggtaaata tctatacaaa atcaagataa taaaggccct ttcaggcttg  7080
aaactatagg caacaacctt agaacaaaag aaaacaaatg aacatcaaaa aactaaaact  7140
ttagtgctct taaatctcaa tgaaaataaa aagtaaatgg taaactgaaa gaaatggaaa  7200
aaaaatatga gactgtgaag ggttaatgtc ctttccacgt aaaaagccct tatatttgaa  7260
gaagaaaata atatattgct caaagggaaa aagagaaata agtgaacaaa agatataaat  7320
aggaaattta caaatggaga cataaaagtg accaataaac atatgaaaaa tattcaattt  7380
cattaataag caaagacatg gaaattatga ccatctattt tattttccgt atatcgaatt  7440
tttattttaa gatcaggcag tatgattagg ttagggagaa aatgtgcatt tcaaacagtg  7500
ttgagaaaag tataaagtgg aataatcttc ctagaaaata atctggcact gtatatcaaa  7560
gctctaaaaa tgtaaattcc atgtgatgtt aaaaattctc ttctaggaat tccaaggaaa  7620
taattatgat ttttgaggaa aaaaatcatt tctgcaagga ttttcatgct tcttattttt  7680
agcaggaaaa taatttgaaa aaaataccca aacatcttat aattggagat agtttgcaaa  7740
aaatatgatg cataaaaatg acatcaaatt taaaaattat actataggaa gagtgcaata  7800
atgtagaatg atattttaat ttaaaattgt gagaaatcag ttgcaaacaa tagtcaggtc  7860
ctaaaataca tttagtttca aagatcacaa tttacaaatg tttatttata agtgatgaga  7920
ttactcctga ctttatactc ttctgatttt tggctcaacc ttataaactc ttctttgaat  7980
tattttgtaa ggaggaaatg ataacaatta gatttaaaag agtagagata aagggacaag  8040
ggaccatgaa gagaatggaa ataaagaaag gaagcagaga aagcaaaaag cagagctcac  8100
ttggtaaggc accctggagc cagcaaatta tttttaccac atgtattagt tccttctcac  8160
actgatttaa agatactctt cgagactggg taatttatta aggaaagagg tttaactgac  8220
tcacagttct acatggctgg ggaggcctca ggaaacttac aatcatggtg gaaggcaaag  8280
gggaaggaac gaccttcttc ccatggtggc aggagagaga agtgcaagca gggaaatgcc  8340
agatacttat aaaaccatct gatctcatga gaactcaccc actatcatga gaacagcatg  8400
ggggaaacca cccccatgat ccaatcacct cccactaggt ctttccctca acacctggga  8460
ttataattca agatgagatt tggatggaga aacaaagcct aaccatacca acacatattg  8520
ctttatttga tatttgacag gtgtttctgt ccctgttttg tgggcaagta gctaaagttc  8580
cagagaaaac agtttttcat agctcgtcaa tgacagactt attctccaag tcacatttga  8640
tggttccaag accagtcttt attcttggtg gagttgggct gagaagaaag aggagaagaa  8700
```

-continued

```
agaagaaaag aaagcttcct tagaaactat gatttgacag tgtaagtagg actatttcct  8760
ccagaagtaa ccataagaag atattaaatg cctattacag tcttatcccc ttagatttat  8820
ttaacactta taaagcaatt atcatgttcc agacactatt ttaagtatat tacgagtatt  8880
atagcattga aggctcagag cggcccaaat aaatcgatca tattattaaa cctattttac  8940
acaggagaaa ctgaggtaca cgccaggtga ataaccttgc ctagggatgc acaattcata  9000
agtgatagag atgggattca gacagaggta ttctgtctcc agaatctggg ctcctcacca  9060
ctttgcaaga gctttaattt cagaaactcc tatgaagtgt catgaggaga agcccattat  9120
gatcccctag aagtaattat agttttagga gcatgcaaag cagacccctc aggaagataa  9180
gttacacaat agacatttgg ataaggtgga tccagcagaa caaagagagg gtggtgacat  9240
cgagattgca gaggaattgg agaaggcaat ggaagtgtac acatgttgcc ctcaaaaaca  9300
tagggtcctc cattgggttc ctatcagggc agcaacatca gagtttctat tctgtattta  9360
tactagaaac ctctctccag ggtttctagg ttttcaccta tgttttaaag actatctata  9420
ggttattagt ctatttaata tttaggtgta tccagaaagc tgatggtcat cagctcatag  9480
caggtgttct ttggctggtg tgtttatgtt gtgggacagt gggttacttg caaggaaagg  9540
atgaatggct ggagtagatg gtgcttgtgc tctgcatgta ttcccttctt acttcccatt  9600
tccatcagac ctaccacttt ttgcctgaca ttatctgttg caacatgagc ccatggatag  9660
gtgtgtttga agtaggggaa tgggagagag ggttccctag ctaatgatgt acagcagtag  9720
gtggataaat acctcagctc tctttgctca ggtaactgaa gcattttcta atatggtcac  9780
ccagtgttcc ttggaaggat tgagtcccag ttgcccctg aggttgcctg cccatgaaca  9840
caccctcttt tattggcttc cttcccattc ttttctcact tccccattcc ttcaattcat  9900
tgagattgtt tccaaataag atgacttgct ctcacatctc tgtgtcattt ttggcttctt  9960
gaagtatgca aaccaggata atagctaact gaaggctata gatagccaca ggcaaattta  10020
agtaacagtg taagaatatt catacttggc agagatttat ttataaaaac tcagaaaatt  10080
cacatggaat tatgaagtta ttattgtatt tattccatca ttcccagaaa gaatatggaa  10140
atcctctcaa gcaagccagt ccttgggaat attgggaaat ctatgcaatt tgttgtggag  10200
tattttttt tttgttaccc tcctaaatat ctggccgcta agcattcctg tctccaggga  10260
cttagaccct agcaaggaag agaagttggg gccaggttca gaaaacgggt tagttatcaa  10320
tctccctgga gaagtgtccc cctcagcagg gtcagtgaga gtaagtgaaa cccattggtg  10380
cccacaggca atggtctggc ctgagtaatt agaatgggcc tccagaaagt tctgggaatt  10440
gctatggtgc catagtctca ttttccccgt tgactctcca gatttattca gagtccaact  10500
tcaagggcct ttctgccctt cctctcacaa ctgtggaata ataataatcc accttattaa  10560
ctgggaccga gaactgagct cgactcttat ttttttgaga cagagtcttg ctctgtcacc  10620
agactggagt gcagtggcac tatctcagct cactgcaacc tctgcctccc aggttcaagc  10680
gattcccctg cctcagcctc ctgggtagct aggactatag gcacgcaccg cgacggctgg  10740
ctaatttttt gtattttagt atagacaggg tttcaccatg ttggccagga tggtcttgat  10800
ctcctgacct catgatctgc ctgccttggc ctcccaaagt gctgggatta catgcgtgag  10860
ccaccgcgcc ctgtctgaac tctacttttt tacactgctg catgtttgta gagtgaccaa  10920
tgaagctata ctttttttcat tttcaaaatg atgatgaata caaggttatc aaataaaaca  10980
cagagggccc attatgtttg aatttcagat aaacaacaaa tcataggtgt cctgtatgtt  11040
tgctcaatct ggcaaccctg gatgaataag agctctcacc tgaggatttc ttgtgaggat  11100
tcatgaaata aatgctagaa atgcttacac actatcttta tttgcccctc agagcccaaa  11160
gtctctgaaa tctttatctt tcacacacaa aaactcactt tcagaaaagt atattccatt  11220
tacatctagt ggaaataaaa attgttcttt ttctttgtga aaaatatttt tattttaagc  11280
tttatgcaga aacctcaggg aaaaaaaggt acttttagga gccaggcttg taatgtaaat  11340
gtccaaaaaa gatgaaattg aaacaaacaa acaaacaaac aaacaaacaa acaaacaaaa  11400
aacagtgcaa gctcctgtgt ggagactgca gtgagtctga gattgcatgt tccatcagaa  11460
gggggcagcc acatcttagc tcttgatgac ccaagggagc agggatgtgg ggttgccaaa  11520
tcttccaaaa ttttaagaag ccagaaatct tgatttctat gtacaatctc ctggttttta  11580
aatgtgggca aataaatcaa aattccctaa aacactgttt ggggcaacaa tgtgtgggcc  11640
aaagtaaata cttttgtggg ctacaagtgt cccctaggct gtacatctgg gacatctgat  11700
ttatgtggaa atttaccgag aactagtttt atttctgtgg caggtcattt tcactttcta  11760
ggattatgtt tcttcattga taaagtgagc tacttgagca agaccagtgg attgaatgcc  11820
acgtcccaag gaggctgggg ttgtttccag ggatcttaca gaacttaggt gtgatactga  11880
gcatgagcta cttgtgttgc attttggtgt tcaaaagaaa agttctttaa atagttctgc  11940
tggaaagaca aaaaaaaaaa aaagaaaaaa ctttcacaac aaaaatctcc aaaaacaaaa  12000
acccagaaaa ctggcataga agtggatgat ctttgcaatt tttttcagta tataaataaa  12060
tgattttgat cccatttaaa attttatcaa atgcaaaaag aaacaattca aagtatagag  12120
ctaccttttc ttactctact gaaatctaca ctttatgtca gccctggagg gtttagacgc  12180
actttatgtc agcccacttc tttcgactgc actatgtcag ccttggaggg tttagatgag  12240
gcagtgagca tttgaatgct tttaatttcc atttttcaaa gtacattctt ggtctatagg  12300
agaggaacaa gatatgtaac tatctctgac tattgctaaa aacacaaacg tctttaataa  12360
atgttgcata aactcagaaa gtgatacttc aaagtcttgt gaaaaatgat gatcaccagc  12420
atttatacag caattagtat gtgccacgca atttgacttt attatttatt catctatctt  12480
taccaccatc ttaaaatatg tgagtgcaaa accctgagaa actttctcca actcctgtgg  12540
gtgtggaaat cgaggcttag agaggttaat gctttgctca gattattaat cacttaggca  12600
gtgctaccta taatatcctg ctctgttact ggtatttcca aacgtcatta actgtagcaa  12660
gaatcctaag gcaagcacta tgctatcatc ttaaaatatt tattgcaaac atcctatgtt  12720
ttattgtttt atctttttaa ctttgagaag ataaaataag ccacagaagt gaaattaatt  12780
gggaaatcat tcgcttttttg caaaatttgg gagcataaac aatgggtcat gaattacaat  12840
caaacaaaag ataaaattct aagaagtctt ttaaagtgga aaaaaataac tgaaaaatac  12900
tgaatggagg gcagtttttc atgcactgtg ttacgaataa aaaatttgat tcaatggatt  12960
acttaatcaa cattttaata gttgtaaatc ttataatatt taagctgttt tataagtgcc  13020
tctacttata atggcacatc cgtttgaaac tctagcagat catttttatt tattttttttg  13080
aatttttttc tttatattct ttaaagaagg atacaaaatt atttctatga atatttaaca  13140
tatggaagga aatagcaata ataaacataa atgctaacac atataaaata ggtggtatca  13200
ttaggctaaa ttttagtctt ccaggataag tagaacatct ctgacttctc aaatatccaa  13260
ttaataaaat gcttactata ccatttggtg ctttaagaac attgccatgg aaacctctca  13320
ggttttatgc acagtagcta taataaaatt ttccttcatc tttcatggag ctacttgaga  13380
tttttttttct ccctttaaac atgagaaatc aaaaagaaag agaaaagaag gattaaatat  13440
```

```
tcatttatcc ttttgcttct gacttgttat gtgggcaagt gccacatgag ggagtgctgg  13500
gacctcatat caagaaaaat taaaacctac ctaatgcgtt ccaggaatgt tcagcatatt  13560
agcaaattct tattaaactg tcaaaaaaaa aaaaagtttt aaaagaaatt ccagcccctg  13620
gatgcaatta gaggctacca cactggattt gatgggccat aaaaccatta aatctaaaca  13680
ctttcttttt gagcctaaaa ggccagaaca ttccaaagtg aagttttggg actcagctat  13740
gacttgacca cctattaaga tgcaggtgga acagattgca gagtaacaca aagagccaca  13800
cagaccccag atgactgcat tagggtgtag gtgagagttt tagctgttga attttctgga  13860
ttttccaaga ttaagtgatc aaccttaaca atgagtgaaa gaccattcaa caggaagaat  13920
tgtcatttcc tttgctctaa acccaaacga tgtatttttt gaaagcttta ttgatttata  13980
tatttatgtg ttgtgctagg cgaccgacta gatatatgtt tcagcatacc tactaggaaa  14040
atatccccat tattctcaat tttacctaat ccaggcaaag cactggactt gctttaagga  14100
acatttttac tctttctgaa gtggagtgcc tgtcatgtat caggtgcaat gcttggactt  14160
tacgttcttg tgattaatcc ttacaatagg cctgtgaagt aattctcatt ctgtttgaca  14220
gtagagaaga aggaagccct tgaccaaggt ctagtgccag taatggtggt gatggggttt  14280
gaacctaagt ctgtttcact ctaaagtgta accaaatttt atgttttaga cttgcttttc  14340
taacaataaa aagtcagtga catgctcttt ctgtgtgtaa gcactcacac acacacacac  14400
aaacacacat ccgtattaca tatgcttata tatgtattaa aagattatgg acatttgata  14460
tatatacata tactaaaatg tataattcat tgctaaagta ttttcatata aatagtggct  14520
tcagtgttaa aatcactttg caatgaaaca agattgttga ttaaaacacc tattaaaaaa  14580
ttagaatcta gccatattaa agacagtcat cgaatggagt gatttctacg attttgcacc  14640
aaaatttaag ctattgggtg gctttcttga gagcatgaga ttgcttcttc tcagaattat  14700
taatgtgcct gatgacatta aaatgtgaca gtgaaaaaag tcagaggctc acatgtgtat  14760
cccaacactg aagttgttaa acactgggag gttggttgaa gttgttgtgt gcaaactcaa  14820
tactccttaa aaccattatt taaaggccta tcactgtgtt atggtctcca tatgatctgc  14880
catttatgcc aggacttgac aattcagtaa aatgacagaa taataacaca ggaatcactg  14940
cagtagagct aatgttttag tctgttgcag agttctgccc tagaaataca gtgaaaacaa  15000
ggaagggaga gctaagatgt ccctgagact aattgttcct tgaaaatatt ttcataagta  15060
aaaaagaggt ctagaggtgt agtggcagtg tgatcactca agattatata gctccggatt  15120
cgttcaatgg gccatgatga aagcacggca acgattaaat ctggtttctt ggtctttctt  15180
ggcagtgttt aaattggttc agttccataa attgtaaatt aagatctgtt tgacaacttt  15240
taagtatttc aagcataatt gtagttgaag gtttgttctt ttagatcact gacttcagaa  15300
ctttattttt ctggttaatc tcaattgtaa ttttagacat tcataaaaca atgttgactg  15360
cgtctatgtg atggtagatc ctctgtgaag acctttatga tggtagttcc cctgtgaaga  15420
taggatgaca cactcaatgg acattatggt gcacagttat acaaacactt cactatgaca  15480
ggccctgagt ttagaaccac acaactgctt ggtacttggt catcgcatat tttccccatt  15540
acgtaatgac ttcctgtgca gatgacaaaa tgcgtttctt caacaaaatt attttcagtg  15600
cagctgtttt gatgactaag ttttgtagga gctttttaat caaatgcacc taagaaaacc  15660
ccaacacttt aggccctttg aacatattac actttttgc ttcctctttc ctctttttcc  15720
ttaaaaccat aatttggaaa tttgattctg ccttcccata aaagagaatt attttcaaag  15780
aaattatttg ggtctaaatt aacatgttac ttaattgttc tgcttgaatc taggtatatg  15840
attagtccca tatgaattga tgttccaaat aatttactct cattgataac taatattttc  15900
tatttccctc tattgttttg tggtggtggt ggtggctgtg gatgaacatc attctcaaat  15960
atattataat tcccttcctc atcaagccca gcatgataaa cttcagtttt gcctgatggt  16020
tcatcatctt atttctgtgt gtaagattgt tggatttgac attaaacatt tggaaactat  16080
tttataattg ataacttgtg ctttctcagc tttgagtaag cgctctcttc ttcatcttat  16140
accattttat ttttatttat tattcacttc tgcttctgat ctgagatcta ggaagctgga  16200
caaatcccag ataagcaagc taaacaaaca aacaacaaca acaacaacaa caacaacaac  16260
aacacaaccc aaactaaacc aaaccaaaat catgggataa tggttaagtg tactgagggg  16320
ccattatgcg aacacagttt aattccttgg ctttaaaact aataagagaa gaatacataa  16380
acaaatgtgg caaatgtacc tgtgaccctc tccagagggt gccaggctag aagaaaggca  16440
gatttatcag caaggcatgg cgggccattg gcaaaccatg ggacaaccac taccaacttc  16500
actgccattg ctccatattt ccctcccgtt ttcaatgagc cccaactttg ctcaggacat  16560
cacacatatt ctactaattt ggatgagtcc ttttgaaaga aaatatctac ctcatggttc  16620
tcaaagtatg gtccttggaa catcagcgtc agcaggactc tggagcttgt tagaaatgca  16680
gatcttaggt cgcactacag acctactgag tcagaatctg aattttgtta acatacccat  16740
gtgattcctc aaagattgag aagccctgat cagagcctgg gatgaaagtt cctgttggtt  16800
ccaagccaaa ggcatagttc aggtcttcac acatgacact attagatgta gatggatatt  16860
gttcccttct gaagaccctc aaggtcttct gagagcctat taagttcaga atgactgcct  16920
gaaatgagtg agaagtcaca aggagactct agataattaa gagatgtgtt cacagtagtc  16980
tttgataaaa acctgggaca ggcaggctta gtatgcaggc ccctaaaatt tatgtacaca  17040
atggatttcc tatttttgct tcttcacatc cagattacct ggatcagaaa taaatgtttt  17100
cattaagact tgatgtgaca aacaaacaaa acaaaactct gccaagctct agaagaacaa  17160
ttgcatttcc cagccagagg gagaacactg ccagtttttg ctgttttcca aagctgttta  17220
cctgtcctag ctcatttaaa tcactgtact ttggagttcc ggattagcgt ccccagaggt  17280
agctgcattc atacttgatg agttctttta aatctcagcc attgattgta ggttccatag  17340
tataggaaat ttagccaacc ctctattgaa tggcagttta gaaaggtcga gctacactta  17400
ccttatgtca ggttattgca gacccttgtg gcatttttcc accctaggac atgtgattta  17460
actctaatag aaatctttat tatgggtggg tctgagatta acttttattc tataaaacag  17520
aaatcatgcc actggccgta gcccattttt tgagatggag tggggggaat ggatgatagt  17580
aaacaaggat attaatctca tttattttta tatcattata tttatagtta cattgcaaat  17640
ggaagagtag agaaaccaaa aacttacact gggaacttta caatttttct tccaagtatt  17700
actgattgat gtttggacta tgcaagtgct gccagcccct tagactcact ctgcagctcc  17760
ccccatggaa atttgtgaac aggttagggt ggggataggg aaaagcatgt tcttgtttca  17820
cttcttggat tatttgttcc aggctctcca aagtaatgtg taccttggga atgcagaaat  17880
tatctcctta gatattctct ccctatatat gtcctcacag ggaattcttg gaattggaga  17940
agattccact ctcctttagg agctttctcc ataaaggtat tgagcattgg acactatatt  18000
tgcaagggaa aagaggaatg ggtctcttga gcatcaaaat cattgtagaa gaatctccaa  18060
actgttttc aaaatgtctg tactaactta cattcctgac atcaatgggt tccctttttct  18120
ccacaagggt tccctttct ttgcatcttc accaacactt gttatcattg gtgtttttga  18180
```

```
taataaccat tctaacagtt ggaggtgata cttcattatg attttaattt aaatttccct  18240
gataattagt gatactgagc ttctttcata tatctattgg ccatttatat ctcttctttt  18300
gagaaatgtc tgttcagatc ctttgccaat ttttttttctt ttttcaactt ttattttaga  18360
atcagggagc catgtgcagg tttgttacaa aggtatattg catgatgctg aggtttggag  18420
tgcaaatgaa tccatcacct aggtagtgac cacaattcca aacaggtagt ttttttcagc  18480
ccttttcccc ctcccaaccc cactgttgta ttccccagca tctattgtta ccattttttt  18540
gaccatgtgt atccaatatt cagcttccat ttataagtga caacatgtgg tatttggttt  18600
ttggttacta cattaattca cttaggttat tgatttccag ctgcatccat gttggtgcaa  18660
aggacattat tttgttattt tttatggcta catagtattc catggtggat atgtaccaca  18720
ttttaaaaat tcaatccacc attggtgggc acctggattg attccatgtc tttgctattg  18780
tgaatagtgc tgtgatgaac atgcaggtgc acgtgtctct ttggtagaat gacttattgt  18840
cctttgggaa tatacccagt tagtgggatt gctggatcga atggtagaaa aactctcagg  18900
tctttgagaa atctccaaac tgctctctat agtggcttat ttaatttaca ttccctacag  18960
cagtgtatca gccttctctt ttctccacag actcaccaac atagtatttt ttgacttttt  19020
aacaaaagta attctgactg gtatgagatg gtatatcatt gtggttttga tttgcatttc  19080
tttgatgatt agagatgatg agcatcattt tcatatattt atcagcctct tttatgcctt  19140
tgtttgagaa gtatctgcaa atgtcctttg cccacttttt aatggggtta tctgttttgt  19200
catgttgatt tgtttaagtt tcttaaagat tctggatatt agacctttgt tggatgcata  19260
gtatgcaaat attttctcca attttgtagg ttgcctgttt actcctttga ttgtttctct  19320
tgctgtcctt tgcctatttt ttaattgggt tatttgtttt ctggctattg agttgtttga  19380
gttccttatt ttttttttttg gatattagca ctcattagat atacacttta caaatatttt  19440
ctcccaatac ctgtgttgtc tcttgattct gttaattgtt ttctttgctg tgcagaaaca  19500
ttttagtttc acacaattcc ttaaaaaact aaaaatagaa ttgccatatg atccagaaat  19560
tctacttctg gatatttatt gagaggaatt gaaatcagca tgttgaagag atatctgcac  19620
ttctatgttc gttatagcat tattcataat agtcatgata tgccatcaac ctaagtatcc  19680
attgacagat gaatggataa agaatgaggt gtatgtacac aaaggaatac tattcagcct  19740
ttaaaaagtg ggaaattctg taacaacatg gatagacaga tactatatga tcttacttat  19800
atgtggaatc taaaaaggta ggtctcacag aaacagatca taaaaaggtg gctaccagag  19860
gctgggagag gaaggaaaag aatgaggaaa gtgacatatt gatcaaagtt gtacaaagtt  19920
tcagtgcgac tggagtaata ggttttagtg atctattgta ctgcatggtg tccacagtta  19980
atagtaatgt attgtatatc ttaaaattac taaacgatta ggtatttaat gttctcccta  20040
caaaaaaatg gtaagttggt gtattagtcc actttcacac tgctataagg aactgcccga  20100
gactaagtaa tttataaaga aaagaggttt actggctcac agttctgtat ggctggggag  20160
gcctcaggaa gcttacaatc atggtgaaag ggaaagcagg tatgtcttac atggtggcag  20220
gtaagagatc ctgtgtgtga agtgaagggg gaagagtccc ttataaaacc atcagatctc  20280
gtgtgagctc actcactagc atgaaaacag catggaggaa atcaccccta tgatccaatc  20340
acctctttcc ctcaacacat ggggattaca gttccctgcc ttgatgcgtg ggattaaaat  20400
ttgagataag atttgggtgg ggacacaaag ccaaacctta tcagttggtg aggtgatgaa  20460
tatggtcatt agcttgtcta aatttgtctg caatgtatac atagatcaaa acatcacttt  20520
gtaccccata aacatgtgca attactattt tccaattaaa aataaatata aataaattaa  20580
aaataattgc aaaggaaagc tggctgtgga gaagattaac aaataatgac attaagaaat  20640
tcaggtcctt ggcaaaatta gaaatacata caaagctatc cagaacttat ttttccaaat  20700
gcattaggcg tcctctcacc ttacccttta caattgcatg gcttcagaga ttacacagaa  20760
aacgttcaga aacattgccc cagtagatga tcttgcaatg ctatgaagta ggcagaacag  20820
ctgtggctat agcaattgtg cagatagaac gtacttcatg gatggcaaga ctgggactct  20880
aggacaggct ttcaatccat tctaccctgt tgttgttctg aaatgaaagt ttttatctccc  20940
agtttatata ggtagcctta tctttgatgc ttcaatacct gagacctggc cagtgtccct  21000
tttagtgatt gtatgtgtgt gtgtgtgtgt catatgcaat ttccttatag caatggcaca  21060
gtgtatcact gtttaattaa agaagagaaa gaaatgccaa acatacgaat aaagtctgaa  21120
tatatctgta acattaaaag tgtaggtgtc tatctttgaa gatatgtctt aaggacaatg  21180
aaagagtcag tgagtaagag aagagagtcc tgggatttca tacaagatca gtgttacttg  21240
atggtgtagg ctcctaggta tttcatcttt aggatatacc gtctattaca aaagccaaga  21300
tttttagatt tggatcaaca ttagggaact tcattctagg caagagccag gttttgcctt  21360
tatgttaata tgacctcagc tgtgagctcc attttgccag gcatcttaaa actgcaacac  21420
atatcattgg aatcttccgt tacagtctaa tacatagcca cacattggga gcaagaatga  21480
aatccaaccc ctgtcctttg caaaatgcaa tgagacagtg tctgctttgg gagcagggag  21540
tcagaatttc attgtggaca atggataagg tgagtaaaag ggcttaaaac atttgtgctt  21600
tcaagccata ggctaggata acgatagtca gaactttttg atgaagtctg accatgctac  21660
gccatttata aaattttgaa gcttgtaagt attaccccaa aatgagcagt gtgaactcaa  21720
agggtttatc attgtctctc aggcaaaggt aatatttgaa ttatttagca aaggactttg  21780
agcaattgga agagatactc agctgctggt ctctagcgct ctaacagggt ggatgccccc  21840
cgctctgccg gcactgatgt ttaagttgct ggattatgag gaagtctggg gattccttgg  21900
ggagaaaagg aagtgatgac atattgaagc acaacgacat attgaagaga ctcgggggct  21960
ggggtgataa acttcagagc cgtggctatt taccaattgg agtgtaagta ttttaatatt  22020
ttaacaaaca taattgccat tctggtatgt accaacttca tctcagatct gtccttaaga  22080
aataggcaaa ttctttattg cctctctgaa tggttcatat aaattcccag gctcccttag  22140
ctcattctaa cataaaactg tattaaaaat aatgaatgta attcatcaat aattttcctt  22200
tgtcatagca aatagtcaca agtggattga gatcagagtg atcactcata tttgttctgg  22260
ggagaaggga gcctgctgtt ttgctcctgt tttctcctag gactagtatt ttagcttcaa  22320
atgataatac cttagcacag actctgatat tcctcctaca tgcaggagca ttctcttgga  22380
ataattttgg ggatgccaat tcaaaatttc agccatgtat gatttactta ttggaaaata  22440
atcactgagc agcaataact ccagcagtta cttgtatcaa ggtagaatca agaaatagat  22500
ggtatggacc aaacttgctt ctctctaaat atgcataccc aagtgatttg ggtaaaatgt  22560
ttgtgaaggg cttacatttc ctgcaagtca gatggtttaa gagaagtaga aattatgtgt  22620
gttttgcagc attttggtaa tctgtgtgga gtgtctgtag atatttctca tgagttcaag  22680
ggaatccttt tgtggatttt gatgttccta ttggcagagc tgctgcttga ctacatgatg  22740
tctttgtatt aactacaaaa acatgcccta tcatctgagt gattttctct gccagacccc  22800
tttgtgcatc cacactctgc acctccagtg tacggaggac cttcccactg gattctaaga  22860
ttccatgcct tcccaatgca tggcagtgtc tctcatgcac atggcaaacc tactctcttg  22920
```

-continued

```
gatgtcactg ccctgaaata ttgagggagt acatttatct aggcatggta ccagggagtc  22980
atttagacat gtagggagtc tagaaagatc attgccctgg gagagtgctc agccatgctg  23040
agttctccta ctttgttgct catttctgtg tgaccttagg taacatcctc ttcaggactt  23100
tttttttttt tttttttttg acagggagtc tcattctgtc atccaggctg gagtacagtg  23160
gtgtgatctc agctcactgc aatctccgcc tcctgggttc aagcaatcct agtgcttcag  23220
tcgcctgagt agctgggatt acaggcatgc gccactacgc ccagctaata tttgtatttt  23280
cagtagagat agggttttat catgttgatc aggctggtct tgaactcctg acctcaaggg  23340
atctgcctac cttggcctcc caaagtgctg ggattacaga tgagagccac caaccctggc  23400
caggacataa tttatttcag gtgaattgat tgttggagga ttttgatcca agcaatcaat  23460
gtcccttggt gttcctttca aacagcagta agtgacctga atttattttc cacatttcca  23520
aatcttaatg aaaatcagac aatggtctat atgttcattt gtgttcttac ttaataaaat  23580
gtgggtttta gacaatattt tgccagtcat gaattcctat agaaggaact ctttgggaga  23640
acagactagt gatctataga catgatgacc tccaactcag atcttctgta gctaaccact  23700
gaccgggaga acatgtatga aaaacatctt caaaggcatt gaaaaattaa catttatcaa  23760
aaacaaaata cattttattt catttgaact tagaccttta ctatctaatg gctatggtac  23820
tatttaaatg tcaaagtgtg atctagcatc agcctaatct ggttagaaat gcaaactctt  23880
gggccacatc tcagacttac tggaccagaa gctctgtggg tgggacccag aaatctgtgt  23940
ttcattcaca tgccctccag gggattgtcc tgctaaagtt tgagaatcat ggaagctttt  24000
taacctctca ttatagcttt ataagcagca actcactgga ttcctatcaa catcctgtga  24060
gtgtcatttg gacaagtata tttataccca tttgatgcat ggtaggcaca cagatgagtc  24120
aaatgacttg aaggaataga gttttacata atatactttt atatatttat acttctaata  24180
tatttatact ttataacaga tttgactgtt ttatatattg catataaaca ttatatcagt  24240
ttctcctcca ctaaggctga ctccaatttt actccaattt tactaccaat ttttggaaga  24300
aagcctacct atcactcatg ttctctcaag taccctctaa aactattagt tagatgactc  24360
tatttaattt tccatttatt tgcccgtttc ttgctacctt tccccccaaa atgtaactgc  24420
taccttgctc aaaaggatgt gtctacttgg gatatctagc acacacattt tatgagattt  24480
taaaagacaa cataaatggt aaactatata tttaatacaa ttttgaaaga caaaatttta  24540
aaattaaaaa ggaagaaaaa aattaaacta accccataat tctcccaccc atcattagca  24600
tgtagtttgt ttagattcat ctaccaataa gtagaattgt acaaatttga tatcatgtaa  24660
tacatgtcat tttgtaaact tttttctttc cttaatatat ctatatatca taaacatttt  24720
tctatgtcta tattatttta aaattgtaat acccagagtt ctccagagaa acagaattaa  24780
taggatctcc cccttggaga tttctcatct ttttctctct cgatagatac agatagatac  24840
atacataagt ctatctctct atctctatct ttatctctaa aacacctatc catagataga  24900
catttttagg aattggctca tgtgtttgtg gaagcttgca agttcaaatg tgcagagtag  24960
gtgggcaagc taccagggaa atgttgatgt tgcagttcca gtctgaaggc aggctccttg  25020
cagaattctt ctttttctta gcagtcttac ttccccttcc tcttcccctt ctccttcccc  25080
tttcccttct tcttctcctt ccccttcttc ttattctcct tcacagactt atttttaagg  25140
ccttgagctg attagataag acccactcac attatgaggg ataatctgct ttacctgtag  25200
tctactaatt aaaatgttaa tctcatctaa aaaacacctt catagcagca ttcagacatg  25260
tttcaccaaa tatctgggca ccatggttta gcatattgat gcagaaaatt gattatcata  25320
ataatattat tttttttga gatgtagttt cactcttgtc acccaggcta gagcgcaatg  25380
ctgcaatctc agctcacttc aacctcttcc tcctaggttc aagcgattct cctgcctcag  25440
cctcctgagt agctgggact acaggcgccc atgaccacgc ccggttaatt ttgtgttttt  25500
ttagtagaga tggggtttca ccacgttggt caggctggtc tcgaactcct gacctcaggt  25560
gatccacccg cctcagcctc ccaaagtgct gggattacag gcgtgagcca ctgtgcccag  25620
caataatatt aattttaatg ggtgtgttca tttcatttta tatatgacct acaatttaac  25680
caatccccta aggctggatg ttcaggttct taatattttt tgcccgtatt tacagacacc  25740
tttgactatt ggatttattt tgttcttcag gaacaatata caaagtgtgg aaagaaatgt  25800
atatttctaa tcattggaaa ataaacactg agcagaaata actccagtag ccatttgtat  25860
cagaggaggt agaatcagga aatagatggt atgggccaga ctttcttctc tctttaagag  25920
atttgacttc atattgccaa attgcccttc tagatgtctt tactcatcca actacaattc  25980
aaaggtttgg gagggtaagc aatgccaggc ccatcttgat catccccttt ctttctcagc  26040
ctgtcagtcc ctgggaacgg gcatgatgtt gagttcctgg gccacctcct caattgaaga  26100
agtggcggaa gctggtcctg aggcacttcg ttggctgcaa ctgtatatct acaaggaccg  26160
agaagtcacc aagaagctag tgcggcaggc agagaagatg ggctacaagg ccatatttgt  26220
gacagtggac acaccttacc tgggcaaccg tctggatgat gtgcgtaaca gattcaaact  26280
gccgccacaa ctcaggtaac catgatcatg tgggccccga gctgaggcga aagggatctt  26340
gactgggaat gttagggtct gggttctact gatagcaacg ttgctaaaca tctagttaat  26400
cttcagctaa tcacatccct tttgtagaca tcactttttt tgagatacac aatagaaaca  26460
gaaatggcct ctataaaagt ccaataaatt ttcagaccag agtgcattaa gggctttggc  26520
tttgggaagt atgaattgct atacagatgg aagatactga attttgccca agcagcagtt  26580
tattattatc atcctggtgc cctatttctt tgttaaagtc aaagagccac ctttaccttt  26640
tatttttaat ggtacatggg acagctaagg ctaagaagat tgaagaaaga aaataatgaa  26700
ggtttaaaaa agccacatct ttgatccctc actgtctact tcttctttca gcaatattcc  26760
tttcactgtg gttcatccat gggtcaagat tcattgattc attcactcaa atcattcatc  26820
ttagcaaaaa caatatatca cataatctga tgttgaacta taaaggtttc atcaggtcat  26880
tcattcaccc tgtccacaag ctgtgaatta ttatctcttt cctggttgta ttttgggatt  26940
acaatcatct tgagtcaaag ctggaaactg agtggaagtc tctgggaaag actcaaacct  27000
ccttaagcta tacacctctt ttccccatca gattttcctt ccttcagttt ccaccaaaat  27060
gtgctcttgg atttttcata tgaatgtata atgtacctca ggcctataag tattttaaaa  27120
gggatcaaaa tcttagtttt aatggaggac atttttatga tggactccta cagcatccat  27180
cagaatatgt aagatgatga ggaatgtctt cctgtgttcc cagatctcat gccacagagg  27240
cccttgctta ctctatgttt gaattgtatt tggaaaaaaa aaaaaaaaca aaaaactagg  27300
gctagcaaaa ttgaaaaaag ataaaagacg aaagaagcca catgtaaaca tactgtgttt  27360
actcttctaa aatattaaaa aatgaaaaga tccaaaatca aattaatatt cccctggaat  27420
ttcatatcta tttcagtgac tgtggagtga atctcaccac gaaagttgct gcagtcttgt  27480
ataagtttca catagtttta ctgtgtttgt gcctatgtga gaataaacta ctgtgcataa  27540
aatcttgctg ttgagccatg tgtgaattag ctgtgtgatg ttacctccct gttactacca  27600
ggctggttta ggatatcatt tctgtatgtg gcaccaggat tagaccaatg acagaaaaag  27660
```

```
aaagtgctct ccctgccaaa ctggccaata aaactgttcc acatatccca gactcagggt  27720
tacctaaaca acctgtgttt aaagagaaca aaaacaaaag cctctgacat agtcttactc  27780
cttgccaaat tcgtcagaaa gctgatggat tcaaattccc ccaatatgaa tcccgtattt  27840
acattatttc tctattttga ctactttttt ttttttttaa agactttcta aatagtttcc  27900
cactatcgag gcttcttaga ggaaacattt ctcattattt ccccttggct atttgaaaag  27960
gaatttgttc ttccttttcc tccatctctt aacactacta ctactaacaa tagtaacaac  28020
aatagtaagt acagtagggt tttttgtttt gtttttaact taagacatac tttcttgttc  28080
tggataccaa aatatgtttc acagaggcat ctacttagat ggggtgcaga tgacacagtt  28140
gttaattctg gcaggtacct cttgcttctt cactgctggg gctactcagt gagtggcagg  28200
aaggttgatt tgctttcccc ccttttcttt tgctcctggg ctccttccca gatgatgtga  28260
cgggccatga aacaaagact cttttcagct gtcggtgtgc atagaactgg ctgcggcttc  28320
ctagcttgtc acatctccgg tctgaagatg atcaaataat gagcaacaca tccaggttat  28380
agggaacacg ggaaacaccc cgcagctggg tgtaccccag cccctcagag tgcacattgg  28440
tgttgtttgt cctagtggac ttcggagtag gccagtgcct tctggtcagt tcctcagtgg  28500
cccacattca gctcttaaag gcagagcatg ctaacgggag gtccaggctt ccgcctgagg  28560
ccaaatacac cccaaaagct catctgttat agcctgatat gaaatcggtt tctttctgca  28620
actgacctga ctcatagaaa gtgaagcctg gcttttcata agtgaagttt ggcaggcaag  28680
ggaggcagga aatccagagg agaatgagcc tgtaaagcat ggctccttcc agcccttgtt  28740
acttcctctg cccaagtgtg ggggagggtc ctgtctcttg gcatctgggc ccagcaagag  28800
ttcagaggtt tggtagtctc tgcttggtcc atatgcaaaa cacatgtatg tgtatacatt  28860
attaatggca agggggttcc tgaaactgag agggagtaag gagacttctc atctgctctt  28920
ggaagaagca aggaatgaag ccagttcagt agactgattc ctgaggcttt ggggcaggaa  28980
ctttttcttt ctccatatcc ccatggagat ggttcattta ccctgaatta agatttggcc  29040
cttcggtgca gtgccaaggc agtttaaaga gaagaaaagt aatttctgat cattgactaa  29100
gatcaaggta aatcatgaca cttatccttt ctatgatttg ccagtgacat gttttcttaa  29160
gcccagaaat gatttattga tcgcagcagc cagaatatat cacactaaaa cagatcagcc  29220
tgccactgtc ttctcaggtc tctcatgatt aaagtggcct gctttaaagt agactcaatg  29280
tgaataggtc tccatgacct ctgcctcact gcgtagcact cacatcctca cccactcttg  29340
cactctggct tccctgcggt tctttcaata tgccaggcat gctggaaccc cggagccttt  29400
gcactggctg ttccctctgt ctgtaacagt cattcgcaga atcaacgcat gactaatagc  29460
ctcacttcca ttgagtcttg acattaggaa tggatataca tgtctatatt gggaaaccac  29520
aataaaaatt gatggtagag atgcaaatat gagcaagata acagggtggg ggcaggggag  29580
agaggtcagt ggaggacttg gcacagtagc ctcttaaatg gcacaatagc ctcttaaatt  29640
tttggttaag aaatcattca cattgataag tatggcagga taaaggtgtc catgagtgaa  29700
tcccgggaac ctgttacttt atgtggcaaa agggactttg cagatgtgat taacttaagg  29760
ggcttgagat gggaagattt ttcctgtttt tatcagtagg cttgatataa ttaaaagggt  29820
ccttataaga gggaagcaag agtgtcagag tcagagaaag agatgaaatg acagatgtag  29880
aggttggaat gatgtggtca ggaaccaggg aaagcagggg gtatctagaa gctggaaaag  29940
acaagggaat agggcttccc ctagattctc cagaaataca gccctattga tatcttgagt  30000
ttagtccagt gagacttatt ttagacttct gacatttgga actgtaatat aataccttca  30060
tgttattttt attgctgttg taacaaataa ccacaaacac agttctacta atttctttct  30120
caaggtagct tctcaatttt gccaacgctg gttaccatac atacttaaag tttcattttg  30180
agtctctgaa aactcacatc tctcttaatc tgctctactt ttttcttggc tttgtatagt  30240
gcttatgttc tgctacactt tgtaatttat tgattatgct taccatgggc agggattctt  30300
aactgtttta tttatttata tatcttaaac attgaaaaca ctggcatgta gtagatgctt  30360
aataagtaat tgttgactca atcgataaaa tatactagaa catacaagat tttcccaatg  30420
taacataact agtaagaggc tgaaccggga tttgaactca aaattcattc cctgaacctt  30480
cttctagcag ccacattgag gaagaaatta ccagggctgt gttctcaaca caagtgtttt  30540
ccgaaccaca gaattaaagg ctggtggccc atgtatcagt gtctgtattt atgagcccct  30600
ctttcaatct ctttcttttc atattgtgtt gatgctgtag cttctactgg tcatgttatt  30660
tttttgtttc ccaagacgga attatgtggc tttatcttta atgttgcatt atcaatactt  30720
ataataaata atattatgta ttactcaata ttcatgatta atagtgttac tattggttat  30780
ttaataatgt ttaacttaca ttagcagttg ttactatttt tatgatgcta aattactaac  30840
agctaaaaca acttctatat taaaaagtat atttgagtgc cactcaagag ataatgagta  30900
ccttacaaag aagaaatctt gtttctcacc tttgcgtcat taaacagatc aggatttgga  30960
gaattaagcc ctaagtaata gtgttattat tttgatctca cccctttttt tcttatgaaa  31020
tggaatactt tggttatcag aagccacttt aagcatatat atatatatat atatatatac  31080
atatatatat atatatatgt cataatccga ataaaaatag cattcatgga ggtttctttt  31140
ggagcctttg gtaaaacact ccatcgtggg tctctgtcaa gatatctgaa aactttttct  31200
tggcttctgg ctttgaacaa agtttcagag taacaacaag gcttcattgt gcactgaaat  31260
ttctgtaagg caacattcat tcaagtgttg attcgcattt caccatccaa gaataacaac  31320
agttatttat ataattttat ccacgtttct gtttttttcct atccatttca ccctttcacc  31380
ccacccctgc tgaaacactg gagcttgttt gggatggggg tggggtgcca tgcagactac  31440
atacacatac agatgttttt ctttttcttt tcccggtctt gctatgggat agacagactg  31500
gactttttct tattaacaat attatttaaa agcttggaat ttattatcat ttaatcattt  31560
gtatgtaatg aaataggtct ccatggtaaa gatgtgttta ttgaccagcg gttagcttta  31620
ttcaaattag ggtgaccata gaagaccaag gactatgata taatgtacaa tcctaagtgg  31680
tttgatttaa ataaaaagaa agaccaggca tttcagctaa aatccccacc aaagcccaat  31740
gactagatgg gcatccatat gactcaatga aattttctat gatcttaaat ggccatctga  31800
gtccgtgaaa ctataggact aactattcaa tccttattga gaaagccttg ttaatagctt  31860
gaattgagtt atatgggata ggaatgttca tatctttatg acaatatatg ccacctaagc  31920
tacataacca gctgtgttag ctaaaatact ctaaagtgta aaaaatcata gttttctatt  31980
aaaggaagtc atgattgtta aaaataattt ttaaatagtg tgcctagatt cttctagtat  32040
aatatataat tttttttttt tttttatttt gagacagagt cttgctctgt cacccaggct  32100
ggagtgcagt ggctggagtt gctcactgca acctcgcctc ccgggttcaa gcgattctcg  32160
tgcctcagcc tcccaagtag ctgagattac acgtgcccac cactatgtcc ggctaatttt  32220
tttgaatttt tagtagagac tgggtttcat catgctggcc agactggtct tgaactcctg  32280
acctcaggtg atctgcccac ctcggcctcc caaagtgctg ggattacagg catgagccat  32340
tgcgcccagc cgatatataa atttttatat ggctccatga tcttctctac atttaatgac  32400
```

```
agaactggtg gaggggaaga aagagatggg actaagccag agatcaatat acatacaact  32460
atactttgac caaaaaaagg gagattgact ggcaggggaa ttaatagtat gcagaagagc  32520
aaggtgagtc cagtcactgt cattattcaa aaacagcctt tcaggagaag tttgcaactg  32580
aatttgggac tgtgggcaga taagtcacag gaatgattct attgtgtatc ctgaagtcat  32640
ccatccagct aggagtcaga ggtgcaggct gaaaagacat tgcccctaga gtggggaact  32700
gccaaaatct agccaggata ttaggccaag agaaaagacc tcaggcacag gggaagccag  32760
cttcaga                                                            32767

SEQ ID NO: 929          moltype = DNA  length = 223
FEATURE                 Location/Qualifiers
misc_feature            1..223
                        note = Synthetic
source                  1..223
                        mol_type = other DNA
                        organism = synthetic construct
SEQUENCE: 929
aacgaactcc atctgggata gcaataacct gtgaaaatgc tccccggct aatttgtatc  60
aatgattatg aacaacatgc taaatcagta cttccaaagt ctatatatga ctattacagg  120
tctggggcaa atgatgaaga aactttggct gataatattg cagcattttc caggtaagaa  180
aatttatttt ttaaaatcat gttttaaaat tacacaaaga ccg                    223

SEQ ID NO: 930          moltype = DNA  length = 252
FEATURE                 Location/Qualifiers
misc_feature            1..252
                        note = Synthetic
source                  1..252
                        mol_type = other DNA
                        organism = synthetic construct
SEQUENCE: 930
tgattctgaa actctaaagc cttttatttt attttatttt ttaattctag atggaagctg  60
tatccaagga tgctccggaa tgttgctgaa acagatctgt cgacttctgt tttaggacag  120
agggtcagca tgccaatatg tgtgggggct acggccatgc agcgcatggc tcatgtggac  180
ggcgagcttg ccactgtgag aggtaggagg aagattgtca ccacagggac agaaggaggc  240
taacgtttat cg                                                      252

SEQ ID NO: 931          moltype = DNA  length = 356
FEATURE                 Location/Qualifiers
misc_feature            1..356
                        note = Synthetic
source                  1..356
                        mol_type = other DNA
                        organism = synthetic construct
SEQUENCE: 931
ggagggtaag caatgccagg cccatcttga tcatcccctt tctttctcag cctgtcagtc  60
cctgggaacg ggcatgatgt tgagttcctg ggccacctcc tcaattgaag aagtggcgga  120
agctggtcct gaggcacttc gttggctgca actgtatatc tacaaggacc gagaagtcac  180
caagaagcta gtgcggcagg cagagaagat gggctacaag gccatatttg tgacagtgga  240
cacaccttac ctgggcaacc gtctggatga tgtgcgtaac agattcaaac tgccgccaca  300
actcaggtaa ccatgatcat gtgggccccg agctgaggcg aaagggatct tgactg      356

SEQ ID NO: 932          moltype = DNA  length = 276
FEATURE                 Location/Qualifiers
misc_feature            1..276
                        note = Synthetic
source                  1..276
                        mol_type = other DNA
                        organism = synthetic construct
SEQUENCE: 932
acgtatttct aatttggcaa atttctcatt ttatgcattt cttattttag gatgaaaaat  60
tttgaaacca gtactttatc attttctcct gaggaaaatt ttggagacga cagtggactt  120
gctgcatatg tggctaaagc aatagaccca tctatcagct gggaagatat caaatggctg  180
agaagactga catcattgcc aattgttgca aagggcattt tgagaggttc gtttatttct  240
ctacttgaat tcatactgac tttgtgatcc tttgtg                            276

SEQ ID NO: 933          moltype = DNA  length = 192
FEATURE                 Location/Qualifiers
misc_feature            1..192
                        note = Synthetic
source                  1..192
                        mol_type = other DNA
                        organism = synthetic construct
SEQUENCE: 933
ctgcctgtta agttacagtt tccctaaggt gcttgtttta ctctctccag gtgatgatgc  60
cagggaggct gttaaacatg gcttgaatgg gatcttggtg tcgaatcatg ggctcgaca  120
actcgatggg gtgccagcca ctgtgagttt tggcagacgc taagatttcc ttttggagtt  180
cccatttcca tc                                                      192

SEQ ID NO: 934          moltype = DNA  length = 444
FEATURE                 Location/Qualifiers
```

```
misc_feature          1..444
                      note = Synthetic
source                1..444
                      mol_type = other DNA
                      organism = synthetic construct
SEQUENCE: 934
taacaattca gtgttaatag agtcacatta ttgaactttt ctttccccag attgatgttc  60
tgccagaaat tgtggaggct gtggaaggga aggtggaagt cttcctggac gggggtgtgc  120
ggaaaggcac tgatgttctg aaagctctgg ctcttggcgc caaggctgtg tttgtgggga  180
gaccaatcgt ttggggctta gctttccagg taactggaca aagaaatgaa tatataaaat  240
agacaacttg acagtaaaac aaatgaataa aacaagtcag actgatttag ttctgaatca  300
ctctgtatct tttcacttgg ttagggggag aaaggtgttc aagatgtcct cgagatacta  360
aaggaagaat tccggttggc catggctctg agtggtaaga ctcattcttg tttacaactt  420
tcttttcttt tatgatcttt aagt                                         444

SEQ ID NO: 935        moltype = DNA  length = 729
FEATURE               Location/Qualifiers
misc_feature          1..729
                      note = Synthetic
source                1..729
                      mol_type = other DNA
                      organism = synthetic construct
SEQUENCE: 935
tgattattat tgcattcagt tcatattaaa tgtatgcatt attttttcag ggtgccagaa  60
tgtgaaagtc atcgacaaga cattggtgag gaaaaaatcct ttggccgttt ccaagatctg  120
acagtgcaca atattttccc atctgtatta tttttttca gcatgtatta cttgacaaag  180
agacactgtg cagagggtga ccacagtctg taattcccca cttcaataca aagggtgtcg  240
ttcttttcca acaaaatagc aatccctttt atttcattgc ttttgacttt tcaatgggtg  300
tcctaggaac cttttagaaa gaaatggact ttcatcctgg aaatatatta actgttaaaa  360
agaaaacatt gaaaatgtgt ttagacaacg tcatcccctg gcaggctaaa gtgctgtatc  420
ctttagtaaa attggaggta gcaaacacta aggtgaaaag ataatgatct cattgtttat  480
taacctgtat tctgtttaca tgtctttaaa acagtggttc ttaaattgta agctcaggtt  540
caaagtgttg gtaatgcctg attcacaact ttgagaaggt agcactggag agaattggaa  600
tgggtggcgg taattggtga tacttctttg aatgtagatt tccaatcaca tctttagtgt  660
ctgaatatat ccaaatgttt taggatgtat gttacttctt agagagaaat aaagcatttt  720
tgggaagaa                                                          729

SEQ ID NO: 936        moltype = RNA  length = 36
FEATURE               Location/Qualifiers
misc_feature          1..36
                      note = Synthetic
source                1..36
                      mol_type = other RNA
                      organism = synthetic construct
SEQUENCE: 936
tctcaacgat agtcagacat gtgtcctcag tgacac                            36

SEQ ID NO: 937        moltype = RNA  length = 36
FEATURE               Location/Qualifiers
misc_feature          1..36
                      note = Synthetic
source                1..36
                      mol_type = other RNA
                      organism = synthetic construct
SEQUENCE: 937
ttttaacaac actcaggcat gtgtccacag tgacac                            36

SEQ ID NO: 938        moltype = RNA  length = 36
FEATURE               Location/Qualifiers
misc_feature          1..36
                      note = Synthetic
source                1..36
                      mol_type = other RNA
                      organism = synthetic construct
SEQUENCE: 938
ttgaacggat actcagacat gtgtttccag tgacac                            36

SEQ ID NO: 939        moltype = RNA  length = 36
FEATURE               Location/Qualifiers
misc_feature          1..36
                      note = Synthetic
source                1..36
                      mol_type = other RNA
                      organism = synthetic construct
SEQUENCE: 939
tgccctcaat agtcagatgt gtgtccacag tgacac                            36

SEQ ID NO: 940        moltype = RNA  length = 36
FEATURE               Location/Qualifiers
```

```
misc_feature           1..36
                       note = Synthetic
source                 1..36
                       mol_type = other RNA
                       organism = synthetic construct
SEQUENCE: 940
tctcaatgat acttagatac gtgtcctcag tgacac                          36

SEQ ID NO: 941         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 941
tctcaatgat actcagacat gtgtccccag tgacac                          36

SEQ ID NO: 942         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 942
tctcaatgat actaagacat gtgtcctcag tgacac                          36

SEQ ID NO: 943         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 943
tctcaactat actcagacat gtgtcctcag tgacac                          36

SEQ ID NO: 944         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 944
tctcaacgat actcagacat gtgtcctcag tgacac                          36

SEQ ID NO: 945         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 945
tctcaacgat actaagatat gtgtcctcag cgacac                          36

SEQ ID NO: 946         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 946
tctcaacgat actaagatat gtgtccccag tgacac                          36

SEQ ID NO: 947         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 947
tctcaacgat actaagatat gtgtccacag tgacac                          36

SEQ ID NO: 948         moltype = RNA  length = 36
```

-continued

```
FEATURE                Location/Qualifiers
misc_feature           1..36
                       note = Synthetic
source                 1..36
                       mol_type = other RNA
                       organism = synthetic construct
SEQUENCE: 948
tctcaacaat actcagacat gtgtccccag tgacac                        36

SEQ ID NO: 949         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 949
tctcaacaat actaaggcat gtgtccccag tgaccc                        36

SEQ ID NO: 950         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 950
tctcaaagat actcagacac gtgtccccag tgacac                        36

SEQ ID NO: 951         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 951
tctcaaaaat actcagacat gtgtcctcag tgacac                        36

SEQ ID NO: 952         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 952
gcgaaacaac agtcagacat gtgtccccag tgacac                        36

SEQ ID NO: 953         moltype = RNA  length = 36
FEATURE                Location/Qualifiers
misc_feature           1..36
                       note = Synthetic
source                 1..36
                       mol_type = other RNA
                       organism = synthetic construct
SEQUENCE: 953
cctcaacgat attaagacat gtgtccgcag tgacac                        36

SEQ ID NO: 954         moltype = RNA  length = 22
FEATURE                Location/Qualifiers
misc_feature           1..22
                       note = Synthetic
source                 1..22
                       mol_type = other RNA
                       organism = synthetic construct
SEQUENCE: 954
agacatgtgt cctcagtgac ac                                       22

SEQ ID NO: 955         moltype = DNA  length = 3222
FEATURE                Location/Qualifiers
misc_feature           1..3222
                       note = Synthetic
source                 1..3222
                       mol_type = other DNA
                       organism = synthetic construct
SEQUENCE: 955
atggcttcca tctctaggcc atacggcacc aagctgcgac cggacgcacg gaagaaggag  60
atgctcgata agttctttaa tacactgact aagggtcagc gcgtgttcgc agacctggcc  120
```

-continued

```
ctgtgcatct atggctccct gaccctggag atggccaagt ctctggagcc agaaagtgat  180
tcagaactgg tgtgcgctat tgggtggttt cggctggtgg acaagaccat ctggtccaag  240
gatggcatca agcaggagaa tctggtgaaa cagtacgaag cctattccgg aaaggaggct  300
tctgaagtgg tcaaaacata cctgaacagc cccagctccg acaagtacgt gtggatcgat  360
tgcaggcaga aattcctgag gtttcagcgc gagctcggca ctcgcaacct gtccgaggac  420
ttcgaatgta tgctctttga acagtacatt agactgacca agggcgagat cgaagggtat  480
gccgctattt caaatatgtt cggaaacggc gagaaggaag accggagcaa gaaaagaatg  540
tacgctacac ggatgaaaga ttggctggag gcaaacgaaa atatcacttg ggagcagtat  600
agagaggccc tgaagaacca gctgaatgct aaaaacctgg agcaggttgt ggccaattac  660
aaggggaacg ctggcggggc agacccottc tttaagtata gcttctccaa agagggaatg  720
gtgagcaaga aagaacatgc acagcagctc gacaagttca aaaccgtcct gaagaacaaa  780
gccccgggacc tgaattttcc aaacaaggag aagctgaagc agtacctgga ggccgaaatc  840
ggcattccgg tcgacgctaa cgtgtactcc cagatgttct ctaacggggt gagtgaggtc  900
cagcctaaga ccacacggaa tatgtctttt agtaacgaga aactggatct gctcactgaa  960
ctgaaggacc tgaacaaggg cgatgggttc gagtacgcca gagaagtgct gaacgggttc  1020
tttgactccg agctccacac taccgaggat aagtttaata tcacctctag gtacctggga  1080
ggcgacaaat caaaccgcct gagcaaactc tataagatct ggaagaaaga gggtgtggac  1140
tgcgaggaag gcattcagca gttctgtgaa gccgtcaaag ataagatggg ccagatcccc  1200
attcgaaatg tgctgaagta cctgtggcag ttccgggaga cagtcagtgc cgaggatttt  1260
gaagcagccg ctaaggctaa ccatctggag gaaaagatca gccgggtgaa agcccaccca  1320
atcgtgatta gcaataggta ctgggctttt gggacttccg cactggtggg aaacattatg  1380
cccgcagaca agaggcatca gggagagtat gccggtcaga atttcaaaat gtggctggag  1440
gctgaactgc actacgatgg caagaaagca aagcaccatc tgccttttta taacgcccgc  1500
ttctttgagg aagtgtactg ctatcacccc tctgtcgccg agatcactcc tttcaaaacc  1560
aagcagtttg gctgtgaaat cgggaaggac attccagatt acgtgagcgt cgctctgaag  1620
gacaatccgt ataagaaagc aaccaaacga atcctgcgtg caatctacaa tcccgtcgcc  1680
aacacaactg gcgttgataa gaccacaaac tgcagcttca tgatcaaacg cgagaatgac  1740
gaatataagc tggtcatcaa ccgaaaaatt tccgtggatc ggcctaagag aatcgaagtg  1800
ggcaggacaa ttatggggta cgaccgcaat cagacagcta gcgatactta ttggattggc  1860
cggctggtgc cacctggaac ccggggcgca taccgcatcg gagagtggag cgtccagtat  1920
attaagtccg ggcctgtcct gtctagtact cagggagtta acaattccac taccgaccag  1980
ctggtgtaca acggcatgcc atcaagctcc gagcggttca aggcctggaa gaaagccaga  2040
atggctttta tccgaaaact cattcgtcag ctgaatgacg agggactgga atctaagggt  2100
caggattata tccccgagaa cccttctagt ttcgatgtgc ggggcgaaac cctgtacgtc  2160
tttaacagta attatctgaa ggccctggtg agcaaacaca gaaaggccaa gaaacctgtt  2220
gaggggatcc tggacgagat tgaagcctgg acatctaaag acaaggattc atgcagcctg  2280
atgcggctga gcagcctgag cgatgcttcc atgcagggaa tcgccagcct gaagagtctg  2340
attaacagct acttcaacaa gaatggctgt aaaaccatcg aggacaaaga aaagtttaat  2400
cccgtgctgt atgccaagct ggttgaggtg gaacagcgga gaacaaacaa gcggtctgag  2460
aaagtgggaa gaatcgcagg tagtctggag cagctggccc tgctgaacgg ggttgaggtg  2520
gtcatcggcg aagctgacct gggggaggtc gaaaaaggaa agagtaagaa acagaattca  2580
cggaacatgg attggtgcgc aaagcaggtg gcacagcggc tggagtacaa actggccttc  2640
catggaatcg gttactttgg agtgaacccc atgtatacca gccaccagga ccctttcgaa  2700
cataggcgcg tggctgatca catcgtcatg cgagcacgtt ttgaggaagt caacgtggag  2760
aacattgccg aatggcacgt gcgaaatttc tcaaactacc tgcgtgcaga cagcggcact  2820
gggctgtact ataagcaggc caccatggac ttcctgaaac attacggtct ggaggaacac  2880
gctgagggcc tggaaaataa gaaaatcaag ttctatgact ttagaaagat cctggaggat  2940
aaaaacctga caagcgtgat cattccaaag aggggcgggc gcatctacat ggccaccaac  3000
ccagtgacat ccgactctac cccgattaca tacgccggca agacttataa taggtgtaac  3060
gctgatgagg tggcagccgc taatatcgtt atttctgtgc tggctccccg cagtaagaaa  3120
aacgaggaac aggacgatat ccctctgatt accaagaaag ccgagagtaa gtcaccaccg  3180
aaagaccgga agagatcaaa aacaagccag ctgcctcaga aa                    3222
```

```
SEQ ID NO: 956          moltype = AA  length = 1074
FEATURE                 Location/Qualifiers
REGION                  1..1074
                        note = Synthetic
source                  1..1074
                        mol_type = protein
                        organism = synthetic construct
SEQUENCE: 956
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLE  480
AELHYDGKKA KHHLPFYNAR FFEEVYCYHP SVAEITPFKT KQFGCEIGKD IPDYVSVALK  540
DNPYKKATKR ILRAIYNPVA NTTGVDKTTN CSFMIKREND EYKLVINRKI SVDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN  1020
ADEVAAANIV ISVLAPRSKK NEEQDDIPLI TKKAESKSPP KDRKRSKTSQ LPQK        1074
```

```
SEQ ID NO: 957          moltype = AA  length = 1074
FEATURE                 Location/Qualifiers
REGION                  1..1074
                        note = Synthetic
source                  1..1074
                        mol_type = protein
                        organism = synthetic construct
SEQUENCE: 957
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLE  480
AELHYDGKKA KHHLPFYNAR FFEEVYCYHP SVAEITPFKT KQFGCEIGKD IPDYVSVALK  540
DNPYKKATKR ILRAIYNPVA NTTGVDKTTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 958          moltype = AA  length = 1074
FEATURE                 Location/Qualifiers
REGION                  1..1074
                        note = Synthetic
source                  1..1074
                        mol_type = protein
                        organism = synthetic construct
SEQUENCE: 958
MASISRPYGT KLRPDARKKE MLDKFFNTLT KGQRVFADLA LCIYGSLTLE MAKSLEPESD  60
SELVCAIGWF RLVDKTIWSK DGIKQENLVK QYEAYSGKEA SEVVKTYLNS PSSDKYVWID  120
CRQKFLRFQR ELGTRNLSED FECMLFEQYI RLTKGEIEGY AAISNMFGNG EKEDRSKKRM  180
YATRMKDWLE ANENITWEQY REALKNQLNA KNLEQVVANY KGNAGGADPF FKYSFSKEGM  240
VSKKEHAQQL DKFKTVLKNK ARDLNFPNKE KLKQYLEAEI GIPVDANVYS QMFSNGVSEV  300
QPKTTRNMSF SNEKLDLLTE LKDLNKGDGF EYAREVLNGF FDSELHTTED KFNITSRYLG  360
GDKSNRLSKL YKIWKKEGVD CEEGIQQFCE AVKDKMGQIP IRNVLKYLWQ FRETVSAEDF  420
EAAAKANHLE EKISRVKAHP IVISNRYWAF GTSALVGNIM PADKRHQGEY AGQNFKMWLR  480
AELHYDGKKA KHHLPFYNAR FFEEVYCYHP SVAEITPFKT KQFGCEIGKD IPDYVSVALK  540
DNPYKKATKR ILRAIYNPVA NTTRVDKTTN CSFMIKREND EYKLVINRKI SRDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN  1020
ADEVAAANIV ISVLAPRSKK NREQDDIPLI TKKAESKSPP KDRKRSKTSQ LPQK        1074

SEQ ID NO: 959          moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 959
gttggaatga ctaatttttg tgcccaccgt tggcac                            36

SEQ ID NO: 960          moltype = RNA  length = 24
FEATURE                 Location/Qualifiers
misc_feature            1..24
                        note = Synthetic
source                  1..24
                        mol_type = other RNA
                        organism = synthetic construct
SEQUENCE: 960
aatttttgtg cccatcgttg gcac                                         24

SEQ ID NO: 961          moltype = RNA  length = 23
FEATURE                 Location/Qualifiers
misc_feature            1..23
                        note = Synthetic
```

```
source                  1..23
                        mol_type = other RNA
                        organism = synthetic construct
SEQUENCE: 961
atttttgtgc ccatcgttgg cac                                  23

SEQ ID NO: 962          moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 962
ctagcaatga cctaatagtg tgtccttagt tgacat                    36

SEQ ID NO: 963          moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 963
cctacaatac ctaagaaatc cgtcctaagt tgacgg                    36

SEQ ID NO: 964          moltype = RNA  length = 22
FEATURE                 Location/Qualifiers
misc_feature            1..22
                        note = Synthetic
source                  1..22
                        mol_type = other RNA
                        organism = synthetic construct
SEQUENCE: 964
atagtgtgtc cttagttgac at                                   22

SEQ ID NO: 965          moltype = AA  length = 1093
FEATURE                 Location/Qualifiers
REGION                  1..1093
                        note = Synthetic
source                  1..1093
                        mol_type = protein
                        organism = synthetic construct
SEQUENCE: 965
MSNKEKNASE TRKAYTTKMI PRSHDRMKLL GNFMDYLMDG TPIFFELWNQ FGGGIDRDII  60
SGTANKDKIS DDLLLAVNWF KVMPINSKPQ GVSPSNLANL FQQYSGSEPD IQAQEYFASN  120
FDTEKHQWKD MRVEYERLLA ELQLSRSDMH HDLKLMYKEK CIGLSLSTAH YITSVMFGTG  180
AKNNRQTKHQ FYSKVIQLLE ESTQINSVEQ LASIILKAGD CDSYRKLRIR CSRKGATPSI  240
LKIVQDYELG TNHDDEVNVP SLIANLKEKL GRFEYECEWK CMEKIKAFLA SKVGPYYLGS  300
YSAMLENALS PIKGMTTKNC KFVLKQIDAK NDIKYENEPF GKIVEGFFDS PYFESDTNVK  360
WVLHPHHIGE SNIKTLWEDL NAIHSKYEED IASLSEDKKE KRIKVYQGDV CQTINTYCEE  420
VGKEAKTPLV QLLRYLYSRK DDIAVDKIID GITFLSKKHK VEKQKINPVI QKYPSFNFGN  480
NSKLLGKIIS PKDKLKHNLK CNRNQVDNYI WIEIKVLNTK TMRWEKHHYA LSSTRFLEEV  540
YYPATSENPP DALAARFRTK TNGYEGKPAL SAEQIEQIRS APVGLRKVKK RQMRLEAARQ  600
QNLLPRYTWG KDFNINICKR GNNFEVTLAT KVKKKKEKNY KVVLGYDANI VRKNTYAAIE  660
AHANGDGVID YNDLPVKPIE SGFVTVESQV RDKSYDQLSY NGVKLLYCKP HVESRRSFLE  720
KYRNGTMKDN RGNNIQIDFM KDFEAIADDE TSLYYFNMKY CKLLQSSIRN HSSQAKEYRE  780
EIFELLRDGK LSVLKLSSLS NLSFVMFKVA KSLIGTYFGH LLKKPKNSKS DVKAPPITDE  840
DKQKADPEMF ALRLALEEKR LNKVKSKKEV IANKIVAKAL ELRDKYGPVL IKGENISDTT  900
KKGKKSSTNS FLMDWLARGV ANKVKEMVMM HQGLEFVEVN PNFTSHQDPF VHKNPENTFR  960
ARYSRCTPSE LTEKNRKEIL SFLSDKPSKR PTNAYYNEGA MAFLATYGLK KNDVLGVSLE  1020
KFKQIMANIL HQRSEDQLLF PSRGGMFYLA TYKLDADATS VNWNGKQFWV CNADLVAAYN  1080
VGLVDIQKDF KKK                                             1093

SEQ ID NO: 966          moltype = AA  length = 1098
FEATURE                 Location/Qualifiers
REGION                  1..1098
                        note = Synthetic
source                  1..1098
                        mol_type = protein
                        organism = synthetic construct
SEQUENCE: 966
MSISNNNILP YNPKLLPDDR KHKMLVDTFN QLDLIRNNLH DMIIALYGAL KYDNIKQFAS  60
KEKPHISADA LCSINWFRLV KTNERKPAIE SNQIISKFIQ YSGHTPDKYA LSHITGNHEP  120
SHKWIDCREY AINYARIMHL SFSQFQDLAT ACLNCKILIL NGTLTSSWAW GANSALFGGS  180
DKENFSVKAK ILNSFIENLK DEMNTTKFQV VEKVCQQIGS SDAADLFDLY RSTVKDGNRG  240
PATGRNPKVM NLFSQDGEIS SEQREDFIES FQKVMQEKNS KQIIPHLDKL KYHLVKQSGL  300
YDIYSWAAAI KNANSTIVAS NSSNLNTILN KTEKQQTFEE LRKDEKIVAC SKILLSVNDT  360
LPEDLHYNPS TSNLGKNLDV FFDLLNENSV HTIENKEEKN KIVKECVNQY MEECKGLNKP  420
```

-continued

```
PMPVLLTFIS DYAHKHQAQD FLSAAKMNFI DLKIKSIKVV PTVHGSSPYT WISNLSKKNK  480
DGKMIRTPNS SLIGWIIPPE EIHDQKFAGQ NPIIWAVLRV YCNNKWEMHH FPFSDSRFFT  540
EVYAYKPNLP YLPGGENRSK RFGYRHSTNL SNESRQILLD KSKYAKANKS VLRCMENMTH  600
NVVFDPKTSL NIRIKTDKNN SPVLDDKGRI TFVMQINHRI LEKYNNTKIE IGDRILAYDQ  660
NQSENHTYAI LQRTEEGSHA HQFNGWYVRV LETGKVTSIV QGLSGPIDQL NYDGMPVTSH  720
KFNCWQADRS AFVSQFASLK ISETETFDEA YQAINAQGAY TWNLFYLRIL RKALRVCHME  780
NINQFREEIL AISKNRLSPM SLGSLSQNSL KMIRAFKSII NCYMSRMSFV DELQKKEGDL  840
ELHTIMRLTD NKLNDKRVEK INRASSFLTN KAHSMGCKMI VGESDLPVAD SKTSKKQNVD  900
RMDWCARALS HKVEYACKLM GLAYRGIPAY MSSHQDPLVH LVESKRSVLR PRFVVADKSD  960
VKQHHLDNLR RMLNSKTKVG TAVYYREAVE LMCEELGIHK TDMAKGKVSL SDFVDKFIGE  1020
KAIFPQRGGR FYMSTKRLTT GAKLICYSGS DVWLSDADEI AAINIGMFVV CDQTGAFKKK  1080
KKEKLDDEEC DILPFRPM                                              1098

SEQ ID NO: 967         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 967
agaaatccgt ctttcattga cggcaaagtc tatatatgac tat                 43

SEQ ID NO: 968         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 968
agaaatccgt ctttcattga cggggaagta ctgatttagc atg                 43

SEQ ID NO: 969         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 969
agaaatccgt ctttcattga cggatcattt gccccagacc tgt                 43

SEQ ID NO: 970         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 970
agaaatccgt ctttcattga cggggctgat aatattgcag cat                 43

SEQ ID NO: 971         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 971
agaaatccgt ctttcattga cgggtatcaa tgattatgaa caa                 43

SEQ ID NO: 972         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 972
agaaatccgt ctttcattga cggtatcaat gattatgaac aac                 43

SEQ ID NO: 973         moltype = RNA  length = 43
FEATURE                Location/Qualifiers
misc_feature           1..43
                       note = Synthetic
source                 1..43
                       mol_type = other RNA
```

```
                       organism = synthetic construct
SEQUENCE: 973
agaaatccgt ctttcattga cggtgaacaa catgctaaat cag                    43

SEQ ID NO: 974         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 974
agaaatccgt ctttcattga cgggcatgtt gttcataatc att                    43

SEQ ID NO: 975         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 975
agaaatccgt ctttcattga cggagcatgt tgttcataat cat                    43

SEQ ID NO: 976         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 976
agaaatccgt ctttcattga cgggaagtac tgatttagca tgt                    43

SEQ ID NO: 977         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 977
agaaatccgt ctttcattga cggcaggtct ggggcaaatg atg                    43

SEQ ID NO: 978         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 978
agaaatccgt ctttcattga cggccccaga cctgtaatag tca                    43

SEQ ID NO: 979         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 979
agaaatccgt ctttcattga cgggccccag acctgtaata gtc                    43

SEQ ID NO: 980         moltype = RNA  length = 43
FEATURE                Location/Qualifiers
misc_feature           1..43
                       note = Synthetic
source                 1..43
                       mol_type = other RNA
                       organism = synthetic construct
SEQUENCE: 980
agaaatccgt ctttcattga cggttcatca tttgccccag acc                    43

SEQ ID NO: 981         moltype = RNA  length = 43
FEATURE                Location/Qualifiers
misc_feature           1..43
                       note = Synthetic
source                 1..43
```

```
                        mol_type = other RNA
                        organism = synthetic construct
SEQUENCE: 981
agaaatccgt ctttcattga cggcttcatc atttgcccca gac                  43

SEQ ID NO: 982          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 982
agaaatccgt ctttcattga cggaatgctg caatattatc agc                  43

SEQ ID NO: 983          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 983
agaaatccgt ctttcattga cggcttacct ggaaaatgct gca                  43

SEQ ID NO: 984          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 984
agaaatccgt ctttcattga cggtcttacc tggaaaatgc tgc                  43

SEQ ID NO: 985          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 985
agaaatccgt ctttcattga cggtgtttta ggacagaggg tca                  43

SEQ ID NO: 986          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 986
agaaatccgt ctttcattga cggctcctac ctctcacagt ggc                  43

SEQ ID NO: 987          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 987
agaaatccgt ctttcattga cggattctag atggaagctg tat                  43

SEQ ID NO: 988          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 988
agaaatccgt ctttcattga cggtagatgg aagctgtatc caa                  43

SEQ ID NO: 989          moltype = RNA  length = 43
FEATURE                 Location/Qualifiers
misc_feature            1..43
                        note = Synthetic
```

```
source                  1..43
                        mol_type = other RNA
                        organism = synthetic construct
SEQUENCE: 989
agaaatccgt ctttcattga cggcggagca tccttggata cag                    43

SEQ ID NO: 990          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 990
agaaatccgt ctttcattga cggctgaaac agatctgtcg act                    43

SEQ ID NO: 991          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 991
agaaatccgt ctttcattga cggagcaaca ttccggagca tcc                    43

SEQ ID NO: 992          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 992
agaaatccgt ctttcattga cggcagcaac attccggagc atc                    43

SEQ ID NO: 993          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 993
agaaatccgt ctttcattga cggtaggaca gagggtcagc atg                    43

SEQ ID NO: 994          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 994
agaaatccgt ctttcattga cggaggacag agggtcagca tgc                    43

SEQ ID NO: 995          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 995
agaaatccgt ctttcattga cggggacaga gggtcagcat gcc                    43

SEQ ID NO: 996          moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 996
agaaatccgt ctttcattga cggctttctc agcctgtcag tcc                    43

SEQ ID NO: 997          moltype = RNA  length = 43
FEATURE                 Location/Qualifiers
misc_feature            1..43
```

```
                         note = Synthetic
source                   1..43
                         mol_type = other RNA
                         organism = synthetic construct
SEQUENCE: 997
agaaatccgt ctttcattga cggctcagcc tgtcagtccc tgg                     43

SEQ ID NO: 998           moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 998
agaaatccgt ctttcattga cggccaggga ctgacaggct gag                     43

SEQ ID NO: 999           moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 999
agaaatccgt ctttcattga cggctgggcc acctcctcaa ttg                     43

SEQ ID NO: 1000          moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 1000
agaaatccgt ctttcattga cggaattgag gaggtggccc agg                     43

SEQ ID NO: 1001          moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 1001
agaaatccgt ctttcattga cggttcaatt gaggaggtgg ccc                     43

SEQ ID NO: 1002          moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 1002
agaaatccgt ctttcattga cggcgccact tcttcaattg agg                     43

SEQ ID NO: 1003          moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 1003
agaaatccgt ctttcattga cgggttggct gcaactgtat atc                     43

SEQ ID NO: 1004          moltype = RNA  length = 43
FEATURE                  Location/Qualifiers
misc_feature             1..43
                         note = Synthetic
source                   1..43
                         mol_type = other RNA
                         organism = synthetic construct
SEQUENCE: 1004
agaaatccgt ctttcattga cggtcggtcc ttgtagatat aca                     43

SEQ ID NO: 1005          moltype = RNA  length = 43
FEATURE                  Location/Qualifiers
```

```
misc_feature            1..43
                        note = Synthetic
source                  1..43
                        mol_type = other RNA
                        organism = synthetic construct
SEQUENCE: 1005
agaaatccgt ctttcattga cggtctgcct gccgcactag ctt                    43

SEQ ID NO: 1006         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1006
agaaatccgt ctttcattga cggtttctca gcctgtcagt ccc                    43

SEQ ID NO: 1007         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1007
agaaatccgt ctttcattga cggtcagcct gtcagtccct ggg                    43

SEQ ID NO: 1008         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1008
agaaatccgt ctttcattga cggagttcct gggccacctc ctc                    43

SEQ ID NO: 1009         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1009
agaaatccgt ctttcattga cggaggaggt ggcccaggaa ctc                    43

SEQ ID NO: 1010         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1010
agaaatccgt ctttcattga cggaagaagt ggcggaagct ggt                    43

SEQ ID NO: 1011         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1011
agaaatccgt ctttcattga cgggctgcaa ctgtatatct aca                    43

SEQ ID NO: 1012         moltype = RNA  length = 43
FEATURE                 Location/Qualifiers
misc_feature            1..43
                        note = Synthetic
source                  1..43
                        mol_type = other RNA
                        organism = synthetic construct
SEQUENCE: 1012
agaaatccgt ctttcattga cggcagccaa cgaagtgcct cag                    43

SEQ ID NO: 1013         moltype = RNA  length = 43
```

```
FEATURE                Location/Qualifiers
misc_feature           1..43
                       note = Synthetic
source                 1..43
                       mol_type = other RNA
                       organism = synthetic construct
SEQUENCE: 1013
agaaatccgt ctttcattga cggtagatat acagttgcag cca                      43

SEQ ID NO: 1014        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1014
agaaatccgt ctttcattga cgggtgactt ctcggtcctt gta                      43

SEQ ID NO: 1015        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1015
agaaatccgt ctttcattga cgggtgacag tggacacacc tta                      43

SEQ ID NO: 1016        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1016
agaaatccgt ctttcattga cggtgacagt ggacacacct tac                      43

SEQ ID NO: 1017        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1017
agaaatccgt ctttcattga cggcctgggc aaccgtctgg atg                      43

SEQ ID NO: 1018        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1018
agaaatccgt ctttcattga cggcccaggt aaggtgtgtc cac                      43

SEQ ID NO: 1019        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1019
agaaatccgt ctttcattga cggcgcacat catccagacg gtt                      43

SEQ ID NO: 1020        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1020
agaaatccgt ctttcattga cggaatctgt tacgcacatc atc                      43
```

```
SEQ ID NO: 1021        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1021
agaaatccgt ctttcattga cgggaatctg ttacgcacat cat                      43

SEQ ID NO: 1022        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1022
agaaatccgt ctttcattga cggtggcggc agtttgaatc tgt                      43

SEQ ID NO: 1023        moltype = RNA  length = 43
FEATURE                Location/Qualifiers
misc_feature           1..43
                       note = Synthetic
source                 1..43
                       mol_type = other RNA
                       organism = synthetic construct
SEQUENCE: 1023
agaaatccgt ctttcattga cggcctgagt tgtggcggca gtt                      43

SEQ ID NO: 1024        moltype = DNA  length = 1113
FEATURE                Location/Qualifiers
misc_feature           1..1113
                       note = Synthetic
source                 1..1113
                       mol_type = other DNA
                       organism = synthetic construct
SEQUENCE: 1024
atgctccccc ggctaatttg tatcaatgat tatgaacaac atgctaaatc agtacttcca  60
aagtctatat atgactatta caggtctggg gcaaatgatg aagaaacttt ggctgataat  120
attgcagcat tttccagatg gaagctgtat ccaaggatgc tccggaatgt tgctgaaaca  180
gatctgtcga cttctgtttt aggacagagg gtcagcatgc caatatgtgt gggggctacg  240
gccatgcagc gcatggctca tgtggacggc gagcttgcca ctgtgagagc ctgtcagtcc  300
ctgggaacgg gcatgatgtt gagttcctgg gccacctcct caattgaaga agtggcggaa  360
gctggtcctg aggcacttcg ttggctgcaa ctgtatatct acaaggaccg agaagtcacc  420
aagaagctag tgcggcaggc agagaagatg ggctacaagg ccatatttgt gacagtggac  480
acaccttacc tgggcaaccg tctggatgat gtgcgtaaca gattcaaact gccgccacaa  540
ctcaggatga aaaattttga aaccagtact ttatcatttt ctcctgagga aaattttgga  600
gacgacagtg gacttgctgc atatgtggct aaagcaatag acccatctat cagctgggaa  660
gatatcaaat ggctgagaag actgacatca ttgccaattg ttgcaaaggg cattttgaga  720
ggtgatgatg ccagggaggc tgttaaacat ggcttgaatg ggatcttggt gtcgaatcat  780
ggggctcgac aactcgatgg ggtgccagcc actattgatg ttctgccaga aattgtggag  840
gctgtggaag ggaaggtgga agtcttcctg gacgggggtg tgcggaaagg cactgatgtt  900
ctgaaagctc tggctcttgg cgccaaggct gtgtttgtgg ggagaccaat cgtttggggc  960
ttagctttcc agggggagaa aggtgttcaa gatgtcctcg agatactaaa ggaagaattc  1020
cggttggcca tggctctgag tgggtgccag aatgtgaaag tcatcgacaa gacattggtg  1080
aggaaaaatc ctttggccgt ttccaagatc tga                                1113

SEQ ID NO: 1025        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1025
caaagtctat atatgactat                                                20

SEQ ID NO: 1026        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1026
ggaagtactg atttagcatg                                                20

SEQ ID NO: 1027        moltype = DNA  length = 20
```

```
FEATURE                Location/Qualifiers
misc_feature           1..20
                       note = Synthetic
source                 1..20
                       mol_type = other DNA
                       organism = synthetic construct
SEQUENCE: 1027
atcatttgcc ccagacctgt                                              20

SEQ ID NO: 1028        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1028
ggctgataat attgcagcat                                              20

SEQ ID NO: 1029        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1029
gtatcaatga ttatgaacaa                                              20

SEQ ID NO: 1030        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1030
tatcaatgat tatgaacaac                                              20

SEQ ID NO: 1031        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1031
tgaacaacat gctaaatcag                                              20

SEQ ID NO: 1032        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1032
gcatgttgtt cataatcatt                                              20

SEQ ID NO: 1033        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1033
agcatgttgt tcataatcat                                              20

SEQ ID NO: 1034        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1034
gaagtactga tttagcatgt                                              20
```

```
SEQ ID NO: 1035         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1035
caggtctggg gcaaatgatg                                              20

SEQ ID NO: 1036         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1036
ccccagacct gtaatagtca                                              20

SEQ ID NO: 1037         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1037
gccccagacc tgtaatagtc                                              20

SEQ ID NO: 1038         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1038
ttcatcattt gccccagacc                                              20

SEQ ID NO: 1039         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1039
cttcatcatt tgccccagac                                              20

SEQ ID NO: 1040         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1040
aatgctgcaa tattatcagc                                              20

SEQ ID NO: 1041         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1041
cttacctgga aaatgctgca                                              20

SEQ ID NO: 1042         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1042
tcttacctgg aaaatgctgc                                              20
```

```
SEQ ID NO: 1043        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1043
tgttttagga cagagggtca                                              20

SEQ ID NO: 1044        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1044
ctcctacctc tcacagtggc                                              20

SEQ ID NO: 1045        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1045
attctagatg gaagctgtat                                              20

SEQ ID NO: 1046        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1046
tagatggaag ctgtatccaa                                              20

SEQ ID NO: 1047        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1047
cggagcatcc ttggatacag                                              20

SEQ ID NO: 1048        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1048
ctgaaacaga tctgtcgact                                              20

SEQ ID NO: 1049        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1049
agcaacattc cggagcatcc                                              20

SEQ ID NO: 1050        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1050
```

```
cagcaacatt ccggagcatc                                                20

SEQ ID NO: 1051       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1051
taggacagag ggtcagcatg                                                20

SEQ ID NO: 1052       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1052
aggacagagg gtcagcatgc                                                20

SEQ ID NO: 1053       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1053
ggacagaggg tcagcatgcc                                                20

SEQ ID NO: 1054       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1054
ctttctcagc ctgtcagtcc                                                20

SEQ ID NO: 1055       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1055
ctcagcctgt cagtccctgg                                                20

SEQ ID NO: 1056       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1056
ccagggactg acaggctgag                                                20

SEQ ID NO: 1057       moltype = DNA  length = 20
FEATURE               Location/Qualifiers
misc_feature          1..20
                      note = Synthetic
source                1..20
                      mol_type = other DNA
                      organism = synthetic construct
SEQUENCE: 1057
ctgggccacc tcctcaattg                                                20

SEQ ID NO: 1058       moltype = DNA  length = 20
FEATURE               Location/Qualifiers
misc_feature          1..20
                      note = Synthetic
source                1..20
                      mol_type = other DNA
                      organism = synthetic construct
```

```
SEQUENCE: 1058
aattgaggag gtggcccagg                                          20

SEQ ID NO: 1059        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1059
ttcaattgag gaggtggccc                                          20

SEQ ID NO: 1060        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1060
cgccacttct tcaattgagg                                          20

SEQ ID NO: 1061        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1061
gttggctgca actgtatatc                                          20

SEQ ID NO: 1062        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1062
tcggtccttg tagatataca                                          20

SEQ ID NO: 1063        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1063
tctgcctgcc gcactagctt                                          20

SEQ ID NO: 1064        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1064
tttctcagcc tgtcagtccc                                          20

SEQ ID NO: 1065        moltype = DNA  length = 20
FEATURE                Location/Qualifiers
misc_feature           1..20
                       note = Synthetic
source                 1..20
                       mol_type = other DNA
                       organism = synthetic construct
SEQUENCE: 1065
tcagcctgtc agtccctggg                                          20

SEQ ID NO: 1066        moltype = DNA  length = 20
FEATURE                Location/Qualifiers
misc_feature           1..20
                       note = Synthetic
source                 1..20
                       mol_type = other DNA
```

```
                        organism = synthetic construct
SEQUENCE: 1066
agttcctggg ccacctcctc                                          20

SEQ ID NO: 1067         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1067
aggaggtggc ccaggaactc                                          20

SEQ ID NO: 1068         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1068
aagaagtggc ggaagctggt                                          20

SEQ ID NO: 1069         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1069
gctgcaactg tatatctaca                                          20

SEQ ID NO: 1070         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1070
cagccaacga agtgcctcag                                          20

SEQ ID NO: 1071         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1071
tagatataca gttgcagcca                                          20

SEQ ID NO: 1072         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1072
gtgacttctc ggtccttgta                                          20

SEQ ID NO: 1073         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1073
gtgacagtgg acacacctta                                          20

SEQ ID NO: 1074         moltype = DNA  length = 20
FEATURE                 Location/Qualifiers
misc_feature            1..20
                        note = Synthetic
source                  1..20
```

```
                        mol_type = other DNA
                        organism = synthetic construct
SEQUENCE: 1074
tgacagtgga cacaccttac                                              20

SEQ ID NO: 1075         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1075
cctgggcaac cgtctggatg                                              20

SEQ ID NO: 1076         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1076
cccaggtaag gtgtgtccac                                              20

SEQ ID NO: 1077         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1077
cgcacatcat ccagacggtt                                              20

SEQ ID NO: 1078         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1078
aatctgttac gcacatcatc                                              20

SEQ ID NO: 1079         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1079
gaatctgtta cgcacatcat                                              20

SEQ ID NO: 1080         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1080
tggcggcagt ttgaatctgt                                              20

SEQ ID NO: 1081         moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1081
cctgagttgt ggcggcagtt                                              20

SEQ ID NO: 1082         moltype = RNA  length = 43
FEATURE                 Location/Qualifiers
misc_feature            1..43
                        note = Synthetic
```

```
modified_base          40..43
                       mod_base = OTHER
                       note = modified with phosphorothioate
modified_base          40..42
                       mod_base = OTHER
                       note = modified with 2'-O-methlyation
source                 1..43
                       mol_type = other RNA
                       organism = synthetic construct
SEQUENCE: 1082
agaaatccgt ctttcattga cggcggagca tccttggata cag                    43

SEQ ID NO: 1083        moltype = RNA  length = 43
FEATURE                Location/Qualifiers
misc_feature           1..43
                       note = Synthetic
modified_base          1..4
                       mod_base = OTHER
                       note = modified with phosphorothioate
modified_base          1..3
                       mod_base = OTHER
                       note = modified with 2'-O-methlyation
modified_base          40..42
                       mod_base = OTHER
                       note = modified with 2'-O-methlyation
source                 1..43
                       mol_type = other RNA
                       organism = synthetic construct
modified_base          40..43
                       mod_base = OTHER
                       note = modified with phosphorothioate
SEQUENCE: 1083
agaaatccgt ctttcattga cggcggagca tccttggata cag                    43

SEQ ID NO: 1084        moltype = RNA  length = 43
FEATURE                Location/Qualifiers
misc_feature           1..43
                       note = Synthetic
modified_base          40..43
                       mod_base = OTHER
                       note = modified with phosphorothioate
modified_base          40..42
                       mod_base = OTHER
                       note = modified with 2'-O-methlyation
source                 1..43
                       mol_type = other RNA
                       organism = synthetic construct
SEQUENCE: 1084
agaaatccgt ctttcattga cggggaagta ctgatttagc atg                    43

SEQ ID NO: 1085        moltype = RNA  length = 43
FEATURE                Location/Qualifiers
misc_feature           1..43
                       note = Synthetic
modified_base          1..4
                       mod_base = OTHER
                       note = modified with phosphorothioate
modified_base          1..3
                       mod_base = OTHER
                       note = modified with 2'-O-methlyation
modified_base          40..42
                       mod_base = OTHER
                       note = modified with 2'-O-methlyation
modified_base          40..43
                       mod_base = OTHER
                       note = modified with phosphorothioate
source                 1..43
                       mol_type = other RNA
                       organism = synthetic construct
SEQUENCE: 1085
agaaatccgt ctttcattga cggggaagta ctgatttagc atg                    43

SEQ ID NO: 1086        moltype = RNA  length = 43
FEATURE                Location/Qualifiers
misc_feature           1..43
                       note = Synthetic
modified_base          40..43
                       mod_base = OTHER
                       note = modified with phosphorothioate
```

```
modified_base          40..42
                       mod_base = OTHER
                       note = modified with 2'-O-methlyation
source                 1..43
                       mol_type = other RNA
                       organism = synthetic construct
SEQUENCE: 1086
agaaatccgt ctttcattga cggcaaagtc tatatatgac tat                  43

SEQ ID NO: 1087        moltype = RNA  length = 43
FEATURE                Location/Qualifiers
misc_feature           1..43
                       note = Synthetic
modified_base          1..4
                       mod_base = OTHER
                       note = modified with phosphorothioate
modified_base          1..3
                       mod_base = OTHER
                       note = modified with 2'-O-methlyation
modified_base          40..42
                       mod_base = OTHER
                       note = modified with 2'-O-methlyation
source                 1..43
                       mol_type = other RNA
                       organism = synthetic construct
modified_base          40..43
                       mod_base = OTHER
                       note = modified with phosphorothioate
SEQUENCE: 1087
agaaatccgt ctttcattga cggcaaagtc tatatatgac tat                  43

SEQ ID NO: 1088        moltype = DNA  length = 122
FEATURE                Location/Qualifiers
misc_feature           1..122
                       note = Synthetic
source                 1..122
                       mol_type = other DNA
                       organism = synthetic construct
SEQUENCE: 1088
attgtgcact gtcagatctt ggaaacggcc aaaggatttt tcctcaccaa tgtcttgtcg  60
atgactttca cattctggca cccactcaga gccatggcca accggaattc ttcctttagt  120
at                                                                 122

SEQ ID NO: 1089        moltype = RNA  length = 3213
FEATURE                Location/Qualifiers
misc_feature           1..3213
                       note = Synthetic
source                 1..3213
                       mol_type = other RNA
                       organism = synthetic construct
SEQUENCE: 1089
atgagctccg ccatcaagtc ctacaagtct gtgctgcggc caaacgagag aaagaatcag  60
ctgctgaagt ccaccatcca gtgcctggag gacggctccg ccttcttttt caagatgctg  120
cagggcctgt ttggcggcat cacccccgag atcgtgagat tcagcacaga gcaggagaag  180
cagcagcagg atatcgccct gtggtgtgcc gtgaattggt tcaggcctgt gagccaggac  240
tccctgaccc acacaatcgc ctccgataac ctggtggaga agtttgagga gtactatggc  300
ggcacagcca gcgacgccat caagcagtac ttcagcgcct ccatcggcga gtcctactat  360
tggaatgact gccgccagca gtactatgat ctgtgtcggg agctgggcgt ggaggtgtct  420
gacctgaccc acgatctgga gatcctgtgc cgggagaagt gtctggccgt ggccacagag  480
agcaaccaga acaattctat catcagcgtg ctgtttggca ccggcgagaa ggaggatagg  540
tctgtgaagc tgcgcatcac aaagaagatc ctggaggcca tcagcaacct gaaggagatc  600
ccaaagaatg tggcccccat ccaggagatc atcctgaatg tggccaaggc caccaaggag  660
acattcagac aggtgtacgc aggaaacctg ggagcaccat ccaccctgga gaagtttatc  720
gccaaggacg gccagaagga gttcgatctg aagaagctgc agacagacct gaagaaagtg  780
atccggggca agtctaagga gagagattgg tgctgtcagg aggagctgag gagctacgtg  840
gagcagaata ccatccagta tgacctgtgg gcctggggcg agatgttcaa caaggcccac  900
accgccctga agatcaagtc cacaagaaac tacaattttg ccaagcagag gctggagcag  960
ttcaaggaga tccagtctct gaacaatctg ctggtggtga agaagctgaa cgactttttc  1020
gatagcgagt ttttctccgg cgaggagacc tacacaatct gcgtgcacca cctgggcggc  1080
aaggacctgt ccaagctgta taaggcctgg gaggacgatc ccgccgatcc tgagaatgcc  1140
atcgtggtgc tgtgcgacga tctgaagaac aattttaaga aggagcctat caggaacatc  1200
ctgcgctaca tcttcaccat ccgccaggag tgtagcgcac aggacatcct ggcagcagca  1260
aagtacaatc agcagctgga tcggtataag agccagaagg ccaacccatc cgtgctgggc  1320
aatcagggct ttacctggac aaacgccgtg atcctgccag agaaggccca gcggaacgac  1380
agacccaatt ctctggatct gcgcatctgg ctgtacctga agctgcggca ccctgacggc  1440
agatggaaga agcaccacat cccattctac gatacccggt ttttccagga gatctatgcc  1500
gccggcaata gccctgtgga cacctgtcag tttaggacac cccgcttcgg ctatcacctg  1560
cctaagctga ccgatcagac agccatccgc gtgaacaaga agcacgtgaa ggcagcaaag  1620
accgaggcac ggatcagact ggccatccag cagggcacac tgccagtgtc caatctgaag  1680
```

-continued

```
atcaccgaga tctccgccac aatcaactct aagggccagg tgcgcatccc cgtgaagttt  1740
cgggtgggaa ggcagaaggg aaccctgcag atcggcgacc ggttctgcgg ctacgatcag  1800
aaccagacag cctctcacgc ctatagcctg tgggaggtgg tgaaggaggg ccagtaccac  1860
aaggagctgg gctgttttgt gcgcttcatc tctagcggcg acatcgtgtc catcaccgag  1920
aaccggggca atcagtttga tcagctgtct tatgagggcc tggcctaccc ccagtatgcc  1980
gactggagaa agaaggcctc caagttcgtg tctctgtggc agatcaccaa gaagaacaag  2040
aagaaggaga tcgtgacagt ggaggccaag gagaagtttg acgccatctg caagtaccag  2100
cctaggctgt ataagttcaa caaggagtac gcctatctgc tgcgggatat cgtgagaggc  2160
aagagcctgg tggagctgca gcagatcagg caggagatct ttcgcttcat cgagcaggac  2220
tgtggagtga cccgcctggg atctctgagc ctgtccaccc tggagacagt gaaggccgtg  2280
aagggcatca tctactccta tttttctaca gccctgaatg cctctaagaa caatcccatc  2340
agcgacgagc agcggaagga gtttgatcct gagctgttcg ccctgctgga gaagctggag  2400
ctgatcagga ctcggaagaa gaagcagaag gtggagagaa tcgccaatag cctgatccag  2460
acatgcctgg agaacaatat caagttcatc aggggcgagg gcgacctgtc caccacaaac  2520
aatgccacca agaagaaggc caactctagg agcatggatt ggctggccag aggcgtgttt  2580
aataagatcc ggcagctggc cccaatgcac aacatcaccc tgttcggctg cggcagcctg  2640
tacacatccc accaggaccc tctggtgcac agaaacccag ataaggccat gaagtgtaga  2700
tgggcagcaa tcccagtgaa ggacatcggc gattgggtgc tgagaaagct gtcccagaac  2760
ctgagggcca agaatcgggg caccggcgag tactatcacc agggcgtgaa ggagttcctg  2820
tctcactatg agctgcagga cctggaggag gagctgctga agtggcggtc tgatagaaag  2880
agcaacatcc cttgctgggt gctgcagaat agactggccg agaagctggg caacaaggag  2940
gccgtggtgt acatcccagt gaggggcggc cgcatctatt ttgcaaccca caaggtggca  3000
acaggagccg tgagcatcgt gttcgaccag aagcaagtgt gggtgtgtaa tgcagatcac  3060
gtggcagcag caaacatcgc actgaccggc aagggcatcg gcgagcagtc ctctgacgag  3120
gagaaccccg atggctccag gatcaagctg cagctgacat ctaaaaggcc ggcggccacg  3180
aaaaaggccg gccaggcaaa aaagaaaaag taa                               3213

SEQ ID NO: 1090        moltype = RNA  length = 3213
FEATURE                Location/Qualifiers
misc_feature           1..3213
                       note = Synthetic
source                 1..3213
                       mol_type = other RNA
                       organism = synthetic construct
SEQUENCE: 1090
atgagctccg ccatcaagtc ctacaagtct gtgctgcggc caaacgagag aaagaatcag  60
ctgctgaagt ccaccatcca gtgcctggag gacggctccg ccttcttttt caagatgctg  120
cagggcctgt ttggcggcat cacccccgag atcgtgagat tcagcacaga gcaggagaag  180
cagcagcagg atatcgccct gtggtgtgcc gtgaattggt tcaggcctgt gagccaggac  240
tccctgaccc acacaatcgc ctccgataac ctggtggaga agtttgagga gtactatggc  300
ggcacagcca gcgacgccat caagcagtac ttcagcgcct ccatcggcga gtcctactat  360
tggaatgact gccgccagca gtactatgat ctgtgtcggg agctgggcgt ggaggtgtct  420
gacctgaccc acgatctgga gatcctgtgc cgggagaagt gtctggccgt ggccacagag  480
agcaaccaga acaattctat catcagcgtg ctgtttggca ccggcgagaa ggaggatagg  540
tctgtgaagc tgcgcatcac aaagaagatc ctggaggcca tcagcaacct gaaggagatc  600
ccaaagaatg tggcccccat ccaggagatc atcctgaatg tggccaaggc caccaaggag  660
acattcagac aggtgtacgc aggaaacctg ggagcaccat ccaccctgga gaagtttatc  720
gccaaggacg gccagaagga gttcgatctg aagaagctgc agacagacct gaagaaagtg  780
atccggggca agtctaagga gagagattgg tgctgtcagg aggagctgag gagctacgtg  840
gagcagaata ccatccagta tgacctgtgg gcctggggcg agatgttcaa caaggcccac  900
accgccctga agatcaagtc cacaagaaac tacaattttg ccaagcagag gctggagcag  960
ttcaaggaga tccagtctct gaacaatctg ctggtggtga agaagctgaa cgactttttc  1020
gatagcgagt tttctccgg cgaggagacc tacacaatct gcgtgcacca cctgggcggc  1080
aaggacctgt ccaagctgta taaggcctgg gaggacgatc ccgccgatcc tgagaatgcc  1140
atcgtggtgc tgtgcgacga tctgaagaac aattttaaga aggagcctat caggaacatc  1200
ctgcgctaca tcttcaccat ccgccaggag tgtagcgcac aggacatcct ggcagcagca  1260
aagtacaatc agcagctgga tcggtataag agccagaagg ccaacccatc cgtgctgggc  1320
aatcagggct ttacctggac aaacgccgtg atcctgccag agaaggccca gcggaacgac  1380
agacccaatt ctctggatct gcgcatctgg ctgtacctga agctgcggca ccctgacggc  1440
agatggaaga agcaccacat cccattctac gatacccggt ttttccagga gatctatgcc  1500
gccggcaata gccctgtgga cacctgtcag tttaggacac cccgcttcgg ctatcacctg  1560
cctaagctga ccgatcagac agccatccgc gtgaacaaga agcacgtgaa ggcagcaaag  1620
accgaggcac ggatcagact ggccatccag cagggcacac tgccagtgtc caatctgaag  1680
atcaccgaga tctccgccac aatcaactct aagggccagg tgcgcatccc cgtgaagttt  1740
cgggtgggaa ggcagaaggg aaccctgcag atcggcgacc ggttctgcgg ctacgatcag  1800
aaccagacag cctctcacgc ctatagcctg tgggaggtgg tgaaggaggg ccagtaccac  1860
aaggagctgc ggtgtcgggt gcgcttcatc tctagcggcg acatcgtgtc catcaccgag  1920
aaccggggca atcagtttga tcagctgtct tatgagggcc tggcctaccc ccagtatgcc  1980
gactggagaa agaaggcctc caagttcgtg tctctgtggc agatcaccaa gaagaacaag  2040
aagaaggaga tcgtgacagt ggaggccaag gagaagtttg acgccatctg caagtaccag  2100
cctaggctgt ataagttcaa caaggagtac gcctatctgc tgcgggatat cgtgagaggc  2160
aagagcctgg tggagctgca gcagatcagg caggagatct ttcgcttcat cgagcaggac  2220
tgtggagtga cccgcctggg atctctgagc ctgtccaccc tggagacagt gaaggccgtg  2280
aagggcatca tctactccta tttttctaca gccctgaatg cctctaagaa caatcccatc  2340
agcgacgagc agcggaagga gtttgatcct gagctgttcg ccctgctgga gaagctggag  2400
ctgatcagga ctcggaagaa gaagcagaag gtggagagaa tcgccaatag cctgatccag  2460
acatgcctgg agaacaatat caagttcatc aggggcgagg gcgacctgtc caccacaaac  2520
aatgccacca agaagaaggc caactctagg agcatggatt ggctggccag aggcgtgttt  2580
aataagatcc ggcagctggc caccatgcac aacatcaccc tgttcggctg cggcagcctg  2640
```

```
tacacatccc accaggaccc tctggtgcac agaaacccag ataaggccat gaagtgtaga  2700
tgggcagcaa tcccagtgaa ggacatcggc gattgggtgc tgagaaagct gtcccagaac  2760
ctgagggcca agaatcgggg caccggcgag tactatcacc agggcgtgaa ggagttcctg  2820
tctcactatg agctgcagga cctggaggag gagctgctga agtggcggtc tgatagaaag  2880
agcaacatcc cttgctgggt gctgcagaat agactggccg agaagctggg caacaaggag  2940
gccgtggtgt acatcccagt gaggggcggc cgcatctatt ttgcaaccca caaggtggca  3000
acaggagccg tgagcatcgt gttcgaccag aagcaagtgt gggtgtgtaa tgcagatcac  3060
gtggcagcag caaacatcgc actgaccggc aagggcatcg gccggcagtc ctctgacgag  3120
gagaaccccg atggcggcag gatcaagctg cagctgacat ctaaaaggcc ggcggccacg  3180
aaaaaggccg gccaggcaaa aaagaaaaag taa                               3213

SEQ ID NO: 1091        moltype = RNA  length = 43
FEATURE                Location/Qualifiers
misc_feature           1..43
                       note = Synthetic
modified_base          40..43
                       mod_base = OTHER
                       note = modified with phosphorothioate
modified_base          40..42
                       mod_base = OTHER
                       note = modified with 2'-O-methlyation
source                 1..43
                       mol_type = other RNA
                       organism = synthetic construct
SEQUENCE: 1091
agaaatccgt ctttcattga cggcggagca tccttggata cag                    43

SEQ ID NO: 1092        moltype = RNA  length = 43
FEATURE                Location/Qualifiers
misc_feature           1..43
                       note = Synthetic
modified_base          1..4
                       mod_base = OTHER
                       note = modified with phosphorothioate
modified_base          1..3
                       mod_base = OTHER
                       note = modified with 2'-O-methlyation
source                 1..43
                       mol_type = other RNA
                       organism = synthetic construct
modified_base          40..42
                       mod_base = OTHER
                       note = modified with 2'-O-methlyation
modified_base          40..43
                       mod_base = OTHER
                       note = modified with phosphorothioate
SEQUENCE: 1092
agaaatccgt ctttcattga cggcggagca tccttggata cag                    43

SEQ ID NO: 1093        moltype = RNA  length = 20
FEATURE                Location/Qualifiers
misc_feature           1..20
                       note = Synthetic
source                 1..20
                       mol_type = other RNA
                       organism = synthetic construct
SEQUENCE: 1093
caaagtctat atatgactat                                              20

SEQ ID NO: 1094        moltype = RNA  length = 20
FEATURE                Location/Qualifiers
misc_feature           1..20
                       note = Synthetic
source                 1..20
                       mol_type = other RNA
                       organism = synthetic construct
SEQUENCE: 1094
ggaagtactg atttagcatg                                              20

SEQ ID NO: 1095        moltype = RNA  length = 20
FEATURE                Location/Qualifiers
misc_feature           1..20
                       note = Synthetic
source                 1..20
                       mol_type = other RNA
                       organism = synthetic construct
SEQUENCE: 1095
tagatggaag ctgtatccaa                                              20
```

-continued

```
SEQ ID NO: 1096        moltype = RNA  length = 20
FEATURE                Location/Qualifiers
misc_feature           1..20
                       note = Synthetic
source                 1..20
                       mol_type = other RNA
                       organism = synthetic construct
SEQUENCE: 1096
cggagcatcc ttggatacag                                              20

SEQ ID NO: 1097        moltype = RNA  length = 20
FEATURE                Location/Qualifiers
misc_feature           1..20
                       note = Synthetic
source                 1..20
                       mol_type = other RNA
                       organism = synthetic construct
SEQUENCE: 1097
aggacagagg gtcagcatgc                                              20
```